(12) United States Patent
Brodney et al.

(10) Patent No.: US 7,781,435 B2
(45) Date of Patent: *Aug. 24, 2010

(54) IMIDAZOLE COMPOUNDS FOR THE TREATMENT OF NEUROLOGICAL DISORDERS

(75) Inventors: Michael A. Brodney, East Lyme, CT (US); Karen J. Coffman, Pawcatuck, CT (US); Edward F. Kleinman, Pawcatuck, CT (US); Brian T. O'Neill, Haddam, CT (US); Yuhpyng L. Chen, Waterford, CT (US)

(73) Assignee: Pfizer Inc, New York, NY (US)

( * ) Notice: Subject to any disclaimer, the term of this patent is extended or adjusted under 35 U.S.C. 154(b) by 431 days.

This patent is subject to a terminal disclaimer.

(21) Appl. No.: 11/524,425

(22) Filed: Sep. 20, 2006

(65) Prior Publication Data

US 2007/0066613 A1 Mar. 22, 2007

Related U.S. Application Data

(60) Provisional application No. 60/719,521, filed on Sep. 22, 2005.

(51) Int. Cl.
| A61K 31/5377 | (2006.01) |
| A61K 31/454 | (2006.01) |
| A61K 31/4178 | (2006.01) |
| A61K 31/4172 | (2006.01) |
| C07D 413/02 | (2006.01) |
| C07D 405/02 | (2006.01) |
| C07D 403/02 | (2006.01) |

(52) U.S. Cl. ............ 514/235.5; 514/326; 514/400; 544/139; 546/210; 548/311.1; 548/335.5

(58) Field of Classification Search ............ 514/235.5, 514/326, 400; 544/139; 546/210; 548/311.1, 548/335.5

See application file for complete search history.

(56) References Cited

U.S. PATENT DOCUMENTS

| 5,760,246 | A |   | 6/1998 | Biller et al. |
| 6,323,315 | B1 |   | 11/2001 | Pettit et al. |
| 6,329,342 | B1 |   | 12/2001 | Kauffman et al. |
| 6,639,076 | B1 |   | 10/2003 | Hauser et al. |
| 6,649,641 | B2 |   | 11/2003 | Behrens et al. |
| 6,828,331 | B1 |   | 12/2004 | Dodge et al. |
| 7,112,599 | B2 |   | 9/2006 | Chen |
| 7,163,942 | B2 |   | 1/2007 | Brodney et al. |
| 7,220,865 | B2 |   | 5/2007 | Chen et al. |
| 7,232,820 | B2 |   | 6/2007 | Chen |
| 7,238,721 | B2 |   | 7/2007 | Chen et al. |
| 7,241,786 | B2 |   | 7/2007 | Chen |
| 7,253,195 | B2 |   | 8/2007 | Chen |
| 7,309,709 | B2 |   | 12/2007 | Zhang |
| 7,342,118 | B2 | * | 3/2008 | Brodney et al. .......... 548/326.5 |
| 7,345,095 | B2 |   | 3/2008 | Brodney et al. |
| 7,384,968 | B2 |   | 6/2008 | Chen |
| 7,408,068 | B2 |   | 8/2008 | Chen |
| 7,521,464 | B2 |   | 4/2009 | Chen et al. |
| 2002/0004512 | A1 |   | 1/2002 | Bakshi et al. |
| 2003/0050314 | A1 |   | 3/2003 | Wehner et al. |
| 2003/0232868 | A1 |   | 12/2003 | Lehmann et al. |
| 2004/0122234 | A1 |   | 6/2004 | Hauser et al. |
| 2004/0152747 | A1 |   | 8/2004 | Chen et al. |
| 2005/0107381 | A1 |   | 5/2005 | Chen |
| 2005/0215610 | A1 | * | 9/2005 | Brodney et al. ............ 514/397 |
| 2005/0222227 | A1 |   | 10/2005 | Chen |
| 2007/0270426 | A1 |   | 11/2007 | Chen |
| 2008/0108675 | A1 |   | 5/2008 | Zhang |
| 2008/0227781 | A1 | * | 9/2008 | Brodney et al. .......... 514/235.5 |

FOREIGN PATENT DOCUMENTS

| EP | 0573271 | 12/1993 |
| EP | 0898963 | 8/1998 |
| EP | 0898963 | 3/1999 |
| JP | 07-101958 | 4/1995 |
| JP | 7-101958 A | 4/1995 |
| JP | WO 2004/089937 A1 | 10/2004 |
| WO | WO 99/08697 | 2/1999 |
| WO | WO 99/08699 | 2/1999 |
| WO | WO 00/49037 | 8/2000 |
| WO | WO 00/49037 A1 | 8/2000 |
| WO | WO 01/81298 | 11/2001 |

(Continued)

OTHER PUBLICATIONS

Golub et al., Science, vol. 286, Oct. 15, 1999, pp. 531-537.*

(Continued)

*Primary Examiner*—Rei-Tsang Shiao
*Assistant Examiner*—Joseph R Kosack
(74) *Attorney, Agent, or Firm*—Jeffrey H. Tidwell

(57) ABSTRACT

The present invention relates to compounds of Formula I

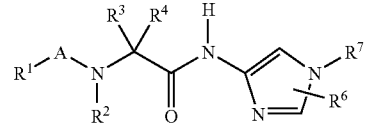

wherein $R^1$, $R^2$, $R^3$, $R^4$, $R^6$, $R^7$ and A are as defined. Compounds of Formula I have activity inhibiting production of Aβ-peptide. The invention also relates to pharmaceutical compositions and methods for treating diseases and disorders, for example, neurodegenerative and/or neurological disorders, e.g., Alzheimer's disease, in a mammal comprising compounds of Formula I.

15 Claims, No Drawings

FOREIGN PATENT DOCUMENTS

| | | |
|---|---|---|
| WO | WO 01/81298 A1 | 11/2001 |
| WO | WO 02/10141 | 2/2002 |
| WO | WO 02/10141 A1 | 2/2002 |
| WO | WO 03/055447 | 7/2003 |
| WO | WO 03/055447 A2 | 7/2003 |
| WO | WO 03/055482 | 7/2003 |
| WO | WO 03/055482 A1 | 7/2003 |
| WO | WO 03/104236 | 12/2003 |
| WO | WO 03/104236 A1 | 12/2003 |
| WO | WO 2004/089937 | 10/2004 |
| WO | WO 2005/058308 | 6/2005 |
| WO | WO 2005/058308 A2 | 6/2005 |
| WO | WO 2005/092864 | 10/2005 |

OTHER PUBLICATIONS

Thompson et al., Current Medicinal Chemistry, Oct. 2002, 9(19), pp. 1751-1763.*

Brown, Neurology, Jun. 25, 2002, 58(12), pp. 1720-1725.*

Li et al., Synthetic Communications, vol. 35, pp. 1017-1026 (2005).

Brown, P., "Drug Therapy In Human And Experimental Transmissible Spongiform Encephalopathy," *Neurology*, 2002, 1720-1725, vol. 58.

Golub, T., et al., "Molecular Classification Of Cancer: Class Discovery And Class Prediction By Gene Expression Monitoring," *Science*, 1999, 531-537, vol. 286.

Li, D., et al., "Synthesis Of Ribavirin Analogues Containing Amino-Acid Residues," *Synthetic Communications*, 2005, 1017-1026, vol. 35.

Thompson, A., et al.,"Protein Conformational Misfolding And Amyloid Formation: Characteristics Of A New Class Of Disorders That Include Alzheimer's And Prion Diseases," *Current Medicinal Chemistry*, 2002, 1751-1762, vol. 9.

* cited by examiner

IMIDAZOLE COMPOUNDS FOR THE TREATMENT OF NEUROLOGICAL DISORDERS

CROSS REFERENCE TO RELATED APPLICATION

The present application claims benefit of U.S. Ser. No. 60/719,521 filed on Sep. 22, 2005 which is incorporated by reference herein in its entirety.

FIELD OF THE INVENTION

The present invention relates to the treatment of neurodegenerative and/or neurological disorders, such as Alzheimer's disease, in mammals, including humans. This invention also relates to inhibiting, in mammals, including humans, the production of Aβ-peptides that can contribute to the formation of neurological deposits of amyloid protein. More particularly, this invention relates to imidazole compounds, pharmaceutical compositions comprising such compounds and methods of using such compounds, i.e., for the treatment of neurodegenerative and/or neurological disorders, such as Alzheimer's disease, related to Aβ-peptide production.

BACKGROUND OF THE INVENTION

Dementia results from a wide variety of distinctive pathological processes. The most common pathological processes causing dementia are Alzheimer's disease (AD), cerebral amyloid angiopathy (CAA) and prion-mediated diseases. AD affects nearly half of all people past the age of 85, the most rapidly growing portion of the United States population. As such, the number of AD patients in the United States is expected to increase from about 4 million to about 14 million by the middle of the next century.

Treatment of AD typically is the support provided by a family member in attendance. Stimulated memory exercises on a regular basis have been shown to slow, but not stop, memory loss. A few drugs, for example Aricep™, provide treatment of AD.

A hallmark of AD is the accumulation in the brain of extracellular insoluble deposits called amyloid plaques and abnormal lesions within neuronal cells called neurofibrillary tangles. Increased plaque formation is associated with an increased risk of AD. Indeed, the presence of amyloid plaques, together with neurofibrillary tangles, is the basis for definitive pathological diagnosis of AD.

The major components of amyloid plaques are the amyloid Aβ-peptides, also called Aβ-peptides, that consist of several proteins including 38, 40, 42 or 43 amino acids, designated as the $A\beta_{1-38}$, $A\beta_{1-40}$, $A\beta_{1-42}$ and $A\beta_{1-43}$ peptides, respectively. The Aβ-peptides are thought to cause nerve cell destruction, in part, because they are toxic to neurons in vitro and in vivo.

The Aβ peptides are derived from larger amyloid precursor proteins (APP proteins), that consist of four proteins containing 695, 714, 751 or 771 amino acids, designated as the $APP_{695}$, $APP_{714}$, $APP_{751}$, and $APP_{771}$, respectively. Proteases are believed to produce the Aβ peptides by cleaving specific amino acid sequences within the various APP proteins. The proteases are named "secretases" because the Aβ-peptides they produce are secreted by cells into the extracellular environment. These secretases are each named according to the cleavage(s) they make to produce the Aβ-peptides. The secretase that forms the amino terminal end of the Aβ-peptides is called the beta-secretase. The secretase that forms the carboxyl terminal end of the Aβ-peptides is called the gamma-secretase.

This invention relates to novel compounds that inhibit Aβ-peptide production, to pharmaceutical compositions comprising such compounds, and to methods of using such compounds to treat neurodegenerative and/or neurological disorders.

SUMMARY OF THE INVENTION

The present invention relates to compounds of Formula I

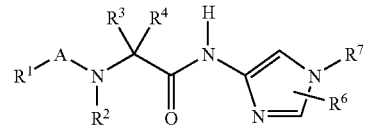

wherein $R^1$, $R^2$, $R^3$, $R^4$, $R^6$, $R^7$ and A are as defined below. Compounds of Formula I have activity inhibiting production of Aβ-peptide. The invention also relates to pharmaceutical compositions and methods for treating diseases and disorders, for example, neurodegenerative and/or neurological disorders, e.g., Alzheimer's disease, in a mammal comprising compounds of Formula I.

DETAILED DESCRIPTION OF THE INVENTION

In one embodiment, the present invention relates to compounds of Formula I wherein A is absent or is selected from

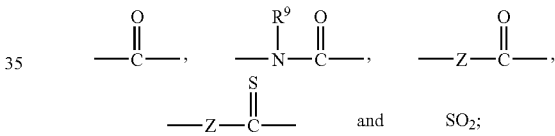

Z is selected from —$CH_2$, —CH(OH), —CH($C_1$-$C_6$ alkyl), —CH($C_1$-$C_6$ alkoxyl), —CH($NR^9R^{10}$), —CH($CH_2$(OH)), —CH(CH($C_1$-$C_4$ alkyl)(OH)) and —CH(C(($C_1$-$C_4$ alkyl)($C_1$-$C_4$alkyl)(OH));

$R^1$ is selected from —$C_1$-$C_{20}$ alkyl, —$C_2$-$C_{20}$ alkenyl, —$C_2$-$C_{20}$ alkynyl, —$C_1$-$C_{20}$ alkoxy, —$C_2$-$C_{20}$ alkenoxy, —$C_1$-$C_{20}$ hydroxyalkyl, —$C_3$-$C_8$ cycloalkyl, benzo($C_3$-$C_8$ cycloalkyl), benzo($C_3$-$C_8$ heterocycloalkyl), —$C_4$-$C_8$ cycloalkenyl, —($C_5$-$C_{11}$)bi- or tricycloalkyl, benzo($C_5$-$C_{11}$) bi- or tricycloalkyl, ($C_7$-$C_{11}$)bi- or tricycloalkenyl, (3-8 membered) heterocycloalkyl, —$C_6$-$C_{14}$ aryl and (5-14 membered) heteroaryl, wherein $R^1$ is optionally substituted by $R^{1a}$;

wherein $R^{1a}$ in each instance is independently selected from —OH, halo, —$C_1$-$C_6$ alkoxy, —CN, —$NO_2$, —$NR^9R^{10}$, —C(=O)$NR^9R^{10}$, —C(=O)$R^{11}$, —C(=O) $OR^{12}$, —$SO_2$—$NR^9R^{10}$, —S(O)$_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy;

wherein said alkoxy, cycloalkyl, cycloalkenyl, bi- or tricycloalkyl, bi- or tricycloalkenyl, heterocycloalkyl, aryl, heteroaryl, aryloxy and heteroaryloxy of $R^{1a}$ are each optionally independently substituted with from one to six substituents independently selected from the group $R^{1b}$;

wherein $R^{1b}$ in each instance is independently selected from —OH, —$C_1$-$C_{12}$ alkyl, —$C_2$-$C_{12}$ alkenyl, —$C_2$-$C_{12}$ alkynyl, —$C_1$-$C_6$ alkoxy, —$C_1$-$C_{12}$ alkoxyalkyl —$C_1$-$C_{12}$ hydroxyalkyl, —$C_2$-$C_6$ alkenoxy, —$C_2$-$C_6$ alkynoxy, halo, —CN, —$NO_2$, —$NR^9R^{10}$, —C(=O)$NR^9R^{10}$, —C(=O)$R^{11}$, —C(=O)$OR^{12}$, —$SO_2$—$NR^9R^{10}$, —S(O)$_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy;

$R^2$ is selected from H, —$C_1$-$C_6$ alkyl, —$C_2$-$C_6$ alkenyl, —$C_3$-$C_8$ cycloalkyl and —$C_3$-$C_8$ cycloalkenyl, wherein $R^2$ is optionally independently substituted with from one to three substituents independently selected from —$C_1$-$C_4$ alkyl optionally substituted with from one to three halo atoms, —$C_1$-$C_4$ alkoxy optionally substituted with from one to three halo atoms, halo and —OH;

or $R^1$ and $R^2$ together with the A group when present and the nitrogen atom to which $R^2$ is attached, or $R^1$ and $R^2$ together with the nitrogen atom to which $R^1$ and $R^2$ are attached when A is absent, may optionally form a four to eight membered ring;

$R^3$ is selected from H, —$C_1$-$C_6$ alkyl, —$C_2$-$C_6$ alkenyl, —$C_2$-$C_6$ alkynyl, —$C_3$-$C_6$ cycloalkyl, —$C_5$-$C_6$ cycloalkenyl and (3-8 membered) heterocycloalkyl, —$C_6$-$C_{14}$ aryl and -(5-14 membered) heteroaryl, wherein said alkyl, alkenyl, alkynyl, cycloalkyl, cycloalkenyl, heterocycloalkyl, aryl or heteroaryl are each optionally independently substituted with from one to three substituents independently selected from —$C_1$-$C_4$ alkoxy, halo, —OH, —S($C_1$-$C_4$)alkyl, —$C_1$-$C_4$ alkyl —C(=O)$OR^9$, —$SO_2R^9$ and -(3-8 membered) heterocycloalkyl wherein said alkyl, alkoxy, and heterocyloalkyl may be further substituted by one to six halo;

$R^4$ is H, —$C_1$-$C_6$ alkyl or halo;

or $R^3$ and $R^4$ may together with the carbon atom to which they are attached optionally form a moiety selected from cyclopropyl, cyclobutyl, cyclopentyl, cyclohexyl, morpholino, piperidino, pyrrolidino, tetrahydrofuranyl and perhydro-2H-pyran, wherein said moiety formed by $R^3$ and $R^4$ is optionally substituted with from one to three substituents independently selected from —$C_1$-$C_6$ alkyl optionally substituted with from one to three halo atoms, —$C_1$-$C_6$ alkoxy optionally substituted with from one to three halo atoms, halo, —OH, —CN and allyl;

$R^6$ is selected from H, —$C_1$-$C_6$ alkyl, —$C_2$-$C_6$ alkylene, —$C_1$-$C_6$ alkoxy, halo, —CN, —$C_3$-$C_{12}$ cycloalkyl, —$C_4$-$C_{12}$ cycloalkenyl (5-10 membered) heteroaryl and —$C_6$-$C_{10}$ aryl, wherein said alkyl, alkylene and alkoxy of $R^6$ are each optionally independently substituted with from one to three substituents independently selected from halo and —CN, and wherein said cycloalkyl, cycloalkenyl, heteroaryl and aryl of $R^6$ are each optionally independently substituted with from one to three substituents independently selected from —$C_1$-$C_4$ alkyl optionally substituted with from one to three halo atoms, —$C_1$-$C_4$ alkoxy optionally substituted with from one to three halo atoms, halo and —CN;

$R^7$ is —$C_1$-$C_{20}$ alkyl substituted by —$C_3$-$C_{12}$ cycloalkyl, —$C_4$-$C_{12}$ cycloalkenyl, —($C_5$-$C_{20}$)bi- or tricycloalkyl, —($C_7$-$C_{20}$)bi- or tricycloalkenyl, -(3-12 membered) heterocycloalkyl, -(7-20 membered) heterobi- or heterotricycloalkyl, —$C_6$-$C_{14}$ aryl, benzo($C_3$-$C_8$ heterocycloalkyl), -(5-15 membered) heteroaryl, —$C_6$-$C_{15}$ aryloxy and -(5-15 membered) heteroaryloxy, wherein $R^7$ is independently substituted with from one to six substituents independently selected from $R^{7a}$;

or $R^7$ is —$C_3$-$C_{20}$ cycloalkyl, —$C_4$-$C_{12}$ cycloalkenyl, —($C_5$-$C_{20}$)bi- or tricycloalkyl, —($C_7$-$C_{20}$)bi- or tricycloalkenyl, -(3-12 membered) heterocycloalkyl, -(7-20 membered) heterobi- or heterotricycloalkyl, —$C_6$-$C_{14}$ aryl, benzo($C_3$-$C_8$ cycloalkyl), -(5-15 membered) heteroaryl, —$C_6$-$C_{15}$ aryloxy and -(5-15 membered) heteroaryloxy substituted by at least one —$C_1$-$C_{20}$ alkyl, wherein said cycloalkyl, cycloalkenyl, bi- or tricycloalkyl, bi- or tricycloalkenyl, heterocycloalkyl, heterobi- or heterotricycloalkyl, aryl, benzocycloalkyl, heteroaryl, aryloxy and heteroaryloxy is optionally independently substituted with from one to six substituents independently selected from $R^{7a}$; and wherein said alkyl is substituted by $R^{7C}$;

wherein $R^{7a}$ in each instance is independently selected from —OH, —$C_1$-$C_{12}$ alkyl, —$C_2$-$C_{12}$ alkenyl, —$C_2$-$C_{12}$ alkynyl, —$C_1$-$C_6$ alkoxy, —$C_1$-$C_{12}$ alkoxyalkyl, —$C_1$-$C_{12}$ hydroxyalkyl, —$C_2$-$C_6$ alkenoxy, —$C_2$-$C_6$ alkynoxy, halo, —CN, —$NO_2$, —$NR^9R^{10}$, —C(=O)$NR^9R^{10}$, —C(=O)$R^{11}$, —C(=O)$OR^{12}$, —$SO_2$—$NR^9R^{10}$, —S(O)$_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy; wherein said alkyl, alkenyl, alkynyl, alkoxy, alkenoxy, alkynoxy, cycloalkyl, cycloalkenyl, bi- or tricycloalkyl, bi- or tricycloalkenyl, heterocycloalkyl, aryl, heteroaryl, aryloxy and heteroaryloxy of $R^{7a}$ are each optionally independently substituted with from one to six substituents independently selected from the group $R^{7b}$;

wherein $R^{7b}$ in each instance is independently selected from —OH, —$C_1$-$C_{12}$ alkyl, —$C_2$-$C_{12}$ alkenyl, —$C_2$-$C_{12}$ alkynyl, —$C_1$-$C_6$ alkoxy, —$C_1$-$C_{12}$ alkoxyalkyl, —$C_1$-$C_{12}$ hydroxyalkyl, —$C_2$-$C_6$ alkenoxy, —$C_2$-$C_6$ alkynoxy, halo, —CN, —$NO_2$, —$NR^9R^{10}$, —C(=O)$NR^9R^{10}$, —C(=O)$R^{11}$, —C(=O)$OR^{12}$, —$SO_2$—$NR^9R^{10}$, —S(O)$_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy;

wherein $R^{7C}$ in each instance is independently selected from —$C_1$-$C_6$ alkoxy, —CN, —$NO_2$, —$NR^9R^{10}$, —C(=O)$NR^9R^{10}$, —C(=O)$R^{11}$, —C(=O)$OR^{12}$, —$SO_2$—$NR^9R^{10}$, —S(O)$_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy; wherein said alkenoxy, cycloalkyl, cycloalkenyl, bi- or tricycloalkyl, bi- or tricycloalkenyl, heterocycloalkyl, aryl, heteroaryl, aryloxy and heteroaryloxy of $R^{7c}$ are each optionally independently substituted with from one to six substituents independently selected from the group $R^{7b}$;

or $R^6$ and $R^7$ may together with the carbon and nitrogen atoms to which they are respectively attached optionally form a -(5-8 membered) heterocycloalkyl ring, a -(5-8 membered) heterocycloalkenyl ring or a -(6-8 membered) heteroaryl ring, wherein said heterocycloalkyl, heterocycloalkenyl and heteroaryl rings are each optionally independently substituted with from one to three substituents independently selected from halo, —$C_1$-$C_6$ alkyl, optionally subsituted with from one to three halo atoms, —$C_1$-$C_6$ alkoxy optionally subsituted with from one to three halo atoms, —$C_1$-$C_6$ hydroxyalkyl, —OH, —($CH_2$)$_{zero-10}$$NR^9R^{10}$, —($CH_2$)$_{zero-10}$C(=O)$NR^9R^{10}$, —$SO_2NR^9R^{10}$ and —$C_3$-$C_{12}$ cycloalkyl;

$R^9$ and $R^{10}$ in each instance are each independently selected from H, —OH, —$C_1$-$C_{12}$ alkyl, —$C_2$-$C_{12}$ alkenyl, —$C_2$-$C_{12}$ alkynyl, —$C_1$-$C_6$ alkoxy, —$C_1$-$C_{12}$ alkoxyalkyl —$C_1$-$C_{12}$ hydroxyalkyl, —$C_2$-$C_6$ alkenoxy, —$C_2$-$C_6$ alkynoxy, —C(=O)$NR^{11}R^{12}$, —C(=O)$R^{11}$, —C(=O)

$OR^{12}$, $-SO_2-NR^{11}R^{12}$, $-S(O)_n-R^{11}$, $-C_3-C_{15}$ cycloalkyl, $-C_4-C_{15}$ cycloalkenyl, $-(C_5-C_{11})$bi- or tricycloalkyl, $-(C_7-C_{11})$bi- or tricycloalkenyl, -(4-20 membered) heterocycloalkyl, $-C_6-C_{15}$ aryl, -(5-15 membered) heteroaryl, $-C_6-C_{15}$ aryloxy and -(5-15 membered) heteroaryloxy, wherein said alkyl, alkenyl, alkynyl, alkoxy, alkenoxy, alkynoxy, cycloalkyl, cycloalkenyl, bi- or tricycloalkyl, bi- or tricycloalkenyl, heterocycloalkyl, aryl, heteroaryl, aryloxy and heteroaryloxy of $R^9$ of $R^{10}$ are each optionally independently substituted with from one to six substituents independently selected from the group $R^{10a}$;

wherein $R^{10a}$ in each instance is independently selected from $-OH$, halo, $-C_1-C_{12}$ hydroxyalkyl, $-C_1-C_6$ alkoxy, $-CN$, $-NO_2$, $-NR^{11}R^{12}$, $-C(=O)NR^{11}R^{12}$, $-C(=O)R^{11}$, $-C(=O)OR^{11}$, $-SO_2-NR^{11}R^{12}$, $-S(O)_nR^{11}$, $-C_3-C_{15}$ cycloalkyl, $-C_4-C_{15}$ cycloalkenyl, $-(C_5-C_{11})$bi- or tricycloalkyl, $-(C_7-C_{11})$bi- or tricycloalkenyl, -(4-20 membered) heterocycloalkyl, $-C_6-C_{15}$ aryl, -(5-15 membered) heteroaryl, $-C_6-C_{15}$ aryloxy and -(5-15 membered) heteroaryloxy; wherein said alkoxy, cycloalkyl, cycloalkenyl, bi- or tricycloalkyl, bi- or tricycloalkenyl, heterocycloalkyl, aryl, heteroaryl, aryloxy and heteroaryloxy of $R^{10a}$ are each optionally independently substituted with from one to six substituents independently selected from the group $R^{10b}$;

wherein $R^{10b}$ in each instance is independently selected from $-OH$, halo; $-C_1-C_{12}$ alkyl, $-C_2-C_{12}$ alkenyl, $-C_2-C_{12}$ alkynyl, $-C_1-C_6$ alkoxy, $-C_1-C_{12}$ alkoxyalkyl $-C_1-C_{12}$ hydroxyalkyl, $-C_2-C_6$ alkenoxy, $-C_2-C_6$ alkynoxy, halo, $-CN$, $-NO_2$, $-NR^{11}R^{12}$, $-C(=O)NR^{11}R^{12}$, $-C(=O)R^{11}$, $-C(=O)OR^{11}$, $-SO_2-NR^{12}$, $-S(O)_nR^{11}$, $-C_3-C_{15}$ cycloalkyl, $-C_4-C_{15}$ cycloalkenyl, $-(C_5-C_{11})$bi- or tricycloalkyl, $-(C_7-C_{11})$bi- or tricycloalkenyl, -(4-20 membered) heterocycloalkyl, $-C_6-C_{15}$ aryl, -(5-15 membered) heteroaryl, $-C_6-C_{15}$ aryloxy and -(5-15 membered) heteroaryloxy;

or $NR^9R^{10}$ may form a (4-20 membered) heterocycloalkyl, (5-18 membered) heterobi- or tricycloalkyl (5-18 membered) heterobi- or tricycloalkenyl, or -(5-15 membered) heteroaryl, wherein said heterocycloalkyl, heterobi- or tricycloalkyl, heterobi- or tricycloalkenyl or heteroaryl are optionally independently substituted with from one to six substituents independently selected from $-C_1-C_6$ alkyl, $-C_2-C_6$ alkenyl, $-C_2-C_6$ alkenyl, $-C_1-C_6$ alkoxy, $-C_2-C_6$ alkenoxy, $-C_2-C_6$ alkynoxy, $-C_1-C_6$ hydroxyalkyl, $-C_2-C_6$ hydroxyalkenyl, $-C_2-C_6$ hydroxyalkenyl, halo, $-OH$, $-CN$, $-NO_2$, $-NR^{11}R^{12}$, $-C(=O)NR^{11}R^{12}$ $-C(=O)R^{11}$, $-C(=O)OR^{11}$, $-S(O)_nR^{11}$ and $-S(O)_n-NR^{11}R^{12}$;

$R^{11}$ and $R^{12}$ in each instance are each independently selected from H, $-C_1-C_8$ alkyl, $-C_3-C_8$ cycloalkyl, $-C_4-C_8$ cycloalkenyl, $-(C_5-C_{11})$bi- or tricycloalkyl, $-(C_7-C_{11})$bi- or tricycloalkenyl, (3-8 membered) heterocycloalkyl, $-C_6-C_{10}$ aryl and -(5-14 membered) heteroaryl, wherein said alkyl of $R^{11}$ is optionally independently substituted with from one to three substituents independently selected from $-OH$, $-CN$ and $-C_3-C_8$ cycloalkyl, and wherein each hydrogen atom of said alkyl is optionally independently replaced with a halo atom, and wherein said cylcoalkyl, cycloalkenyl, heterocycloalkyl, aryl and hetereoaryl of $R^{11}$ are each optionally independently substituted with from one to three substituents independently selected from halo, $-C_1-C_8$ alkyl optionally substituted with from one to three halo atoms, $-OH$, $-CN$ and $-C_3-C_8$ cycloalkyl; and n is in each instance an integer independently selected from zero, 1 and 2;

or a pharmaceutically acceptable salt thereof.

In one aspect of the above embodiment, $R^7$ is a $-C_4-C_8$ cycloalkyl, -(4-10 membered) heterocycloalkyl, $-C_6-C_{14}$ aryl or -(5-15 membered) heteroaryl substituted by a $-C_1-C_4$ alkyl and wherein said alkyl is further substituted by $R^{7C}$, wherein $R^{7C}$ is $-NR^9R^{10}$.

In another aspect of the above embodiment, $R^9$ is hydrogen or methyl, $R^{10}$ is $-C_1-C_8$ alkyl or $-C_4-C_8$ cycloalkyl, wherein said alkyl or cycloalkyl of $R^{10}$ is optionally substituted with from one to six substituents selected from $R^{10a}$ wherein $R^{10a}$ is selected from halo, $-C_1-C_4$ alkyl, $-C_4-C_8$ cycloalkyl, -(5-15 membered) heteroaryl or $-C_1-C_4$ hydroxyalkyl; or $-NR^9R^{10}$ is a -(4-6 membered) heterocycloalkyl optionally substituted with from one to six substituents selected from halo, $-C_1-C_4$ alkyl or $-C_1-C_4$ hydroxyalkyl.

In another aspect of the above embodiment, $R^7$ is a $-C_1-C_8$ alkyl substituted by a $-C_4-C_8$ cycloalkyl; $-(C_5-C_{20})$bi- or tricycloalkyl, -(4-8 membered) heterocycloalkyl, -(7-12 membered) heterobi- or heterotricycloalkyl, $-C_6-C_{14}$ aryl, benzo($C_3-C_8$ cycloalkyl), -(5-15 membered) heteroaryl, wherein $R^7$ is optionally independently substituted with from one to six substituents independently selected from $R^{7a}$, wherein $R^{7a}$ is $-NR^9R^{10}$, halo, $-C_1-C_4$ alkyl or $-C_1-C_4$ hydroxyalkyl.

In another aspect of the above embodiment, $R^7$ is a $-C_1-C_6$ alkyl substituted by a -(4-8 membered) heterocycloalkyl or $-C_6-C_{14}$ aryl, wherein $R^7$ is optionally independently substituted with from one to six substituents independently selected from $R^{7a}$, wherein $R^{7a}$ is $-NR^9R^{10}$, halo, $-OH$, $-C_1-C_4$ alkyl or $-C_1-C_4$ hydroxyalkyl, wherein said alkyl or hydroxyalkyl is optional substituted with from one to six halo.

In another aspect of the above embodiment, A is absent and $R^1$ is benzo($C_5-C_6$ cycloalkyl) optionally substituted with from one to three substituents independently selected from $-C_1-C_6$ alkyl, halo and $-OH$; or A is

Z is $-CH_2$, $-CH(OH)$ or $-CH(C_1-C_6$ alkyl) and $R^1$ is $-C_1-C_{10}$ alkyl, $-C_6-C_{10}$ aryl or (6-10 membered) heteroaryl, wherein said alkyl, aryl and heteroaryl are optionally independently substituted with from one to three substituents independently selected from $-C_1-C_6$ alkyl, halo and $-OH$; $R^1$ is H or $-C_1-C_6$ alkyl; $R^3$ is H, $-CH_2CH_2SCH_3$, $-CH_2CH_2OCH_3$ or $-C_1-C_6$ alkyl; $R^4$ is H and $R^6$ is H or $-C_1-C_6$ alkyl.

In an another embodiment, the present invention relates to compounds of Formula I wherein A is absent or is selected from

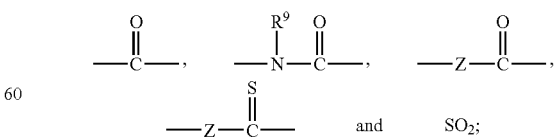

Z is selected from $-CH_2$, $-CH(OH)$, $-CH(C_1-C_6$ alkyl), $-CH(C_1-C_6$ alkoxyl), $-CH(NR^9R^{10})$, $-CH(CH_2(OH))$, $-CH(CH(C_1-C_4$ alkyl)(OH)) and $-CH(C(C_1-C_4$ alkyl)($C_1-C_4$alkyl)(OH));

$R^1$ is selected from —$C_1$-$C_{20}$ alkyl, —$C_2$-$C_{20}$ alkenyl, —$C_2$-$C_{20}$ alkynyl, —$C_1$-$C_{20}$ alkoxy, —$C_2$-$C_{20}$ alkenoxy, —$C_1$-$C_{20}$ hydroxyalkyl, —$C_3$-$C_8$ cycloalkyl, benzo($C_3$-$C_8$ cycloalkyl), benzo($C_3$-$C_8$ heterocycloalkyl), —$C_4$-$C_8$ cycloalkenyl, —($C_5$-$C_{11}$)bi- or tricycloalkyl, benzo($C_5$-$C_{11}$) bi- or tricycloalkyl, $C_7$-$C_{11}$)bi- or tricycloalkyl, -(3-8 membered) heterocycloalkyl, —$C_6$-$C_{14}$ aryl and -(5-14 membered) heteroaryl, wherein $R^1$ is optionally substituted by $R^{1a}$;

wherein $R^{1a}$ in each instance is independently selected from —OH, halo, —$C_1$-$C_6$ alkoxy, —CN, —$NO_2$, —$NR^9R^{10}$, —C(=O)$NR^9R^{10}$, —C(=O)$R^{11}$, —C(=O)$OR^{12}$, —$SO_2$—$NR^9R^{10}$, —S(O)$_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy;

wherein said alkoxy, cycloalkyl, cycloalkenyl, bi- or tricycloalkyl, bi- or tricycloalkenyl, heterocycloalkyl, aryl, heteroaryl, aryloxy and heteroaryloxy of $R^{1a}$ are each optionally independently substituted with from one to six substituents independently selected from the group $R^{1b}$;

wherein $R^{1b}$ in each instance is independently selected from —OH, —$C_1$-$C_{12}$ alkyl, —$C_2$-$C_{12}$ alkenyl, —$C_2$-$C_{12}$ alkynyl, —$C_1$-$C_6$ alkoxy, —$C_1$-$C_{12}$ alkoxyalkyl —$C_1$-$C_{12}$ hydroxyalkyl, —$C_2$-$C_6$ alkenoxy, —$C_2$-$C_6$ alkynoxy, halo, —CN, —$NO_2$, —$NR^9R^{10}$, —C(=O)$NR^9R^{10}$, —C(=O)$R^{11}$, —C(=O)$OR^{12}$, —$SO_2$—$NR^9R^{10}$, —S(O)$_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy;

$R^2$ is selected from H, —$C_1$-$C_6$ alkyl, —$C_2$-$C_6$ alkenyl, —$C_3$-$C_8$ cycloalkyl and $C_3$-$C_8$ cycloalkenyl, wherein $R^2$ is optionally independently substituted with from one to three substituents independently selected from —$C_1$-$C_4$ alkyl optionally substituted with from one to three halo atoms, —$C_1$-$C_4$ alkoxy optionally substituted with from one to three halo atoms, halo and —OH;

or $R^1$ and $R^1$ together with the A group when present and the nitrogen atom to which $R^2$ is attached, or $R^1$ and $R^2$ together with the nitrogen atom to which $R^1$ and $R^2$ are attached when A is absent, may optionally form a four to eight membered ring;

$R^3$ is selected from H, —$C_1$-$C_6$ alkyl, —$C_2$-$C_6$ alkenyl, —$C_2$-$C_6$ alkynyl, —$C_3$-$C_6$ cycloalkyl, —$C_5$-$C_6$ cycloalkenyl and (3-8 membered) heterocycloalkyl —$C_6$-$C_{14}$ aryl and (5-14 membered) heteroaryl, wherein said alkyl, alkenyl, alkynyl, cycloalkyl, cycloalkenyl, heterocycloalkyl aryl or heteroaryl are each optionally independently substituted with from one to three substituents independently selected from —$C_1$-$C_4$ alkoxy, halo, —OH, —S($C_1$-$C_4$)alkyl —$C_1$-$C_4$ alkyl —C(=O)$OR^9$, —$SO_2R^9$ and -(3-8 membered) heterocycloalkyl wherein said alkyl, alkoxy, and heterocyloalkyl may be further substituted by one to six halo;

$R^4$ is H, —$C_1$-$C_6$ alkyl or halo;

or $R^3$ and $R^4$ may together with the carbon atom to which they are attached optionally form a moiety selected from cyclopropyl, cyclobutyl, cyclopentyl, cyclohexyl, morpholino, piperidino, pyrrolidino, tetrahydrofuranyl and perhydro-2H-pyran, wherein said moiety formed by $R^3$ and $R^4$ is optionally substituted with from one to three substituents independently selected from —$C_1$-$C_6$ alkyl optionally substituted with from one to three halo atoms, —$C_1$-$C_6$ alkoxy optionally substituted with from one to three halo atoms, halo, —OH, —CN and allyl;

$R^6$ is selected from H, —$C_1$-$C_6$ alkyl, —$C_2$-$C_6$ alkylene, —$C_1$-$C_6$ alkoxy, halo, —CN, —$C_3$-$C_{12}$ cycloalkyl, —$C_4$-$C_{12}$ cycloalkenyl -(5-10 membered) heteroaryl and —$C_6$-$C_{10}$ aryl, wherein said alkyl, alkylene and alkoxy of $R^6$ are each optionally independently substituted with from one to three substituents independently selected from halo and —CN, and wherein said cycloalkyl, cycloalkenyl, heteroaryl and aryl of $R^6$ are each optionally independently substituted with from one to three substituents independently selected from —$C_1$-$C_4$ alkyl optionally substituted with from one to three halo atoms, —$C_1$-$C_4$ alkoxy optionally substituted with from one to three halo atoms, halo and —CN;

$R^7$ is selected from —$C_1$-$C_{20}$ alkyl, —$C_1$-$C_{20}$ alkoxy, —$C_1$-$C_{20}$ hydroxyalkyl, —$C_3$-$C_{12}$ cycloalkyl, —$C_4$-$C_{12}$ cycloalkenyl, —($C_5$-$C_{20}$)bi- or tricycloalkyl, —($C_7$-$C_{20}$)bi- or tricycloalkenyl, (3-12 membered) heterocycloalkyl, -(7-20 membered) heterobi- or heterotricycloalkyl, —$C_6$-$C_{14}$ aryl, -(5-15 membered) heteroaryl —$C_6$-$C_{15}$ aryloxy and -(5-15 membered) heteroaryloxy, wherein said alkyl, alkenyl, alkynyl, alkoxy, alkenoxy, alkynoxy, cycloalkyl, cycloalkenyl, bi- or tricycloalkyl, bi- or tricycloalkenyl, heterocycloalkyl, aryl, heteroaryl, aryloxy and heteroaryloxy of $R^7$ are each independently substituted with from one to six substituents independently selected from the group $R^{7a}$ or are each independently optionally substituted with from one to six substituents independently selected from the group $R^{7d}$ wherein $R^{7a}$ in each instance is independently selected from —$C_1$-$C_6$ alkoxy, —$C_1$-$C_{12}$ alkoxyalkyl, —$NR^9R^{10}$, —C(=O)$NR^9R^{10}$, —$C_3$-$C_{15}$ cycloalkyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy, wherein said alkyl, alkoxy, alkoxyalkyl, cycloalkyl, heterocycloalkyl, aryl heteroaryl, aryloxy, and heteroaryloxy of $R^{7a}$ are each independently substituted by $R^{7b}$;

wherein $R^{7d}$ in each instance is independently selected from: —$C_2$-$C_{12}$ alkenyl, —$C_2$-$C_{12}$ alkynyl, —$C_1$-$C_{12}$ hydroxyalkyl, —$C_2$-$C_6$ alkenoxy, —$C_2$-$C_6$ alkynoxy, —$NR^9R^{10}$, —C(=O)$NR^9R^{10}$, —$SO_2$—$NR^9R^{10}$, —$C_4$-$C_{15}$ cycloalkenyl, —($C_5$-$C_{11}$)bi- or tricycloalkyl, —($C_7$-$C_{11}$)bi- or tricycloalkenyl; wherein said alkenyl, alkynyl, hydroxyalkyl, alkenoxy, alkynoxy, cycloalkenyl, bi- or tricycloalkyl, bi- or tricycloalkenyl, of $R^{7d}$ are each optionally independently substituted with from one to six substituents independently selected from the group $R^{7b}$;

wherein $R^{7b}$ in each instance is independently selected from —$C_2$-$C_{12}$ alkenyl, —$C_2$-$C_{12}$ alkynyl, —$C_1$-$C_6$ alkoxy, —$C_1$-$C_{12}$ alkoxyalkyl —$C_1$-$C_{12}$ hydroxyalkyl, —$C_2$-$C_6$ alkenoxy, —$C_2$-$C_6$ alkynoxy, halo, —CN, —$NO_2$, —$NR^9R^{10}$, —C(=O)$NR^9R^{10}$, —C(=O)$R^{11}$, —C(=O)$OR^{12}$, —$SO_2$—$NR^9R^{10}$, —S(O)$_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy;

or $R^6$ and $R^7$ may together with the carbon and nitrogen atoms to which they are respectively attached optionally form a (5-8 membered) heterocycloalkyl ring, a (5-8 membered) heterocycloalkenyl ring or a (6-8 membered) heteroaryl ring, wherein said heterocycloalkyl, heterocycloalkenyl and heteroaryl rings are each optionally independently substituted with from one to three substituents independently selected from halo, —$C_1$-$C_6$ alkyl, optionally subsituted with from one to three halo atoms, —$C_1$-$C_6$ alkoxy optionally subsituted with from one to three halo atoms, —$C_1$-$C_6$ hydroxyalkyl, —OH, —(CH$_2$)$_{zero-10}$NR$^9$R$^{10}$, —(CH$_2$)$_{zero-10}$C(=O)NR$^9$R$^{10}$, —SO$_2$NR$^9$R$^{10}$ and —C$_3$-C$_{12}$ cycloalkyl;

R$^9$ and R$^{10}$ in each instance are each independently selected from —H, —C(=O)R$^{13}$ or —C$_1$-C$_{20}$ alkyl, wherein at least one of R$^9$ and R$^{10}$ are —C(=O)R$^{13}$ or —C$_1$-C$_{20}$ alkyl, and wherein each —C$_1$-C$_{20}$ alkyl is substituted with R$^{10a}$ wherein R$^{10a}$ in each instance is independently selected from —C$_1$-C$_6$ alkoxy, —CN, —NO$_2$, —NR$^{11}$R$^{11}$, —C(=O)NR$^{11}$R$^{12}$, —C(=O)R$^{11}$, —C(=O)OR$^{11}$, —SO$_2$—NR$^{11}$R$^{12}$, —S(O)$_n$—R$^{11}$, —C$_3$-C$_{15}$ cycloalkyl, —C$_4$-C$_{15}$ cycloalkenyl, —(C$_5$-C$_{11}$)bi- or tricycloalkyl, —(C$_7$-C$_{11}$)bi- or tricycloalkenyl, -(4-20 membered) heterocycloalkyl, —C$_6$-C$_{15}$ aryl, -(5-15 membered) heteroaryl, —C$_6$-C$_{15}$ aryloxy and -(5-15 membered) heteroaryloxy; wherein said alkoxy, cycloalkyl, cycloalkenyl, bi- or tricycloalkyl, bi- or tricycloalkenyl, heterocycloalkyl, aryl, heteroaryl, aryloxy and heteroaryloxy of R$^{10a}$ are each optionally independently substituted with from one to six substituents independently selected from the group R$^{10b}$ wherein R$^{10b}$ in each instance is independently selected from —OH, —C$_1$-C$_{12}$ alkyl, —C$_2$-C$_{12}$ alkenyl, —C$_2$-C$_{12}$ alkynyl, —C$_1$-C$_6$ alkoxy, —C$_1$-C$_{12}$ alkoxyalkyl —C$_1$-C$_{12}$ hydroxyalkyl, —C$_2$-C$_6$ alkenoxy, —C$_2$-C$_6$ alkynoxy, halo, —CN, —NO$_2$, —NR$^{11}$R$^{12}$, —C(=O)NR$^{11}$R$^{12}$, —C(=O)R$^{11}$, —C(=O)OR$^{11}$, —SO$_2$—NR$^{11}$R$^{12}$, —S(O)$_n$R$^{11}$, —C$_3$-C$_{15}$ cycloalkyl, —C$_4$-C$_{15}$ cycloalkenyl, —(C$_5$-C$_{11}$)bi- or tricycloalkyl, —(C$_7$-C$_{11}$)bi- or tricycloalkenyl, -(4-20 membered) heterocycloalkyl, —C$_6$-C$_{15}$ aryl, -(5-15 membered) heteroaryl, —C$_6$-C$_{15}$ aryloxy and -(5-15 membered) heteroaryloxy or NR$^9$R$^{10}$ may form a (4-20 membered) heterocycloalkyl, (5-18 membered) heterobi- or tricycloalkyl, (5-18 membered) heterobi- or tricycloalkenyl, or -(5-15 membered) heteroaryl, wherein said heterocycloalkyl, heterobi- or tricycloalkyl, heterobi- or tricycloalkenyl or heteroaryl are optionally independently substituted with from one to six substituents independently selected from —C$_1$-C$_6$ alkyl, —C$_2$-C$_6$ alkenyl, —C$_2$-C$_6$ alkenyl, —C$_1$-C$_6$ alkoxy, —C$_2$-C$_6$ alkenoxy, —C$_2$-C$_6$ alkynoxy, —C$_1$-C$_6$ hydroxyalkyl, —C$_2$-C$_6$ hydroxyalkenyl, —C$_2$-C$_6$ hydroxyalkenyl, halo, —OH, —CN, —NO$_2$, —NR$^{11}$R$^{12}$, —C(=O)NR$^{11}$R$^{12}$, —C(=O)R$^{11}$, —C(=O)OR$^{11}$, —S(O)$_n$R$^{11}$ and —S(O)$_n$NR$^{11}$R$^{12}$;

R$^{11}$ and R$^{12}$ in each instance are each independently selected from H, —C$_1$-C$_8$ alkyl, —C$_3$-C$_8$ cycloalkyl, —C$_4$-C$_8$ cycloalkenyl, (C$_5$-C$_{11}$)bi- or tricycloalkyl, —(C$_7$-C$_{11}$)bi- or tricycloalkenyl, (3-8 membered) heterocycloalkyl, —C$_6$-C$_{10}$ aryl and (5-14 membered) heteroaryl, wherein said alkyl of R$^{11}$ and R$^{12}$ is optionally independently substituted with from one to three substituents independently selected from —OH, —CN and —C$_3$-C$_8$ cycloalkyl, and wherein each hydrogen atom of said alkyl is optionally independently replaced with a halo atom, and wherein said cylcoalkyl, cycloalkenyl, heterocycloalkyl, aryl and hetereoaryl of R$^{11}$ and R$^{12}$ are each optionally independently substituted with from one to three substituents independently selected from halo, —C$_1$-C$_8$ alkyl optionally substituted with from one to three halo atoms, —OH, —CN and —C$_3$-C$_8$ cycloalkyl;

R$^{13}$ is in each instance is independently selected from alkyl substituted by —C$_1$-C$_{12}$ alkoxy, —C$_3$-C$_{15}$ cycloalkyl, —C$_4$-C$_{15}$ cycloalkenyl, —(C$_5$-C$_{11}$)bi- or tricycloalkyl, —(C$_7$-C$_{11}$)bi- or tricycloalkenyl, -(4-20 membered) heterocycloalkyl, —C$_6$-C$_{15}$ aryl, -(5-15 membered) heteroaryl, —C$_6$-C$_{15}$ aryloxy and -(5-15 membered) heteroaryloxy; wherein said alkoxy, cycloalkyl, cycloalkenyl, bi- or tricycloalkyl, bi- or tricycloalkenyl, heterocycloalkyl, aryl, heteroaryl, aryloxy and heteroaryloxy of R$^{13}$ is optionally substituted by one to three substituents independently selected from halo, —C$_1$-C$_8$ alkyl optionally substituted with from one to three halo atoms, —OH, —CN and —C$_3$-C$_8$ cycloalkyl;

n is in each instance an integer independently selected from zero, 1 and 2;

or a pharmaceutically acceptable salt thereof.

In one aspect of the above embodiment, R$^7$ is a —C$_1$-C$_8$ alkyl substituted by R$^{7a}$; R$^{7a}$ is —NR$^9$R$^{10}$; R$^9$ is H or methyl; R$^{10}$ is a —C$_1$-C$_8$ alkyl; R$^{10a}$ is —C$_1$-C$_6$ alkoxy, —C$_4$-C$_8$ cycloalkyl, -(4-8 membered) heterocycloalkyl, —C$_6$-C$_{15}$ aryl or -(5-15 membered) heteroaryl, wherein said alkoxy, cycloalkyl, heterocycloalkyl, aryl, heteroaryl of R$^{10a}$ are each optionally independently substituted with from one to six substituents independently selected from the group R$^{10b}$; wherein R$^{10b}$ is halo, —OH, —C$_1$-C$_4$ alkyl or —C$_1$-C$_4$ hydroxyalkyl, wherein said alkyl or hydroxyalkyl of R$^{10b}$ is optionally substituted by one to six halo.

In another aspect of the above embodiment, R$^7$ is a —C$_1$-C$_8$ alkyl substituted by R$^{7a}$; R$^{7a}$ is —C(=O)NR$^9$R$^{10}$; R$^9$ is H or methyl; R$^{10}$ is a —C$_1$-C$_8$ alkyl; R$^{10a}$ is —C$_1$-C$_6$ alkoxy, —C$_4$-C$_8$ cycloalkyl, -(4-8 membered) heterocycloalkyl, —C$_6$-C$_{15}$ aryl or -(5-15 membered) heteroaryl, wherein said alkoxy, cycloalkyl, heterocycloalkyl, aryl, heteroaryl, aryloxy and heteroaryloxy of R$^{10a}$ are each optionally independently substituted with from one to six substituents independently selected from the group R$^{10b}$; wherein R$^{10b}$ is halo, —OH, —C$_1$-C$_4$ alkyl or —C$_1$-C$_4$ hydroxyalkyl, wherein said alkyl or hydroxyalkyl of R$^{10b}$ is optionally substituted by one to six halo.

In another aspect of the above embodiment A is absent and R$^1$ is benzo(C$_5$-C$_6$ cycloalkyl) optionally substituted with from one to three substituents independently selected from C$_1$-C$_6$ alkyl, halo and OH; or A is

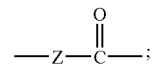

Z is —CH$_2$, —CH(OH) or —CH(C$_1$-C$_6$ alkyl) and R$^1$ is C$_1$-C$_{10}$ alkyl, C$_6$-C$_{10}$ aryl or (6-10 membered) heteroaryl, wherein said alkyl, aryl and heteroaryl are optionally independently substituted with from one to three substituents independently selected from C$_1$-C$_6$ alkyl, halo and OH; R$^2$ is H or C$_1$-C$_6$ alkyl; R$^3$ is H, —CH$_2$CH$_2$SCH$_3$, —CH$_2$CH$_2$OCH$_3$ or C$_1$-C$_6$ alkyl; R$^4$ is H and R$^6$ is H or C$_1$-C$_6$ alkyl.

In an another embodiment, the present invention relates to compounds of Formula I wherein A is absent or is selected from

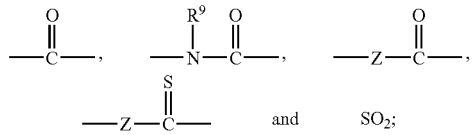

Z is selected from —CH$_2$, —CH(OH), —CH(C$_1$-C$_6$ alkyl), —CH(C$_1$-C$_6$ alkoxyl), —CH(NR$^9$R$^{10}$), —CH(CH$_2$(OH)), —CH(CH(C$_1$-C$_4$ alkyl)(OH)) and —CH(C(C$_1$-C$_4$ alkyl)(C$_1$-C$_4$alkyl)(OH));

R$^1$ is selected from —C$_1$-C$_{20}$ alkyl, —C$_2$-C$_{20}$ alkenyl, —C$_2$-C$_{20}$ alkynyl, —C$_1$-C$_{20}$ alkoxy, —C$_2$-C$_{20}$ alkenoxy, —C$_1$-C$_{20}$ hydroxyalkyl, —C$_3$-C$_8$ cycloalkyl, benzo(C$_3$-C$_8$ cycloalkyl), benzo(C$_3$-C$_8$ heterocycloalkyl), —C$_4$-C$_8$ cycloalkenyl, —(C$_5$-C$_{11}$)bi- or tricycloalkyl, benzo(C$_5$-C$_{11}$)

bi- or tricycloalkyl, —($C_7$-$C_{11}$)bi- or tricycloalkenyl, -(3-8 membered) heterocycloalkyl, —$C_6$-$C_{14}$ aryl and -(5-14 membered) heteroaryl, wherein $R^1$ is optionally substituted by $R^{1a}$;

wherein $R^{1a}$ in each instance is independently selected from —OH, halo, —$C_1$-$C_6$ alkoxy, —CN, —$NO_2$, —$NR^9R^{10}$, —C(=O)$NR^9R^{10}$, —C(=O)$R^{11}$, —C(=O)$OR^{12}$, —$SO_2$—$NR^9R^{10}$, —S(O)$_n$—$R^{11}$, —$C_3$-$C_{15}$ cycloalkyl, —$C_4$-$C_{15}$ cycloalkenyl, —($C_5$-$C_{15}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy, wherein said alkoxy, cycloalkyl, cycloalkenyl, bi- or tricycloalkyl, bi- or tricycloalkenyl, heterocycloalkyl, aryl, heteroaryl, aryloxy and heteroaryloxy of $R^{1a}$ are each optionally independently substituted with from one to six substituents independently selected from the group $R^{1b}$;

wherein $R^{1b}$ in each instance is independently selected from —OH, —$C_1$-$C_{12}$ alkyl, —$C_2$-$C_{12}$ alkenyl, —$C_2$-$C_{12}$ alkynyl, —$C_1$-$C_6$ alkoxy, —$C_1$-$C_{12}$ alkoxyalkyl —$C_1$-$C_{12}$ hydroxyalkyl, —$C_2$-$C_6$ alkenoxy, —$C_2$-$C_6$ alkynoxy, halo, —CN, —$NO_2$, —$NR^9R^{10}$, —C(=O)$NR^9R^{10}$, —C(=O)$R^{11}$, —C(=O)$OR^{12}$, —$SO_2$—$NR^9R^{10}$, —S(O)$_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy;

$R^2$ is selected from H, —$C_1$-$C_6$ alkyl, —$C_2$-$C_6$ alkenyl, —$C_3$-$C_8$ cycloalkyl and —$C_3$-$C_8$ cycloalkenyl, wherein $R^2$ is optionally independently substituted with from one to three substituents independently selected from —$C_1$-$C_4$ alkyl optionally substituted with from one to three halo atoms, —$C_1$-$C_4$ alkoxy optionally substituted with from one to three halo atoms, halo and —OH;

or $R^1$ and $R^2$ together with the A group when present and the nitrogen atom to which $R^2$ is attached, or $R^1$ and $R^2$ together with the nitrogen atom to which $R^1$ and $R^2$ are attached when A is absent, may optionally form a four to eight membered ring;

$R^3$ is selected from —$C_6$-$C_{14}$ aryl and (5-14 membered) heteroaryl, wherein said aryl or heteroaryl are each optionally independently substituted with from one to three substituents independently selected from —$C_1$-$C_4$ alkoxy, halo, —OH, —S($C_1$-$C_4$)alkyl —$C_1$-$C_4$ alkyl —C(=O)$OR^9$, —$SO_2R^9$ and (3-8 membered) heterocycloalkyl wherein said alkyl, alkoxy, and heterocyloalkyl may be further substituted by one to six halo;

$R^4$ is H, —$C_1$-$C_6$ alkyl or halo;

or $R^3$ and $R^4$ may together with the carbon atom to which they are attached optionally form a moiety selected from cyclopropyl, cyclobutyl, cyclopentyl, cyclohexyl, morpholino, piperidino, pyrrolidino, tetrahydrofuranyl and perhydro-2H-pyran, wherein said moiety formed by $R^3$ and $R^4$ is optionally substituted with from one to three substituents independently selected from —$C_1$-$C_6$ alkyl optionally substituted with from one to three halo atoms, —$C_1$-$C_6$ alkoxy optionally substituted with from one to three halo atoms, halo, —OH, —CN and allyl;

$R^6$ is selected from H, —$C_1$-$C_6$ alkyl, —$C_2$-$C_6$ alkylene, —$C_1$-$C_6$ alkoxy, halo, —CN, —$C_3$-$C_{12}$ cycloalkyl, —$C_4$-$C_{12}$ cycloalkenyl (5-10 membered) heteroaryl and —$C_6$-$C_{10}$ aryl, wherein said alkyl, alkylene and alkoxy of $R^6$ are each optionally independently substituted with from one to three substituents independently selected from halo and —CN, and wherein said cycloalkyl, cycloalkenyl, heteroaryl and aryl of $R^6$ are each optionally independently substituted with from one to three substituents independently selected from —$C_1$-$C_4$ alkyl optionally substituted with from one to three halo atoms, —$C_1$-$C_4$ alkoxy optionally substituted with from one to three halo atoms, halo and —N;

$R^7$ is selected from H, —$C_1$-$C_{20}$ alkyl, —$C_1$-$C_{20}$ alkoxy, —$C_1$-$C_{20}$ hydroxyalkyl, —$C_3$-$C_{12}$ cycloalkyl, —$C_4$-$C_{12}$ cycloalkenyl, ($C_5$-$C_{20}$)bi- or tricycloalkyl, —($C_7$-$C_{20}$)bi- or tricycloalkenyl, (3-12 membered) heterocycloalkyl, -(7-20 membered) heterobi- or heterotricycloalkyl, —$C_6$-$C_{14}$ aryl and -(5-15 membered) heteroaryl, wherein said alkyl, alkenyl, alkynyl, alkoxy, alkenoxy, alkynoxy, cycloalkyl, cycloalkenyl, bi- or tricycloalkyl, bi- or tricycloalkenyl, heterocycloalkyl, aryl, heteroaryl, aryloxy and heteroaryloxy of $R^7$ are each optionally independently substituted with from one to six substituents independently selected from the group $R^{7a}$;

wherein $R^{7a}$ in each instance is independently selected from —OH, —$C_1$-$C_{12}$ alkyl, —$C_2$-$C_{12}$ alkenyl, —$C_2$-$C_{12}$ alkynyl, —$C_1$-$C_6$ alkoxy, —$C_1$-$C_{12}$ alkoxyalkyl, —$C_1$-$C_{12}$ hydroxyalkyl, —$C_2$-$C_6$ alkenoxy, —$C_2$-$C_6$ alkynoxy, halo, —CN, —$NO_2$, —$NR^9R^{10}$, —C(=O)$NR^9R^{10}$, —C(=O)$R^{11}$, —C(=O)$OR^{12}$, —$SO_2$—$NR^9R^{10}$, —S(O)$_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy; wherein said alkyl, alkenyl, alkynyl, alkoxy, alkenoxy, alkynoxy, cycloalkyl, cycloalkenyl, bi- or tricycloalkyl, bi- or tricycloalkenyl, heterocycloalkyl, aryl, heteroaryl, aryloxy and heteroaryloxy of $R^{7a}$ are each optionally independently substituted with from one to six substituents independently selected from the group $R^{7b}$;

wherein $R^{7b}$ in each instance is independently selected from —OH, —$C_1$-$C_{12}$ alkyl, —$C_2$-$C_{12}$ alkenyl, —$C_2$-$C_{12}$ alkynyl, —$C_1$-$C_6$ alkoxy, —$C_1$-$C_{12}$ alkoxyalkyl —$C_1$-$C_{12}$ hydroxyalkyl, —$C_2$-$C_6$ alkenoxy, —$C_2$-$C_6$ alkynoxy, halo, —CN, —$NO_2$, —$NR^9R^{10}$, —C(=O)$NR^9R^{10}$, —C(=O)$R^{11}$, —C(=O)$OR^{11}$, —$SO_2$—$NR^9R^{10}$, —S(O)$_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy;

or $R^6$ and $R^7$ may together with the carbon and nitrogen atoms to which they are respectively attached optionally form a (5-8 membered) heterocycloalkyl ring, a (5-8 membered) heterocycloalkenyl ring or a (6-8 membered) heteroaryl ring, wherein said heterocycloalkyl, heterocycloalkenyl and heteroaryl rings are each optionally independently substituted with from one to three substituents independently selected from halo, —$C_1$-$C_6$ alkyl, optionally subsituted with from one to three halo atoms, —$C_1$-$C_6$ alkoxy optionally subsituted with from one to three halo atoms, —$C_1$-$C_6$ hydroxyalkyl, —OH, —($CH_2$)$_{zero-10}$($NR^9R^{10}$, —($CH_2$)$_{zero-10}$C(=O)$NR^9R^{10}$, —$SO_2NR^9R^{10}$ and —$C_3$-$C_{12}$ cycloalkyl;

$R^9$ and $R^{10}$ in each instance are each independently selected from H, —OH, —$C_1$-$C_{12}$ alkyl, —$C_2$-$C_{12}$ alkenyl, —$C_2$-$C_{12}$ alkynyl, —$C_1$-$C_6$ alkoxy, —$C_1$-$C_{12}$ alkoxyalkyl —$C_1$-$C_{12}$ hydroxyalkyl, —$C_2$-$C_6$ alkenoxy, —$C_2$-$C_6$ alkynoxy, —C(=O)$NR^{11}R^{12}$, —C(=O)$R^{11}$, —C(=O)$OR^{12}$, —$SO_2$—$NR^{10}R^{11}$, —S(O)$_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy, wherein said alkyl, alkenyl, alkynyl, alkoxy, alkenoxy, alkynoxy, cycloalkyl, cycloalkenyl, bi- or tricycloalkyl, bi- or tricycloalkenyl, heterocycloalkyl, aryl, heteroaryl, aryloxy and heteroaryloxy of $R^9$ of $R^{10}$ are each optionally independently substituted with from one to six substituents independently selected from the group $R^{10a}$;

wherein $R^{10a}$ in each instance is independently selected from —OH, halo, —$C_1$-$C_6$ alkoxy, —CN, —$NO_2$, —$NR^{11}R^{12}$, —C(=O)$NR^{11}R^{12}$, —C(=O)$R^{11}$, —C(=O)$OR^{12}$, —$SO_2$—$NR^{11}R^{12}$, —S(O)$_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy; wherein said alkoxy, cycloalkyl, cycloalkenyl, bi- or tricycloalkyl, bi- or tricycloalkenyl, heterocycloalkyl, aryl, heteroaryl, aryloxy and heteroaryloxy of $R^{10a}$ are each optionally independently substituted with from one to six substituents independently selected from the group $R^{10b}$;

wherein $R^{10b}$ in each instance is independently selected from —OH, halo; —$C_1$-$C_{12}$ alkyl, —$C_2$-$C_{12}$ alkenyl, —$C_2$-$C_{12}$ alkynyl, —$C_1$-$C_6$ alkoxy, —$C_1$-$C_{12}$ alkoxyalkyl —$C_1$-$C_{12}$ hydroxyalkyl, —$C_2$-$C_6$ alkenoxy, —$C_2$-$C_6$ alkynoxy, halo, —CN, —$NO_2$, —$NR^{11}R^{12}$, —C(=O)$NR^{11}R^{12}$, —C(=O)$R^{11}$, —C(=O)$OR^{12}$, —$SO_2$—$NR^{11}R^{12}$, —S(O)$_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy;

or $NR^9R^{10}$ may form may form a -(4-20 membered) heterocycloalkyl, -(5-18 membered) heterobi- or tricycloalkyl, -(5-18 membered) heterobi- or tricycloalkenyl, or -(5-15 membered) heteroaryl, wherein said heterocycloalkyl, heterobi- or tricycloalkyl, heterobi- or tricycloalkenyl or heteroaryl are optionally independently substituted with from one to six substituents independently selected from —$C_1$-$C_6$ alkyl, —$C_2$-$C_6$ alkenyl, —$C_2$-$C_6$ alkenyl, —$C_1$-$C_6$ alkoxy, —$C_2$-$C_6$ alkenoxy, —$C_2$-$C_6$ alkynoxy, —$C_1$-$C_6$ hydroxyalkyl, —$C_2$-$C_6$ hydroxyalkenyl, —$C_2$-$C_6$ hydroxyalkenyl, halo, —OH, —CN, —$NO_2$, —$NR^{11}R^{12}$, —C(=O)$NR^{11}R^{12}$, —C(=O)$R^{11}$, —C(=O)$OR^{11}$, —S(O)$_n$$R^{11}$ and —S(O)$_n$$NR^{11}R^{12}$;

wherein $R^{11}$ and $R^{12}$ in each instance are each independently selected from H, —$C_1$-$C_8$ alkyl, —$C_3$-$C_8$ cycloalkyl, —$C_4$-$C_8$ cycloalkenyl, —($C_5$-$C_{11}$)bi- or tricycloalkyl, —($C_7$-$C_{11}$)bi- or tricycloalkenyl, -(3-8 membered) heterocycloalkyl, —$C_6$-$C_{10}$ aryl and -(5-14 membered) heteroaryl, wherein said alkyl of $R^{11}$ is optionally independently substituted with from one to three substituents independently selected from —OH, —CN and —$C_3$-$C_8$ cycloalkyl, and wherein each hydrogen atom of said alkyl is optionally independently replaced with a halo atom, and wherein said cycloalkyl, cycloalkenyl, heterocycloalkyl, aryl and hetereoaryl of $R^{11}$ are each optionally independently substituted with from one to three substituents independently selected from halo, —$C_1$-$C_8$ alkyl optionally substituted with from one to three halo atoms, —OH, —CN and —$C_3$-$C_8$ cycloalkyl; and n is in each instance an integer independently selected from zero, 1 and 2;

or a pharmaceutically acceptable salt thereof.

In an another embodiment, the present invention relates to compounds of Formula I, wherein A is absent;

$R^1$ is —$C_1$-$C_{20}$ alkyl; wherein $R^1$ is independently substituted with from one to six substituents independently selected from $R^{1a}$;

wherein $R^{1a}$ in each instance is independently selected from —$C_1$-$C_6$ alkoxy, —CN, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy;

wherein said cycloalkyl, cycloalkenyl, bi- or tricycloalkyl, bi- or tricycloalkenyl, heterocycloalkyl, aryl, heteroaryl, aryloxy and heteroaryloxy of $R^{1a}$ are each optionally independently substituted with from one to six substituents independently selected from the group $R^{1b}$;

wherein $R^{1b}$ in each instance is independently selected from —OH, —$C_1$-$C_{12}$ alkyl, —$C_2$-$C_{12}$ alkenyl, —$C_2$-$C_{12}$ alkynyl, —$C_1$-$C_6$ alkoxy, —$C_1$-$C_{12}$ alkoxyalkyl —$C_1$-$C_{12}$ hydroxyalkyl, —$C_2$-$C_6$ alkenoxy, —$C_2$-$C_6$ alkynoxy, halo, —CN, —$NO_2$, —$NR^9R^{10}$, —C(=O)$NR^9R^{10}$, —C(=O)$R^{11}$, —C(=O)$OR^{12}$, —$SO_2$—$NR^9R^{10}$, —S(O)$_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy;

$R^2$ is selected from H, —$C_1$-$C_6$ alkyl, —$C_2$-$C_6$ alkenyl, —$C_3$-$C_8$ cycloalkyl and —$C_3$-$C_8$ cycloalkenyl, wherein $R^2$ is optionally independently substituted with from one to three substituents independently selected from —$C_1$-$C_4$ alkyl optionally substituted with from one to three halo atoms, —$C_1$-$C_4$ alkoxy optionally substituted with from one to three halo atoms, halo and —OH;

$R^3$ is selected from H, —$C_1$-$C_6$ alkyl, —$C_2$-$C_6$ alkenyl, —$C_2$-$C_6$ alkynyl, —$C_3$-$C_6$ cycloalkyl, —$C_5$-$C_6$ cycloalkenyl and (3-8 membered) heterocycloalkyl, —$C_6$-$C_{14}$ aryl and (5-14 membered) heteroaryl, wherein said alkyl, alkenyl, alkynyl, cycloalkyl, cycloalkenyl, heterocycloalkyl aryl or heteroaryl are each optionally independently substituted with from one to three substituents independently selected from —$C_1$-$C_4$ alkoxy, halo, —OH, —S($C_1$-$C_4$)alkyl —$C_1$-$C_4$ alkyl —C(=O)$OR^9$, —$SO_2R^9$ and (3-8 membered) heterocycloalkyl wherein said alkyl, alkoxy, and heterocyloalkyl may be further substituted by one to six halo;

$R^4$ is H, —$C_1$-$C_6$ alkyl or halo;

or $R^3$ and $R^4$ may together with the carbon atom to which they are attached optionally form a moiety selected from cyclopropyl, cyclobutyl, cyclopentyl, cyclohexyl, morpholino, piperidino, pyrrolidino, tetrahydrofuranyl and perhydro-2H-pyran, wherein said moiety formed by $R^3$ and $R^4$ is optionally substituted with from one to three substituents independently selected from —$C_1$-$C_6$ alkyl optionally substituted with from one to three halo atoms, —$C_1$-$C_6$ alkoxy optionally substituted with from one to three halo atoms, halo, —OH, —CN and allyl;

$R^6$ is selected from H, —$C_1$-$C_6$ alkyl, —$C_2$-$C_6$ alkylene, —$C_1$-$C_6$ alkoxy, halo, —CN, —$C_3$-$C_{12}$ cycloalkyl, —$C_4$-$C_{12}$ cycloalkenyl (5-10 membered) heteroaryl and —$C_6$-$C_{10}$ aryl, wherein said alkyl, alkylene and alkoxy of $R^6$ are each optionally independently substituted with from one to three substituents independently selected from halo and —CN, and wherein said cycloalkyl, cycloalkenyl, heteroaryl and aryl of $R^6$ are each optionally independently substituted with from one to three substituents independently selected from —$C_1$-$C_4$ alkyl optionally substituted with from one to three halo atoms, —$C_1$-$C_4$ alkoxy optionally substituted with from one to three halo atoms, halo and —CN;

$R^7$ is selected from H, —$C_1$-$C_{20}$ alkyl, —$C_1$-$C_{20}$ alkoxy, —$C_1$-$C_{20}$ hydroxyalkyl, —$C_3$-$C_{12}$ cycloalkyl, —$C_4$-$C_{12}$ cycloalkenyl, —($C_5$-$C_{20}$)bi- or tricycloalkyl, —($C_7$-$C_{20}$)bi- or tricycloalkenyl, (3-12 membered) heterocycloalkyl, (-7-20 membered) heterobi- or heterotricycloalkyl, —$C_6$-$C_{14}$ aryl and (5-15 membered) heteroaryl, wherein said alkyl, alkenyl, alkynyl, alkoxy, alkenoxy, alkynoxy, cycloalkyl, cycloalkenyl, bi- or tricycloalkyl, bi- or tricycloalkenyl, heterocycloalkyl, aryl, heteroaryl, aryloxy and heteroaryloxy of $R^7$ are each optionally independently substituted with from one to six substituents independently selected from the group $R^{7a}$;

wherein $R^{7a}$ in each instance is independently selected from —OH, —$C_1$-$C_{12}$ alkyl, —$C_2$-$C_{12}$ alkenyl, —$C_2$-$C_{12}$ alkynyl, —$C_1$-$C_6$ alkoxy, —$C_1$-$C_{12}$ alkoxyalkyl, —$C_1$-$C_{12}$ hydroxyalkyl, —$C_2$-$C_6$ alkenoxy, —$C_2$-$C_6$ alkynoxy, halo, —CN, —$NO_2$, —$NR^9R^{10}$, —C(=O)$NR^9R^{10}$, —C(=O)$R^{11}$, —C(=O)$OR^{12}$, —$SO_2$-$NR^9R^{10}$, —S(O)$_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy; wherein said alkyl, alkenyl, alkynyl, alkoxy, alkenoxy, alkynoxy, cycloalkyl, cycloalkenyl, bi- or tricycloalkyl, bi- or tricycloalkenyl, heterocycloalkyl, aryl, heteroaryl, aryloxy and heteroaryloxy of $R^{7a}$ are each optionally independently substituted with from one to six substituents independently selected from the group $R^{7b}$;

wherein $R^{7b}$ in each instance is independently selected from —OH, —$C_1$-$C_{12}$ alkyl, —$C_2$-$C_{12}$ alkenyl, —$C_2$-$C_{12}$ alkynyl, —$C_1$-$C_6$ alkoxy, —$C_1$-$C_{12}$ alkoxyalkyl —$C_1$-$C_{12}$ hydroxyalkyl, —$C_2$-$C_6$ alkenoxy, —$C_2$-$C_6$ alkynoxy, halo, —CN, —$NO_2$, —$NR^9R^{10}$, —C(=O)$NR^9R^{10}$, —C(=O)$R^{11}$, —C(=O)$OR^{11}$, —$SO_2$—$NR^9R^{10}$, —S(O)$_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy;

or $R^6$ and $R^7$ may together with the carbon and nitrogen atoms to which they are respectively attached optionally form a -(5-8 membered) heterocycloalkyl ring, a -(5-8 membered) heterocycloalkenyl ring or a -(6-8 membered) heteroaryl ring, wherein said heterocycloalkyl, heterocycloalkenyl and heteroaryl rings are each optionally independently substituted with from one to three substituents independently selected from halo, —$C_1$-$C_6$ alkyl, optionally subsituted with from one to three halo atoms, —$C_1$-$C_6$ alkoxy optionally subsituted with from one to three halo atoms, —$C_1$-$C_6$ hydroxyalkyl, —OH, —($CH_2$)$_{zero-10}$$NR^9R^{10}$, —($CH_2$)$_{zero-10}$C(=O)$NR^9R^{10}$, —$SO_2NR^9R^{10}$ and —$C_3$-$C_{12}$ cycloalkyl;

$R^9$ and $R^{10}$ in each instance are each independently selected from H, —OH, —$C_1$-$C_{12}$ alkyl, —$C_2$-$C_{12}$ alkenyl, —$C_2$-$C_{12}$ alkynyl, —$C_1$-$C_6$ alkoxy, —$C_1$-$C_{12}$ alkoxyalkyl —$C_1$-$C_{12}$ hydroxyalkyl, —$C_2$-$C_6$ alkenoxy, —$C_2$-$C_6$ alkynoxy, —C(=O)$NR^{11}R^{12}$, —C(=O)$R^{11}$, —C(=O)$OR^{11}$, —$SO_2$—$NR^{11}R^{12}$, —S(O)$_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy, wherein said alkyl, alkenyl, alkynyl, alkoxy, alkenoxy, alkynoxy, cycloalkyl, cycloalkenyl, bi- or tricycloalkyl, bi- or tricycloalkenyl, heterocycloalkyl, aryl, heteroaryl, aryloxy and heteroaryloxy of $R^9$ of $R^{10}$ are each optionally independently substituted with from one to six substituents independently selected from the group $R^{10a}$;

wherein $R^{10a}$ in each instance is independently selected from —OH, Halo, —$C_1$-$C_6$ alkoxy, —CN, —$NO_2$, —$NR^{11}R^{12}$, —C(=O)$NR^{11}R^{12}$, —C(=O)$R^{11}$, —C(=O)$OR^{12}$, —$SO_2$—$NR^{11}R^{12}$, —S(O)$_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy; wherein said alkoxy, cycloalkyl, cycloalkenyl, bi- or tricycloalkyl, bi- or tricycloalkenyl, heterocycloalkyl, aryl, heteroaryl, aryloxy and heteroaryloxy of $R^{10a}$ are each optionally independently substituted with from one to six substituents independently selected from the group $R^{10b}$;

wherein $R^{10b}$ in each instance is independently selected from —OH, halo; —$C_1$-$C_{12}$ alkyl, —$C_2$-$C_{12}$ alkenyl, —$C_2$-$C_{12}$ alkynyl, —$C_1$-$C_6$ alkoxy, —$C_1$-$C_{12}$ alkoxyalkyl —$C_1$-$C_{12}$ hydroxyalkyl, —$C_2$-$C_6$ alkenoxy, —$C_2$-$C_6$ alkynoxy, halo, —CN, —$NO_2$, —$NR^{11}R^{12}$, —C(=O)$NR^{11}R^{12}$, —C(=O)$R^{11}$, —C(=O)$OR^{11}$, —$SO_2$—$NR^{11}R^{12}$, —S(O)$_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy;

or $NR^9R^{10}$ may form a (4-20 membered) heterocycloalkyl, (5-18 membered) heterobi- or tricycloalkyl (5-18 membered) heterobi- or tricycloalkenyl, or -(5-15 membered) heteroaryl, wherein said a heterocycloalkyl, heterobi- or tricycloalkyl, heterobi- or tricycloalkenyl or heteroaryl are optionally independently substituted with from one to six substituents independently selected from —$C_1$-$C_6$ alkyl, —$C_2$-$C_6$ alkenyl, —$C_2$-$C_6$ alkenyl, —$C_1$-$C_6$ alkoxy, —$C_2$-$C_6$ alkenoxy, —$C_2$-$C_6$ alkynoxy, —$C_1$-$C_6$ hydroxyalkyl, —$C_2$-$C_6$ hydroxyalkenyl, —$C_2$-$C_6$ hydroxyalkenyl, halo, —OH, —CN, —$NO_2$, —$NR^{11}R^{12}$, —C(=O)$NR^{11}R^{12}$, —C(=O)$R^{11}$, —C(=O)$OR^{11}$, —S(O)$_n$$R^{11}$ and —S(O)$_n$$NR^{11}R^{12}$;

$R^{11}$ and $R^{12}$ in each instance are each independently selected from H, —$C_1$-$C_8$ alkyl, —$C_3$-$C_8$ cycloalkyl, —$C_4$-$C_8$ cycloalkenyl, —($C_5$-$C_{11}$)bi- or tricycloalkyl, —($C_7$-$C_{11}$) bi- or tricycloalkenyl, -(3-8 membered) heterocycloalkyl, —$C_6$-$C_{10}$ aryl and -(5-14 membered) heteroaryl, wherein said alkyl of $R^{11}$ is optionally independently substituted with from one to three substituents independently selected from —OH, —CN and —$C_3$-$C_8$ cycloalkyl, and wherein each hydrogen atom of said alkyl is optionally independently replaced with a halo atom, and wherein said cycloalkyl, cycloalkenyl, heterocycloalkyl, aryl and hetereoaryl of $R^{11}$ are each optionally independently substituted with from one to three substituents independently selected from halo, —$C_1$-$C_8$ alkyl optionally substituted with from one to three halo atoms, —OH, —CN and —$C_3$-$C_8$ cycloalkyl; and n is in each instance an integer independently selected from zero, 1 and 2;

or a pharmaceutically acceptable salt thereof.

Compounds of Formula I may have optical centers and therefore may occur in different enantiomeric and diastereomeric configurations. The present invention includes all enantiomers, diastereomers, and other stereoisomers of such compounds of Formula I, as well as racemic compounds and racemic mixtures and other mixtures of stereoisomers thereof.

Pharmaceutically acceptable salts of the compounds of Formula I include the acid addition and base salts thereof.

Suitable acid addition salts are formed from acids which form non-toxic salts. Examples include, but are not limited to, the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mandelates mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, salicylate, saccharate, stearate, succinate, sulfonate, stannate, tartrate, tosylate, trifluoroacetate and xinofoate salts.

Suitable base salts are formed from bases which form non-toxic salts. Examples include, but are not limited to, the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see Handbook of Pharmaceutical Salts: Properties, Selection, and Use by Stahl and Wermuth (Wiley-VCH, 2002).

Pharmaceutically acceptable salts of compounds of Formula I may be prepared by one or more of three methods:

(i) by reacting the compound of Formula I with the desired acid or base;

(ii) by removing an acid- or base-labile protecting group from a suitable precursor of the compound of Formula I or by ring-opening a suitable cyclic precursor, for example, a lactone or lactam, using the desired acid or base; or (iii) by converting one salt of the compound of Formula I to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionization in the resulting salt may vary from completely ionised to almost non-ionised.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

The compounds of the invention may also exist in unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see Polymorphism in Pharmaceutical Solids by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO$^-$K$^+$, or —SO$_3^-$Na$^+$) or non-ionic (such as —N$^-$N$^+$(CH$_3$)$_3$) polar head group. For more information, see Crystals and the Polarizing Microscope by N. H. Hartshorne and A. Stuart, 4$^{th}$ Edition (Edward Arnold, 1970).

Hereinafter all references to compounds of Formula I include references to salts, solvates, multi-component complexes and liquid crystals thereof and to solvates, multi-component complexes and liquid crystals of salts thereof.

The compounds of the invention include compounds of Formula I as hereinbefore defined, including all polymorphs and crystal habits thereof, prodrugs and isomers thereof (including optical, geometric and tautomeric isomers) as hereinafter defined and isotopically-labeled compounds of Formula I.

Unless otherwise indicated, as used herein, the term "A is absent" means a direct bond between the nitrogen and R$^1$ (i.e., —N—R$^1$).

Unless otherwise indicated, as used herein, the terms "halogen" and "halo" include F, Cl, Br, and I.

Unless otherwise indicated, as used herein, the term "alkyl" includes saturated monovalent hydrocarbon radicals having straight or branched moieties. Examples of alkyl groups include, but are not limited to, methyl, ethyl, n-propyl, isopropyl, and t-butyl.

Unless otherwise indicated, as used herein, the term "alkenyl" includes alkyl moieties having at least one carbon-carbon double bond wherein alkyl is as defined above. Examples of alkenyl include, but are not limited to, ethenyl and propenyl.

Unless otherwise indicated, as used herein, the term "alkynyl" includes alkyl moieties having at least one carbon-carbon triple bond wherein alkyl is as defined above. Examples of alkynyl groups include, but are not limited to, ethynyl and 2-propynyl.

Unless otherwise indicated, as used herein, the term "alkoxy", means "alkyl-O—", wherein "alkyl" is as defined above. Examples of "alkoxy" groups include, but are not limited to, methoxy, ethoxy, propoxy, butoxy, pentoxy and allyloxy.

Unless otherwise indicated, as used herein, the term "alkenoxy", means "alkenyl-O—", wherein "alkenyl" is as defined above.

Unless otherwise indicated, as used herein, the term "cycloalkyl" includes non-aromatic saturated cyclic alkyl moieties wherein alkyl is as defined above. Examples of cycloalkyl include, but are not limited to, cyclopropyl, cyclobutyl, cyclopentyl, cyclohexyl and cycloheptyl. "Bicycloalkyl" and "tricycloalkyl" groups are non-aromatic saturated carbocyclic groups consisting of two or three rings respectively, wherein said rings share at least one carbon atom. Unless otherwise indicated, for purposes of the present invention, bicycloalkyl groups include spiro groups and fused ring groups. Examples of bicycloalkyl groups include, but are not limited to, bicyclo-[3.1.0]-hexyl, bicyclo-2.2.1]-hept-1-yl, norbornyl, spiro[4.5]decyl, spiro[4.4]nonyl, spiro[4.3]octyl, and spiro[4.2]heptyl. An example of a tricycloalkyl group is adamantanyl. Other cycloalkyl, bicycloalkyl, and tricycloalkyl groups are known in the art, and such groups are encompassed by the definitions "cycloalkyl", "bicycloalkyl" and "tricycloalkyl" herein.

"Cycloalkenyl", "bicycloalkenyl", and "tricycloalkenyl" refer to non-aromatic carbocyclic cycloalkyl, bicycloalkyl, and tricycloalkyl moieties as defined above, except comprising one or more carbon-carbon double bonds connecting carbon ring members (an "endocyclic" double bond) and/or one or more carbon-carbon double bonds connecting a carbon ring member and an adjacent non-ring carbon (an "exocyclic" double bond). Examples of cycloalkenyl groups include, but are not limited to, cyclopentenyl, cyclobutenyl, and cyclohexenyl, and a non-limiting example of a bicycloalkenyl group is norbornenyl. Other cycloalkenyl, bicycloalkenyl, and tricycloalkenyl groups are known in the art, and such groups are included within the definitions "cycloalkenyl", "bicycloalkenyl" and "tricycloalkenyl" herein.

Cycloalkyl, cycloalkenyl, bicycloalkyl, and bicycloalkenyl groups also include groups that are substituted with one or more oxo moieties. Examples of such groups with oxo moieties are oxocyclopentyl, oxocyclobutyl, oxocyclopentenyl, and norcamphoryl.

As used herein, the term "benzocycloalkyl" includes, without limitation, moieties such as tetrahydronaphthyl, indanyl, 1,2-benzocylcoheptanyl and the like.

Unless otherwise indicated, as used herein, the term "aryl" includes an organic radical derived from an aromatic hydrocarbon by removal of one hydrogen, such as phenyl, naphthyl, indenyl, indanyl, and fluorenyl. "Aryl" encompasses fused ring groups wherein at least one ring is aromatic.

Unless otherwise indicated, as used herein, the terms "heterocyclic" and "heterocycloalkyl" refer to non-aromatic cyclic groups containing one or more heteroatoms, prefereably from one to four heteroatoms, each selected from O, S and N. "Heterobicycloalkyl" groups are non-aromatic two-ringed cyclic groups, wherein said rings share one or two atoms, and wherein at least one of the rings contains a heteroatom (O, S, or N). Heterobicycloalkyl groups for purposes of the present invention, and unless otherwise indicated, include spiro groups and fused ring groups. "Heterotricycloalkyl" groups are non-aromatic three-ringed cyclic groups, wherein said rings are fused to one another or form a spiro group (in other words, at least two of said rings share one or two atoms and the third ring shares one or two atoms with at least one of said two rings). The heterotricycloalkyl groups of the compounds of the present invention can include one or more O, S and/or N heteroatoms. In one embodiment, each ring in the heterobicycloalkyl or heterotricycloalkyl contains up to four heteroatoms (i.e. from zero to four heteroatoms, provided that at least one ring contains at least one heteroatom). The heterocycloalkyl, heterobicycloalky and heterotricycloalkyl groups of the present invention can also include ring systems substituted with one or more oxo moieties. The heterocyclic groups, including the heterobicyclic and heterotricyclic groups, may comprise double or triple bonds, e.g. heterocycloalkenyl, heterobicycloalkenyl, and heterotricycloalkenyl. Examples of non-aromatic heterocyclic groups are aziridinyl, azetidinyl, pyrrolidinyl, piperidinyl, azepinyl, piperazinyl, 1,2,3,6-tetrahydropyridinyl, oxiranyl, oxetanyl, tetrahydrofuranyl, tetrahydrothienyl, tetrahydropyranyl, tetrahydrothiopyranyl, morpholino, thiomorpholino, thioxanyl, pyrrolinyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, quinolizinyl, quinuclidinyl, 1,4-dioxaspiro[4.5]decyl, 1,4-dioxaspiro[4.4]nonyl, 1,4-dioxaspiro[4.3]octyl, and 1,4-dioxaspiro[4.2]heptyl.

Unless otherwise indicated, as used herein, "heteroaryl" refers to aromatic groups containing one or more heteroatoms (O, S, or N), preferably from one to four heteroatoms. A multicyclic group containing one or more heteroatoms wherein at least one ring of the group is aromatic is a "heteroaryl" group. The heteroaryl groups of this invention can also include ring systems substituted with one or more oxo moieties. Examples of heteroaryl groups are pyridinyl, pyridazinyl, imidazolyl, pyrimidinyl, pyrazolyl, triazolyl, pyrazinyl, quinolyl, isoquinolyl, 1,2,3,4-tetrahydroquinolyl, tetrazolyl, furyl, thienyl, isoxazolyl, thiazolyl, oxazolyl, isothiazolyl, pyrrolyl, indolyl, benzimidazolyl, benzofuranyl, cinnolinyl, indazolyl, indolizinyl, phthalazinyl, triazinyl, 1,2,4-trizainyl, 1,3,5-triazinyl, isoindolyl, 1-oxoisoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl.

Unless otherwise indicated to the contrary, all the foregoing groups derived from hydrocarbons may be optionally substituted by one or more halogen atoms (e.g., —$CH_2F$, —$CHF_2$—$CF_3$, -PhCl, etc.).

Unless otherwise indicated, the term "one or more substituents", as used herein, refers to from one to the maximum number of substituents possible based on the number of available bonding sites.

Unless otherwise indicated, all the foregoing groups derived from hydrocarbons may have up to about 1 to about 20 carbon atoms (e.g. $C_1$-$C_{20}$ alkyl, $C_2$-$C_{20}$ alkenyl, $C_3$-$C_{20}$ cycloalkyl, 3-20 membered heterocycloalkyl; $C_6$-$C_{20}$ aryl, 5-20 membered heteroaryl, etc.) or 1 to about 15 carbon atoms (e.g., $C_1$-$C_{15}$ alkyl, $C_2$-$C_{15}$ alkenyl, $C_3$-$C_{15}$ cycloalkyl, 3-15 membered heterocycloalkyl, $C_6$-$C_{15}$ aryl, 5-15 membered heteroaryl, etc.), or 1 to about 12 carbon atoms, or 1 to about 8 carbon atoms, or 1 to about 6 carbon atoms.

As appreciated by the artisan, the use of Formula I is a convenience, and the invention is understood to envision and embrace each and every species thereunder as though individually identified and set forth herein. Thus, the present invention contemplates each species separately and any and all combinations and permutations of species falling within Formula I.

The foregoing groups, as derived from the compounds listed above, may be C-attached or N-attached where such is possible. For instance, a group derived from pyrrole may be pyrrol-1-yl (N-attached) or pyrrol-3-yl (C-attached). The terms referring to the groups also encompass all possible tautomers.

As indicated, so-called 'prodrugs' of the compounds of Formula I are also within the scope of the invention. Thus certain derivatives of compounds of Formula I which may have little or no pharmacological activity themselves can, when administered into or onto the body, be converted into compounds of Formula I having the desired activity, for example, by hydrolytic cleavage. Such derivatives are referred to as 'prodrugs'. Further information on the use of prodrugs may be found in Pro-drugs as Novel Delivery Systems, Vol. 14, ACS Symposium Series (T. Higuchi and W.

Stella) and Bioreversible Carriers in Drug Design, Pergamon Press, 1987 (Ed. E. B. Roche, American Pharmaceutical Association).

Prodrugs in accordance with the invention can, for example, be produced by replacing appropriate functionalities present in the compounds of Formula I with certain moieties known to those skilled in the art as 'pro-moieties' as described, for example, in Design of Prodrugs by H. Bundgaard (Elsevier, 1985).

Some examples of prodrugs in accordance with the invention include, but are not limited to, (i) where the compound of Formula I contains a carboxylic acid functionality (—COOH), an ester thereof, for example, a compound wherein the hydrogen of the carboxylic acid functionality of the compound of Formula (I) is replaced by ($C_1$-$C_8$)alkyl;

(ii) where the compound of Formula I contains an alcohol functionality (—OH), an ether thereof, for example, a compound wherein the hydrogen of the alcohol functionality of the compound of Formula I is replaced by ($C_1$-$C_6$)alkanoyloxymethyl; and (iii) where the compound of Formula I contains a primary or secondary amino functionality (—$NH_2$ or —$NHR^1$ where R≠H), an amide thereof, for example, a compound wherein, as the case may be, one or both hydrogens of the amino functionality of the compound of Formula I is/are replaced by ($C_1$-$C_{10}$)alkanoyl.

Further examples of replacement groups in accordance with the foregoing examples and examples of other prodrug types may be found in the aforementioned references.

Moreover, certain compounds of Formula I may themselves act as prodrugs of other compounds of Formula I.

Also included within the scope of the invention are metabolites of compounds of Formula I, that is, compounds formed in vivo upon administration of the drug. Some examples of metabolites in accordance with the invention include, but are not limited to, (i) where the compound of Formula I contains a methyl group, an hydroxymethyl derivative thereof (—$CH_3$->—$CH_2OH$):

(ii) where the compound of Formula I contains an alkoxy group, an hydroxy derivative thereof (—$OR^1$->—OH);

(iii) where the compound of Formula I contains a tertiary amino group, a secondary amino derivative thereof (—$NR^1R^2$->—$NHR^1$ or —$NHR^2$);

(iv) where the compound of Formula I contains a secondary amino group, a primary derivative thereof (—$NHR^1$->—$NH_2$);

(v) where the compound of Formula I contains a phenyl moiety, a phenol derivative thereof (-Ph->-PhOH); and (vi) where the compound of Formula I contains an amide group, a carboxylic acid derivative thereof (—$CONH_2$->COOH).

Compounds of Formula I containing one or more asymmetric carbon atoms can exist as two or more stereoisomers. Where a compound of Formula I contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of Formula I containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of Formula I, including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of Formula I contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, Stereochemistry of Organic Compounds by E. L. Eliel and S. H. Wilen (Wiley, 1994).

The present invention includes all pharmaceutically acceptable isotopically-labelled compounds of Formula I wherein one or more atoms are replaced by atoms having the same atomic number, but an atomic mass or mass number different from the atomic mass or mass number which predominates in nature.

Examples of isotopes suitable for inclusion in the compounds of the invention include, but are not limited to, isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of Formula I, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of Formula I can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Specific embodiments of the present invention include the compounds exemplified in the Examples below and the pharmaceutically acceptable salts thereof, complexes thereof, and derivatives thereof that convert into a pharmaceutically active compound upon administration:

Compounds of Formula I of this invention, and their pharmaceutically acceptable salts, have useful pharmaceutical and medicinal properties. The compounds of Formula I, and their pharmaceutically acceptable salts inhibit the production of Aβ-peptide (thus, gamma-secretase activityl) in mammals, including humans. Compounds of Formula I, and their pharmaceutically acceptable salts, are therefore able to function as therapeutic agents in the treatment of the neurodegenerative and/or neurological disorders and diseases representatively enumerated below, for example Alzheimer's disease, in an afflicted mammal, including a human.

The present invention also relates to a pharmaceutical composition for inhibiting Aβ-peptide production in a mammal, including a human, comprising an amount of a compound of Formula I, or a pharmaceutically acceptable salt thereof, that is effective in inhibiting Aβ-production, and a pharmaceutically acceptable carrier.

The present invention also relates to a pharmaceutical composition for treating a disease or condition selected from the group consisting of Alzheimer's disease, hereditary cerebral hemorrhage with amyloidosis, cerebral amyloid angiopathy, a prion-mediated disease, inclusion body myositis, stroke, multiple sclerosis, head trauma, mild cognitive impairment and Down's Syndrome in a mammal, including a human, comprising an amount of a compound of Formula I, or a pharmaceutically acceptable salt thereof, that is effective in inhibiting Aβ-peptide production, and a pharmaceutically acceptable carrier.

The present invention also relates to a pharmaceutical composition for treating a disease or condition selected from the group consisting of Alzheimer's disease and Down's Syndrome in a mammal, including a human, comprising an amount of a compound of Formula I, or a pharmaceutically acceptable salt thereof, that is effective in inhibiting Aβ-peptide production, and a pharmaceutically acceptable carrier.

The present invention also relates to a pharmaceutical composition for treating a disease or a condition selected from the group consisting of Alzheimer's disease, hereditary cerebral hemorrhage with amyloidosis, cerebral amyloid angiopathy, a prion-mediated disease, inclusion body myositis, stroke, multiple sclerosis, head trauma, mild cognitive impairment and Down's Syndrome in a mammal, including a human, comprising an amount of a compound of Formula I, or a pharmaceutically acceptable salt thereof, that is effective in treating such disease or condition, and a pharmaceutically acceptable carrier.

The present invention also relates to a pharmaceutical composition for treating a disease or a condition selected from the group consisting of Alzheimer's disease and Down's Syndrome in a mammal, including a human, comprising an amount of a compound of Formula I, or a pharmaceutically acceptable salt thereof, that is effective in treating such disease or condition, and a pharmaceutically acceptable carrier.

The present invention also relates to a method of inhibiting Aβ-peptide production in a mammal, including a human, comprising administering to said mammal an amount of a compound of Formula I, or a pharmaceutically acceptable salt thereof, that is effective in inhibiting Aβ-production.

The present invention also relates to a method of treating a disease or condition selected from Alzheimer's disease, hereditary cerebral hemorrhage with amyloidosis, cerebral amyloid angiopathy, a prion-mediated disease, inclusion body myositis, stroke, multiple sclerosis, head trauma, mild cognitive impairment and Down's Syndrome in a mammal, including a human, comprising administering to said mammal an amount of a compound of Formula I, or a pharmaceutically acceptable salt thereof, that is effective in inhibiting Aβ-production.

The present invention also relates to a method of treating a disease or condition selected from Alzheimer's disease and Down's Syndrome in a mammal, including a human, comprising administering to said mammal an amount of a compound of Formula I, or a pharmaceutically acceptable salt thereof, that is effective in inhibiting Aβ-production.

The present invention also relates to a method of treating a disease or condition selected from Alzheimer's disease, hereditary cerebral hemorrhage with amyloidosis, cerebral amyloid angiopathy, a prion-mediated disease, inclusion body myositis, stroke, multiple sclerosis, head trauma, mild cognitive impairment and Down's Syndrome in a mammal, including a human, comprising administering to said mammal an amount of a compound of Formula I, or a pharmaceutically acceptable salt thereof, that is effective in treating such condition.

The present invention also relates to a method of treating a disease or condition selected from Alzheimer's disease and Down's Syndrome in a mammal, including a human, comprising administering to said mammal an amount of a compound of Formula I, or a pharmaceutically acceptable salt thereof, that is effective in treating such condition.

The compounds of Formula I may be used alone or used in combination with any other drug, including, but not limited to, any memory enhancement agent, e.g., Aricept™ and/or Namenda™, antidepressant agent, e.g., Zoloft™, anxiolytic, antipsychotic agent, e.g., Geodon™, sleep disorder agent, anti-inflammatory agent, e.g., Celebrex™, Bextra™, etc., anti-oxidant agent, cholesterol modulating agent (for example, an agent that lowers LDL or increases HDL), e.g., Lipitor™, Caduet™, etc., Histamine (H2) antagonist, e.g., Cimetadine™, and anti-hypertension agent, e.g., Norvasc™, Caduet™, etc. Accordingly, the present invention also relates to the following pharmaceutical compositions and methods of treatment comprising a compound of Formula I in combination with other drugs, such as those of the type described above.

The present invention also relates to a pharmaceutical composition for treating a disease or condition associated with Aβ-peptide production in a mammal, including a human, comprising (a) a compound of Formula I, or a pharmaceutically acceptable salt thereof; (b) a memory enhancement agent, e.g., Aricept™ and/or Namenda™, antidepressant, e.g., Zoloft™, anxiolytic, antipsychotic agent, e.g., Geodon™, sleep disorder agent, anti-inflammatory agent, e.g., Celebrex™, Bextra™, etc., anti-oxidant agent, cholesterol modulating agent (for example, an agent that lowers LDL or increases HDL), e.g., Lipitor™, Caduet™, etc., Histamine (H2) antagonist, e.g., Cimetadine™, and anti-hypertensive agent, e.g., Norvasc™, Caduet™, etc.; and (c) a pharmaceutically acceptable carrier; wherein the active agents "a" and "b" above are present in amounts that render the composition effective in treating such disease or condition.

The present invention also relates to a pharmaceutical composition for treating a disease or condition selected from the group consisting of Alzheimer's disease, hereditary cerebral hemorrhage with amyloidosis, cerebral amyloid angiopathy, a prion-mediated disease, inclusion body myositis, stroke, multiple sclerosis, head trauma, mild cognitive impairment and Down's Syndrome, in a mammal, including a human, comprising (a) a compound of Formula I, or a pharmaceutically acceptable salt thereof; (b) a memory enhancement agent, e.g., Aricept™ and/or Namenda™, antidepressant, e.g., Zoloft™, anxiolytic, antipsychotic agent, e.g., Geodon™, sleep disorder agent, anti-inflammatory agent, e.g., Celebrex™, Bextra™, etc., anti-oxidant agent, cholesterol modulating agent (for example, an agent that lowers LDL or increases HDL), e.g., Lipitor™, Caduet™, etc., Histamine (H2) antagonist, e.g., Cimetadine™, and anti-hypertensive agent, e.g., Norvasc™, Caduet™, etc.; and (c) a pharmaceutically acceptable carrier; wherein the active agents "a" and "b" above are present in amounts that render the composition effective in treating such disease or condition.

The present invention also relates to a pharmaceutical composition for treating a disease or condition selected from the group consisting of Alzheimer's disease and Down's Syndrome, in a mammal, including a human, comprising (a) a compound of Formula I, or a pharmaceutically acceptable salt thereof; (b) a memory enhancement agent, e.g., Aricept™ and/or Namenda™, antidepressant, e.g., Zoloft™, anxiolytic, antipsychotic agent, e.g., Geodon™, sleep disorder agent, anti-inflammatory agent, e.g., Celebrex™, Bextra™, etc., anti-oxidant agent, cholesterol modulating agent (for example, an agent that lowers LDL or increases HDL), e.g., Lipitor™, Caduet™, etc., Histamine (H2) antagonist, e.g., Cimetadine™, and anti-hypertensive agent, e.g., Norvasc™, Caduet™, etc.; and (c) a pharmaceutically acceptable carrier; wherein the active agents "a" and "b" above are present in amounts that render the composition effective in treating such disease or condition.

The present invention also relates to a method of treating a disease or condition associated with Aβ-peptide production in a mammal, including a human, comprising administering to said mammal (a) a compound of Formula I, or a pharmaceutically acceptable salt thereof; and (b) a memory enhancement agent, e.g., Aricept™ and/or Namenda™, antidepressant, e.g., Zoloft™, anxiolytic, antipsychotic agent, e.g., Geodon™, sleep disorder agent, anti-inflammatory agent, e.g., Celebrex™, Bextra™, etc., anti-oxidant agent, cholesterol modulating agent (for example, an agent that lowers LDL or increases HDL), e.g., Lipitor™, Caduet™, etc., Histamine (H2) antagonist, e.g., Cimetadine™, and anti-hypertensive agent, e.g., Norvasc™, Caduet™, etc.; wherein the active agents "a" and "b" above are present in amounts that render the composition effective in treating such disease or condition.

The present invention also relates to a method of treating a disease or condition selected from the group consisting of Alzheimer's disease, hereditary cerebral hemorrhage with amyloidosis, cerebral amyloid angiopathy, a prion-mediated disease, inclusion body myositis, stroke, multiple sclerosis, head trauma, mild cognitive impairment and Down's Syndrome, in a mammal, including a human, comprising administering to said mammal (a) a compound of Formula I, or a pharmaceutically acceptable salt thereof; and (b) a memory enhancement agent, e.g., Aricept™ and/or Namenda™, antidepressant, e.g., Zoloft™, anxiolytic, antipsychotic agent, e.g., Geodon™, sleep disorder agent, anti-inflammatory agent, e.g., Celebrex™, Bextra™, etc., anti-oxidant agent, cholesterol modulating agent (for example, an agent that lowers LDL or increases HDL), e.g., Lipitor™, Caduet™, etc., Histamine (H2) antagonist, e.g., Cimetadine™, and anti-hypertensive agent, e.g., Norvasc™, Caduet™, etc.; wherein the active agents "a" and "b" above are present in amounts that render the composition effective in treating such disease or condition.

The present invention also relates to a method of treating a disease or condition selected from the group consisting of Alzheimer's disease and Down's Syndrome, in a mammal, including a human, comprising administering to said mammal (a) a compound of Formula I, or a pharmaceutically acceptable salt thereof; and (b) a memory enhancement agent, e.g., Aricept™ and/or Namenda™, antidepressant, e.g., Zoloft™, anxiolytic, antipsychotic agent, e.g., Geodon™, sleep disorder agent, anti-inflammatory agent, e.g., Celebrex™, Bextra™, etc., anti-oxidant agent, cholesterol modulating agent (for example, an agent that lowers LDL or increases HDL), e.g., Lipitor™, Caduet™, etc., Histamine (H2) antagonist, e.g., Cimetadine™, and anti-hypertensive agent, e.g., Novasc™; Caduet™, etc.; wherein the active agents "a" and "b" above are present in amounts that render the composition effective in treating such disease or condition.

Compounds of Formula I, or any of the combinations described in the immediately preceding paragraphs, may optionally be used in conjunction with a known β-glycoprotein inhibitor, such as verapamil.

References herein to diseases and conditions "associated with Aβ-peptide production" relate to diseases or conditions that are caused, at least in part, by Aβ-peptide and/or the production thereof. Thus, Aβ-peptide is a contributing factor, but not necessarily the only contributing factor, to "a disease or condition associated with Aβ-peptide production."

The compounds of Formula I, or their pharmaceutically acceptable salts may also be used to modulate or inhibit the Notch signaling pathway in organisms, including humans. The Notch signaling pathway is an evolutionarily conserved mechanism utilized by organisms, ranging from worms through humans, to regulate fate determination of various cell lineages. Notch belongs to the family of epidermal growth factor-like homeotic genes, which encode transmembrane proteins with variable numbers of epidermal growth factor-like repeats in the extracellular domain. There is increasing evidence for a role of the Notch pathway in human disease. All of the components of the pathway have yet to be identified, but among those identified to date, mutations that affect their interaction with each other can lead to a variety of syndromes and pathological conditions.

For example, Notch signaling is typically associated with cell fate decision. The finding that Notch activation stimulates capillary outgrowth suggests that Notch receptors must be activated to allow this process to occur. Therefore, Notch modulation provides a method for regulating angiogenesis. Specifically, modulation of Notch signaling can be used to modulate angiogenesis (e.g., by blocking Notch signaling to block angiogenesis). This inhibition of angiogenesis in vivo can be used as a therapeutic means to treat a variety of diseases, including but not limited to cancer, diabetic retinopathy, rheumatoid arthritis, psoriasis, inflammatory bowel disease and arteriosclerosis.

The Notch pathway is also implicated in the development and maturation of T cells, as described in Radtke, F. et al., Immunity 10:547-558, 1999. The compounds of Formula I, and their pharmaceutically acceptable salts are therefore useful candidates for modulating the immune system, including the treatment of inflamamation, asthma, graft rejection, graft versus host disease, autoimmune disease and transplant rejection.

In addition, a number of studies published between 2002 and 2004 have provided convincing evidence that Notch signaling is frequently elevated in a variety of human tumors (including, but not limited to breast, prostate, pancreas and T-cell acute lymphoblastic leukemia). One key study provides a strong genetic link to Notch's role in important tumor types. Specifically, Weijzen et al. demonstrated that Notch signaling maintains the neoplastic phenotype in human Ras-transformed cells. Weijzen et al. (2002) *Nature Med* 8: 979. Because 30% of human malignancies may carry activating mutations in at least one of the three isoforms of Ras, this finding raises the possibility that Notch inhibitors would be a powerful addition to anti-cancer therapy. Another study's findings support a central role for aberrant Notch signaling in the pathogenesis of human T cell acute lymphoblastic leukemia/lymphoma. Pear et al., *Current Opinion in Hematology* (2004), 11(6), 426-433.

Accordingly, the compounds of Formula I, or their pharmaceutically acceptable salts, may be used for treating a disease or condition selected from the group consisting of cancer, arteriosclerosis, diabetic retinopathy, rheumatoid arthritis, psoriasis, inflammatory bowel disease inflammation, asthma, graft rejection, graft versus host disease, autoimmune disease and transplant rejection.

As used herein, the term "treating" refers to reversing, alleviating or inhibiting the progress of a disease, disorder or condition, or one or more symptoms of such disease, disorder or condition, to which such term applies. As used herein, "treating" may also refer to decreasing the probability or incidence of the occurrence of a disease, disorder or condition in a mammal as compared to an untreated control population, or as compared to the same mammal prior to treatment. For example, as used herein, "treating" may refer to preventing a disease, disorder or condition, and may include delaying or preventing the onset of a disease, disorder or condition, or delaying or preventing the symptoms associated with a disease, disorder or condition. As used herein, "treating" may also refer to reducing the severity of a disease, disorder or condition or symptoms associated with such disease, disorder or condition prior to a mammal's affliction with the disease, disorder or condition. Such prevention or reduction of the severity of a disease, disorder or condition prior to affliction relates to the administration of the composition of the present invention, as described herein, to a subject that is not at the time of administration afflicted with the disease, disorder or condition. As used herein "treating" may also refer to preventing the recurrence of a disease, disorder or condition or of one or more symptoms associated with such disease, disorder or condition. The terms "treatment" and "therapeutically," as used herein, refer to the act of treating, as "treating" is defined above.

Compounds of Formula I, and their pharmaceutically acceptable salts, may be prepared as described in the following reaction Schemes and discussion. Unless otherwise indicated, as referred to in the reaction schemes and discussion that follow, $R^1$, $R^2$, $R^3$, $R^4$, $R^6$, $R^7$, $R^8$, $R^9$, $R^{10}$, $R^{11}$, A, Z and n are as defined above.

The compounds of Formula I may have asymmetric carbon atoms and may therefore exist as racemic mixtures, diasteroisomers, or as individual optical isomers.

Separation of a mixture of isomers of compounds of Formula I into single isomers may be accomplished according to conventional methods known in the art.

The compounds of Formula I may be prepared by the methods described below, together with synthetic methods known in the art of organic chemistry, or modifications and derivatisations that are familiar to those of ordinary skill in the art. Preferred methods include, but are not limited to, those described below.

The reactions described below are performed in solvents that are appropriate to the reagents and materials employed and that are suitable for use in the reactions described. In the description of the synthetic methods described below, it is also to be understood that all reaction conditions, whether actual or proposed, including choice of solvent, reaction temperature, reaction duration time, reaction pressure, and other reaction conditions (such as anhydrous conditions, under argon, under nitrogen, etc.), and work up procedures, are those conditions that are standard for that reaction, as would be readily recognized by one of skill in the art. Alternate methods may also be used.

Compounds of formula II wherein $R^7$ contains an alcohol moiety may be oxidized using standard oxidation method known in art, such as, e.g., Dess-Martin reagents, Swern oxidation, or use of $SO_3$-pyridine, $CrO_3$, to provide compounds of formula II wherein $R^7$ contains a ketone or aldehyde. Compounds of formula II wherein $R^7$ is a ketone or aldehyde may convert to the corresponding compounds of formula II wherein $R^7$ is an imine (by reaction with an amine), olefin (by a Wittig reaction), alcohol (by a Grignard reaction), or other derivative (by standard reactions).

The compounds of formula I of the present invention and their salts can be prepared by a reaction process comprising a compound of formula II

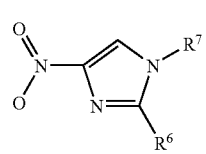

(II)

with a compound of formula III

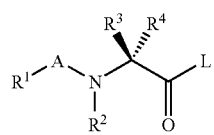

(III)

or reacting a compound of formula IV

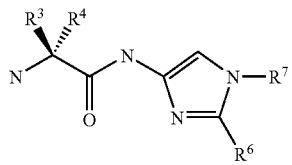

with a compound of formula V

wherein $R^1$, $R^3$, $R^4$, $R^6$, $R^7$, and A are as defined above and L is hydroxy or a suitable leaving group. If desired, the 4-amino-imidazole derivative of formula I or synthetic intermediate of formula IV may be converted into a salt by methods known to those of ordinary skill in the art.

Examples of specific compounds of formula III and V wherein L is hydroxy or a suitable leaving group are those wherein L represents a halogen atom, such as Cl, Br, or I, or A-L is an alkyl or aryl ester.

Compounds in formula I can be prepared by reacting a compound of formula II and a carboxylic acid of formula III, or a compound of formula IV with a compound of formula V. Compounds of formula IV can be prepared by reacting a compound of formula II with a compound of formula VI.

The reaction between compounds of formula II and compounds of formula III, between compounds of formula IV and compounds of formula V, and between compounds of formula II and compounds of formula VI, can be carried out by standard methods. For example, wherein L is a hydroxy group, these reactions can be carried out in the presence of a coupling agent or a polymer supported coupling agent, such as, for example, carbodiimide, i.e. 1,3-dicyclohexylcarbodiimide (DCC), 1,3-diisopropylcarbodiimide, 1-(3-dimethylaminopropyl)-3-ethylcarbodiimide (EDC), N-cyclohexylcarbodiimide, or N'-methylpolystyrene in the presence or absence of HOBt, in a suitable solvent such as, for instance, a single solvent or a combination of several solvents selected from dichloromethane ($CH_2$—$Cl_2$), chloroform ($CHCl_3$), tetrahydrofuran (THF), diethyl ether ($Et_2O$), 1,4-dioxane, acetonitrile, ($CH_3CN$), toluene, N,N-dimethylformamide (DMF), or dimethylsulfoxide (DMSO), at a suitable temperature such as from about $-10°$ C. to about reflux, for a suitable time monitored by chromatography or LC-MS. An alternative method wherein L is OH is carried out by converting OH to a leaving group by reaction with oxalyl chloride, thionyl chloride or a mixed anhydride method, using an alkyl chloroformate, such as $C_1$-$C_4$ alkyl chloroformate, in the presence of a base such as triethylamine, N,N-diisopropylethylamine, pyridine, or dimethylaminopyridine, in a suitable solvent such as, for example, methylene chloride, chloroform, tetrahydrofuran (THF), toluene, diethyl ether, acetonitrile, 1,4-dioxane, n,N-dimethylformamide, dimethylsulfoxide (DMSO), N-methyl pyrrolidinone (NMP), or xylene, at a temperature of from about $-30°$ C. to about room temperature.

Alternatively, aminoimidazole coupling may be achieved as follows. A compound of formula I may be prepared by coupling an amino-imidazole II with III wherein C(=O)L is an ester, in the presence of trialkylaluminium preferably trimethylaluminum in an appropriate solvent such as methylene chloride, THF, dioxane, toluene, etc., at an appropriate temperature, such as from about room temperature to about reflux, or in a sealed reactor (such as sealed tube or inscrewed vials). Similarly, compound IV may be prepared by reacting an amino-imidazole II, triamethylaluminum and N-Boc of an alpha-amino acid ester, followed by removal of the Boc group using standard methods.

The protected amino compounds of formula VI, where $P^1$ is a blocking group such as an N-Boc group, can be prepared by methods well known in the literature, for example the methods described in Theodora W. Greene's book "Protective Groups in Organic Synthesis". Compounds of formula IV can be prepared in an analogous method as above by reacting compound of formula II with a compound of formula VI, followed by deblocking the $P^1$ group. Deprotection can be performed by well-known methods, for example when $P^1$ is N-Boc, removal by any methods well-known in the literature, for example HCl(g) in an appropriate solvent such as 1,4-dioxane, diethylether or trifluoroacetic acid in methylene chloride. Many other amino protecting groups are known and may also be used, such as benzyl or p-methoxy-benzyl, trimethylsilyl, t-butyldimethylsilyl, etc. Methods for deblocking such groups are also well-known in the literature and may be used.

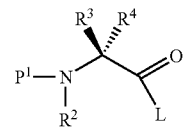

The compounds of formula II, III, IV, V and VI, in certain circumstances, are known compounds or can be obtained according to methods well known to one of skill in the art.

Compounds of formula III and V, wherein L is a leaving group as defined above, can be obtained according to conventional methods from the corresponding carboxylic acids of formula III where X is hydroxy.

Compounds of formula IV can be prepared by reacting a compound of formula II with a compound of formula V using known methods.

An ester group of $R^7$ in compounds of formula I or II may be converted to the corresponding amide using a similar method for amide bond formation, preferably employing trimethylaluminum in an appropriate solvent or a mixture of solvents, such as THF/toluene.

A keto group of $R^7$ in compounds of formula I or II may be converted to the corresponding amine using a well-estabished reductive amination method by reacting such ketone with an appropriate amine, with or without acid catalyst/ammonium acetate/dry agents (such as anhydrous $Na_2SO_4$ or $MgSO_4$), and a reducing agent, such as sodium triacetoxy borohydride, sodium cyanoborohydride, or sodium borohydride, or the corresponding polymer bound-$NaBH_4$, polymer bound-$NaBH_3CN$, or polymer bound-$NaB(OAc)_3H$, or any reducing agent (e.g., hydrogenation) that is known in the literature for reducing an imine bond to an amine, in an appropriate solvent, such as dichloroethane, chloroform, THF, MeOH, ethanol, isopropanol, t-butanol or toluene, at a temperature from about room temperature to about reflux, preferably from about room temperature to about 65° C.

Compounds wherein $R^6$ is a halo group may be generated by reacting the starting material wherein $R^6$ is H with NBS (N-bromosuccinamide), NCS (N-chlorosuccinamide), or $SO_2Cl_2$, $I_2$ in an appropriate solvent such as methylene chloride, carbontetrachloride or chloroform. The halo group may then be replaced with another group using methods known in the art, such as halogen-metal exchange, followed by quenching with an electrophile, or using typical Suzuki coupling conditions employing a catalyst such as a palladium complex, e.g., tetrakis(triphenylphosphine)-palladium, with sodium carbonate as a base, in a suitable solvent such as THF, DME, or ethanol, and a boronic acid.

4-amino-imidazole II may be prepared by the following methods known in the chemical literature (e. g., Tetrahedron, 1995, 51, 2875-2894; J. Chem. Soc. Perkin 1, 1987, 2819-2828; Bull. Chem. Soc. Fr. 1994, 131, 200-209; Tetrahedron Lett. 1996, 4423-4426; Tetrahedron 1996, 37, 4423-4426; Tetrahedron, 1994, 50, 5741-5752; Heterocycles, 1994, 37, 1511-1520; Tetrahedron Lett. 1999, 1623-1626; Organic Lett. 2002, 4, 4133-4134; Organic Lett. 2000, 2, 1233-1236; J. Med. Chem. 1990, 33, 1091-1097;or by the methods described below.

Scheme 1 illustrates methods suitable for preparing amino-imidazole compounds of formula I. Referring to Scheme 1, treatment of a solution of 1,4-dinitroimidazole (*J. Phys. Chem.* (1995) Vol. 99, pp. 5009-5015) in dimethylsulfoxide (DMSO), pyridine-water, water, an alcohol, or an alcohol-water solvent system, but preferably in a lower alcohol such as methanol, from about −20° C. to about 50° C., preferably from about −5° C. to 35° C., with a primary alkyl or aryl amine ($NR^9R^{10}$) affords 1-N-substituted-4-nitroimidazoles of formula 2A. 1,4-dinitroimidazole is a highly energetic, semi-stable substance and should be stored in a freezer at all times it is not in use. Thermodynamic measurements have shown that it can potentially generate enough energy at 35° C. under adiabatic conditions to violently explode. Extreme caution should be exercised at all time using this material. Reduction of the nitro compound of formula 2A to the amine of formula 3A may be accomplished by exposing a mixture of a compound of formula 2A and a noble metal catalyst, in a solvent such as ethyl acetate, tetrahydrofuran, dioxane, or a mixture thereof, to an atmosphere of hydrogen gas at a pressure of about 1 to 100 atmospheres, where a preferred pressure of hygrogen gas is about one to about ten atmospheres. Palladium is the preferred noble metal catalyst. The metal may be conveniently suspended on an inert solid support such as charcoal and filtered to provide the amine of formula 3A. Alternatively, the nitro group of formula 2A to the amine of formula 3A may be accomplished by exposing a mixture of a compound of formula 2A to zinc/HCl or iron/HCl or with $NaBH_4/NiCl_2$ or with $NaBH_2S_3$.

The resulting amine of formula 3A is reacted immediately with an acid chloride, acid anhydride, or an activated carboxylic acid derivative (defined by Formula III), in the presence of a base, such as triethylamine, diisopropylethylamine, pyridine, or 2,6-lutidine, from about −78° C. to 40° C. The reaction between compounds of formula 3A and compounds of formula III can be carried out by standard methods. For example, wherein L of formula III is a hydroxy group, these reactions can be carried out in the presence of a coupling agent or a polymer supported coupling agent, such as, for example, carbodiimide, i.e. 1,3-dicyclohexylcarbodiimide (DCC), 1,3-diisopropylcarbodiimide, 1-(3-dimethylaminopropyl)-3-ethylcarbodiimide (EDC), N-cyclohexylcarbodiimide, or N'-methylpolystyrene in the presence or absence of HOBt, in a suitable solvent such as, for instance, a single solvent or a combination of several solvents selected from dichloromethane ($CH_2Cl_2$), chloroform ($CHCl_3$), tetrahydrofuran (THF), diethyl ether ($Et_2O$), 1,4-dioxane, acetonitrile, ($CH_3CN$), toluene, N,N-dimethylformamide (DMF), or dimethylsulfoxide (DMSO), at a suitable temperature such as from about −10° C. to about reflux, for a suitable time monitored by chromatography or LC-MS. An alternative method wherein L is OH is carried out by converting OH to a leaving group by reaction with oxalyl chloride, thionyl chloride or a mixed anhydride method, using an alkyl chloroformate, such as $C_1$-$C_4$ alkyl chloroformate, in the presence of a base such as triethylamine, N,N-diisopropylethylamine, pyridine, or dimethylaminopyridine, in a suitable solvent such as, for example, methylene chloride, chloroform, tetrahydrofuran (THF), toluene, diethyl ether, acetonitrile, 1,4-dioxane, N,N-dimethylformamide, dimethylsulfoxide (DMSO), N-methyl pyrrolidinone (NMP), or xylene, at a temperature of from about −30° C. to about room temperature.

Alternatively, aminoimidazole coupling may be achieved as follows. A compound of formula I may be prepared by coupling an amino-imidazole 3A with a compound of formula III wherein C(=O)L is an ester, in the presence of trialkylaluminium preferably trimethylaluminum in an appropriate solvent such as methylene chloride, THF, dioxane, toluene, etc., at an appropriate temperature, such as from about room temperature to about reflux, or in a sealed reactor (such as sealed tube or inscrewed vials).

Alternatively, the resulting amine of formula 3A is reacted immediately with an acid chloride, acid anhydride, or an activated carboxylic acid derivative (defined by Formula IV), in the presence of a base, such as triethylamine, diisopropylethylamine, pyridine, or 2,6-lutidine, from about −78° C. to 40° C. to form a compound of formula 4A. The reaction between compounds of formula 3A and compounds of formula IV can be carried out by standard methods. For example, wherein L of formula IV is a hydroxy group, these reactions can be carried out in the presence of a coupling agent or a polymer supported coupling agent, such as, for example, carbodiimide, i.e. 1,3-dicyclohexylcarbodiimide (DCC), 1,3-diisopropylcarbodiimide, 1-(3-dimethylaminopropyl)-3-ethylcarbodiimide (EDC), N-cyclohexylcarbodiimide, or N'-methylpolystyrene in the presence or absence of HOBt, in a suitable solvent such as, for instance, a single solvent or a combination of several solvents selected from dichloromethane ($CH_2Cl_2$), chloroform ($CHCl_3$), tetrahydrofuran (THF), diethyl ether ($Et_2O$), 1,4-dioxane, acetonitrile, ($CH_3CN$), toluene, N,N-dimethylformamide (DMF), or dimethylsulfoxide (DMSO), at a suitable temperature such as from about −10° C. to about reflux, for a suitable time monitored by chromatography or LC-MS. An alternative method wherein L is OH is carried out by converting OH to a leaving group by reaction with oxalyl chloride, thionyl chloride or a mixed anhydride method, using an alkyl chloroformate, such as $C_1$-$C_4$ alkyl chloroformate, in the presence of a base such as triethylamine, N,N-diisopropylethylamine, pyridine, or dimethylaminopyridine, in a suitable solvent such as, for example, methylene chloride, chloroform, tetrahydrofuran (THF), toluene, diethyl ether, acetonitrile, 1,4-dioxane, N,N-dimethylformamide, dimethylsulfoxide (DMSO), N-methyl pyrrolidinone (NMP), or xylene, at a temperature of from about −30° C. to about room temperature.

Alternatively, aminoimidazole coupling may be achieved as follows. A compound of formula 4A may be prepared by coupling an amino-imidazole 3A with a compound of formula IV wherein C(=O)L is an ester, in the presence of trialkylaluminium preferably trimethylaluminum in an appropriate solvent such as methylene chloride, THF, dioxane, toluene, etc., at an appropriate temperature, such as from about room temperature to about reflux, or in a sealed reactor (such as sealed tube or inscrewed vials). The protected amino compounds defined as PG, such as a compound with an Boc group, of formula IV can be prepared by methods well known in the literature, for example the methods described in Theodora W. Greene's book "Protective Groups in Organic Synthesis".

Compounds defined as by Formula 5A can be prepared from compounds of formula 4A by deblocking the PG group. Deprotection can be performed by well-known methods, for example when PG is N-Boc, removal by any methods well-known in the literature, for example HCl(g) in an appropriate solvent such as 1,4-dioxane, diethylether or trifluoroacetic acid in methylene chloride. Many other amino protecting groups are known and may also be used, such as benzyl or p-methoxy-benzyl, trimethylsilyl, t-butyldimethylsilyl, etc. Methods for deblocking such groups are also well-known in the literature and may be used.

Compounds of Formula I can be formed by reaction between compounds of formula 5A and compounds of formula V can be carried out by standard methods. For example, wherein L is a hydroxy group, these reactions can be carried out in the presence of a coupling agent or a polymer supported coupling agent, such as, for example, carbodiimide, i.e. 1,3-dicyclohexylcarbodiimide (DCC), 1,3-diisopropylcarbodiimide, 1-(3-dimethylaminopropyl)-3-ethylcarbodiimide (EDC), N-cyclohexylcarbodiimide, or N'-methylpolystyrene in the presence or absence of HOBt, in a suitable solvent such as, for instance, a single solvent or a combination of several solvents selected from dichloromethane ($CH_2Cl_2$), chloroform ($CHCl_3$), tetrahydrofuran (THF), diethyl ether ($Et_2O$), 1,4-dioxane, acetonitrile, ($CH_3CN$), toluene, N,N-dimethylformamide (DMF), or dimethylsulfoxide (DMSO), at a suitable temperature such as from about $-10°$ C. to about reflux, for a suitable time monitored by chromatography or LC-MS. An alternative method wherein L is OH is carried out by converting OH to a leaving group by reaction with oxalyl chloride, thionyl chloride or a mixed anhydride method, using an alkyl chloroformate, such as $C_1$-$C_4$ alkyl chloroformate, in the presence of a base such as triethylamine, N,N-diisopropylethylamine, pyridine, or dimethylaminopyridine, in a suitable solvent such as, for example, methylene chloride, chloroform, tetrahydrofuran (THF), toluene, diethyl ether, acetonitrile, 1,4-dioxane, n,N-dimethylformamide, dimethylsulfoxide (DMSO), N-methyl pyrrolidinone (NMP), or xylene, at a temperature of from about $-30°$ C. to about room temperature.

Alternatively, aminoimidazole coupling may be achieved as follows. A compound of formula I may be prepared by coupling an amino-imidazole 5A with V wherein L is an ester, in the presence of trialkylaluminium preferably trimethylaluminum in an appropriate solvent such as methylene chloride, THF, dioxane, toluene, etc., at an appropriate temperature, such as from about room temperature to about reflux, or in a sealed reactor (such as sealed tube or inscrewed vials).

Alternatively, compounds of Formula I can be formed by reaction between compounds of formula 5A and compounds of formula V when L is an aldehyde or ketone by using a well-established reductive amination method by reacting such ketone or aldehyde with an appropriate amine 5A, with or without acid catalyst/ammonium acetate/dry agents (such as anhydrous $Na_2SO_4$ or $MgSO_4$), and a reducing agent, such as sodium triacetoxy borohydride, sodium cyanoborohydride, or sodium borohydride, or the corresponding polymer bound-$NaBH_4$, polymer bound-$NaBH_3CN$, or polymer bound-$NaB(OAc)_3H$, or any reducing agent (e.g., hydrogenation) that is known in the literature for reducing an imine bond to an amine, in an appropriate solvent, such as dichloroethane, chloroform, THF, MeOH, ethanol, isopropanol, t-butanol or toluene, at a temperature from about room temperature to about reflux, preferably from about room temperature to about $65°$ C.

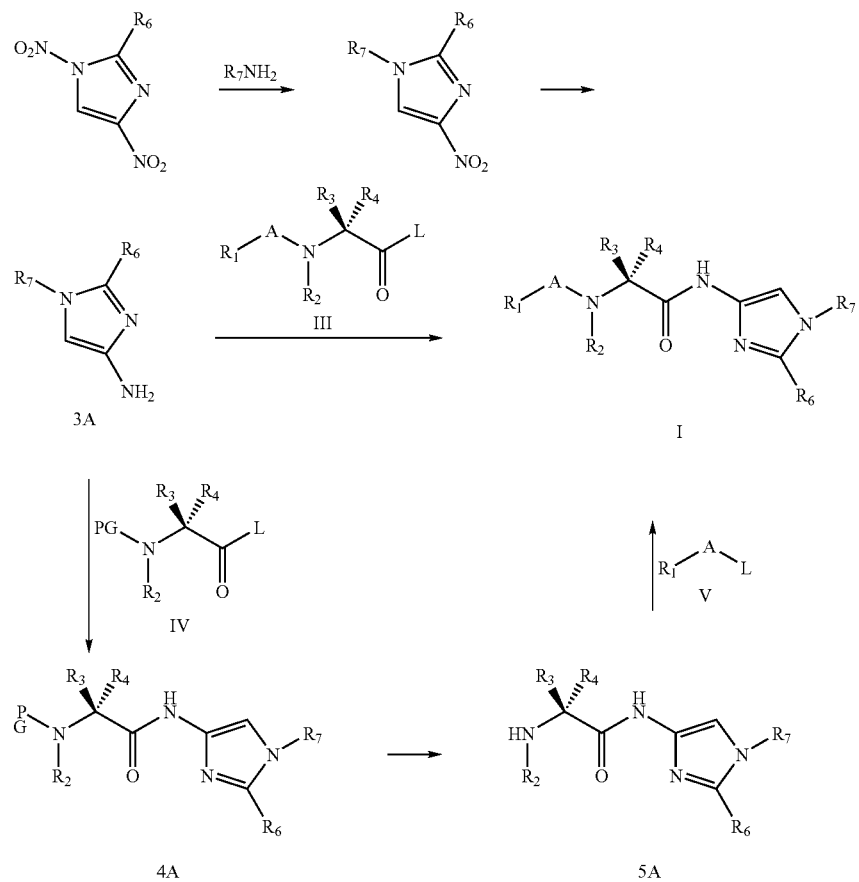

Scheme 1

Scheme 2 illustrates additional methods for the synthesis of imidazole compounds defined as Formula 2A. Treatment of nitroimidazole 6A with a base such as sodium hydride, potassium hydride, alkyl lithium, alkoxides, in a solvent such as tetrahydrofuran, dimethylformamide, methylene chloride, ether, preferably dimethylformamide, from about −60° C. to 40° C., where from −10° C. to 20° C. is preferred, followed by addition of R7-X wherein X is defined as Cl, Br, I, F, alkylsulfonate, or arylsulfonate followed by warming the reaction from 23° C. to 150° C. where 30-80° C. is preferrable, affords imidazoles of formula 2A. Reduction of the nitro compound and coupling reaction is carried out in a similar manner described above and is useful for preparing compounds of Formula I. Alternatively, $R^7$ can be further functionalized by procedures described within or using methods known to one skilled in the art.

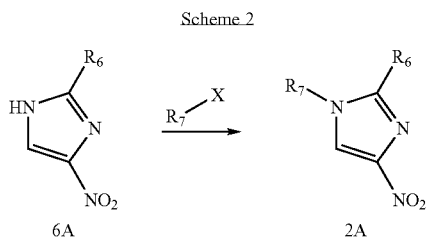

Scheme 2

Scheme 3 illustrates additional methods for the synthesis of nitro-imidazole compounds defined as Formula 2A. A key starting material for the synthesis is the double-bond compound (a compound of Formula 16 or 17) substituted with the group $ER^8$ and one to three groups selected from $R^8$, where $ER^8$ is defined as an electron-withdrawing group chosen from $C(=O)R^9$, $C(=O)OR^9$, $C_9=O)NR^9R^{10}$, $S(=O)_2R^9$, $S(=O)_2NR^9R^{10}$, $S(=O)_2OR^9$, cyano, and heteroaryl. Additionally, compounds of formula 16 or 17 may be defined wherein $ER^8$ is connected to one of the groups $R^8$ or directly to the carbon-carbon double bond to form a ring and thus includes comopunds such as 2-cyclopentene-1-one and 2-cyclohexene-1-one. Alternatively, compounds of formula 17 where L is defined as Cl, Br, I, OC(=O)R^9, or OS(=O)_2R^9 may be used as starting materials; examples of such compounds are 3-chloro-1-cyclopentanone, 3-acetoxy-1-cyclobutanone. Thus, referring to Scheme 3, treatment of -=4-nitroimidazole 6A, with a base such as sodium hydride, potassium hydride, cesium carbonate, 1,8-diazabicyclo[5.4.0]undec-7-ene (DBU) or tetraalkylammonium chloride, where DBU is the preferred base, with intermediates 16 or 17 in a solvent such as acetonitrile, methylene chloride, 1,2-dichloroethane, or chloroform, where acetonitrile is the preferred solvent, at a temperature from about 60° C. to about 50° C., where −20° C. to 23° C. is the preferred range, affords addition products of formula 2A. Reduction of the nitro compound and coupling to give compounds of formula I is carried out in a similar manner described above.

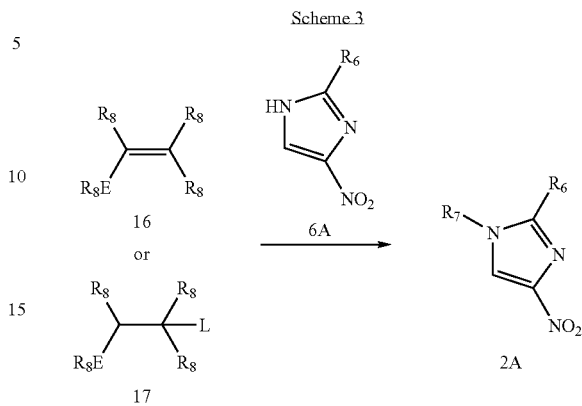

Scheme 3

Scheme 4 below illustrates additional methods for the synthesis of amino-imidazole compounds defined as Formula 2A. Treatment of ethyl-2-isocyano-3-N,N-dimethylamino acrylate or benzyl-2-isocyano-3-N-N-dimethylamino acrylate with a primary amine, R7-NH$_2$, in a solvent such as n-butanol, n-propanol, l-propanol, or ethanol, or in the absence of solvent, where n-propanol or no solvent are preferred, from about 23° C. to about 200° C., where from about 60° C. to 150° C. is preferred, affords imidazoles of formula 18. Treatment of ester 18 with a base such as potassium hydroxide, lithium hydroxide, or sodium hydroxide in a—solvent such as tetrahydrofuran, water, methanol, ethanol, propanol, wherein methanol is preferred provides the acid 19. The acid is converted to the acylazide 20 using methods known to one skilled in the art such as treatment of acid 19 with thionyl chloride or oxalyl chloride from −20 to 50° C. followed by removal of the residual solvent and quenching with sodium or potassium azide in a solvent such as toluene, tetrahydrofuran, methlene chloride, dioxane. The azide 20 undergoes Curtius rearrangement to the Boc 21 by heating from 5° C.-200° C. in a solvent such as t-butanol, benzyl alcohol, and ethanol. If t-butanol is used, deprotection of the N-Boc protecting group can be accomplished with HCl or triflouroacetic acid in a solvent such as ether, tetrahydrofuran, where HCl in methanol is preferred affords the desired aminoimidazole compounds of formula 2A. If benzyl alcohol is used, deprotection can be accomplished by the use of a noble metal catalyst, in a solvent such as ethyl acetate, tetrahydrofuran, dioxane, or a mixture thereof, to an atmosphere of hydrogen gas at a pressure of about 1 to 100 atmospheres, where a preferred pressure of hygrogen gas is about one to about ten atmospheres. Palladium is the preferred noble metal catalyst which affords the desired aminoimidazole compounds of formula 2A. Alternatively, ester 18 can be treated with hydrazine in a solvent such as water from a temperature from 50° C. to 200° C. where 80° C. to 120° C. is preferred provides the hydrazide 22. The hydrazide 22 can be converted to the acylazide 20 using t-butylnitrite in a solvent or combination of solvent such as ether, methylene chloride, dichloroethane, chloroform, where in ether/methylene chloride is preferred at a temperature from −50° C. to 23° C. wherein −30° C. to 10° C. is preferred. The acylazide is then converted onto aminoimidazole compounds of formula 2A as described above.

Scheme 4

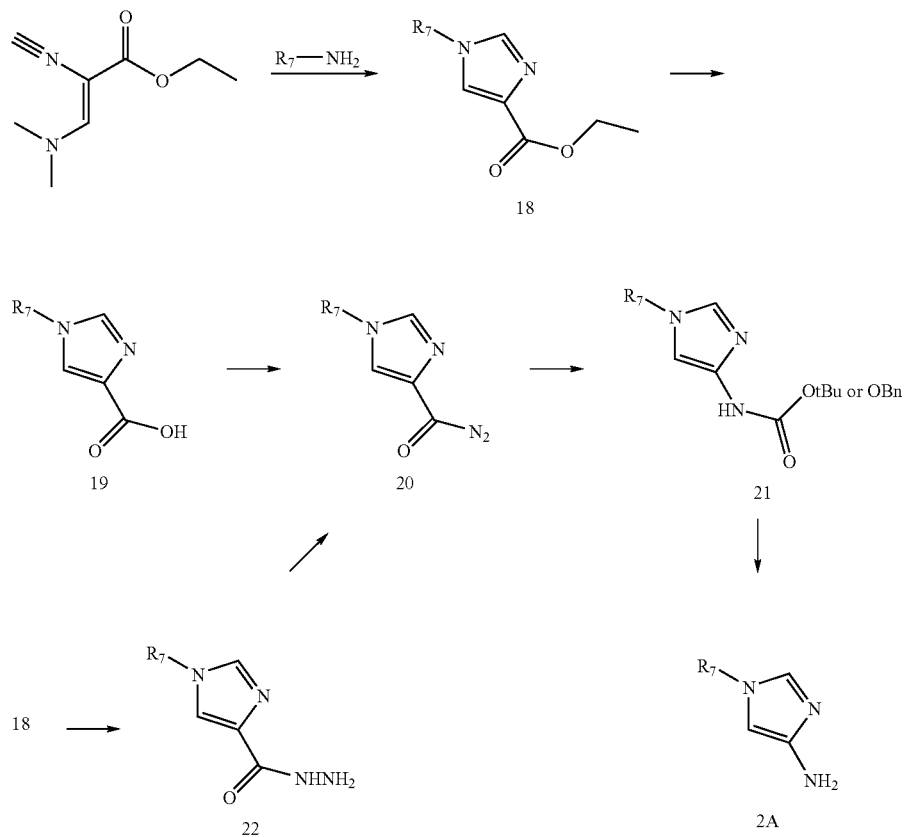

Scheme 5 below illustrates additional methods for the synthesis of amino-imidazole compounds defined as Formula I. Treatment of N-O-dimethyl hydroxyl amine hydrochloride with trimethylaluminum in 1,2-dichloroethane followed by the addition of ester 18, prepared as described above and heating at about 30° C. to about 80° C., where a temperature of about 50° C. is preferred, affords imidazole 23. Addition of an organometallic reagent 24 wherein Z is defined as lithium halide, magnesium halide, potassium halide, where lithium halide is preferred, to a solution of amide 23 in a solvent such as tetrahydrofuran, methylene chloride, or diethyl ether, from a temperature about −78° C. to about 30° C., where a range of about −20° C. to about 0° C. is preferred affords 25. Addition of 25 to a mixture of hydroxyl amine hydrochloride and potassium acetate in a lower alcoholic solvent, where in ethanol is preferred, at about 23° C., yields oxime 26 as a mixture of isomers. Treatment of an acetone solution of oxime 26 at about 0° C. with aqueous hydroxide followed by paratoluenesulfonyl chloride yields a mixture of O-sulfonyl compound following extractive workup. Dissolution of the crude material in a non-polar solvent such as benzene, hexanes, or toluene, wherein benzene is preferred, and application to a column of alumina followed by elution with chloroform-methanol (about 10:1) after approximately five minutes provides a compound of Formula I.

Scheme 5

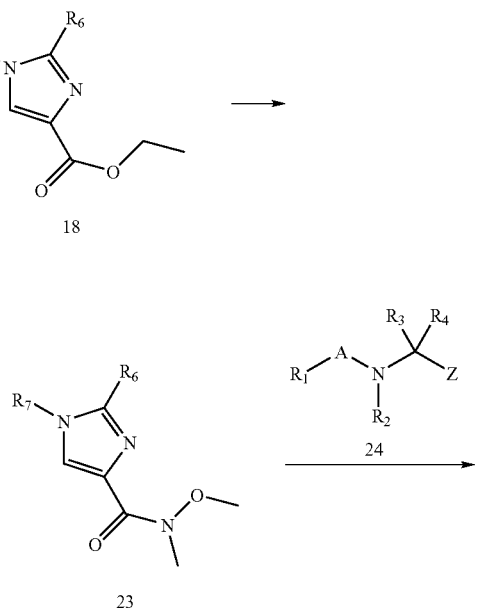

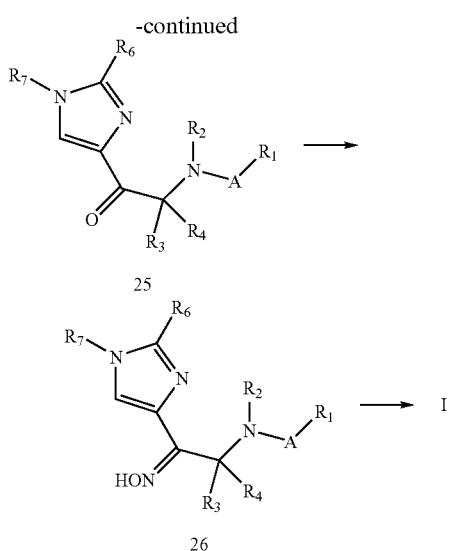

Scheme 6 illustrates methods suitable for preparing amino-imidazole compounds of formula I. Compound of Formula I, 27 can be prepared using methods described above. Conversion of ester I, 27 to alcohol of compounds I, 28 can be accomplished by treatment of ester I, 27 with an appropriate reducing agent such as sodium borohydride or lithium aluminum hydride using conditions well known to one skilled in the art. Compounds of formula I, 28 may be oxidized using standard oxidation method known in art, such as, e.g., Dess-Martin reagents, Swern oxidation, or use of $SO_3$-pyridine, $CrO_3$, where Swern oxidation is preferred to provide compounds containing an aldehyde. The aldehyde can be converted onto compounds of formula I, 29 using well-established reductive amination method by reacting the aldehyde with an appropriate amine 5A, with or without acid catalyst/ammonium acetate/dry agents (such as anhydrous $Na_2SO_4$ or $MgSO_4$), and a reducing agent, such as sodium triacetoxy borohydride, sodium cyanoborohydride, or sodium borohydride, or the corresponding polymer bound-$NaBH_4$, polymer bound-$NaBH_3CN$, or polymer bound-$NaB(OAc)_3H$, or any reducing agent (e.g., hydrogenation) that is known in the literature for reducing an imine bond to an amine, in an appropriate solvent, such as dichloroethane, chloroform, THF, MeOH, ethanol, isopropanol, t-butanol or toluene, at a temperature from about room temperature to about reflux, preferably from about room temperature to about 65° C. Alternatively, the alcohol of I, 28 can be converted to the corresponding alkyl or aryl sulfonate I, 30 by treatment of the alcohol with alkyl or aryl sulfonyl chloride (where in mesyl chloride is preferred) in a solvent such as methylene chloride, tetrahydrofuran, toluene wherein methylene chloride in the presence of an amide such as triethylamine, diisopropyamine, pyridine, 2,6-lutidine, where in triethylamine is preferred at a temperature from −50° C. to 23° C. wherein −0° C. to 30° C. is preferred. The aryl or alkyl sulfonate is then reacted with an alkali metal azide (wherein sodium azide is preferred), in a polar solvent such as dimethylformamide, dimethylsulfoxide, alcohol, wherein ethanol is preferred produces a compound containing an azide. This intermediate azide may be reduced by exposing the azide to a noble metal catalyst, in a solvent such as ethyl acetate, tetrahydrofuran, dioxane, or a mixture thereof, to an atmosphere of hydrogen gas at a pressure of about 1 to 100 atmospheres, where a preferred pressure of hygrogen gas is about one to about ten atmospheres. Palladium is the preferred noble metal catalyst and the reaction affords the amine group. The amine group can then be converted to compounds of Formula I, 29 using the reductive amination conditions described above.

Scheme 6

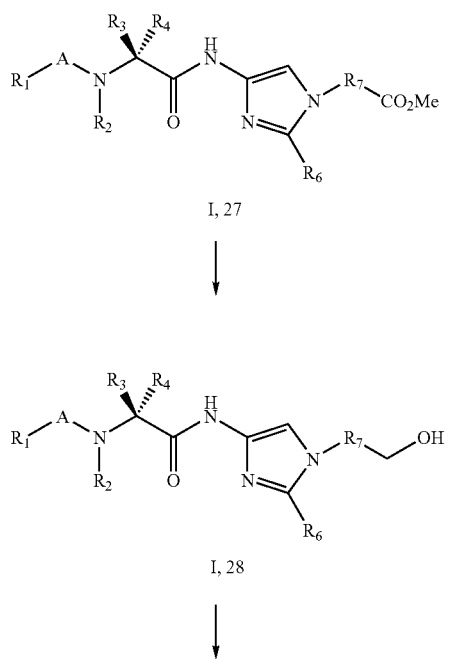

-continued

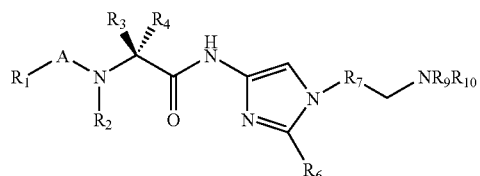

I, 29

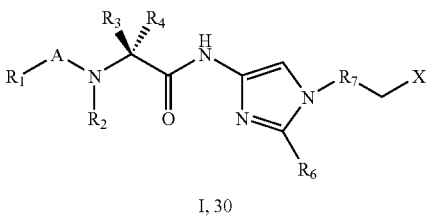

I, 30

Referring to Scheme 7, treatment of a solution of bromoimidazole 30 with a base, such as sodium hydride, potassium hydride, lithium hydride, cesium carbonate, sodium hydroxide, potassium hydroxide, cesium hydroxide, lithium diisopropyl amide, sodium amide, potassium hexamethyldisilazide, sodium hexamethyldisilazide, sodium tert-butoxide, or potassium tert-butoxide, in a reaction inert solvent such as tetrahydrofuran, 1,4-dioxane, N,N-dimethylformamide, dimethylsulfoxide, or toluene, from about −20° C. to 150° C., where 20° C. to 100° C. is preferred, in the absence or presence of a phase transfer catalyst, such as tetra-n-butylammonium chloride, tetra-n-butylammonium bromide, tetra-n-butylammonium iodide, benzyltrimethyl ammonium chloride, benzyltrimethyl ammonium bromide, or benzyltrimethyl ammonium fluoride, followed by the addition of an alkyl, allylic, or benzylic chloride, bromide, iodide, alkyl sulfonate, aryl sulfonate, or triflate, affords imidazoles 31.

Treatment of 1-substituted-4-bromoimidazole (31) with an intermediate of the formula 32 or PG-NH$_2$ (where PG is defined as (C=O)alkyl or benzoyl) and a palladium catalyst such as palladium (II) acetate, allyl palladium chloride dimer, tris(dibenzylideneacetone)dipalladium (0), tris(dibenzylideneacetone)dipalladium (0) chloroform adduct, or palladium (II) chloride, where palladium (II) acetate, tris(dibenzylideneacetone)dipalladium (0), and tris(dibenzylideneacetone)dipalladium (0) chloroform adduct are preferred, and a phosphine ligand, preferably 9,9-dimethyl-4,5-bis(diphenylphosphino)xanthene (XANTPHOS) is preferred, and a base, such as cesium carbonate, or potassium phosphate (K$_3$PO$_4$), where potassium phosphate is preferred, in a reaction inert solvent, such as toluene, 1,4-dioxane, or tetrahydrofuran, from about 0° C. to 150° C., where 20° C. to 110° C. is preferred, affords the coupled product 1. Alternatively, treatment of 1-substituted-4-bromoimidazole (31) with an intermediate of the formula 32 or PG-NH2 (where PG is defined as (C=O)alkyl or benzoyl) and a diamine, such as 1,2-ethylenediamine, N,N'-dimethylethylenediamine, or cis-1,2-diaminocyclohexane, preferably N,N'-dimethylethylenediamine, and cuprous chloride, bromide or iodide, preferably cuprous iodide, in the presence of a small amount of water, preferably about 1% to about 4% water, in a reaction inert solvent such as 1,2-dimethoxyethane, diglyme, t-butyl methyl ether, tetrahydrofuran, benzene or toluene, preferably toluene, at a temperature of about 40° C. to about 150° C., preferably about 80° C. to about 120° C. to yield the compound of formula I or compounds of formula 33. In the case of compound 33, this can be converted to compounds of formula 2A using standard methods described above.

Scheme 7

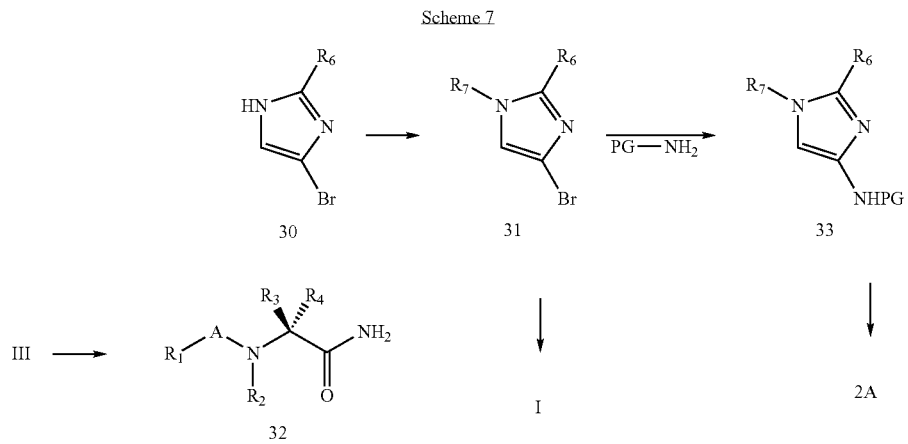

The starting materials used in the procedures of the above Schemes, the syntheses of which are not described above, are either commercially available, known in the art or readily obtainable from known compounds using methods that will be apparent to those skilled in the art.

The compounds of Formula I, and the intermediates shown in the above reaction schemes, may be isolated and purified by conventional procedures, such as recrystallization or chromatographic separation, such as on silica gel, either with an ethyl acetate/hexane elution gradient, a methylene chloride/methanol elution gradient, or a chloroform/methanol elution gradient. Alternatively, a reverse phase preparative HPLC or chiral HPLC separation technique may be used.

In each of the reactions discussed or illustrated above, pressure is not critical unless otherwise indicated. Pressures from about 0.5 atmospheres to about 5 atmospheres are generally acceptable, and ambient pressure, i.e., about 1 atmosphere, is preferred as a matter of convenience.

The compounds of Formula I of the present invention are useful in inhibiting Aβ-peptide production (thus, gamma-secretase activityl) in mammals, and therefore they are able to function as therapeutic agents in the treatment of the aforementioned disorders and diseases in an afflicted mammal.

A specific compound of Formula I can be determined to inhibit Aβ-peptide production using biological assays known to those of ordinary skill in the art, for example the assays described below.

For testing efficacy in vitro, the effect of test compounds on the secretion of Aβ from cells in tissue culture was determined. H4 cells (human brain neuroglioma) were stably transfected with human APP695 containing the Swedish Familial Alzheimers Disease mutation. Cells were distributed into 96-well plates at a density of about 30,000 cells/well and allowed to attach to the plate surface for approximately 6 hours at 37° C. After this time, cells were washed to remove secreted Aβ and fresh media containing test compound was added. Following incubation with compound overnight at 37° C., media was harvested and subjected to immunoassay to determine the amount of Aβ secreted from the cells. Various assays for Aβ peptides known to those skilled in the art can be applied to these samples for quantitation of Aβ secretion. In this application, a two-site sandwich ELISA utilizing commercially available monoclonal antibodies, 6E10 and 4G8-biotinylated, were employed to provide an estimate of the amount of most of the physiologically relevant forms of Aβ, e.g., Aβ1-40, Aβ1-42. Signals from these samples were compared to standard curves generated with synthetic Aβ1-40 peptide and used to calculate $IC_{50}$ values for each test compound.

Using such assay, compounds of the present invention were determined to have an $IC_{50}$ activity for inhibiting gamma-secretase activity of less than about 800 micromolar. Preferred compounds of the invention are compounds that were determined to have an $IC_{50}$ activity for inhibiting gamma-secretase activity of less than about 1 micromolar.

The following Examples illustrate the present invention. It is to be understood, however, that the invention, as fully described herein and as recited in the claims, is not intended to be limited by the details of the following Examples.

EXAMPLES

General Procedure A:
Coupling Method for Amide Formation
a) EDC/HOBt/Trialkylamine Coupling Procedure A mixture of a carboxylic acid (1.0 e.q.), amine (1.0 e.q.), HOBt (1.1-1.5 eq.), EDC (1.2-1.8 eq.) and a trialkylamine (triethylamine or diisopropylethylamine) (3-6 eq.) in an appropriate solvent or a mixture of solvents, for example methylene chloride, dichloroethane, THF, or DMF, was stirred at room temperature until product formation or disappearance of starting material. The solvent was removed under reduced pressure, the residue taken up in ethyl acetate (or similar selected solvent such as methylene chloride or chloroform) and water. The organic layer was separated, washed with dilute HCl (if the desired product contains a basic functional group, washing with dilute HCl may be omitted), brine, and dried over sodium sulfate. The solvent was then removed at reduced pressure to provide product.

b) HATU/Trialkylamine Coupling Procedure

A mixture of a carboxylic acid (1.0 e.q.), amine (1.0 e.q.), HATU (1.1-1.5 eq.) and a trialkylamine (triethylamine or diisopropylethylamine) (3-6 eq.) in an appropriate solvent or a mixture of solvents, for example methylene chloride, dichloroethane, THF, or DMF, was stirred at room temperature until product formation or disappearance of starting material. The solvent was removed under reduced pressure, the residue taken up in ethyl acetate (or similar selected solvent such as methylene chloride or chloroform) and water. The organic layer was separated, washed with dilute HCl (if the desired product contains a basic functional group, washing with dilute HCl may be omitted), brine, and dried over sodium sulfate. The solvent was then removed at reduced pressure to provide product.

c) PyBOP/Trialkylamine Coupling Procedure

A mixture of a carboxylic acid (1.0 e.q.), amine (1.0 e.q.), PyBOP (1.1-1.5 eq.) and a trialkylamine (triethylamine or diisopropylethylamine) (3-6 eq.) in an appropriate solvent or a mixture of solvents, for example methylene chloride, dichloroethane, THF, or DMF, was stirred at room temperature until product formation or disappearance of starting material. The solvent was removed under reduced pressure, the residue taken up in ethyl acetate (or similar selected solvent such as methylene chloride or chloroform) and water. The organic layer was separated, washed with dilute HCl (if the desired product contains a basic functional group, washing with dilute HCl may be omitted), brine, and dried over sodium sulfate. The solvent was removed at reduced pressure to provide product.

d) HBTU/Trialkylamine Coupling Procedure

A mixture of a carboxylic acid (1.0 e.q.), amine (1.0 e.q.), HBTU (1.1-1.5 eq.), and a trialkylamine (triethylamine or diisopropylethylamine) (3-6 eq.) in an appropriate solvent or a mixture of solvents, for example methylene chloride, dichloroethane, THF, or DMF, was stirred at room temperature until product formation or disappearance of starting material. The solvent was removed under reduced pressure, the residue taken up in ethyl acetate (or similar selected solvent such as methylene chloride or chloroform) and water. The organic layer was separated, washed with dilute HCl (if the desired product contains a basic functional group, washing with dilute HCl may be omitted), brine, and dried over sodium sulfate. The solvent was removed at reduced pressure to provide product.

e) Chloro-alkylformate Coupling Procedure

A mixture of a carboxylic acid (1 eq.) and triethylamine (eq.) was dissolved in an appropriate solvent, such as DMF and cooled to −23° C. Isobutyl formate (1 eq.) was added dropwise with stirring. After stirring for a period of time (form 15 min to 2 hr), a 2-amino-thiazole or an amine (1 eq.) was added and stirring continued for an additional 30 min at −23° C. The mixture was then warmed to room temperature until amide formation (typically overnight). The mixture was quenched with water and brine and extracted with an appropriate solvent such as ethyl acetate, methylene chloride or chloroform. The organic layer was washed with dilute $NaHSO_4$, $NaHCO_3$ and brine and the solvent was removed under reduced pressure to provide product. Purification may be necessary.

f) TPTU Coupling Procedure

To the acid (1 equiv) was suspended in dry DMF, Diisoproplyethyl amine (2-4 equiv) and TPTU (1 equiv) were added and the resulting mixture was stirred at room temperature for 1 to 2 hour. To an aliquot of this solution was added the appropriate amine and the mixture was stirred at room temperature over night. 1N NaOH was added and the resulting mixture was extracted with ethyl acetate. The organic extracts were loaded onto SCX SPE (Silicycle, 1 g) which was washed with MeOH. The product was then eluted with 1N triethyl amine in MeOH and the resulting fraction was concentrated. Purification was on Waters XTerra PrepMS C18 OBD column (19×100 mm) and provided the title compound. Gradient elution with water/acetonitrile (18 ml/min) with a 1% trifluoroacetic acid modifier (2 ml/min).

General Procedure B:
Method for Reductive Amination
a) Sodium Triacetoxyborohydride An amine (14 eq.) in dichloroethane or THF was added to a solution of a ketone (1 eq.), NaBH(OAc)$_3$ (1-3 eq.) and acetic acid (1-3 eq.) in dichloroethane or THF. The mixture was stirred at room temperature until product formation or disappearance of starting material. The mixture was quenched with diluted base, extracted with methylene chloride or other appropriate solvent such as chloroform or ethyl acetate. The organic layer was separated, dried and concentrated to give the desired amide. Purification may be necessary.

b) Sodium Cyanoborohydride

A mixture of a ketone or aldehyde (1 eq.), an amine (1-20 eq.), sodium cyanoborohydride (1-5 eq.), acetic acid (1-3 eq.), sodium acetate (1-3 eq.), anhydrous sodium sulfate in dichloroethane or THF was stirred at room temperature to 60° C., preferably heated at 35-50° C. until product formation. The mixture was quenched with diluted base, extracted with methylene chloride or other appropriate solvent such as chloroform or ethyl acetate. The organic layer was separated, dried and concentrated to give the desired amide. Purification may be necessary.

c) Potassium Formate and Palladium Acetate

A solution of an aldehyde or a ketone (1 eq.) and an amine (1 eq.) in dry DMF was stirred at room temperature for 4 hr, in the presence of molecular sieves. To the resulting reaction mixture were added potassium formate (2 eq.) and palladium acetate (catalytic amount, 0.02 eq.). The mixture was heated at 40-60° C. to complete reaction (TLC) and after cooling it was diluted with ice-water. The mixture was extracted with an appropriate solvent (such as methylene chloride, ethyl acetate, or chloroform). The organic layer was separated, dried and concentrated to give the desired amide. Purification may be necessary.

General Procedure C:
Sodium Borohydride Reduction of Ketone or Aldehyde

A mixture of an aldehyde or a ketone (1 eq.) and sodium borohydride (1-10 eq.) in an appropriate solvent (methanol or ethanol) was stirred at 0° C. to room temperature for 10 minutes to complete reaction (TLC). The mixture was concentrated to a small volume, quenched with water, extracted with an appropriate solvent (such as methylene chloride, ethyl acetate, or chloroform). The organic layer was separated, dried and concentrated to give the desired amide. Purification may be necessary.

General Procedure D:
N-tBOC Deprotecting Procedure

To a solution of N-tBOC compound in 1,4-dioxane (0.03-0.09 M) was added 4 N HCl in 1,4-dioxane or anhydrous HCl gas under nitrogen. The reaction mixture was stirred at room temperature for 1-24 hrs until all the starting material consumed (TLC). The solution was concentrated and pumped in vacuo. The final HCl salt of the corresponding amine was typically used without further purification.

General Procedure E:
Conjugate Addition to Nitroimidazole

To a suspension of 4-nitroimidazole (2.0 equiv.) in acetonitrile is added DBU (1.0 equiv) followed by enone (1.0 equiv.). The reaction is heated for 12-24 hrs and the solvent removed in vacuo. The resultant solids are removed by filtration with methylene chloride and the resultant oil concentrated and purified by silica gel chromatography to provide the desired nitroimidazole.

General Proceudre F:
Alkylation of Nitroimidazole Using Sodium Hydride

To a suspension of 4-nitroimidazole (1.0 equiv.) in dimethylformamide at rt under a nitrogen atmosphere is added sodium hydride (1.2 equiv.) portionwise. The reaction is stirred for 15-30 min. And then the appropriate alkylhalide or alkyl mesylate is added. The mixture is stirred for 12-24 h at 50° C., cooled to 0° C., and quenched with water. The aqueous layer is extrated with methylene chloride, dried, and purified by silica gel chromatography to provide the desired nitroimidazole.

Alkylation of Nitroimidazole Using Potassium Carbonate

To a suspension of 4-nitroimidazole (1.0 equiv.) in dimethylformamide at rt under a nitrogen atmosphere is added potassium carbonate (1-4 equiv.) portionwise. The reaction is stirred for 15-30 min. And then the appropriate alkylhalide or alkyl mesylate is added. The mixture is stirred for 12-24 h at 50° C. to 90° C., cooled to rt, and quenched with water. The aqueous layer is extrated with methylene chloride, dried, and purified by silica gel chromatography or recrystalized to provide the desired nitroimidazole.

General Procedure G:
Reduction of Nitroimidazole A

To a solution of the nitroimidazole (1.0 equiv.) in ethylacetate is added palladium on carbon (0.25 w/w %). The reaction is hydrogenated @ 40-60 psi for 2-6 hrs and filtered over a pad of celite using ethyl acetate. The majority of the ethylacetate is removed in vacuo and the solution of the amine in the remaining ethylacetate is used without further purification.

Reduction of Nitroimidazole B

A Parr bottle was charged with nitroimidazole (1 equiv), dioxane and (1-3 equiv) of Raney nickel which had been washed with water until the supernatant was at pH=7. The mixture was placed under 50 psi of hydrogen pressure and shaken for 45 minutes. After filtration and evaporation, the product, was used directly in the next step without further purification.

General Procedure H:
Reduction of Nitroimidazole-ester Followed by Reductive Amination To a solution of appropriate ester such as 3-Methyl-3-(4-nitro-imidazol-1-yl)-butyric acid methyl ester (1.0 equiv.) in methylene chloride at −78° C. is added DIBAL (2 equiv.) dropwise. The reaction is stirred for 1 h, quenched with ethylacetate, removed from cooling bath, and stirred for 10 min. To the reaction is added water and allowed to warm to rt and stir for 1 h. The reaction is diluted with methylene chloride, Na$_2$SO$_4$ is added and the reaction filtered through celite. The solvent is removed to afford the aldehyde such as 2-Methyl-2-(4-nitro-imidazol-1-yl)-propionaldehyde which is used in the next step without further purification.

To a solution of the appropriate aldehyde such as 2-Methyl-2-(4-nitro-imidazol-1-yl)-propionaldehyde (1 equiv.) in methylene chloride is added an appropriate amine (2 equiv.) and 4A molecular sieves. The reaction is stirred for 4-6 hours and an appropriate hydride reducing agent such as sodium triacetoxyborohydride (2 equiv.) is added. The reaction is stirred for 6-24 h, quenched with sodium bicarbonate, and the aqueous layer extracted with methylene chloride. The solvent is removed and residue purified by silica gel chromatography to provide the desired nitroimidazole.

General Procedure I:

Ester Reduction

To a solution of ester (1 equiv) in an appropriate solvent such as diethyl ether or tetrahydrofuran at −78° C. to 0° C. is added lithium aluminum hydride (1 equiv) and the reaction is stirred at 0° C. for 15 min and warmed to rt for 1 h. The reaction is slowly quenched with water and ethyl acetate. The reaction is filtered and the aqueous is extracted with ethylacetate, dried, and concentrated. Alternatively, the reaction is quenched with water, 1N NaOH and water, stirred and filtered through celite. The filtrate was concentrated to dryness. Using either workup, the resultant residue is purified by silica gel chromatography to provide the title alcohol.

General Procedure J

Swern Oxidation

To a solution of oxalyl chloride (1.2 equiv) in methylene chloride at −78° C. is added DMSO (3 equiv) dropwise. The reaction is stirred for 20 min. and the alcohol (1 equiv) is added in methylene chloride. The reaction is stirred for 1 h, triethylamine (4-5 equiv) is added, and the reaction warmed to 0° C. for 20 min to 2 hours. The reaction is quenched with 100 mL of sodium bicarbonate, extracted with methylene chloride, dried, and concentrated to afford the title compound.

Dess Martin Oxidation

A mixture of 1 eq. of an alcohol and 1 to 1.5 eq. of Dess-Martin oxidizing agent in methylene chloride (2 mL per mmole reaction) was stirred at rt until reaction done. The mixture was quenched with water, filtered. The organic layer was separated, dried and concentrated to give the corresponding aldehyde.

General Procedure K:

Epoxide Opening:

Isopropanol was added to the appropriate amine followed by the addition of Hunig's base (2 equiv) and the appropriate epoxide (1 equiv), the reaction mixture was heated at 60-100° C. overnight. The mixture was quenched with dilute aq bicarb solution and extracted with dichloromethane. The organic extracts were dried ($Na_2SO_4$) and concentrated to afford 200 mg crude material which was purified on a silica get flash column to afford the desired compound.

General Procedure M:

Substitution of Dinitroimidazole

A solution of (1 equiv) of 1,4-dinitro-1H-imidazole (WO99/08699) and appropriate amine (1-2 equiv) in 1:1 MeOH—water was stirred at room temperature for 48 hrs. The solvent was removed in vacuo. The residue was taken up in methylene chloride and chromatographed on silica gel to provide the desired compound.

General Procedure N:

Mesylate Formation (A)

The appropriate alcohol (1 equiv) was dissolved in pyridine and treated with methansulfonyl chloride (2.2 equiv) at 0° C. The reaction was warmed to rt and stirred for 4 h, quenched with sodium bicarbonate, and extracted with methylene chloride. The extracts were dried and concentrated to provide the appropriate mesylate which was used without further purification.

Mesylate Formation (B)

To the appropriate alcohol (1 equiv), methanesulfonyl chloride (1 equiv), triethylamine (1 equiv) in methylene chloride was stirred at rt for 1 to 8 hr. The reaction mixture was quenched with waster, the organic layer was separated and concentrated to give the desired mesylate which was used without further purification.

General Procedure O:

Mesylate Displacement:

A 0.1 M solution of mesylate in acetonitrile was treated with 3 equiv. of amine and 3 equiv. of $K_2CO_3$ and heated at 65-80 C with stirring for 24-75 hrs. Once judged complete by APCI or TLC, the reaction was quenched with $H_2O$ and extracted with DCM. Silica gel chromatography or HPLC afforded pure product in 30-75% yield.

General Procedure P:

Benzyl Halide Displacement:

A 0.1 M solution of imidazole in DMF was treated with 1.1-2.1 equiv of benzyl halide and 2.1 equiv of $K_2CO_3$ and heated at 65 C with stirring for 18-30 hrs. In some cases, reaction was facilitated by the addition of 0.05 equiv of $Et_3NBnCl$. Once judged complete by APCI or TLC, the reaction was quenched with $H_2O$ and extracted with EtOAc. The combined extracts were washed with $H_2O$ and brine, dried over $MgSO_4$, filtered and concentrated. Alternatively, reactions were worked up by extraction with DCM. Extracts were loaded onto an SCX SPE (1 g, Silicycle) cartridge. After washing with MeOH, crude product was eluted with 1 N TEA in MeOH. Silica gel chromatography or HPLC afforded pure product in 30-75% yield.

General Proceudre R:

Ester Hydrolysis

The ester (1 equiv) is dissolved in THF:water (5:1) and LiOH (1.2 equiv) is added. The reaction is stirred overnight at rt, the solvent is removed, water added, and the pH is adjusted to 7 using 1 N hydrochloric acid. The solid is filtered, washed with water and diethyl ether, and dried to afford the desired acid.

The following intermediates were prepared by methods analogous to those described above for General Method F;

1-(3-Methyl-oxetan-3-ylmethyl)-4-nitro-1H-imidazole; H1 NMR, (400 MHz), CDCl3) δ 1.25 (s, 3H), 4.28 (s, 2H), 4.42 (dd, J=6.6 Hz, 37.3 Hz, 4H), 7.44 (s, 1H), 7.80 (s, 1H).

4-Nitro-1-[1-(4-trifluoromethyl-phenyl)-ethyl]-1H-imidazole: H1 NMR, (400 MHz), CDCl3): δ 1.96 (d, 3H), 5.49 (q, 1H), 7.33 (d, 2H), 7.53 (s, 1H), 7.67 (d, 2H), 7.78 (s, 1H).

1-Benzyl-4-nitro-1H-imidazole; was prepared according to the procedure of Searcey, M.; Pye, P. L.; Lee, J. B.; Synth. Commun.; EN; 19; 7,8; 1989; 1309-1316.

1-(4-Nitro-imidazol-1-yl)-cyclobutanecarboxylic acid methyl ester; MS 240 m/z (M+1).

2-(4-Nitro-imidazol-1-yl)-cyclobutanecarboxylic acid methyl ester; MS 240 m/z (M+1).

The following intermediates were prepared from dinitroimidazole by methods analogous to those described above for General Method M;

1-Indan-1-yl-4-nitro-1H-imidazole; MS 230 m/z (M+1).

(1R,2S)-(1-(4-Nitro-imidazol-1-yl)-indan-2-ol; MS 246 m/z (M+1).

(1S,2R)-(1-(4-Nitro-imidazol-1-yl)-indan-2-ol; MS 246 m/z (M+1).

2-(4-fluorophenyl)-2-(4-nitro-1H-imidazol-1-yl)ethanol; MS 252 m/z (M+1).

(2-(4-nitro-1H-imidazol-1-yl)phenyl)methanol; MS 220 m/z (M+1).

Methyl 2-(4-nitro-1H-imidazol-1-yl)-2-phenylacetate; MS 262 m/z (M+1).

The following nitroimidazoles were prepared by methods analogous to those described above for General Method H:

2,2-dimethyl-N-(2-(4-nitro-1H-imidazol-1-yl)-2-phenylethyl)propan-1-amine

Methyl 2-(4-nitro-1H-imidazol-1-yl)-2-phenylacetate was converted to the title compound using a method analogous to the general procedure H to afford the title compound: MS 303 m/z (M+1).

The following prepared as descripted:

4-Nitro-1-(2-pyrrolidin-1-ylmethyl-cyclobutyl)-1H-imidazole

A mixture of the 2-(4-Nitro-imidazol-1-yl)-cyclobutanecarboxylic acid methyl ester (2.640 g, 0.01105 mol), borane-dimethyl sulfide complex (1M in tetrahydrofuran) (33.2 mL, 0.0332 mol) and tetrahydrofuran (10 mL) was heated at reflux for 17 hours. The reaction was quenched by water. The volatile solvent was evaporated under reduced pressure. The residue was diluted with water and extracted with ethyl acetate three times. The combined extracts were washed with brine and dried over sodium sulfate. The solvent was then evaporated under reduced pressure to yield [2-(4-Nitro-imidazol-1-yl)-cyclobutyl]-methanol (0.825 g, 0.00419 mol) as a white solid. M+1=198.1.

[2-(4-Nitro-imidazol-1-yl)-cyclobutyl]-methanol was converted to Methanesulfonic acid 2-(4-nitro-imidazol-1-yl)-cyclobutylmethyl ester following General Procedure N; MS 276.3 m/z (M+1).

Methanesulfonic acid 2-(4-nitro-imidazol-1-yl)-cyclobutylmethyl ester was converted to the title compound following General Procedure O; MS 251.5 m/z (M+1).

The following mesylates were prepared by methods analogous to those described above for General Method N:

Methanesulfonic acid 2-(4-{2-[2-(3,5-difluoro-phenyl)-acetylamino]-pentanoylamino}-imidazol-1-yl)-ethyl ester 2-[2-(3,5-Difluoro-phenyl)-acetylamino]-pentanoic acid [1-(2-hydroxy-ethyl)-1H-imidazol-4-yl]-amide amide (U.S. Ser. No. 11/078,898 filed Mar. 11, 2005) was converted to the title compound; MS 459.0 m/z (M+1).

Methanesulfonic acid 3-{4-[2-(6,8-difluoro-1,2,3,4-tetrahydro-naphthalen-2-ylamino)-pentanoylamino]-imidazol-1-yl}-propyl ester 2-(6,8-Difluoro-1,2,3,4-tetrahydro-naphthalen-2-ylamino)-pentanoic acid [1-(3-hydroxy-propyl)-1H-imidazol-4-yl]-amide was converted to the title compound; MS 485 m/z (M+1).

Methanesulfonic acid 2-{4-[2-(6,8-difluoro-1,2,3,4-tetrahydro-naphthalen-2-ylamino)-pentanoylamino]-imidazol-1-yl}-propyl ester 2-(6,8-Difluoro-1,2,3,4-tetrahydro-naphthalen-2-ylamino)-pentanoic acid [1-(2-hydroxy-1-methyl-ethyl)-1H-imidazol-4-yl]-amide was converted to the title compound; MS 485.5 m/z (M+1).

Methanesulfonic acid 3-{4-[2-(6,8-difluoro-1,2,3,4-tetrahydro-naphthalen-2-ylamino)-pentanoylamino]-imidazol-1-yl}-3-methyl-butyl ester 2-(6,8-Difluoro-1,2,3,4-tetrahydro-naphthalen-2-ylamino)-pentanoic acid [1-(3-hydroxy-1,1-dimethyl-propyl)-1H-imidazol-4-yl]-amide was converted to the title compound; MS 513 m/z (M+1).

The following intermediates were prepared by methods analogous to those described above for the reduction of the appropriate nitroimidazole using General Method G followed by coupling to the appropriate acid using General Procedure A, method F.

2-[2-(3,5-Difluoro-phenyl)-acetylamino]-pentanoic acid (1-benzyl-1H-imidazol-4-yl)-amide 1-Benzyl-4-nitro-1H-imidazole was reduced and coupled with 2-[2-(3,5-Difluoro-phenyl)-acetylamino]-pentanoic acid to afford the title compound; MS 470 m/z (M+1).

(4-{2-[2-(3,5-Difluoro-phenyl)-acetylamino]-pentanoylamino}-imidazol-1-yl)-acetic acid methyl ester (4-Nitro-imidazol-1-yl)-acetic acid methyl ester was reduced and coupled with 2-[2-(3,5-Difluoro-phenyl)-acetylamino]-pentanoic acid to afford the title compound; MS 409.1 m/z (M+1).

1-(4-{2-[2-(3,5-Difluoro-phenyl)-acetylamino]-pentanoylamino}-imidazol-1-yl)-cyclobutanecarboxylic acid methyl ester 1-(4-Nitro-imidazol-1-yl)-cyclobutanecarboxylic acid methyl ester was reduced and coupled with 2-[2-(3,5-Difluoro-phenyl)-acetylamino]-pentanoic acid to afford the title compound; MS 463.0 m/z (M+1).

2-(4-{2-[2-(3,5-Difluoro-phenyl)-acetylamino]-pentanoylamino}-imidazol-1-yl)-cyclobutanecarboxylic acid methyl ester 2-(4-Nitro-imidazol-1-yl)-cyclobutanecarboxylic acid methyl ester was reduced and coupled with 2-[2-(3,5-Difluoro-phenyl)-acetylamino]-pentanoic acid to afford the title compound; MS 463.1 m/z (M+1).

1-{4-[2-(5,7-Difluoro-1,2,3,4-tetrahydro-naphthalen-2-ylamino)-pentanoylamino]-imidazol-1-yl}-cyclobutanecarboxylic acid methyl ester 1-(4-Nitro-imidazol-1-yl)-cyclobutanecarboxylic acid methyl ester was reduced and coupled with 2-(6,8-Difluoro-1,2,3,4-tetrahydro-naphthalen-2-ylamino)-pentanoic acid to afford the title compound; MS 475.5 m/z (M+1).

2-{4-[2-(6,8-Difluoro-1,2,3,4-tetrahydro-naphthalen-2-ylamino)-propionylamino]-imidazol-1-yl}-2-methyl-propionic acid methyl ester 2-Methyl-2-(4-nitro-imidazol-1-yl)-propionic acid methyl ester was reduced and coupled with 2-(6,8-Difluoro-1,2,3,4-tetrahydro-naphthalen-2-ylamino)-propionic acid to afford the title compound; MS 421.5 m/z (M+1).

2-{4-[2-(6,8-Difluoro-1,2,3,4-tetrahydro-naphthalen-2-ylamino)-pentanoylamino]-imidazol-1-yl}-propionic acid methyl ester 2-(4-Nitro-imidazol-1-yl)-propionic acid methyl ester was reduced and coupled with 2-(6,8-Difluoro-1,2,3,4-tetrahydro-naphthalen-2-ylamino)-pentanoic acid to afford the title compound; MS 435.5 m/z (M+1).

3-{4-[2-(6,8-Difluoro-1,2,3,4-tetrahydro-naphthalen-2-ylamino)-pentanoylamino]-imidazol-1-yl}-3-methyl-butyric acid methyl ester 3-Methyl-3-(4-nitro-imidazol-1-yl)-butyric acid methyl ester was reduced and coupled with 2-(6,8-Difluoro-1,2,3,4- tetrahydro-naphthalen-2-ylamino)-pentanoic acid to afford the title compound; MS 463.5 m/z (M+1).

2-{4-[2-(6,8-Difluoro-1,2,3,4-tetrahydro-naphthalen-2-ylamino)-pentanoylamino]-imidazol-1-yl}-2-methyl-propionic acid methyl ester 2-Methyl-2-(4-nitro-imidazol-1-yl)-propionic acid methyl ester was reduced and coupled with 2-(6,8-Difluoro-1,2,3,4-tetrahydro-naphthalen-2-ylamino)-pentanoic acid to afford the title compound; MS 449.3 m/z (M+1).

{1-[1-(3-oxo-butyl)-1H-imidazol-4-ylcarbamoyl]-butyl}-carbamic acid tert-butyl ester 4-(4-nitro-1H-imidazol-1-yl)butan-2-one was reduced and coupled with 2-[(tert-butoxycarbonyl)amino]pentanoic acid to afford the title compound; MS 353 m/z (M+1).

3-{4-[2-(6,8-Difluoro-1,2,3,4-tetrahydro-naphthalen-2-ylamino)-pentanoylamino]-imidazol-1-yl}-propionic acid methyl ester; MS 435 m/z (M+1).

2-(6,8-Difluoro-1,2,3,4-tetrahydro-naphthalen-2-ylamino)-pentanoic acid [1-(1-methyl-3-oxo-butyl)-1H-imidazol-4-yl]-amide; MS 433 m/z (M+1).

The following Boc groups were removed following general method D;

2-Amino-ientanoic acid [1-(3-oxo-butyl)-1H-imidazol-4-yl]-amide hydrochloride; MS 253 m/z (M+1).

2-Amino-pentanoic acid {1-[2-(2,6-dimethyl-morpholin-4-yl)-1,1-dimethyl-ethyl]-1H-imidazol-4-yl}-amide: MS 352.3 m/z (M+1).

2-Amino-pentanoic acid (1-{1,1-dimethyl-3-[(pyridin-2-ylmethyl)-amino]-proyl}-1H-imidazol-4-yl)-amide; MS 359 m/z (M+1).

2-Amino-pentanoic acid {1-[1,1-dimethyl-3-(2,2,2-trifluoro-1-phenyl-ethylamino)-propyl]-1H-imidazol-4-yl}-amide; MS 426 m/z (M+1).

2-Amino-pentanoic acid {1-[1,1-dimethyl-3-(1-phenyl-ethylamino)-propyl]-1H-imidazol-4-yl}-amide; MS 372 m/z (M+1).

The following alcohols were prepared by reduction of the corresponding esters using methods analogous to those described above using General Method I;

2-[2-(3,5-Difluoro-phenyl)-acetylamino]-pentanoic acid [1-(2-hydroxy-ethyl)-1H-imidazol-4-yl]-amide; MS 381.1 m/z (M+1).

2-(6,8-Difluoro-1,2,3,4-tetrahydro-naphthalen-2-ylamino)-pentanoic acid [1-(3-hydroxy-propyl)-1H-imidazol-4-yl]-amide; MS 407 m/z (M+1).

2-(6,8-Difluoro-1,2,3,4-tetrahydro-naphthalen-2-ylamino)-pentanoic acid [1-(2-hydroxy-1-methyl-ethyl)-1H-imidazol-4-yl]-amide; MS 407.5 m/z (M+1).

{1-[1-(3-Hydroxy-1,1-dimethyl-propyl)-1H-imidazol-4-ylcarbamoyl]-butyl}-carbamic acid tert-butyl ester; MS 369 m/z (M+1).

The following aldehydes were prepared by oxidation from corresponding alcohol using methods analogous to those described above using General Method J;

2-[2-(3,5-Difluoro-phenyl)-acetylamino]-pentanoic acid [1-(1-formyl-cyclobutyl)-1H-imidazol-4-yl]-amide; MS 419.1 m/z (M+1).

2-(5,7-Difluoro-1,2,3,4-tetrahydro-naphthalen-2-ylamino)-pentanoic acid [1-(1-formyl-cyclobutyl)-1H-imidazol-4-yl]-amide; MS 431.5 m/z (M+1).

(2S)-2-(5,7-difluoro-1,2,3,4-tetrahydronaphthalen-3-ylamino)-N-(1-(2-formylphenyl)-1H-imidazol-4-yl)pentanamide;

{1-[1-(1,1-Dimethyl-3-oxo-propyl)-1H-imidazol-4-ylcarbamoyl]-butyl}-carbamic acid tert-butyl ester; MS 367 m/z (M+1).

The following acids were prepared by hydrolysis from corresponding esters using methods analogous to those described above using General Method R;

3-{4-[2-(6,8-Difluoro-1,2,3,4-tetrahydro-naphthalen-2-ylamino)-pentanoylamino]-imidazol-1-yl}-3-methyl-butyric acid methyl ester; MS 449.6 m/z (M+1).

2-{4-[2-(6,8-Difluoro-1,2,3,4-tetrahydro-naphthalen-2-ylamino)-pentanoylamino]-imidazol-1-yl}-2-methyl-propionic acid; MS 435.4 m/z (M+1).

2-{4-[2-(6,8-Difluoro-1,2,3,4-tetrahydro-naphthalen-2-ylamino)-propionylamino]-imidazol-1-yl}-2-methyl-propionic acid; MS 407.5 m/z (M+1).

Procedure for Synthesis of 2-(6,8-Difluoro-1,2,3,4-tetrahydro-naphthalen-2-ylamino)-pentanoic acid; General procedure Q:

Combine L-norvaline methyl ester-hydrochloride (1 equiv) with 6,8-difluoro-3,4-dihydro-1H-naphthalen-2-one (1 equiv) in methylene chloride and stir 30 min. and add sodium triacetoxy borohydride (1.1 equiv) and stir at rt overnight. The reaction is quenched with aqueous sodium bicarbonate, extracted with methylene chloride, dried, and concentrated. The resultant material is purified by silica gel chromatography to afford the separated diastereomers of 2-(6,8-Difluoro-1,2,3,4-tetrahydro-naphthalen-2-ylamino)-pentanoic acid methyl ester: Diastereomer 1; 13C NMR (100 MHz, CDCl3) 14.0, 19.4, 27.7, 28.2, 29.5, 29.6, 36.3, 51.1, 58.7, 100.7, 100.9, 101.2, 110.5, 110.7, 110.8, 118.5, 118.6, 141.1, 159.7, 159.8, 162.1, 176.7; MS m/z 298.3 (M+1). Diastereomer 2; Diagnostic 13C NMR (100 MHz, CDCl3) 14.0, 19.3, 28.3, 28.4, 28.5, 30.3, 36.4, 51.1, 52.0, 58.5, 100.7, 100.9, 101.2, 110.5, 110.7, 176.8; MS m/z 298.3 (M+1).

2-(6,8-Difluoro-1,2,3,4-tetrahydro-naphthalen-2-ylamino)-pentanoic acid methyl ester (1 equiv) is dissolved in THF:water (5:1) and LiOH (1.2 equiv) is added. The reaction is stirred overnight at rt, the solvent is removed, water added, and the pH is adjusted to 7 using 1N hydrochloric acid. The solid is filtered, washed with water and diethyl ether, and dried to afford 2-(6,8-Difluoro-1,2,3,4-tetrahydro-naphthalen-2-ylamino)-pentanoic acid; Acid derived from diastereomer 1: H1 NMR (400 MHz, CD3OD) 0.99 (t, 3H, J=7.5), 1.48 (m, 2H), 1.82 (m, 3H), 2.36 (m, 1H), 2.65 (m, 1H), 2.95 (m, 2H), 3.28 (s, 1H), 3.42 (m, 1H), 3.74 (m, 1H), 6.80 (m, 2H); (MS m/z 284.3 (M+1). Acid derived from diastereomer 2: H1 NMR (400 MHz, CD3OD) 0.94 (t, 3H, J=7.6), 1.42 (m, 2H), 1.56 (m, 3H), 1.96 (m, 1H), 2.25 (m, 1H), 2.85 (m, 3H), 3.15 (m, 1H), 3.25 (m, 1H), 6.64 (m, 2H); MS m/z 284.2 (M+1).

The following intermdediates were prepared in an analogous manner to Method Q starting with an appropriate amino acid and ketone or starting amino-ester and ketone; or the aminoester is acylated using general procedure A followed by hydrolysis.

(S)-2-(2-(3,5-difluorophenyl)acetamido)-2-phenylacetic acid; MS 304 m/z (M−1).

(S)-2-(2-(3,5-difluorophenyl)acetamido)-2-(pyridin-3-yl)acetic acid; MS 305 m/z (M−1).

(S)-2-(2-(3,5-difluorophenyl)acetamido)-2-(4-fluorophenyl)acetic acid; MS 322 m/z (M−1).

(S)-2-(6,8-difluoro-1,2,3,4-tetrahydronaphthalen-3-ylamino)-2-phenylacetic acid; MS 316 m/z (M−1).

(S)-2-(6,8-Difluoro-1,2,3,4-tetrahydro-naphthalen-2-ylamino)-propionic acid; MS 256.5 m/z (M+1).

(S)-2-(1,2,3,4-Tetrahydro-naphthalen-2-ylamino)-pentanoic acid; MS 246.5 m/z (M−1).

The following intermediates were prepared in an analogous manner to Method B starting with an appropriate amine and ketone/aldehyde.

(1-{1-[2-(2,6-Dimethyl-morpholin-4-yl)-1,1-dimethyl-ethyl]-1H-imidazol-4-ylcarbamoyl}-butyl)-carbamic acid tert-butyl ester; MS 452.1 m/z (M+1).

2-(6,8-Difluoro-1,2,3,4-tetrahydro-naphthalen-2-ylamino)-pentanoic acid [1-(3-oxo-butyl)-1H-imidazol-4-yl]-amide; MS 419 m/z (M+1).

[1-(1-{1,1-Dimethyl-3-[(pyridin-2-ylmethyl)-amino]-propyl}-1H-imidazol-4-ylcarbamoyl)-butyl]-carbamic acid tert-butyl ester; MS 459 m/z (M+1).

[1-(1-{1,1-Dimethyl-3-(2,2,2-trifluoro-1-phenyl-ethylamino)-propyl]-1H-imidazol-4-ylcarbamoyl}-butyl)-carbamic acid tert-butyl ester; MS 526 m/z (M+1).

(1-{1-[1,1-Dimethyl-3-(1-phenyl-ethylamino)-propyl]-1H-imidazol-4-ylcarbamoyl}-butyl)-carbamic acid tert-butyl ester; MS 472 m/z (M+1).

The following Examples were prepared by methods analogous to those described above for General Procedure O;

Example 1

(S)-2-[2-(3,5-Difluoro-phenyl)-acetylamino]-pentanoic acid {1-[2-(3-ethoxy-propylamino)-ethyl]-1H-imidazol-4-yl}-amide Methanesulfonic acid 2-(4-{2-[2-(3,5-difluoro-phenyl)-acetylamino]-pentanoylamino}-imidazol-1-yl)-ethyl ester was reacted with 3-ethoxypropyl amine to provide the title compound: MS 446.2 m/z (M+1).

Example 2

(S)-2-[2-(3,5-Difluoro-phenyl)-acetylamino]-pentanoic acid {1-[2-(octahydro-pyrazino[1,2-a]azepin-2-yl)-ethyl]-1H-imidazol-4-yl}-amide Methanesulfonic acid 2-(4-{2-[2-(3,5-difluoro-phenyl)-acetylamino]-pentanoylamino}-imidazol-1-yl)-ethyl ester was reacted with appropriate amine to provide the title compound: MS 517.2 m/z (M+1).

Example 3

(S)-2-[2-(3,5-Difluoro-phenyl)-acetylamino]-pentanoic acid {1-[2-([1,4]dioxan-2-ylmethyl-methyl-amino)-ethyl]-1H-imidazol-4-yl}-amide Methanesulfonic acid 2-(4-{2-[2-(3,5-difluoro-phenyl)-acetylamino]-pentanoylamino}-imidazol-1-yl)-ethyl ester was reacted with appropriate amine to provide the title compound: MS 494.2 m/z (M+1).

Example 4

(S)-2-[2-(3,5-Difluoro-phenyl)-acetylamino]-pentanoic acid {1-[2-(2-methoxy-1-methyl-ethylamino)-ethyl]-1H-imidazol-4-yl}-amide Methanesulfonic acid 2-(4-{2-[2-(3,5-difluoro-phenyl)-acetylamino]-pentanoylamino}-imidazol-1-yl)-ethyl ester was reacted with appropriate amine to provide the title compound: MS 452.2 m/z (M+1).

Example 5

(S)-2-[2-(3,5-Difluoro-phenyl)-acetylamino]-pentanoic acid {1-[2-(3-oxo-piperazin-1-yl)-ethyl]-1H-imidazol-4-yl}-amide Methanesulfonic acid 2-(4-{2-[2-(3,5-difluoro-phenyl)-acetylamino]-pentanoylamino}-imidazol-1-yl)-ethyl ester was reacted with appropriate amine to provide the title compound: MS 463.2 m/z (M+1).

Example 6

(S)-2-[2-(3,5-Difluoro-phenyl)-acetylamino]-pentanoic acid [1-(2-benzylamino-ethyl)-1H-imidazol-4-yl]-amide Methanesulfonic acid 2-(4-{2-[2-(3,5-difluoro-phenyl)-acetylamino]-pentanoylamino}-imidazol-1-yl)-ethyl ester was reacted with appropriate amine to provide the title compound: MS 470.2 m/z (M+1).

Example 7

(S)-2-[2-(3,5-Difluoro-phenyl)-acetylamino]-pentanoic acid {1-[2-(3-butoxy-propylamino)-ethyl]-1H-imidazol-4-yl}-amide Methanesulfonic acid 2-(4-{2-[2-(3,5-difluoro-phenyl)-acetylamino]-pentanoylamino}-imidazol-1-yl)-ethyl ester was reacted with appropriate amine to provide the title compound: MS 494.2 m/z (M+1).

Example 8

(S)-2-[2-(3,5-Difluoro-phenyl)-acetylamino]-pentanoic acid {1-[2-((1R,2S)-2-hydroxymethyl-cyclohexylamino)-ethyl]-1H-imidazol-4-y}-amide Methanesulfonic acid 2-(4-{2-[2-(3,5-difluoro-phenyl)-acetylamino]-pentanoylamino}-imidazol-1-yl)-ethyl ester was reacted with appropriate amine to provide the title compound: MS 492.2 m/z (M+1).

Example 9

2-[2-(3,5-Difluoro-phenyl)-acetylamino]-pentanoic acid {1-[(4aS,8aS)-2-(octahydro-isoquinolin-2-yl)-ethyl]-1H-imidazol-4-yl}-amide Methanesulfonic acid 2-(4-{2-[2-(3,5-difluoro-phenyl)-acetylamino]-pentanoylamino}-imidazol-1-yl)-ethyl ester was reacted with appropriate amine to provide the title compound: MS 502.2 m/z (M+1).

Example 10

(S)-2-[2-(3,5-Difluoro-phenyl)-acetylamino]-pentanoic acid {1-[2-(3-isopropoxy-propylamino)-ethyl]-1H-imidazol-4-yl}-amide Methanesulfonic acid 2-(4-{2-[2-(3,5-difluoro-phenyl)-acetylamino]-pentanoylamino}-imidazol-1-yl)-ethyl ester was reacted with appropriate amine to provide the title compound: MS 480.2 m/z (M+1).

Example 11

(S)-2-[2-(3,5-Difluoro-phenyl)-acetylamino]-pentanoic acid {1-[2-(octahydro-isoquinolin-2-yl)-ethyl]-1H-imidazol-4-yl}-amide Methanesulfonic acid 2-(4-{2-[2-(3,5-difluoro-phenyl)-acetylamino]-pentanoylamino}-imidazol-1-yl)-ethyl ester was reacted with appropriate amine to provide the title compound: MS 502.2 m/z (M+1).

Example 12

(S)-2-[2-(3,5-Difluoro-phenyl)-acetylamino]-pentanoic acid {1-[2-(3,4,5,6-tetrahydro-2H-[4,4']bipyridinyl-1-yl)-ethyl]-1H-imidazol-4-yl}-amide Methanesulfonic acid 2-(4-{2-[2-(3,5-difluoro-phenyl)-acetylamino]-pentanoylamino}-imidazol-1-yl)-ethyl ester was reacted with appropriate amine to provide the title compound: MS 525.2 m/z (M+1).

Example 13

S)-2-[2-(3,5-Difluoro-phenyl)-acetylamino]-pentanoic acid {1-[2-(2-hydroxy-2-phenyl-ethylamino)-ethyl]-1H-imidazol-4-yl}-amide Methanesulfonic acid 2-(4-{2-[2-(3,5-difluoro-phenyl)-acetylamino]-pentanoylamino}-imidazol-1-yl)-ethyl ester was reacted with appropriate amine to provide the title compound: MS 500.2 m/z (M+1).

Example 14

(S)-2-[2-(3,5-Difluoro-phenyl)-acetylamino]-pentanoic acid {1-[2-(indan-1-ylamino)-ethyl]-1H-imidazol-4-yl}-amide Methanesulfonic acid 2-(4-{2-[2-(3,5-difluoro-phenyl)-acetylamino]-pentanoylamino}-imidazol-1-yl)-ethyl ester was reacted with appropriate amine to provide the title compound: MS 496.2 m/z (M+1).

Example 15

(S)-2-[2-(3,5-Difluoro-phenyl)-acetylamino]-pentanoic acid {1-[2-(benzyl-methyl-amino)-ethyl]-1H-imidazol-4-yl}-amide Methanesulfonic acid 2-(4-{2-[2-(3,5-difluoro-phenyl)-acetylamino]-pentanoylamino}-imidazol-1-yl)-ethyl ester was reacted with appropriate amine to provide the title compound: MS 484.2 m/z (M+1).

Example 16

(S)-2-[2-(3,5-Difluoro-phenyl)-acetylamino]-pentanoic acid {1-[2-(indan-2-ylamino)-ethyl]-1H-imidazol-4-yl}-amide Methanesulfonic acid 2-(4-{2-[2-(3,5-difluoro-phenyl)-acetylamino]-pentanoylamino}-imidazol-1-yl)-ethyl ester was reacted with appropriate amine to provide the title compound: MS 496.2 m/z (M+1).

Example 17

(S)-2-[2-(3,5-Difluoro-phenyl)-acetylamino]-pentanoic acid {1-[2-(3,4-dihydro-1#H!-isoquinolin-2-yl)-ethyl]-1H-imidazol-4-yl}-amide Methanesulfonic acid 2-(4-{2-[2-(3,5-difluoro-phenyl)-acetylamino]-pentanoylamino}-imidazol-1-yl)-ethyl ester was reacted with appropriate amine to provide the title compound: MS 496.2 m/z (M+1).

Example 18

(S)-2-[2-(3,5-Difluoro-phenyl)-acetylamino]-pentanoic acid {1-[2-(2-propoxy-ethylamino)-ethyl]-1H-imidazol-4-yl}-amide Methanesulfonic acid 2-(4-{2-[2-(3,5-difluoro-phenyl)-acetylamino]-pentanoylamino}-imidazol-1-yl)-ethyl ester was reacted with appropriate amine to provide the title compound: MS 466.2 m/z (M+1).

Example 19

(S)-2-[2-(3,5-Difluoro-phenyl)-acetylamino]-pentanoic acid {1-[2-(3-benzyl-pyrrolidin-1-yl)-ethyl]-1H-imidazol-4-yl}-amide Methanesulfonic acid 2-(4-{2-[2-(3,5-difluoro-phenyl)-acetylamino]-pentanoylamino}-imidazol-1-yl)-ethyl ester was reacted with appropriate amine to provide the title compound: MS 524.2 m/z (M+1).

Example 20

(S)-2-[2-(3,5-Difluoro-phenyl)-acetylamino]-pentanoic acid {1-[2-(3-pyridin-2-yl-pyrrolidin-1-yl)-ethyl]-1H-imidazol-4-yl}-amide Methanesulfonic acid 2-(4-{2-[2-(3,5-difluoro-phenyl)-acetylamino]-pentanoylamino}-imidazol-1-yl)-ethyl ester was reacted with appropriate amine to provide the title compound: MS 511.2 m/z (M+1).

Example 21

(S)-2-[2-(3,5-Difluoro-phenyl)-acetylamino]-pentanoic acid {1-[2-(methyl-pyridin-4-ylmethyl-amino)-ethyl]-1H-imidazol-4-yl}-amide Methanesulfonic acid 2-(4-{2-[2-(3,5-difluoro-phenyl)-acetylamino]-pentanoylamino}-imidazol-1-yl)-ethyl ester was reacted with appropriate amine to provide the title compound: MS 485.2 m/z (M+1).

Example 22

(S)-2-[2-(3,5-Difluoro-phenyl)-acetylamino]-nentanoic acid (1-{2-[(2-methanesulfonyl-ethyl)-methyl-amino]-ethyl}-1H-imidazol-4-yl)-amide Methanesulfonic acid 2-(4-{2-[2-(3,5-difluoro-phenyl)-acetylamino]-pentanoylamino}-imidazol-1-yl)-ethyl ester was reacted with appropriate amine to provide the title compound: MS 500.1 m/z (M+1).

Example 23

(S)-2-[2-(3,5-Difluoro-phenyl)-acetylamino]-pentanoic acid {1-[2-(2-tert-butoxy-ethylamino)-ethyl]-1H-imidazol-4-yl}-amide Methanesulfonic acid 2-(4-{2-[2-(3,5-difluoro-phenyl)-acetylamino]-pentanoylamino}-imidazol-1-yl)-ethyl ester was reacted with appropriate amine to provide the title compound: MS 480.2 m/z (M+1).

Example 23A (S)-2-[2-(3,5-Difluoro-phenyl)-acetylamino]-nentanoic acid {1-[2-(3-pyridin-4-yl-pyrrolidin-1-yl)-ethyl]-1H-imidazol-4-yl}-amide Methanesulfonic acid 2-(4-{2-[2-(3,5-difluoro-phenyl)-acetylamino]-pentanoylamino}-imidazol-1-yl)-ethyl ester was reacted with appropriate amine to provide the title compound: MS 511.2 m/z (M+1).

The following Examples were prepared by methods analogous to those described above for General Procedure P;

Example 24

(S)-2-[2-(3,5-Difluoro-phenyl)-acetylamino]-pentanoic acid [1-(2-fluoro-benzyl)-1H-imidazol-4-yl]-amide 2-[2-(3,5-Difluoro-phenyl)-acetylamino]-pentanoic acid (1H-imidazol-4-yl)-amide was reacted with appropriate benzyl halide to provide the title compound: MS 445.1 m/z (M+1).

Example 25

(S)-2-[2-(3,5-Difluoro-phenyl)-acetylamino]-nentanoic acid [1-(3-fluoro-benzyl)-1H-imidazol-4-yl]-amide 2-[2-(3,5-Difluoro-phenyl)-acetylamino]-pentanoic acid (1H-imidazol-4-yl)-amide was reacted with appropriate benzyl halide to provide the title compound: MS 445.1 m/z (M+1).

Example 26

(S)-2-[2-(3,5-Difluoro-phenyl)-acetylamino]-pentanoic acid [1-(4-methyl-benzyl)-1H-imidazol-4-yl]-amide 2-[2-(3,5-Difluoro-phenyl)-acetylamino]-pentanoic acid (1H-imidazol-4-yl)-amide was reacted with appropriate benzyl halide to provide the title compound: MS 441.1 m/z (M+1).

Example 27

(S)-2-[2-(3,5-Difluoro-phenyl)-acetylamino]-pentanoic acid [1-(4-methoxy-benzyl)-1H-imidazol-4-yl]-amide 2-[2-(3,5-Difluoro-phenyl)-acetylamino]-pentanoic acid (1H-imidazol-4-yl)-amide was reacted with appropriate benzyl halide to provide the title compound: MS 457.3 m/z (M+1).

Example 28

(S)-2-[2-(3,5-Difluoro-phenyl)-acetylamino]-pentanoic acid [1-(4-tert-butyl-benzyl)-1H-imidazol-4-yl]-amide 2-[2-(3,5-Difluoro-phenyl)-acetylamino]-pentanoic acid (1H-imidazol-4-yl)-amide was reacted with appropriate benzyl halide to provide the title compound: MS 483.3 m/z (M+1).

The following Examples were prepared by methods analogous to those described above for General Procedure B;

Example 29

(S)-2-[2-(3,5-Difluoro-phenyl)-acetylamino]-pentanoic acid [1-(1-pyrrolidin-1-ylmethyl-cyclobutyl)-1H-imidazol-4-yl]-amide 2-[2-(3,5-Difluoro-phenyl)-acetylamino]-pentanoic acid [1-(1-formyl-cyclobutyl)-1H-imidazol-4-yl]-amide was reacted with appropriate amine to provide the title compound: MS 474.1 m/z(M+1).

Example 30

(S)-2-[2-(3,5-Difluoro-phenyl)-acetylamino]-pentanoic acid [1-(1-dimethylaminomethyl-cyclobutyl)-1H-imidazol-4-yl]-amide 2-[2-(3,5-Difluoro-phenyl)-acetylamino]-pentanoic acid [1-(1-formyl-cyclobutyl)-1H-imidazol-4-yl]-amide was reacted with appropriate amine to provide the title compound: MS 448.5 m/z (M+1).

Example 31

(S)-2-[2-(3,5-Difluoro-phenyl)-acetylamino]-pentanoic acid [1-(1-piperidin-1-ylmethyl-cyclobutyl)-1H-imidazol-4-yl]-amide 2-[2-(3,5-Difluoro-phenyl)-acetylamino]-pentanoic acid [1-(1-formyl-cyclobutyl)-1H-imidazol-4-yl]-amide was reacted with appropriate amine to provide the title compound: MS 488.5 m/z (M+1).

Example 32

(S)-2-[2-(3,5-Difluoro-phenyl)-acetylamino]-pentanoic acid [1-(1-morpholin-4-ylmethyl-cyclobutyl)-1H-imidazol-4-yl]-amide 2-[2-(3,5-Difluoro-phenyl)-acetylamino]-pentanoic acid [1-(1-formyl-cyclobutyl)-1H-imidazol-4-yl]-amide was reacted with appropriate amine to provide the title compound: MS 490.5 m/z (M+1).

Example 31A (S)-2-[2-(3,5-Difluoro-phenyl)-acetylamino]-pentanoic acid (1-{1-[((2R,6S)-2,6-dimethyl-morpholin-4-yl)methyl]-cyclobutyl}-1H-imidazol-4-yl)-amide 2-[2-(3,5-Difluoro-phenyl)-acetylamino]-pentanoic acid [1-(1-formyl-cyclobutyl)-1H-imidazol-4-yl]-amide was reacted with appropriate amine to provide the title compound: MS 518.5 m/z (M+1).

Example 32A (S)-2-[2-(3,5-Difluoro-phenyl)-acetylamino]-pentanoic acid (1-{1-[(2,2,2-trifluoro-ethylamino)-methyl]-cyclobutyl}-1H-imidazol-4-yl)-amide 2-[2-(3,5-Difluoro-phenyl)-acetylamino]-pentanoic acid [1-(1-formyl-cyclobutyl)-1H-imidazol-4-yl]-amide was reacted with appropriate amine to provide the title compound: MS 502.4 m/z (M+1).

Example 33

(S)-2-[2-(3,5-Difluoro-phenyl)-acetylamino]-pentanoic acid (1-{1-[((R)-1-cyclohexyl-ethylamino)-methyl]-cyclobutyl}-1H-imidazol-4-yl)-amide 2-[2-(3,5-Difluoro-phenyl)-acetylamino]-pentanoic acid [1-(1-formyl-cyclobutyl)-1H-imidazol-4-yl]-amide was reacted with appropriate amine to provide the title compound: MS 530.5 m/z (M+1).

Example 34

(S)-2-(5,7-Difluoro-1,2,3,4-tetrahydro-naphthalen-2-ylamino)-pentanoic acid [1-(1-pyrrolidin-1-ylmethyl-cyclobutyl)-1H-imidazol-4-yl]-amide 2-(5,7-Difluoro-1,2,3,4-tetrahydro-naphthalen-2-ylamino)-pentanoic acid [1-(1-formyl-cyclobutyl)-1H-imidazol-4-yl]-amide was reacted with appropriate amine to provide the title compound: MS 486.5 m/z (M+1).

Example 35

(S)-2-[2-(3,5-Difluoro-phenyl)-acetylamino]-pentanoic acid (1-{1-[(2,2-dimethyl-propylamino)-methyl]-cyclobutyl}-1H-imidazol-4-yl)-amide 2-[2-(3,5-Difluoro-phenyl)-acetylamino]-pentanoic acid [1-(1-formyl-cyclobutyl)-1H-imidazol-4-yl]-amide was reacted with appropriate amine to provide the title compound: MS 490.5 m/z (M+1).

Example 36

(S)-2-(6,8-Difluoro-1,2,3,4-tetrahydro-naphthalen-2-ylamino)-pentanoic acid (1-{1-[(2,2,2-trifluoro-ethylamino)-methyl]-cyclobutyl}-1H-imidazol-4-yl)-amide 2-(5,7-Difluoro-1,2,3,4-tetrahydro-naphthalen-2-ylamino)-pentanoic acid [1-(1-formyl-cyclobutyl)-1H-imidazol-4-yl]-amide was reacted with appropriate amine to provide the title compound: MS 514.5 m/z (M+1).

Example 37

(S)-2-(6,8-Difluoro-1,2,3,4-tetrahydro-naphthalen-2-ylamino)-pentanoic acid (1-{1-[(2,2-dimethyl-propylamino)-methyl]-cyclobutyl}-1H-imidazol-4-yl)-amide 2-(5,7-Difluoro-1,2,3,4-tetrahydro-naphthalen-2-ylamino)-pentanoic acid [1-(1-formyl-cyclobutyl)-1H-imidazol-4-yl]-amide was reacted with appropriate amine to provide the title compound: MS 502.6 m/z (M+1).

Example 38

(S)-2-(6,8-Difluoro-1,2,3,4-tetrahydro-naphthalen-2-ylamino)-pentanoic acid (1-{1-[((R)-1-cyclohexyl-ethylamino)-methyl]-cyclobutyl}-1H-imidazol-4-yl)-amide 2-(5,7-Difluoro-1,2,3,4-tetrahydro-naphthalen-2-ylamino)-pentanoic acid [1-(1-formyl-cyclobutyl)-1H-imidazol-4-yl]-amide was reacted with appropriate amine to provide the title compound: MS 542.6 m/z (M+1).

Example 39

(S)-2-(6,8-Difluoro-1,2,3,4-tetrahydro-naphthalen-2-ylamino)-ientanoic acid [1-(1-dimethylaminomethyl-cyclobutyl)-1H-imidazol-4-yl]-amide 2-(5,7-Difluoro-1,2,3,4-tetrahydro-naphthalen-2-ylamino)-pentanoic acid [1-(1-formyl-cyclobutyl)-1H-imidazol-4-yl]-amide was reacted with appropriate amine to provide the title compound: MS 460.6 m/z (M+1).

Example 40

(S)-2-(6,8-Difluoro-1,2,3,4-tetrahydro-naphthalen-2-ylamino)-pentanoic acid [1-(1-piperidin-1-ylmethyl-cyclobutyl)-1H-imidazol-4-yl]-amide 2-(5,7-Difluoro-1,2,3,4-tetrahydro-naphthalen-2-ylamino)-pentanoic acid [1-(1-formyl-cyclobutyl)-1H-imidazol-4-yl]-amide was reacted with appropriate amine to provide the title compound: MS 500.6 m/z (M+1).

Example 41

(S)-2-(6,8-Difluoro-1,2,3,4-tetrahydro-naphthalen-2-ylamino)-pentanoic acid [1-(1-morpholin-4-ylmethyl-cyclobutyl)-1H-imidazol-4-yl]-amide 2-(5,7-Difluoro-1,2,3,4-tetrahydro-naphthalen-2-ylamino)-pentanoic acid [1-(1-formyl-cyclobutyl)-1H-imidazol-4-yl]-amide was reacted with appropriate amine to provide the title compound: MS 502.6 m/z (M+1).

Example 42

(S)-2-(6,8-Difluoro-1,2,3,4-tetrahydro-naphthalen-2-ylamino)-pentanoic acid (1-{1-[((2R,6S)-2,6-dimethyl-morpholin-4-yl)methyl]-cyclobutyl}-1H-imidazol-4-yl)-amide 2-(5,7-Difluoro-1,2,3,4-tetrahydro-naphthalen-2-ylamino)-pentanoic acid [1-(1-formyl-cyclobutyl)-1H-imidazol-4-yl]-amide was reacted with appropriate amine to provide the title compound: MS 530.6 m/z (M+1).

Example 43

(S)-2-(6,8-Difluoro-1,2,3,4-tetrahydro-naphthalen-2-ylamino)-pentanoic acid {1-[2-((R)-1-cyclohexyl-ethylamino)-1,1-dimethyl-ethyl]-1H-imidazol-4-yl}-amide 2-(6,8-Difluoro-1,2,3,4-tetrahydro-naphthalen-2-ylamino)-pentanoic acid [1-(1,1-dimethyl-2-oxo-ethyl)-1H-imidazol-4-yl]-amide (U.S. Ser. No. 11/078,898 filed Mar.

11, 2005) was treated with the appropriate amine to afford the title compound MS 530.4 m/z (M+1).

Example 44

(S)-2-(6,8-Difluoro-1,2,3,4-tetrahydro-naphthalen-2-ylamino)-pentanoic acid (1-{1,1-dimethyl-2-[(tetrahydro-pyran-4-ylmethyl)-amino]-ethyl}-1H-imidazol-4-yl)-amide 2-(6,8-Difluoro-1,2,3,4-tetrahydro-naphthalen-2-ylamino)-pentanoic acid [1-(1,1-dimethyl-2-oxo-ethyl)-1H-imidazol-4-yl]-amide (U.S. Ser. No. 11/078,898 filed Mar. 11, 2005) was treated with the appropriate amine to afford the title compound MS 518.4 m/z (M+1).

Example 45

(S)-2-(6,8-Difluoro-1,2,3,4-tetrahydro-naphthalen-2-ylamino)-pentanoic acid (1-{2-[(1-hydroxy-cyclohexylmethyl)-amino]-1,1-dimethyl-ethyl}-1H-imidazol-4-yl)-amide 2-(6,8-Difluoro-1,2,3,4-tetrahydro-naphthalen-2-ylamino)-pentanoic acid [1-(1,1-dimethyl-2-oxo-ethyl)-1H-imidazol-4-yl]-amide (U.S. Ser. No. 11/078,898 filed Mar. 11, 2005) was treated with the appropriate amine to afford the title compound MS 532.6 m/z (M+1).

Example 46

(S)-2-(6,8-Difluoro-1,2,3,4-tetrahydro-naphthalen-2-ylamino)-pentanoic acid (1-{2-[(4-hydroxy-tetrahydro-pyran-4-ylmethyl)-amino]-1,1-dimethyl-ethyl}-1H-imidazol-4-yl)-amide 2-(6,8-Difluoro-1,2,3,4-tetrahydro-naphthalen-2-ylamino)-pentanoic acid [1-(1,1-dimethyl-2-oxo-ethyl)-1H-imidazol-4-yl]-amide (U.S. Ser. No. 11/078,898 filed Mar. 11, 2005) was treated with the appropriate amine to afford the title compound MS 534.6 m/z (M+1).

Example 47

(S)-2-(6,8-Difluoro-1,2,3,4-tetrahydro-naphthalen-2-ylamino)-pentanoic acid {1-[2-(2-methoxy-2-methyl-propylamino)-1,1-dimethyl-ethyl]-1H-imidazol-4-yl}-amide 2-(6,8-Difluoro-1,2,3,4-tetrahydro-naphthalen-2-ylamino)-pentanoic acid [1-(1,1-dimethyl-2-oxo-ethyl)-1H-imidazol-4-yl]-amide (U.S. Ser. No. 11/078,898 filed Mar. 11, 2005) was treated with the appropriate amine to afford the title compound MS 506.5 m/z (M+1).

Example 48

(S)-2-(6,8-Difluoro-1,2,3,4-tetrahydro-naphthalen-2-ylamino)-pentanoic acid (1-{1,1-dimethyl-2-[(3-methyl-oxetan-3-ylmethyl)-amino]-ethyl}-1H-imidazol-4-yl)-amide 2-(6,8-Difluoro-1,2,3,4-tetrahydro-naphthalen-2-ylamino)-pentanoic acid [1-(1,1-dimethyl-2-oxo-ethyl)-1H-imidazol-4-yl]-amide (U.S. Ser. No. 11/078,898 filed Mar. 11, 2005) was treated with the appropriate amine to afford the title compound MS 504.5 m/z (M+1).

Example 49

(S)-2-(6,8-Difluoro-1,2,3,4-tetrahydro-naphthalen-2-ylamino)-pentanoic acid {1-[2-(cyclohexylmethyl-amino)-1,1-dimethyl-ethyl]-1H-imidazol-4-yl}-amide 2-(6,8-Difluoro-1,2,3,4-tetrahydro-naphthalen-2-ylamino)-pentanoic acid [1-(1,1-dimethyl-2-oxo-ethyl)-1H-imidazol-4-yl]-amide (U.S. Ser. No. 11/078,898 filed Mar. 11, 2005) was treated with the appropriate amine to afford the title compound MS 516.6 m/z (M+1).

Example 50

(S)-2-[2-(3,5-Difluoro-phenyl)-acetylamino]-pentanoic acid {1-[2-((R)-1-cyclohexyl-ethylamino)-1,1-dimethyl-ethyl]-1H-imidazol-4-yl}-amide 2-[2-(3,5-Difluoro-phenyl)-acetylamino]-pentanoic acid [1-(1,1-dimethyl-2-oxo-ethyl)-1H-imidazol-4-yl]-amide (U.S. Ser. No. 11/078,898 filed Mar. 11, 2005) was treated with the appropriate amine to afford the title compound MS 518.2 m/z (M+1).

Example 51

(S)-2-[2-(3,5-Difluoro-phenyl)-acetylamino]-pentanoic acid (1-{1,1-dimethyl-2-[(tetrahydro-pyran-4-ylmethyl)-amino]-ethyl}-1H-imidazol-4-yl)-amide 2-[2-(3,5-Difluoro-phenyl)-acetylamino]-pentanoic acid [1-(1,1-dimethyl-2-oxo-ethyl)-1H-imidazol-4-yl]-amide (U.S. Ser. No. 11/078,898 filed Mar. 11, 2005) was treated with the appropriate amine to afford the title compound MS 506.4 m/z (M+1).

Example 52

(S)-2-(6,8-Difluoro-1,2,3,4-tetrahydro-naphthalen-2-ylamino)-pentanoic acid {1-[3-((S)-1-phenyl-ethylamino)-butyl]-1H-imidazol-4-yl}-amide 2-(6,8-Difluoro-1,2,3,4-tetrahydro-naphthalen-2-ylamino)-pentanoic acid [1-(3-oxo-butyl)-1H-imidazol-4-yl]-amide was treated with the appropriate amine to afford the title compound MS 524.1 m/z (M+1).

Example 53

(S)-2-(Dicyclopropylmethyl-amino)-pentanoic acid [1-(1,1-dimethyl-2-pyrrolidin-1-yl-ethyl)-1H-imidazol-4-yl]-amide 2-Amino-pentanoic acid [1-(1,1-dimethyl-2-pyrrolidin-1-yl-ethyl)-1H-imidazol-4-yl]-amide (U.S. Ser. No. 11/078,898 filed Mar. 11, 2005) was treated with the appropriate ketone to afford the title compound MS 402.6 m/z (M+1).

The following Examples were prepared by methods analogous to those described above for General Procedure I;

Example 54

(S)-2-[2-(3,5-Difluoro-phenyl)-acetylamino]-pentanoic acid [1-(1-hydroxymethyl-cyclobutyl)-1H-imidazol-4-yl]-amide 1-(4-{2-[2-(3,5-Difluoro-phenyl)-acetylamino]-pentanoylamino}-imidazol-1-yl)-cyclobutanecarboxylic acid methyl ester was reduced to afford the title compound: MS 421.1 m/z (M+1).

Example 55

(S)-2-[2-(3,5-Difluoro-phenyl)-acetylamino]-pentanoic acid [1-(2-hydroxymethyl-cyclobutyl)-1H-imidazol-4-yl]-amide 2-(4-{2-[2-(3,5-Difluoro-phenyl)-acetylamino]-pentanoylamino}-imidazol-1-yl)-cyclobutanecarboxylic acid methyl ester was reduced to afford the title compound: MS 421.1 m/z (M+1).

Example 56

(S)-2-(5,7-Difluoro-1,2,3,4-tetrahydro-naphthalen-2-ylamino)-pentanoic acid [1-(1-hydroxymethyl-cyclobutyl)-1H-imidazol-4-yl]-amide 1-{4-[2-(5,7-Difluoro-1,2,3,4-tetrahydro-naphthalen-2-ylamino)-pentanoylamino]-imidazol-1-yl}-cyclobutanecarboxylic acid methyl ester was reduced to afford the title compound: MS 433.5 m/z (M+1).

The following Examples were prepared by methods analogous to those described above for General Procedure K;

Example 57

(S)-2-[2-(2,4-Difluoro-phenyl)-2-hydroxy-ethylamino]-pentanoic acid [1-(1,1-dimethyl-2-pyrrolidin-1-yl-ethyl)-1H-imidazol-4-yl]-amide 2-Amino-pentanoic acid [1-(1,1-dimethyl-2-pyrrolidin-1-yl-ethyl)-1H-imidazol-4-yl]-amide (U.S. Ser. No. 11/078, 898 filed Mar. 11, 2005) was treated with the appropriate epoxide to afford the title compound: MS 464.3 m/z (M+1).

Example 58

(S)-2-[2-(3,4-Difluoro-phenyl)-2-hydroxy-ethylamino]-pentanoic acid [1-(1,1-dimethyl-2-pyrrolidin-1-yl-ethyl)-1H-imidazol-4-yl]-amide 2-Amino-pentanoic acid [1-(1,1-dimethyl-2-pyrrolidin-1-yl-ethyl)-1H-imidazol-4-yl]-amide (U.S. Ser. No. 11/078, 898 filed Mar. 11, 2005) was treated with the appropriate epoxide to afford the title compound: MS 464.3 m/z (M+1).

Example 59

(S)-2-[2-(3,5-Difluoro-phenyl)-2-hydroxy-ethylamino]-pentanoic acid [1-(1,1-dimethyl-2-pyrrolidin-1-yl-ethyl)-1H-imidazol-4-yl]-amide 2-Amino-pentanoic acid [1-(1,1-dimethyl-2-pyrrolidin-1-yl-ethyl)-1H-imidazol-4-yl]-amide (U.S. Ser. No. 11/078, 898 filed Mar. 11, 2005) was treated with the appropriate epoxide to afford the title compound: MS 464.5 m/z (M+1).

Example 60

(S)-2-[2-(2,4-Difluoro-phenyl)-2-hydroxy-ethylamino]-pentanoic acid {1-[2-((2R,6S)-2,6-dimethyl-morpholin-4-yl)-1,1-dimethyl-ethyl]-1H-imidazol-4-yl}-amide 2-Amino-pentanoic acid [1-(1,1-dimethyl-2-(2,6-dimethylmorpholino-1-yl-ethyl)-1H-imidazol-4-yl]-amide was treated with the appropriate epoxide to afford the title compound: MS 508.5 m/z (M+1).

Example 61

(S)-2-[(1-Hydroxy-cyclohexylmethyl)-amino]-pentanoic acid [1-(1,1-dimethyl-2-pyrrolidin-1-yl-ethyl)-1H-imidazol-4-yl]-amide 2-Amino-pentanoic acid [1-(1,1-dimethyl-2-pyrrolidin-1-yl-ethyl)-1H-imidazol-4-yl]-amide (U.S. Ser. No. 11/078, 898 filed Mar. 11, 2005) was treated with the appropriate epoxide to afford the title compound: MS 420.6 m/z (M+1).

The following Examples were prepared by methods analogous to those described above for General Procedure O;

Example 62

(S)-2-(6,8-Difluoro-1,2,3,4-tetrahydro-naphthalen-2-ylamino)-pentanoic acid {1-[3-((R)-1-phenyl-ethylamino)-propyl]-1H-imidazol-4-yl}-amide Methanesulfonic acid 3-{4-[2-(6,8-difluoro-1,2,3,4-tetrahydro-naphthalen-2-ylamino)-pentanoylamino]-imidazol-1-yl}-propyl ester was treated with the appropriate amine to afford the title compound: MS 510.1 m/z (M+1).

Example 63

(S)-2-(6,8-Difluoro-1,2,3,4-tetrahydro-naphthalen-2-ylamino)-ientanoic acid {1-[3-(3-methyl-benzylamino)-propyl]-1H-imidazol-4-yl}-amide Methanesulfonic acid 3-{4-[2-(6,8-difluoro-1,2,3,4-tetrahydro-naphthalen-2-ylamino)-pentanoylamino]-imidazol-1-yl}-propyl ester was treated with the appropriate amine to afford the title compound: MS 510.53 m/z (M+1).

Example 64

(S)-2-(6,8-Difluoro-1,2,3,4-tetrahydro-naphthalen-2-ylamino)-pentanoic acid {1-[3-(2-hydroxy-2-phenyl-ethylamino)-propyl]-1H-imidazol-4-yl}-amide Methanesulfonic acid 3-{4-[2-(6,8-difluoro-1,2,3,4-tetrahydro-naphthalen-2-ylamino)-pentanoylamino]-imidazol-1-yl}-propyl ester was treated with the appropriate amine to afford the title compound: MS 526.54 m/z (M+1).

Example 65

(S)-2-(6,8-Difluoro-1,2,3,4-tetrahydro-naphthalen-2-ylamino)-pentanoic acid {1-[3-(2-chloro-benzylamino)-propyl]-1H-imidazol-4-yl}-amide Methanesulfonic acid 3-{4-[2-(6,8-difluoro-1,2,3,4-tetrahydro-naphthalen-2-ylamino)-pentanoylamino]-imidazol- 1-yl}-propyl ester was treated with the appropriate amine to afford the title compound: MS 530.5 m/z (M+1).

Example 66

(S)-2-(6,8-Difluoro-1,2,3,4-tetrahydro-naphthalen-2-ylamino)-pentanoic acid {1-[3-(3,4-dihydro-1H-isoquinolin-2-yl)-propyl]-1H-imidazol-4-yl}-amide Methanesulfonic acid 3-{4-[2-(6,8-difluoro-1,2,3,4-tetrahydro-naphthalen-2-ylamino)-pentanoylamino]-imidazol-1-yl}-propyl ester was treated with the appropriate amine to afford the title compound: MS 522.53 m/z (M+1).

Example 67

(S)-2-(6,8-Difluoro-1,2,3,4-tetrahydro-naphthalen-2-ylamino)-pentanoic acid {1-[3-(indan-2-ylamino)-propyl]-1H-imidazol-4-yl}-amide Methanesulfonic acid 3-{4-[2-(6,8-difluoro-1,2,3,4-tetrahydro-naphthalen-2-ylamino)-pentanoylamino]-imidazol-1-yl}-propyl ester was treated with the appropriate amine to afford the title compound: MS 522.52 m/z (M+1).

Example 68

(S)-2-(6,8-Difluoro-1,2,3,4-tetrahydro-naphthalen-2-ylamino)-pentanoic acid {1-[3-(1-methoxymethyl-propylamino)-propyl]-1H-imidazol-4-yl}-amide Methanesulfonic acid 3-{4-[2-(6,8-difluoro-1,2,3,4-tetrahydro-naphthalen-2-ylamino)-pentanoylamino]-imidazol-1-yl}-propyl ester was treated with the appropriate amine to afford the title compound: MS 492.53 m/z (M+1).

Example 69

(S)-2-(6,8-Difluoro-1,2,3,4-tetrahydro-naphthalen-2-ylamino)-pentanoic acid {1-[3-(4-chloro-benzylamino)-propyl]-1H-imidazol-4-yl}-amide Methanesulfonic acid 3-{4-[2-(6,8-difluoro-1,2,3,4-tetrahydro-naphthalen-2-ylamino)-pentanoylamino]-imidazol-1-yl}-propyl ester was treated with the appropriate amine to afford the title compound: MS 530.5 m/z (M+1).

Example 70

(S)-2-(6,8-Difluoro-1,2,3,4-tetrahydro-naphthalen-2-ylamino)-pentanoic acid {1-[3-(2-methyl-benzylamino)-propyl]-1H-imidazol-4-yl}-amide Methanesulfonic acid 3-{4-[2-(6,8-difluoro-1,2,3,4-tetrahydro-naphthalen-2-ylamino)-pentanoylamino]-imidazol-1-yl}-propyl ester was treated with the appropriate amine to afford the title compound: MS 510.5 m/z (M+1).

Example 71

(S)-2-(6,8-Difluoro-1,2,3,4-tetrahydro-naphthalen-2-ylamino)-pentanoic acid {1-[3-(2-methoxy-ethylamino)-propyl]-1H-imidazol-4-yl}-amide Methanesulfonic acid 3-{4-[2-(6,8-difluoro-1,2,3,4-tetrahydro-naphthalen-2-ylamino)-pentanoylamino]-imidazol-1-yl}-propyl ester was treated with the appropriate amine to afford the title compound: MS 464.2 m/z (M+1).

Example 72

(S)-2-(6,8-Difluoro-1,2,3,4-tetrahydro-naphthalen-2-ylamino)-pentanoic acid (1-{3-[(pyridin-3-ylmethyl)-amino]-propyl}-1H-imidazol-4-yl)-amide Methanesulfonic acid 3-{4-[2-(6,8-difluoro-1,2,3,4-tetrahydro-naphthalen-2-ylamino)-pentanoylamino]-imidazol-1-yl}-propyl ester was treated with the appropriate amine to afford the title compound: MS 497.5 m/z (M+1).

Example 73

(S)-2-(6,8-Difluoro-1,2,3,4-tetrahydro-naphthalen-2-ylamino)-pentanoic acid {1-[3-((S)-1-p-tolyl-ethylamino)-propyl]-1H-imidazol-4-yl}-amide Methanesulfonic acid 3-{4-[2-(6,8-difluoro-1,2,3,4-tetrahydro-naphthalen-2-ylamino)-pentanoylamino]-imidazol-1-yl}-propyl ester was treated with the appropriate amine to afford the title compound: MS 524.6 m/z (M+1).

Example 74

(S)-2-(6,8-Difluoro-1,2,3,4-tetrahydro-naphthalen-2-ylamino)-pentanoic acid {1-[3-(4-methoxy-benzylamino)-propyl]-1H-imidazol-4-yl}-amide Methanesulfonic acid 3-{4-[2-(6,8-difluoro-1,2,3,4-tetrahydro-naphthalen-2-ylamino)-pentanoylamino]-imidazol-1-yl}-propyl ester was treated with the appropriate amine to afford the title compound: MS 526.5 m/z (M+1).

Example 75

(S)-2-(6,8-Difluoro-1,2,3,4-tetrahydro-naphthalen-2-ylamino)-pentanoic acid {1-[3-(cyclopropylmethyl-amino)-propyl]-1H-imidazol-4-yl}-amide Methanesulfonic acid 3-{4-[2-(6,8-difluoro-1,2,3,4-tetrahydro-naphthalen-2-ylamino)-pentanoylamino]-imidazol-1-yl}-propyl ester was treated with the appropriate amine to afford the title compound: MS 460.5 m/z (M+1).

Example 76

(S)-2-(6,8-Difluoro-1,2,3,4-tetrahydro-naphthalen-2-ylamino)-pentanoic acid {1-[3-(4-methyl-benzylamino)-propyl-]1H-imidazol-4-yl}-amide Methanesulfonic acid 3-{4-[2-(6,8-difluoro-1,2,3,4-tetrahydro-naphthalen-2-ylamino)-pentanoylamino]-imidazol-1-yl}-propyl ester was treated with the appropriate amine to afford the title compound: MS 510.5 m/z (M+1).

The following Examples were prepared by methods analogous to those described above for General Procedure A, method F using 2-{4-[2-(6,8-Difluoro-1,2,3,4-tetrahydro-naphthalen-2-ylamino)-pentanoylamino]-imidazol-1-yl}-2-methyl-propionic acid and an appropriate amine.

Example 77

(S)-2-(6,8-Difluoro-1,2,3,4-tetrahydro-naphthalen-2-ylamino)pentanoic acid {1-[1-methyl-1-(methyl-phenethyl-carbamoyl)-ethyl]-1H-imidazol-4-yl}-amide MS 552.58 m/z (M+1).

Example 78

(S)-2-(6,8-Difluoro-1,2,3,4-tetrahydro-naphthalen-2-ylamino)-pentanoic acid {1-[1-(1,3-dihydro-isobenzofuran-5-ylcarbamoyl)-1-methyl-ethyl]-1H-imidazol-4-yl}-amide MS 552.55 m/z (M+1).

Example 79

(S)-2-(6,8-Difluoro-1,2,3,4-tetrahydro-naphthalen-2-ylamino)-pentanoic acid {1-[1-(indan-1-ylcarbamoyl)-1-methyl-ethyl]-1H-imidazol-4-yl}-amide MS 550.53 m/z (M+1).

Example 80

(S)-2-(6,8-Difluoro-1,2,3,4-tetrahydro-naphthalen-2-ylamino)-pentanoic acid {1-[1,1-dimethyl-2-oxo-2-(3-pyridin-4-yl-pyrrolidin-1-yl)-ethyl]-1H-imidazol-4-yl}-amide MS 565.6 m/z (M+1).

Example 81

(S)-2-(6,8-Difluoro-1,2,3,4-tetrahydro-naphthalen-2-ylamino)-pentanoic acid (1-{1-[2-(3-fluoro-phenyl)-ethylcarbamoyl]-1-methyl-ethyl}-1H-imidazol-4-yl)-amide MS 556.54 m/z (M+1).

Example 82

(S)-2-(6,8-Difluoro-1,2,3,4-tetrahydro-naphthalen-2-ylamino)-pentanoic acid {1-[2-(3-cyano-piperidin-1-yl)-1,1-dimethyl-2-oxo-ethyl]-1H-imidazol-4-yl}-amide MS 527.57 m/z (M+1).

Example 83

(S)-2-(6,8-Difluoro-1,2,3,4-tetrahydro-naphthalen-2-ylamino)-pentanoic acid (1-{1-methyl-1-[methyl-(tetrahydro-pyran-2-ylmethyl)-carbamoyl]-ethyl}-1H-imidazol-4-yl)-amide MS 546.58 m/z (M+1).

Example 84

(S)-2-(6,8-Difluoro-1,2,3,4-tetrahydro-naphthalen-2-ylamino)-pentanoic acid (1-{1-[ethyl-(2-pyrazol-1-yl-ethyl)-carbamoyl]-1-methyl-ethyl}-1H-imidazol-4-yl)-amide MS 556.61 m/z (M+1).

Example 85

(S)-2-(6,8-Difluoro-1,2,3,4-tetrahydro-naphthalen-2-ylamino)-pentanoic acid {1-[1,1-dimethyl-2-oxo-2-(2-phenyl-pyrrolidin-1-yl)-ethyl]-1H-imidazol-4-yl}-amide MS 564.59 m/z (M+1).

Example 86

(S)-2-(6,8-Difluoro-1,2,3,4-tetrahydro-naphthalen-2-ylamino)-pentanoic acid (1-{1-[(furan-2-ylmethyl)-carbamoyl]-1-methyl-ethyl}-1H-imidazol-4-yl)-amide MS 514.51 m/z (M+1).

Example 87

(S)-2-(6,8-Difluoro-1,2,3,4-tetrahydro-naphthalen-2-ylamino)-pentanoic acid (1-{2-[3-(acetyl-methyl-amino)-pyrrolidin-1-yl]-1,1-dimethyl-2-oxo-ethyl}-1H-imidazol-4-yl)-amide MS 559.57 m/z (M+1).

Example 88

(S)-2-(6,8-Difluoro-1,2,3,4-tetrahydro-naphthalen-2-ylamino)-pentanoic acid {1-[1-methyl-1-((3R,4S)-4-methylsulfanyl-tetrahydro-furan-3-ylcarbamoyl)-ethyl]-1H-imidazol-4-yl}-amide MS 550.53 m/z (M+1).

Example 89

(S)-2-(6,8-Difluoro-1,2,3,4-tetrahydro-naphthalen-2-ylamino)-pentanoic acid {1-[2-(4-acetyl-[1.4]diazepan-1-yl)-1,1-dimethyl-2-oxo-ethyl]-1H-imidazol-4-yl}-amide MS 559.31 m/z (M+1).

Example 90

(S)-2-(6,8-Difluoro-1,2,3,4-tetrahydro-naphthalen-2-ylamino)-pentanoic acid (1-{1-methyl-1-[1-(1-methyl-1H-pyrazol-4-yl)-ethylcarbamoyl]-ethyl}-1H-imidazol-4-yl)-amide MS 542.56 m/z (M+1).

Example 91

(S)-2-(6,8-Difluoro-1,2,3,4-tetrahydro-naphthalen-2-ylamino)-pentanoic acid {1-[1-(3-methoxy-propyl-carbamoyl)-1-methyl-ethyl]-1H-imidazol-4-yl}-amide MS 506.52 m/z (M+1).

Example 92

(S)-2-(6,8-Difluoro-1,2,3,4-tetrahydro-naphthalen-2-ylamino)-pentanoic acid (1-{1-methyl-1-[(3-methyl-[1.2.4]oxadiazol-5-ylmethyl)-carbamoyl]-ethyl}-1H-imidazol-4-yl)-amide MS 530.54 m/z (M+1).

Example 93

(S)-2-(6,8-Difluoro-1,2,3,4-tetrahydro-naphthalen-2-ylamino)-pentanoic acid (1-{1-[(2-cyano-ethyl)-methyl-carbamoyl]-1-methyl-ethyl}-1H-imidazol-4-yl)-amide MS 501.51 m/z (M+1).

Example 94

(S)-2-(6,8-Difluoro-1,2,3,4-tetrahydro-naphthalen-2-ylamino)-pentanoic acid {1-[1,1-dimethyl-2-(3-methyl-5,6-dihydro-8H-[1,2,4]triazolo[4,3-a]pyrazin-7-yl)-2-oxo-ethyl]-1H-imidazol-4-yl}-amide MS 555.55 m/z (M+1).

Example 95

(S)-2-(6,8-Difluoro-1,2,3,4-tetrahydro-naphthalen-2-ylamino)-pentanoic acid (1-{1-methyl-1-[methyl-(1-methyl-1H-imidazol-2-ylmethyl)-carbamoyl]-ethyl}-1H-imidazol-4-yl)-amide MS 542.48 m/z (M+1).

Example 96

(S)-2-(6,8-Difluoro-1,2,3,4-tetrahydro-naphthalen-2-ylamino)-pentanoic acid (1-{1-[(2-diethylamino-ethyl)-methyl-carbamoyl]-1-methyl-ethyl}-1H-imidazol-4-yl)-amide MS 547.62 m/z (M+1).

The following Examples were prepared by methods analogous to those described above for General Procedure A, method F using 2-{4-[2-(6,8-Difluoro-1,2,3,4-tetrahydro-naphthalen-2-ylamino)-propionylamino]-imidazol-1-yl}-2-methyl-propionic acid and an appropriate amine.

Example 97

2-{4-[(S)-2-(6,8-Difluoro-1,2,3,4-tetrahydro-naphthalen-2-ylamino)-propionylamino]-imidazol-1-yl}-N-indan-1-yl-isobutyramide MS 522.56 m/z (M+1).

Example 98

(S)-2-(6,8-Difluoro-1,2,3,4-tetrahydro-naphthalen-2-ylamino)-N-{1-[1,1-dimethyl-2-oxo-2-(3-pyridin-4-yl-pyrrolidin-1-yl)-ethyl]-1H-imidazol-4-yl}-propionamide MS 537.53 m/z (M+1).

Example 99

(S)-2-(6,8-Difluoro-1,2,3,4-tetrahydro-naphthalen-2-ylamino)-N-{1-[2-(4-hydroxymethyl-4-methyl-piperidin-1-yl)-1,1-dimethyl-2-oxo-ethyl]-1H-imidazol-4-yl}-propionamide MS 528.51 m/z (M+1).

Example 100

2-{4-[(S)-2-(6,8-Difluoro-1,2,3,4-tetrahydro-naphthalen-2-ylamino)-propionylamino]-imidazol-1-yl}-N-methyl-N-phenethyl-isobutyramide MS 524.54 m/z (M+1).

Example 101

2-{4-[(S)-2-(6,8-Difluoro-1,2,3,4-tetrahydro-naphthalen-2-ylamino)-propionylamino]-imidazol-1-yl}-N-ethyl-N-(2-pyrazol-1-yl-ethyl)-isobutyramide MS 528.49 m/z (M+1).

Example 102

(S)-2-(6,8-Difluoro-1,2,3,4-tetrahydro-naphthalen-2-ylamino)-N-{1-[2-(4-hydroxymethyl-4-methyl-piperidin-1-yl)-1,1-dimethyl-2-oxo-ethyl]-1H-imidazol-4-yl}-propionamide MS 518.53 m/z (M+1).

Example 103

2-{4-[(S)-2-(6,8-Difluoro-1,2,3,4-tetrahydro-naphthalen-2-ylamino)-propionylamino]-imidazol-1-yl}-N-(4-methyl-benzyl)-isobutyramide MS 510.49 m/z (M+1).

Example 104

2-{4-[(S)-2-(6,8-Difluoro-1,2,3,4-tetrahydro-naphthalen-2-ylamino)-propionylamino]-imidazol-1-yl}-N-(1,3-dihydro-isobenzofuran-5-yl)-isobutyramide MS 524.47 m/z (M+1).

Example 105

(S)-2-(6,8-Difluoro-1,2,3,4-tetrahydro-naphthalen-2-ylamino)-N-{1-[1,1-dimethyl-2-oxo-2-(2-phenyl-pyrrolidin-1-yl)-ethyl]-1H-imidazol-4-yl}-propionamide MS 536.55 m/z (M+1).

Example 106

(S)-N-{1-[2-(3-Cyano-piperidin-1-yl)-1,1-dimethyl-2-oxo-ethyl]-1H-imidazol-4-yl}-2-(6,8-difluoro-1,2,3,4-tetrahydro-naphthalen-2-ylamino)-propionamide MS 499.46 m/z (M+1).

Example 107

(S)-N-(1-{2-[3-(Acetyl-methyl-amino)-pyrrolidin-1-yl]-1,1-dimethyl-2-oxo-ethyl}-1H-imidazol-4-yl)-2-(6,8-difluoro-1,2,3,4-tetrahydro-naphthalen-2-ylamino)-propionamide MS 531.53 m/z (M+1).

Example 108

2-{4-[(S)-2-(6,8-Difluoro-1,2,3,4-tetrahydro-naphthalen-2-ylamino)-propionylamino]-imidazol-1-yl}-N-((1R,2S)-2-hydroxymethyl-cyclohexyl)-isobutyramide MS 518.53 m/z (M+1).

Example 109

2-{4-[(S)-2-(6,8-Difluoro-1,2,3,4-tetrahydro-naphthalen-2-ylamino)-propionylamino]-imidazol-1-yl}-N-(3-methyl-[1,2,4]oxadiazol-5-ylmethyl)-isobutyramide MS 502.43 m/z (M+1).

Example 110

2-{4-[(S)-2-(6,8-Difluoro-1,2,3,4-tetrahydro-naphthalen-2-ylamino)-propionylamino]-imidazol-1-yl}-N-((S)-2-methoxy-1-methyl-ethyl)-isobutyramide MS 478.51 m/z (M+1).

Example 111

2-{4-[(S)-2-(6,8-Difluoro-1,2,3,4-tetrahydro-naphthalen-2-ylamino)-propionylamino]-imidazol-1-yl}-N-(3-methoxy-propyl)-isobutyramide MS 478.58 m/z (M+1).

Example 112

2-{4-[(S)-2-(6,8-Difluoro-1,2,3,4-tetrahydro-naphthalen-2-ylamino)-propionylamino]-imidazol-1-yl}-N-[1-(1-methyl-1H-pyrazol-4-yl)-ethyl]-isobutyramide MS 514.51 m/z (M+1).

Example 113

2-{4-[(S)-2-(6,8-Difluoro-1,2,3,4-tetrahydro-naphthalen-2-ylamino)-propionylamino]-imidazol-1-yl}-N-(3-imidazol-1-yl-propyl)-isobutyramide MS 514.56 m/z (M+1).

Example 114

2-{4-[(S)-2-(6,8-Difluoro-1,2,3,4-tetrahydro-naphthalen-2-ylamino)-propionylamino]-imidazol-1-yl}-N-(3-morpholin-4-yl-propyl)-isobutyramide MS 533.58 m/z (M+1).

The following Examples were prepared by methods analogous to those described above for the reduction of the appropriate nitroimdiazole using General Method G followed by coupling to the appropriate acid using General Procedure A, method F.

Example 115

(S)-2-(6,8-Difluoro-1,2,3,4-tetrahydro-naphthalen-2-ylamino)-pentanoic acid [1-(3-methyl-oxetan-3-ylmethyl)-1H-imidazol-4-yl]-amide 1-(3-Methyl-oxetan-3-ylmethyl)-4-nitro-1H-imidazole was reduced and then coupled with 2-(6,8-Difluoro-1,2,3,4-tetrahydro-naphthalen-2-ylamino)-pentanoic acid (U.S. Ser. No. 11/078,898 filed Mar. 11, 2005) to afford the title compound: MS 433.3 m/z (M+1).

Example 116

(S)-2-[2-(3,5-Difluoro-phenyl)-acetylamino]-pentanoic acid [1-(3-methyl-oxetan-3-ylmethyl)-1H-imidazol-4-yl]-amide 1-(3-Methyl-oxetan-3-ylmethyl)-4-nitro-1H-imidazole was reduced and then coupled with 2-[2-(3,5-Difluoro-phenyl)-acetylamino]-pentanoic acid (U.S. Ser. No. 11/078,898 filed Mar. 11, 2005) to afford the title compound: MS 421.3 m/z (M+1).

Example 117

(S)-2-(6,8-Difluoro-1,2,3,4-tetrahydro-naphthalen-2-ylamino)-pentanoic acid {1-[1-(4-trifluoromethyl-phenyl)-ethyl]-1H-imidazol-4-yl}-amide 4-Nitro-1-[1-(4-trifluoromethyl-phenyl)-ethyl]-1H-imidazole was reduced and then coupled with 2-(6,8-Difluoro-1,2,3,4-tetrahydro-naphthalen-2-ylamino)-pentanoic acid (U.S. Ser. No. 11/078,898 filed Mar. 11, 2005) to afford the title compound: MS 521.5 m/z (M+1).

Example 118

(S)-2-[2-(3,5-Difluoro-phenyl)-acetylamino]-pentanoic acid {1-[1-(4-trifluoromethyl-phenyl)-ethyl]-1H-imidazol-4-yl}-amide 4-Nitro-1-[1-(4-trifluoromethyl-phenyl)-ethyl]-1H-imidazole was reduced and then coupled with 2-[2-(3,5-Difluoro-phenyl)-acetylamino]-pentanoic acid (U.S. Ser. No. 11/078,898 filed Mar. 11, 2005) to afford the title compound: MS 509.5 m/z (M+1).

Example 120

(S)-2-[2-(3,5-Difluoro-phenyl)-acetylamino]-pentanoic acid [1-(2-pyrrolidin-1-ylmethyl-cyclobutyl)-1H-imidazol-4-yl]-amide 4-Nitro-1-(2-pyrrolidin-1-ylmethyl-cyclobutyl)-1H-imidazole was reduced and then coupled with 2-[2-(3,5-Difluoro-phenyl)-acetylamino]-pentanoic acid (U.S. Ser. No. 11/078,898 filed Mar. 11, 2005) to afford the title compound: MS 474.6 m/z (M+1).

Example 121

(S)-2-(6,8-Difluoro-1,2,3,4-tetrahydro-naphthalen-2-ylamino)-pentanoic acid [1-2-pyrrolidin-1-ylmethyl-cyclobutyl)-1H-imidazol-4-yl]-amide 4-Nitro-1-(2-pyrrolidin-1-ylmethyl-cyclobutyl)-1H-imidazole was reduced and then coupled with 2-(6,8-Difluoro-1,2,3,4-tetrahydro-naphthalen-2-ylamino)-pentanoic acid (U.S. Ser. No. 11/078,898 filed Mar. 11, 2005) to afford the title compound: MS 486.6 m/z (M+1).

Example 122

(S)-2-(1,2,3,4-Tetrahydro-naphthalen-2-ylamino)-pentanoic acid (1-{1,1-dimethyl-2-[(tetrahydro-pyran-4-ylmethyl)-amino]-ethyl}-1H-imidazol-4-yl)-amide

[2-(4-Nitro-imidazol-1-yl)-propyl]-(tetrahydro-pyran-4-ylmethyl)-amine was reduced and then coupled with 2-(1,2,3,4-Tetrahydro-naphthalen-2-ylamino)-pentanoic acid to afford the title compound: MS 482.6 m/z (M+1).

Example 123

(S)-2-(6,8-Difluoro-1,2,3,4-tetrahydro-naphthalen-2-ylamino)-pentanoic acid {1-[2-(2-ethoxy-ethylamino)-1,1-dimethyl-ethyl]-1H-imidazol-4-yl}-amide (2-Ethoxy-ethyl)-[2-methyl-2-(4-nitro-imidazol-1-yl)-propyl]-amine was reduced and then coupled with 2-(6,8-Difluoro-1,2,3,4-tetrahydro-naphthalen-2-ylamino)-pentanoic acid (U.S. Ser. No. 11/078,898 filed Mar. 11, 2005) to afford the title compound: MS 492.6 m/z (M+1).

Example 124

(S)-2-(6,8-Difluoro-1,2,3,4-tetrahydro-naphthalen-2-ylamino)-N-{1-[2-(2-ethoxy-ethylamino)-1,1-dimethyl-ethyl]-1H-imidazol-4-yl}-propionamide (2-Ethoxy-ethyl)-[2-methyl-2-(4-nitro-imidazol-1-yl)-propyl]-amine was reduced and then coupled with 2-(6,8-Difluoro-1,2,3,4-tetrahydro-naphthalen-2-ylamino)-propionic acid to afford the title compound: MS 464.6 m/z (M+1).

The following Examples were prepared by methods analogous to those described above for General Procedure A, method F Example 125

(S)-2-(6,8-Difluoro-1,2,3,4-tetrahydro-naphthalen-2-ylamino)-pentanoic acid (1-{2-[(1-hydroxy-cyclohexylmethyl)-carbamoyl]-1,1-dimethyl-ethyl}-1H-imidazol-4-yl)-amide 3-{4-[2-(6,8-Difluoro-1,2,3,4-tetrahydro-naphthalen-2-ylamino)-pentanoylamino]-imidazol-1-yl}-3-methyl-butyric acid was coupled with the appropriate amine to afford the title compound: MS 560.5 m/z (M+1).

Example 126

(S)-2-(6,8-Difluoro-1,2,3,4-tetrahydro-naphthalen-2-ylamino)-pentanoic acid (1-{1-[(1-hydroxy-cyclohexylmethyl)-carbamoyl]-1-methyl-ethyl}-1H-imidazol-4-yl)-amide 2-{4-[2-(6,8-Difluoro-1,2,3,4-tetrahydro-naphthalen-2-ylamino)-pentanoylamino]-imidazol-1-yl}-2-methyl-propionic acid was coupled with the appropriate amine to afford the title compound: MS 546.6 m/z (M+1).

Example 127

(S)-2-(6,8-Difluoro-1,2,3,4-tetrahydro-naphthalen-2-ylamino)-pentanoic acid (1-{1-methyl-1-[(tetrahydro-pyran-4-ylmethyl)-carbamoyl]-ethyl}-1H-imidazol-4-yl)-amide 2-{4-[2-(6,8-Difluoro-1,2,3,4-tetrahydro-naphthalen-2-ylamino)-pentanoylamino]-imidazol-1-yl}-2-methyl-propionic acid was coupled with the appropriate amine to afford the title compound: MS 532.6 m/z (M+1).

Example 128

(S)-2-(6,8-Difluoro-1,2,3,4-tetrahydro-naphthalen-2-ylamino)-ientanoic acid {1-[1-methyl-1-(2-methyl-benzylcarbamoyl)-ethyl]-1H-imidazol-4-yl}-amide 2-{4-[2-(6,8-Difluoro-1,2,3,4-tetrahydro-naphthalen-2-ylamino)-pentanoylamino]-imidazol-1-yl}-2-methyl-propionic acid was coupled with the appropriate amine to afford the title compound: MS 538.52 m/z (M+1).

Example 129

(S)-2-(6,8-Difluoro-1,2,3,4-tetrahydro-naphthalen-2-ylamino)-pentanoic acid {1-[1-2-methoxy-1-methyl-ethylcarbamoyl)-1-methyl-ethyl]-1H-imidazol-4-yl}-amide 2-{4-[2-(6,8-Difluoro-1,2,3,4-tetrahydro-naphthalen-2-ylamino)-pentanoylamino]-imidazol-1-yl}-2-methyl-propionic acid was coupled with the appropriate amine to afford the title compound: MS 505.9 m/z (M+1).

The following Examples were prepared by methods analogous to those described above for General Procedure O;

Example 129a (S)-2-(6,8-Difluoro-1,2,3,4-tetrahydro-naphthalen-2-ylamino)-pentanoic acid (1-{1-methyl-2-[(tetrahydro-pyran-4-ylmethyl)-amino]-ethyl}-1H-imidazol-4-yl)-amide Methanesulfonic acid 2-{4-[2-(6,8-difluoro-1,2,3,4-tetrahydro-naphthalen-2-ylamino)-pentanoylamino]-imidazol-1-yl}-propyl ester was reacted with appropriate amine to afford the title compound: MS 504.6 m/z (M+1); The diastereomers were separated using Chiral HPLC conditions (OD-H column (2.1×250 cm); 10 mL/min; 95/5 Heptane/EtOH+0.2% DEA)

Example 130

(S)-2-(6,8-Difluoro-1,2,3,4-tetrahydro-naphthalen-2-ylamino)-pentanoic acid (1-{2-[(1-hydroxy-cyclohexylmethyl)-amino]-ethyl}-1H-imidazol-4-yl)-amide Methanesulfonic acid 2-{4-[2-(6,8-difluoro-1,2,3,4-tetrahydro-naphthalen-2-ylamino)-pentanoylamino]-imidazol-1-yl}-ethyl ester was reacted with the appropriate amine to afford the title: MS 504.6 m/z (M+1).

Example 131

(S)-2-(6,8-Difluoro-1,2,3,4-tetrahydro-naphthalen-2-ylamino)-pentanoic acid (1-{2-[(4-hydroxy-tetrahydro-pyran-4-ylmethyl)-amino]-ethyl}-1H-imidazol-4-yl)-amide Methanesulfonic acid 2-{4-[2-(6,8-difluoro-1,2,3,4-tetrahydro-naphthalen-2-ylamino)-pentanoylamino]-imidazol-1-yl}-ethyl ester was reacted with the appropriate amine to afford the title: MS 506.6 m/z (M+1).

Example 132

(S)-2-(6,8-Difluoro-1,2,3,4-tetrahydro-naphthalen-2-ylamino)-pentanoic acid (1-{2-[(tetrahydro-pyran-4-ylmethyl)-amino]-ethyl}-1H-imidazol-4-yl)-amide Methanesulfonic acid 2-{4-[2-(6,8-difluoro-1,2,3,4-tetrahydro-naphthalen-2-ylamino)-pentanoylamino]-imidazol-1-yl}-ethyl ester was reacted with the appropriate amine to afford the title: 490.5 m/z (M+1).

Example 133

(S)-2-(6,8-Difluoro-1,2,3,4-tetrahydro-naphthalen-2-ylamino)-pentanoic acid (1-{2-[(3-methyl-oxetan-3-ylmethyl)-amino]-ethyl}-1H-imidazol-4-yl)-amide Methanesulfonic acid 2-{4-[2-(6,8-difluoro-1,2,3,4-tetrahydro-naphthalen-2-ylamino)-pentanoylamino]-imidazol-1-yl}-ethyl ester was reacted with the appropriate amine to afford the title: 476.6 m/z (M+1).

Example 133A (S)-2-(6,8-Difluoro-1,2,3,4-tetrahydro-naphthalen-2-ylamino)-pentanoic acid (1-{2-[(1-hydroxy-cyclohexylmethyl)-amino]-1-methyl-ethyl}-1H-imidazol-4-yl)-amide Methanesulfonic acid 2-{4-[2-(6,8-difluoro-1,2,3,4-tetrahydro-naphthalen-2-ylamino)-pentanoylamino]-imidazol-1-yl}-propyl ester was reacted with the appropriate amine to afford the title: 518.3 m/z (M+1).

Example 134

(S)-2-(6,8-Difluoro-1,2,3,4-tetrahydro-naphthalen-2-ylamino)-pentanoic acid {1-[2-(2-ethoxy-ethylamino)-ethyl]-1H-imidazol-4-yl}-amide Methanesulfonic acid 2-{4-[2-(6,8-difluoro-1,2,3,4-tetrahydro-naphthalen-2-ylamino)-pentanoylamino]-imidazol-1-yl}-ethyl ester was reacted with the appropriate amine to afford the title: 464.6 m/z (M+1).

Example 135

(S)-2-(6,8-Difluoro-1,2,3,4-tetrahydro-naphthalen-2-ylamino)-pentanoic acid [1-(3-benzylamino-propyl)-1H-imidazol-4-yl]-amide Methanesulfonic acid 3-{4-[2-(6,8-difluoro-1,2,3,4-tetrahydro-naphthalen-2-ylamino)-pentanoylamino]-imidazol-1-yl}-propyl ester was reacted with the appropriate amine to afford the title: 496.3 m/z (M+1);

The following Examples were prepared by methods analogous to those described above for General Procedure B;

Example 136

(S)-2-(6,8-Difluoro-1,2,3,4-tetrahydro-naphthalen-2-ylamino)-pentanoic acid (1-{1,1-dimethyl-3-[(pyridin-2-ylmethyl)-amino]-propyl}-1H-imidazol-4-yl)-amide 2-Amino-pentanoic acid (1-{1,1-dimethyl-3-[(pyridin-2-ylmethyl)-amino]-propyl}-1H-imidazol-4-yl)-amide was reacted with 6,8-Difluoro-3,4-dihydro-1H-naphthalen-2-one to afford the title: 525.5 m/z (M+1).

Example 137

(S)-2-(6,8-Difluoro-1,2,3,4-tetrahydro-naphthalen-2-ylamino)-pentanoic acid {1-[1,1-dimethyl-3-((S)-2,2,2-trifluoro-1-phenyl-ethylamino)-propyl]-1H-imidazol-4-yl}-amide 2-Amino-pentanoic acid {1-[1,1-dimethyl-3-(2,2,2-trifluoro-1-phenyl-ethylamino)-propyl]-1H-imidazol-4-yl}-amide 6,8-Difluoro-3,4-dihydro-1H-naphthalen-2-one to afford the title: 592.3 m/z (M+1).

Example 138

(S)-2-(6,8-Difluoro-1,2,3,4-tetrahydro-naphthalen-2-ylamino)-pentanoic acid {1-[1,1-dimethyl-3-((R)-1-phenyl-ethylamino)-propyl]-1H-imidazol-4-yl}-amide 2-Amino-pentanoic acid {1-[1,1-dimethyl-3-(1-phenyl-ethylamino)-propyl]-1H-imidazol-4-yl}-amide was reacted with 6,8-Difluoro-3,4-dihydro-1H-naphthalen-2-one to afford the title: 538.6 m/z (M+1).

Example 139

(S)-2-(2-Trifluoromethyl-benzylamino)-pentanoic acid {1-[2-((2R,6S)-2,6-dimethyl-morpholin-4-yl)-1,1-dimethyl-ethyl]-1H-imidazol-4-yl}-amide 2-Amino-pentanoic acid {1-[2-(2,6-dimethyl-morpholin-4-yl)-1,1-dimethyl-ethyl]-1H-imidazol-4-yl}-amide was reacted with the appropriate aldehyde to afford the title compound: 510.5 m/z (M+1).

Example 140

(S)-2-{[(2-Fluoro-3-trifluoromethyl-phenyl)methyl]-amino}-pentanoic acid {1-[2-((2R,6S)-2,6-dimethyl-morpholin-4-yl)-1,1-dimethyl-ethyl]-1H-imidazol-4-yl}-amide 2-Amino-pentanoic acid {1-[2-(2,6-dimethyl-morpholin-4-yl)-1,1-dimethyl-ethyl]-1H-imidazol-4-yl}-amide was reacted with the appropriate aldehyde to afford the title compound: 528.6 m/z (M+1).

The following Examples were prepared by methods analogous to those described above for the reduction of the appropriate nitroimdiazole using General Method G followed by coupling to the appropriate acid using General Procedure A, method F.

Example 140a (S)-2-[2-(3,5-Difluoro-phenyl)-acetylamino]-N-[1-(1,1-dimethyl-2-pyrrolidin-1-yl-ethyl)-1H-imidazol-4-yl]-2-phenyl-acetamide 1-(2-methyl-1-(pyrrolidin-1-yl)propan-2-yl)-4-nitro-1H-imidazole (U.S. Ser. No. 11/078,898 filed Mar. 11, 2005) was reduced and coupled with (S)-2-(2-(3,5-difluorophenyl)acetamido)-2-phenylacetic acid to afford the title compound: MS 496 m/z (M+1).

Example 141

(S)-2-[2-(3,5-Difluoro-phenyl)-acetylamino]-N-{1-[2-((2S,6R)-2,6-dimethyl-morpholin-4-yl)-1,1-dimethyl-ethyl]-1H-imidazol-4-yl}-2-phenyl-acetamide 2,6-Dimethyl-4-[2-methyl-2-(4-nitro-imidazol-1-yl)-propyl]-morpholine (U.S. Ser. No. 11/078,898 filed Mar. 11, 2005) was reduced and coupled with (S)-2-(2-(3,5-difluorophenyl)acetamido)-2-phenylacetic acid to afford the title compound: MS 540 m/z (M+1).

Example 142

(S)-2-(6,8-Difluoro-1,2,3,4-tetrahydro-naphthalen-2-ylamino)-N-{1-[2-(2,2-dimethyl-propylamino)-1,1-dimethyl-ethyl]-1H-imidazol-4-yl}-2-phenyl-acetamide 2-methyl-N-neopentyl-2-(4-nitro-1H-imidazol-1-yl)propan-1-amine (U.S. Ser. No. 11/078,898 filed Mar. 11, 2005) was reduced and coupled with (S)-2-(5,7-difluoro-1,2,3,4-tetrahydronaphthalen-3-ylamino)-2-phenylacetic acid to afford the title compound: MS 524 m/z (M+1).

Example 143

(S)-2-[2-(3,5-Difluoro-phenyl)-acetylamino]-pentanoic acid (1-indan-1-yl-1H-imidazol-4-yl)-amide 1-(2,3-dihydro-1H-inden-1-yl)-4-nitro-1H-imidazole was reduced and coupled with (S)-2-[2-(3,5-Difluoro-phenyl)-acetylamino]-pentanoic acid (U.S. Ser. No. 11/078,898 filed Mar. 11, 2005) to afford the title compound: MS 453 m/z (M+1).

Example 144

(S)-2-[2-(3,5-Difluoro-phenyl)-acetylamino]-pentanoic acid [(S)-1-((1S,2R)-2-hydroxy-indan-1-yl)-1H-imidazol-4-yl]-amide (1S,2R)-2,3-dihydro-1-(4-nitro-1H-imidazol-1-yl)-1H-inden-2-ol was reduced and coupled with (S)-2-[2-(3,5-Difluoro-phenyl)-acetylamino]-pentanoic acid (U.S. Ser. No. 11/078,898 filed Mar. 11, 2005) to afford the title compound: MS 469 m/z (M+1).

Example 145

(S)-2-[2-(3,5-Difluoro-phenyl)-acetylamino]-pentanoic acid [(R)-1-((1R,2S)-2-hydroxy-indan-1-yl)-1H-imidazol-4-yl]-amide (1R,2S)-2,3-dihydro-1-(4-nitro-1H-imidazol-1-yl)-1H-inden-2-ol was reduced and coupled with (S)-2-[2-(3,5-Difluoro-phenyl)-acetylamino]-pentanoic acid (U.S. Ser. No. 11/078,898 filed Mar. 11, 2005) to afford the title compound: MS 469 m/z (M+1).

Example 146

(S)-2-[2-(3,5-Difluoro-phenyl)-acetylamino]-pentanoic acid {1-[1-(4-fluoro-phenyl)-2-hydroxy-ethyl]-1H-imidazol-4-yl}-amide 2-(4-amino-1H-imidazol-1-yl)-2-(4-fluorophenyl)ethanol was reduced and coupled with (S)-2-[2-(3,5-Difluoro-phenyl)-acetylamino]-pentanoic acid (U.S. Ser. No. 11/078,898 filed Mar. 11, 2005) to afford the title compound: MS 475 m/z (M+1).

Example 147

(S)-2-[2-(3,5-Difluoro-phenyl)-acetylamino]-pentanoic acid {(R)-1-[(R)-1-(4-fluoro-phenyl)-2-hydroxy-ethyl]-1H-imidazol-4-yl}-amide (R)-2-(4-amino-1H-imidazol-1-yl)-2-(4-fluorophenyl)ethanol was reduced and coupled with (S)-2-[2-(3,5-Difluoro-phenyl)-acetylamino]-pentanoic acid (U.S. Ser. No. 11/078,898 filed Mar. 11, 2005) to afford the title compound: MS 475 m/z (M+1).

Example 148

(S)-2-[2-(3,5-Difluoro-phenyl)-acetylamino]-pentanoic acid [1-(2-hydroxymethyl-phenyl)-1H-imidazol-4-yl]-amide (2-(4-nitro-1H-imidazol-1-yl)phenyl)methanol was reduced and coupled with (S)-2-[2-(3,5-Difluoro-phenyl)-acetylamino]-pentanoic acid (U.S. Ser. No. 11/078,898 filed Mar. 11, 2005) to afford the title compound: MS 443 m/z (M+1).

Example 149

(S)-2-[2-(3,5-Difluoro-phenyl)-acetylamino]-N-{1-[2-(2,2-dimethyl-propylamino)-1,1-dimethyl-ethyl]-1H-imidazol-4-yl}-2-phenyl-acetamide 2-methyl-N-neopentyl-2-(4-nitro-1H-imidazol-1-yl)propan-1-amine (U.S. Ser. No. 11/078,898 filed Mar. 11, 2005) was reduced and coupled with (S)-2-(2-(3,5-difluorophenyl)acetamido)-2-phenylacetic acid to afford the title compound: MS 512 m/z (M+1).

Example 150

(S)-2-(6,8-Difluoro-1,2,3,4-tetrahydro-naphthalen-2-ylamino)-pentanoic acid {(S)-1-[2-(2,2-dimethyl-propylamino)-1-phenyl-ethyl]-1H-imidazol-4-yl}-amide (S)-2,2-dimethyl-N-(2-(4-nitro-1H-imidazol-1-yl)-2-phenylethyl)propan-1-amine was reduced and coupled with (S)-2-(6,8-Difluoro-1,2,3,4-tetrahydro-naphthalen-2-ylamino)-pentanoic acid (U.S. Ser. No. 11/078,898 filed Mar. 11, 2005) to afford the title compound: MS 538 m/z (M+1).

Example 151

(S)-2-(6,8-Difluoro-1,2,3,4-tetrahydro-naphthalen-2-ylamino)-pentanoic acid {(S)-1-[2-(2,2-dimethyl-propylamino)-1-phenyl-ethyl]-1H-imidazol-4-yl}-amide (R)-2,2-dimethyl-N-(2-(4-nitro-1H-imidazol-1-yl)-2-phenylethyl)propan-1-amine was reduced and coupled with (S)-2-(6,8-Difluoro-1,2,3,4-tetrahydro-naphthalen-2-ylamino)-pentanoic acid (U.S. Ser. No. 11/078,898 filed Mar. 11, 2005) to afford the title compound: MS 538 m/z (M+1).

Example 152

2-[2-(3,5-Difluoro-phenyl)-acetylamino]-N-{1-[2-(2,2-dimethyl-propylamino)-1,1-dimethyl-ethyl]-1H-imidazol-4-yl}-2-(4-fluoro-phenyl)-acetamide 2-methyl-N-neopentyl-2-(4-nitro-1H-imidazol-1-yl)propan-1-amine (U.S. Ser. No. 11/078,898 filed Mar. 11, 2005) was reduced and coupled with (S)-2-(2-(3,5-difluorophenyl)acetamido)-2-(4-fluorophenyl)acetic acid to afford the title compound: MS 530 m/z (M+1).

Example 153

2-[2-(3,5-Difluoro-phenyl)-acetylamino]-N-{1-[2-(2,2-dimethyl-propylamino)-1,1-dimethyl-ethyl]-1H-imidazol-4-yl}-2-pyridin-3-yl-acetamide 2-methyl-N-neopentyl-2-(4-nitro-1H-imidazol-1-yl)propan-1-amine (U.S. Ser. No. 11/078,898 filed Mar. 11, 2005) was reduced and coupled with (S)-2-(2-(3,5-difluorophenyl)acetamido)-2-(pyridin-3-yl)acetic acid to afford the title compound: MS 513 m/z (M+1).

The following Examples were prepared by methods analogous to those described using General Method B

Example 154

(S)-2-(6,8-Difluoro-1,2,3,4-tetrahydro-naphthalen-2-ylamino)-pentanoic acid (1-{2-[(2,2-dimethyl-propylamino)-methyl]-phenyl}-1H-imidazol-4-yl)-amide (2S)-2-(5,7-difluoro-1,2,3,4-tetrahydronaphthalen-3-ylamino)-N-(1-(2-formylphenyl)-1H-imidazol-4-yl)pentanamide was treated with the appropriate amine to afford the title compound: MS 524 m/z (M+1).

Example 155

(S)-2-(6,8-Difluoro-1,2,3,4-tetrahydro-naphthalen-2-ylamino)-pentanoic acid (1-{2-[(2-hydroxy-butylamino)-methyl]-phenyl}-1H-imidazol-4-yl)-amide (2S)-2-(5,7-difluoro-1,2,3,4-tetrahydronaphthalen-3-ylamino)-N-(1-(2-formylphenyl)-1H-imidazol-4-yl)pentanamide was treated with the appropriate amine to afford the title compound: MS 526 m/z (M+1).

The following Examples were prepared by methods analogous to those described above.

| Ex | Structure | MS or NMR data | IUPACNAME |
|---|---|---|---|
| 156 | 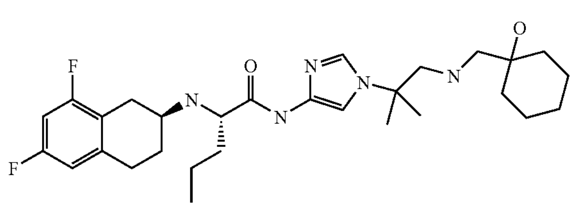 | M + 1 = 532.6 | N-2-[(2S)-6,8-difluoro-1,2,3,4-tetrahydronaphthalen-2-yl]-N-[1-(2-{[(1-hydroxycyclohexyl)methyl]-amino}-11-dimethylethyl)-1H-imidazol-4-yl]-L-norvalinamide |

-continued

| Ex | Structure | MS or NMR data | IUPACNAME |
|---|---|---|---|
| 157 | 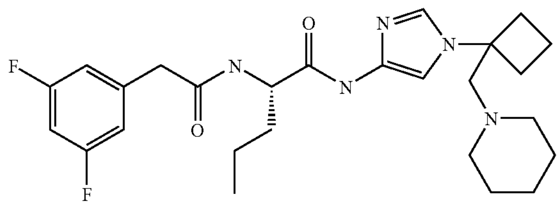 | M + 1 = 488.5 | N-2-[(3,5-difluorophenyl)acetyl]-N-{1-[1-(piperidin-1-ylmethyl)cyclobutyl]-1H-imidazol-4-yl}-L-norvalinamide |
| 158 | 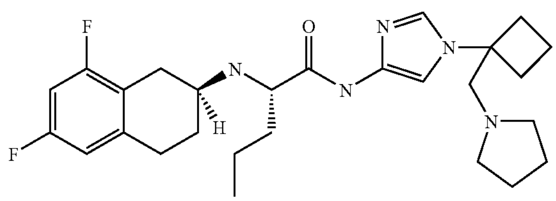 | M + 1 = 486.5 | N-2-[(2S)-6,8-difluoro-1,2,3,4-tetrahydronaphthalen-2-yl]-N-{1-[1-(pyrrolidin-1-ylmethyl)cyclobutyl]-1H-imidazol-4-yl}-L-norvalinamide |
| 159 | 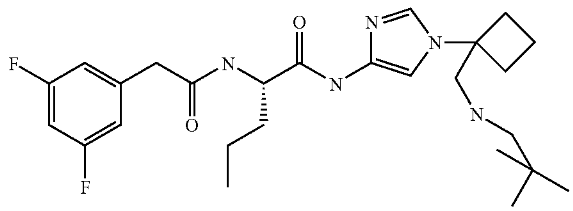 | M + 1 = 490.1 | N-2-[(3,5-difluorophenyl)acetyl]-N-[1-(1-{[(2,2-dimethylpropyl)amino]-methyl}cyclobutyl)-1H-imidazol-4-yl]-L-norvalinamide |
| 160 | 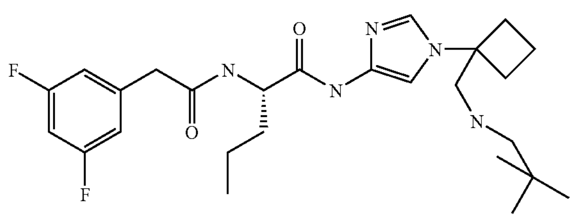 | M + 1 = 490.1 | N-2-[(3,5-difluorophenyl)acetyl]-N-[1-(1-{[(2,2-dimethylpropyl)amino]-methyl}cyclobutyl)-1H-imidazol-4-yl]-L-norvalinamide |
| 161 | 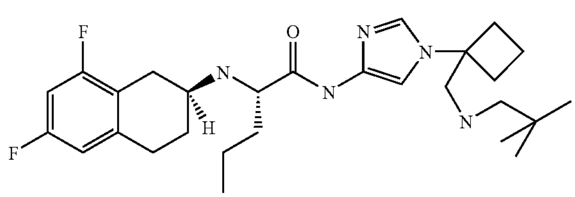 | M + 1 = 502.6 | N-2-[(2S)-6,8-difluoro-1,2,3,4-tetrahydronaphthalen-2-yl]-N-[1-(1-{[(22-dimethylpropyl)amino]-methyl}cyclobutyl)-1H-imidazol-4-yl]-L-norvalinamide |

-continued

| Ex | Structure | MS or NMR data | IUPACNAME |
|---|---|---|---|
| 162 | 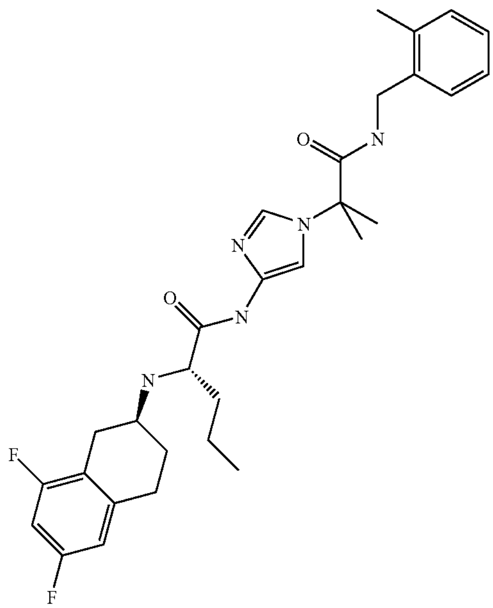 | M + 1 = 538.26 | N-2-[(2S)-6,8-difluoro-1,2,3,4-tetrahydronaphthalen-2-yl]-N-(1-{1,1-dimethyl-2-[(2-methylbenzyl)amino]-2-oxoethyl}-1H-imidazol-4-yl)-L-norvalinamide |
| 163 | 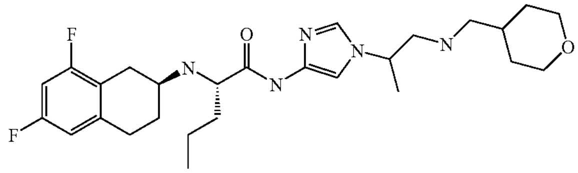 | M + 1 = 504.1 | N-2-[(2S)-6,8-difluoro-1,2,3,4-tetrahydronaphthalen-2-yl]-N-(1-{1-methyl-2-[(tetrahydro-2H-pyran-4-ylmethyl)amino]ethyl}-1H-imidazol-4-yl)-L-norvalinamide |
| 164 | 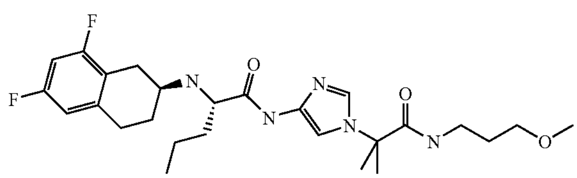 | M + 1 = 506.52 | N-2-[(2S)-6,8-difluoro-1,2,3,4-tetrahydronaphthalen-2-yl]-N-(1-{2-[(3-methoxypropyl)amino]-1,1-dimethyl-2-oxoethyl}-1H-imidazol-4-yl)-L-norvalinamide |
| 165 | 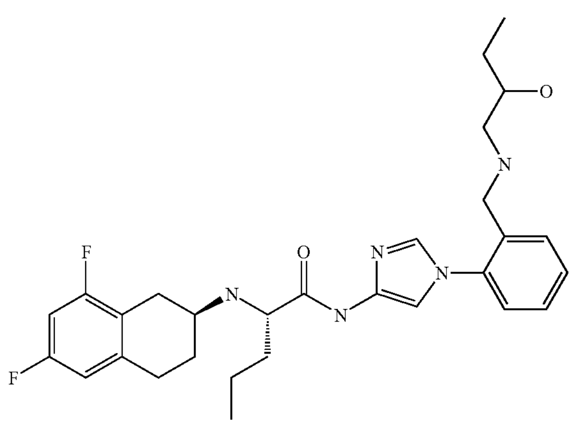 | M + 1 = 526.64 | N-2-[(2S)-6,8-difluoro-1,2,3,4-tetrahydronaphthalen-2-yl]-N-[1-(2-{[(2-hydroxybutyl)amino]methyl}phenyl)-1H-imidazol-4-yl]-L-norvalinamide |

-continued

| Ex | Structure | MS or NMR data | IUPACNAME |
|---|---|---|---|
| 166 | 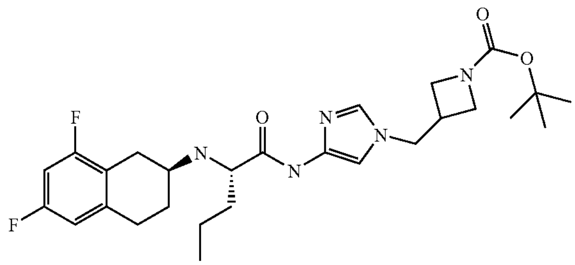 | M + 1 = 518.5 | tert-butyl 3-{[4-({N-[(2S)-6,8-difluoro-1,2,3,4-tetrahydronaphthalen-2-yl]-L-norvalyl}amino)-1H-imidazol-1-yl]methyl}azetidine-1-carboxylate |
| 167 | 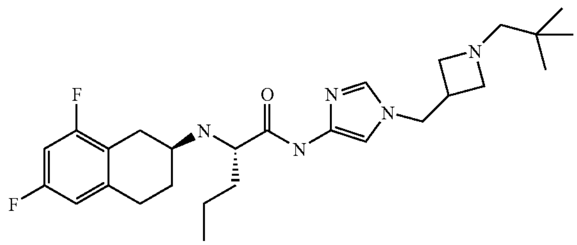 | M + 1 = 488.5 | N-2-[(2S)-6,8-difluoro-1,2,3,4-tetrahydronaphthalen-2-yl]-N-(1-{[1-(2,2-dimethylpropyl)azetidin-3-yl]methyl}-1H-imidazol-4-yl)-L-norvalinamide |
| 168 | 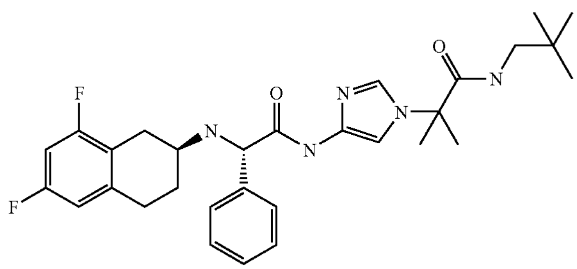 | M + 1 = 538.65 | 2-[4-({(2S)-2-[(6,8-difluoro-1,2,3,4-tetrahydronaphthalen-2-yl)amino]-2-phenylacetyl}amino)-1H-imidazol-1-yl]-N-(2,2-dimethylpropyl)-2-methylpropanamide |
| 169 | 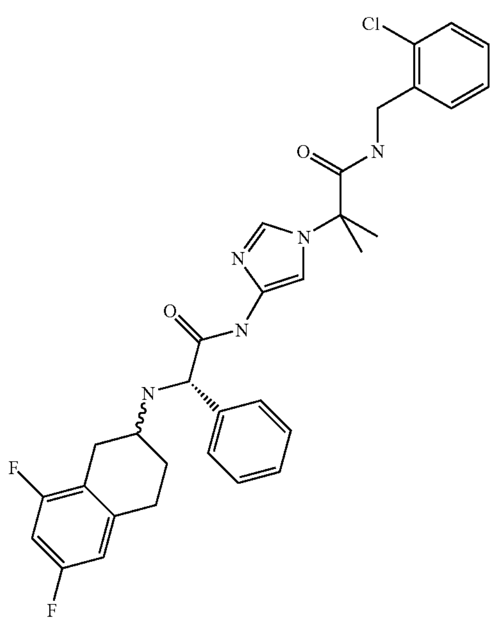 | M + 1 = 593.09 | N-(2-chlorobenzyl)-2-[4-({(2S)-2-[(6,8-difluoro-1,2,3,4-tetrahydronaphthalen-2-yl)amino]-2-phenylacetyl}amino)-1H-imidazol-1-yl]-2-methylpropanamide |

-continued
| Ex | Structure | MS or NMR data | IUPACNAME |
|---|---|---|---|
| 170 | 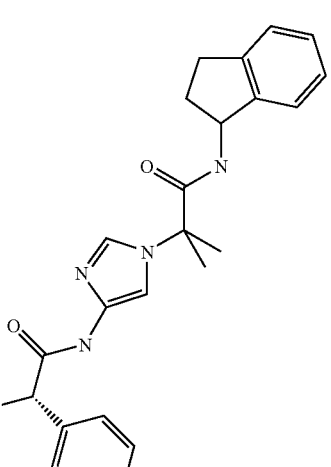 | M + 1 = 584.68 | 2-[4-({(2S)-2-[(6,8-difluoro-1,2,3,4-tetrahydronaphthalen-2-yl)amino]-2-phenylacetyl}amino)-1H-imidazol-1-yl]-N-(2,3-dihydro-1H-inden-1-yl)-2-methylpropanamide |
| 171 | 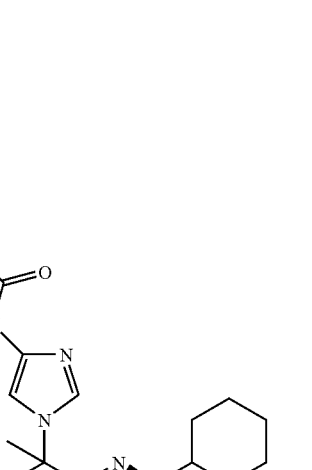 | M + 1 = 578.72 | N-[(1R)-1-cyclohexylethyl]-2-[4-({(2S)-2-[(6,8-difluoro-1,2,3,4-tetrahydronaphthalen-2-yl)amino]-2-phenylacetyl}amino)-1H-imidazol-1-yl]-2-methylpropanamide |

-continued

| Ex | Structure | MS or NMR data | IUPAC NAME |
|---|---|---|---|
| 172 | 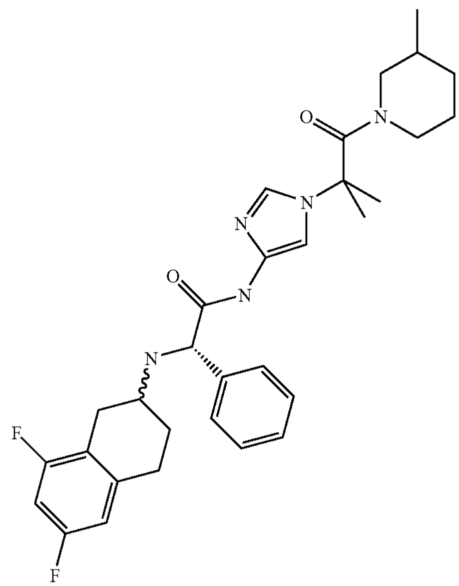 | M + 1 = 550.66 | (2S)-2-[(6,8-difluoro-1,2,3,4-tetrahydronaphthalen-2-yl)amino]-N-{1-[11-dimethyl-2-(3-methylpiperidin-1-yl)-2-oxoethyl]-1H-imidazol-4-yl}-2-phenylacetamide |
| 173 | 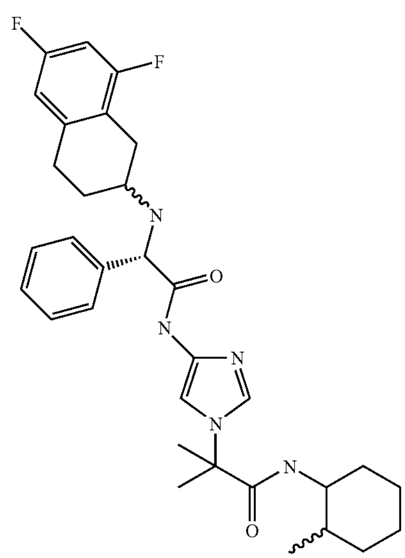 | M + 1 = 564.69 | 2-[4-({(2S)-2-[(6,8-difluoro-1,2,3,4-tetrahydronaphthalen-2-yl)amino]-2-phenylacetyl}amino)-1H-imidazol-1-yl]-2-methyl-N-(2-methylcyclohexyl)-propanamide |

-continued
| Ex | Structure | MS or NMR data | IUPACNAME |
|---|---|---|---|
| 174 | 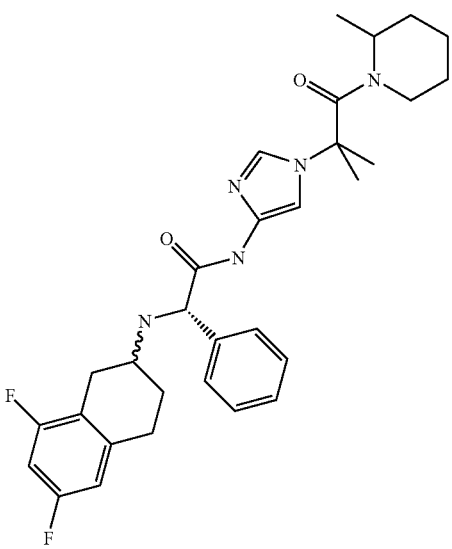 | M + 1 = 550.66 | (2S)-2-[(6,8-difluoro-1,2,3,4-tetrahydronaphthalen-2-yl)amino]-N-{1-[1,1-dimethyl-2-(2-methylpiperidin-1-yl)-2-oxoethyl]-1H-imidazol-4-yl}-2-phenylacetamide |
| 175 | 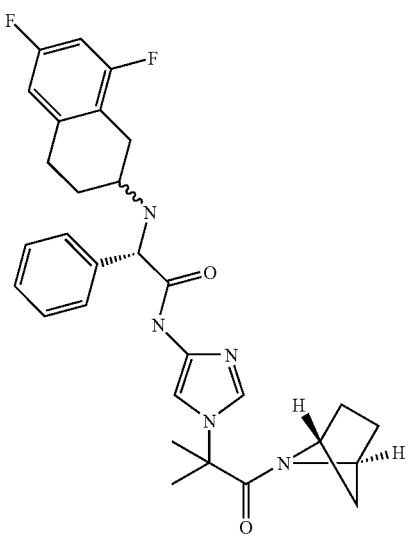 | M + 1 = 548.65 | (2S)-N-(1-{2-[(1R, 4S)-2-azabicyclo[2.2.1]hept-2-yl]-1,1-dimethyl-2-oxoethyl}-1H-imidazol-4-yl)-2-[(6,8-difluoro-1,2,3,4-tetrahydronaphthalen-2-yl)amino]-2-phenylacetamide |

-continued
| Ex | Structure | MS or NMR data | IUPACNAME |
|---|---|---|---|
| 176 | 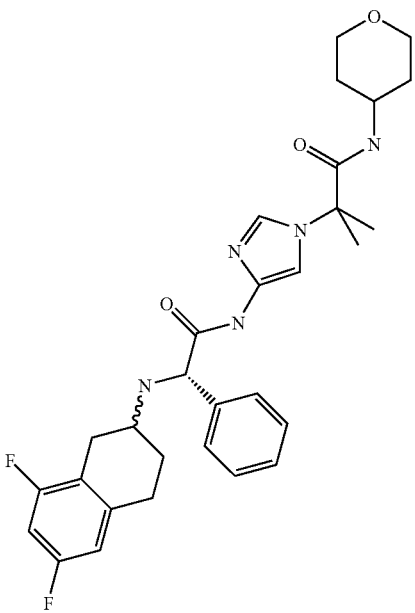 | M + 1 = 552.64 | 2-[4-({(2S)-2-[(6,8-difluoro-1,2,3,4-tetrahydronaphthalen-2-yl)amino]-2-phenylacetyl}amino)-1H-imidazol-1-yl]-2-methyl-N-(tetrahydro-2H-pyran-4-yl)propanamide |
| 177 | 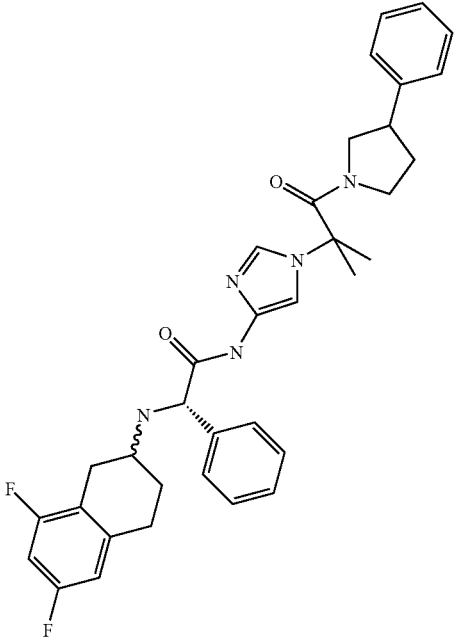 | M + 1 = 598.71 | (2S)-2-[(6,8-difluoro-1,2,3,4-tetrahydronaphthalen-2-yl)amino]-N-{1-[1,1-dimethyl-2-oxo-2-(3-phenylpyrrolidin-1-yl)ethyl]-1H-imidazol-4-yl}-2-phenylacetamide |

-continued

| Ex | Structure | MS or NMR data | IUPAC NAME |
|---|---|---|---|
| 178 | 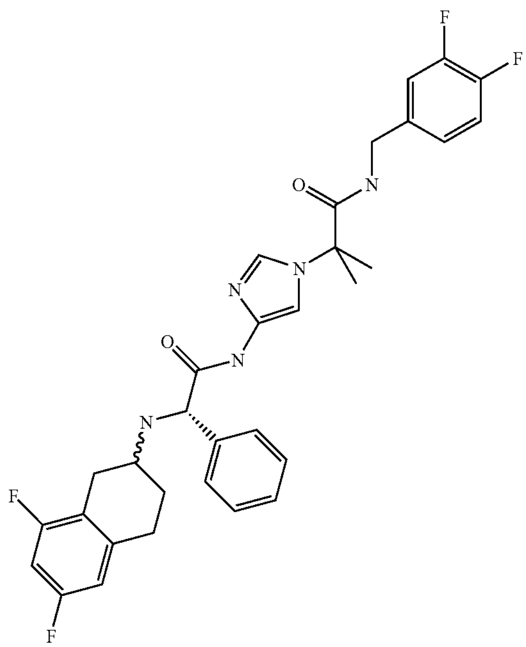 | M + 1 = 594.62 | N-(3,4-difluorobenzyl)-2-[4-({(2S)-2-[(6,8-difluoro-1,2,3,4-tetrahydronaphthalen-2-yl)amino]-2-phenylacetyl}amino)-1H-imidazol-1-yl]-2-methylpropanamide |
| 179 | 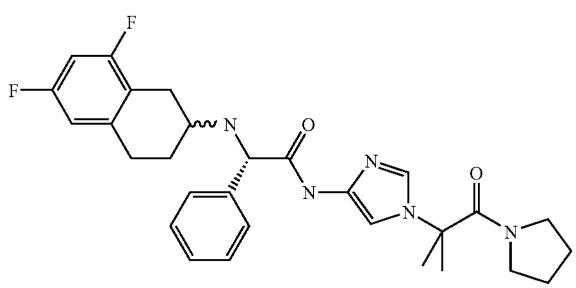 | M + 1 = 522.61 | (2S)-2-[(6,8-difluoro-1,2,3,4-tetrahydronaphthalen-2-yl)amino]-N-[1-(1,1-dimethyl-2-oxo-2-pyrrolidin-1-ylethyl)-1H-imidazol-4-yl]-2-phenylacetamide |
| 180 | 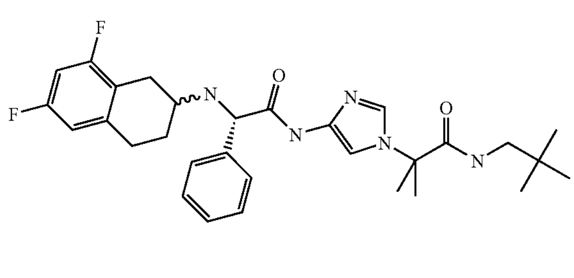 | M + 1 = 538.65 | 2-[4-({(2S)-2-[(6,8-difluoro-1,2,3,4-tetrahydronaphthalen-2-yl)amino]-2-phenylacetyl}amino)-1H-imidazol-1-yl]-N-(2,2-dimethylpropyl)-2-methylpropanamide |

-continued
| Ex | Structure | MS or NMR data | IUPACNAME |
|---|---|---|---|
| 181 | 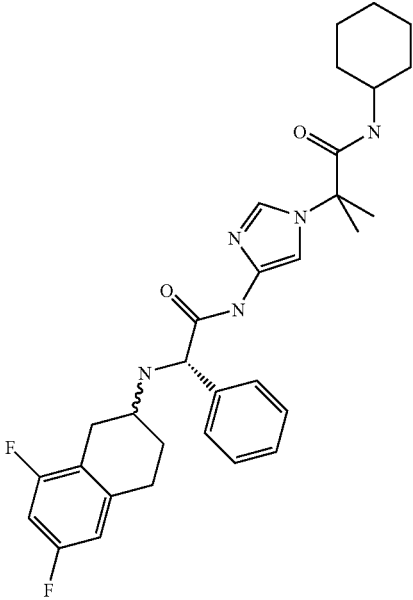 | M + 1 = 550.66 | N-cyclohexyl-2-[4-({(2S)-2-[(6,8-difluoro-1,2,3,4-tetrahydronaphthalen-2-yl)amino]-2-phenylacetyl}amino)-1H-imidazol-1-yl]-2-methylpropanamide |
| 182 | 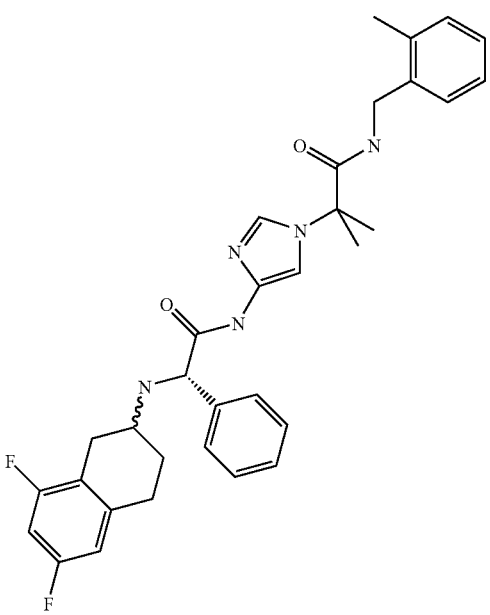 | M + 1 = 572.67 | 2-[4-({(2S)-2-[(6,8-difluoro-1,2,3,4-tetrahydronaphthalen-2-yl)amino]-2-phenylacetyl}amino)-1H-imidazol-1-yl]-2-methyl-N-(2-methylbenzyl)propanamide |

-continued

| Ex | Structure | MS or NMR data | IUPACNAME |
|---|---|---|---|
| 183 | 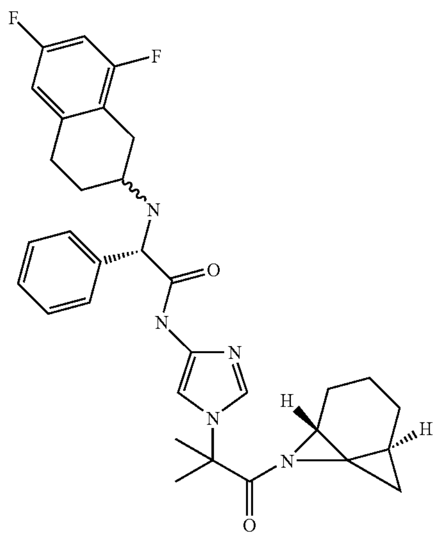 | M + 1 = 562.67 | (2S)-N-(1-{2-[(1S5R)-6-azabicyclo[3.2.1]oct-6-yl]-11-dimethyl-2-oxoethyl}-1H-imidazol-4-yl)-2-[(6,8-difluoro-1,2,3,4-tetrahydronaphthalen-2-yl)amino]-2-phenylacetamide |
| 184 | 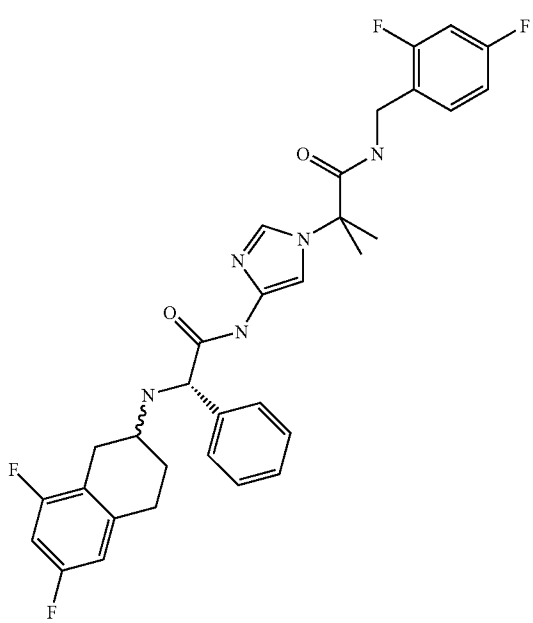 | M + 1 = 594.62 | N-(2,4-difluorobenzyl)-2-[4-({(2S)-2-[(6,8-difluoro-1,2,3,4-tetrahydronaphthalen-2-yl)amino]-2-phenylacetyl}amino)-1H-imidazol-1-yl]-2-methylpropanamide |

-continued

| Ex | Structure | MS or NMR data | IUPACNAME |
|---|---|---|---|
| 185 | 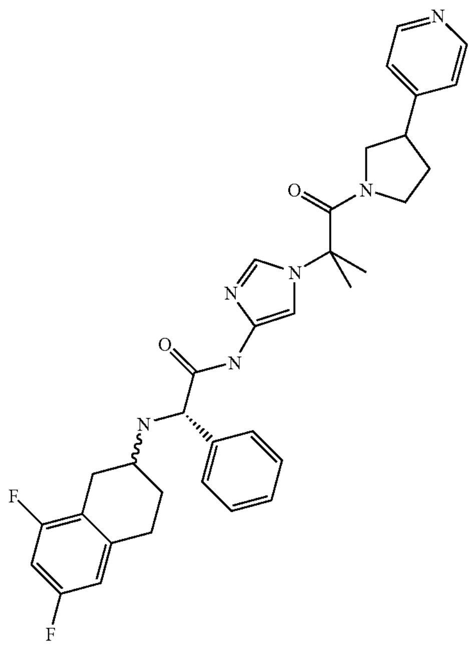 | M + 1 = 599.69 | (2S)-2-[(6,8-difluoro-1,2,3,4-tetrahydronaphthalen-2-yl)amino]-N-{1-[1,1-dimethyl-2-oxo-2-(3-pyridin-4-ylpyrrolidin-1-yl)ethyl]-1H-imidazol-4-yl}-2-phenylacetamide |
| 186 | 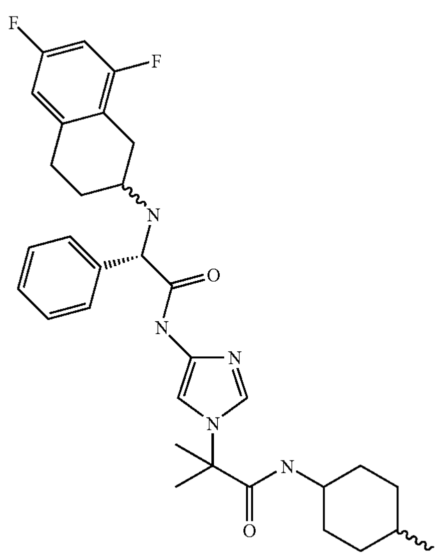 | M + 1 = 564.69 | 2-[4-({(2S)-2-[(6,8-difluoro-1,2,3,4-tetrahydronaphthalen-2-yl)amino]-2-phenylacetyl}amino)-1H-imidazol-1-yl]-2-methyl-N-(4-methylcyclohexyl)-propanamide |

-continued

| Ex | Structure | MS or NMR data | IUPACNAME |
|---|---|---|---|
| 187 | 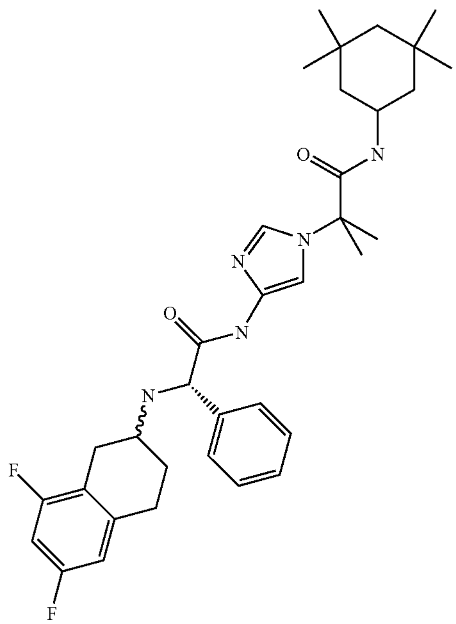 | M + 1 = 606.77 | 2-[4-({(2S)-2-[(6,8-difluoro-1,2,3,4-tetrahydronaphthalen-2-yl)amino]-2-phenylacetyl}amino)-1H-imidazol-1-yl]-2-methyl-N-(3,3,5,5-tetramethylcyclohexyl)-propanamide |
| 188 | 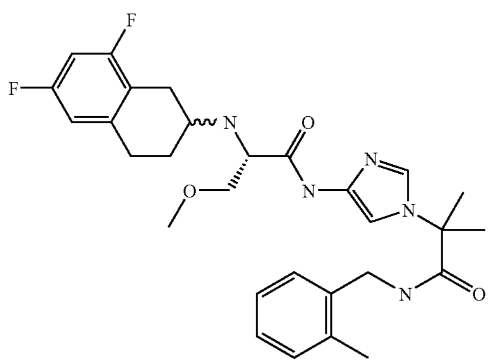 | M + 1 = 540.04 | N-2-(6,8-difluoro-1,2,3,4-tetrahydronaphthalen-2-yl)-N-(1-{1,1-dimethyl-2-[(2-methylbenzyl)amino]-2-oxoethyl}-1H-imidazol-4-yl)-O-methyl-L-serinamide |
| 189 | 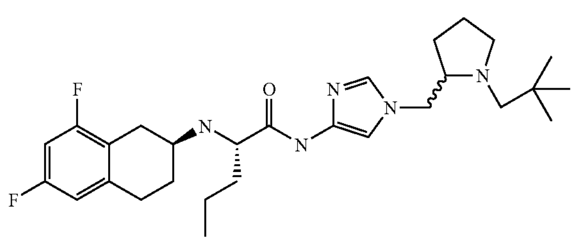 | M + 1 = 502.5 | N-2-[(2S)-6,8-difluoro-1,2,3,4-tetrahydronaphthalen-2-yl]-N-(1-{[1-(2,2-dimethylpropyl)pyrrolidin-2-yl]methyl}-1H-imidazol-4-yl)-L-norvalinamide |
| 190 | 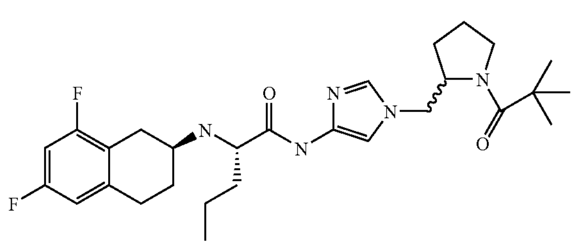 | M + 1 = 516.5 | N-2-[(2S)-6,8-difluoro-1,2,3,4-tetrahydronaphthalen-2-yl]-N-(1-{[1-(2,2-dimethylpropanoyl)-pyrrolidin-2-yl]methyl}-1H-imidazol-4-yl)-L-norvalinamide |

-continued

| Ex | Structure | MS or NMR data | IUPACNAME |
|---|---|---|---|
| 191 | 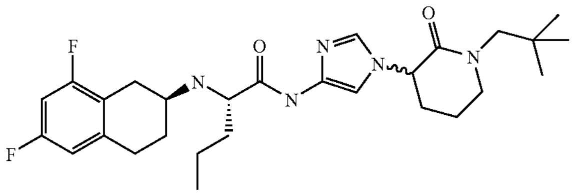 | M + 1 = 516.4 | (2S)-2-{[(2S)-6,8-difluoro-1,2,3,4-tetrahydronaphthalen-2-yl]amino}-N-{1-[1-(2,2-dimethylpropyl)-2-oxopiperidin-3-yl]-1H-imidazol-4-yl}pentanamide |
| 192 | 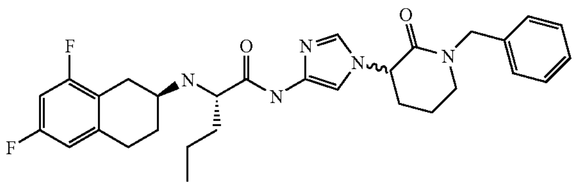 | M + 1 = 536.3 | (2S)-N-[1-(1-benzyl-2-oxopiperidin-3-yl)-1H-imidazol-4-yl]-2-{[(2S)-6,8-difluoro-1,2,3,4-tetrahydronaphthalen-2-yl]amino}pentanamide |
| 193 | 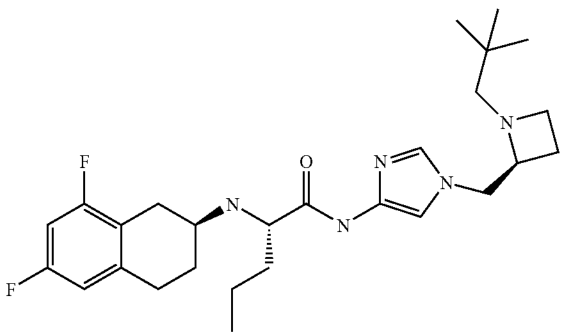 | M + 1 = 488.4 | N-2-[(2S)-6,8-difluoro-1,2,3,4-tetrahydronaphthalen-2-yl]-N-(1-{[(2S)-1-(2,2-dimethylpropyl)azetidin-2-yl]methyl}-1H-imidazol-4-yl)-L-norvalinamide |
| 194 | 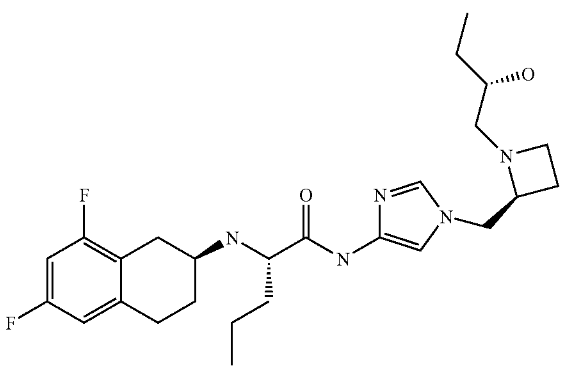 | M + 1 = 490.3 | N-2-[(2S)-6,8-difluoro-1,2,3,4-tetrahydronaphthalen-2-yl]-N-[1-({(2S)-1-[(2S)-2-hydroxybutyl]azetidin-2-yl}methyl)-1H-imidazol-4-yl]-L-norvalinamide |
| 195 | 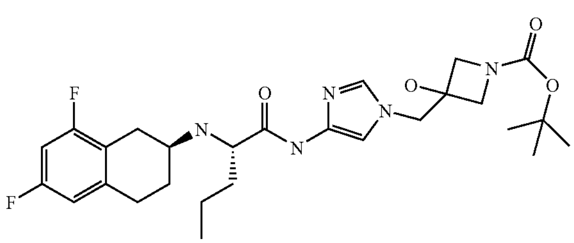 | M + 1 = 534.4 | tert-butyl 3-{[4-({N-[(2S)-6,8-difluoro-1,2,3,4-tetrahydronaphthalen-2-yl]-L-norvalyl}amino)-1H-imidazol-1-yl]methyl}-3-hydroxyazetidine-1-carboxylate |
| 196 | 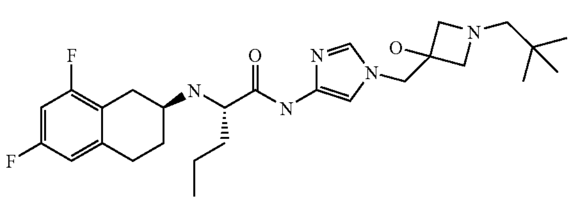 | M + 1 = 504.4 | N-2-[(2S)-6,8-difluoro-1,2,3,4-tetrahydronaphthalen-2-yl]-N-(1-{[1-(2,2-dimethylpropyl)-3-hydroxyazetidin-3-yl]methyl}-1H-imidazol-4-yl)-L-norvalinamide |

-continued

| Ex | Structure | MS or NMR data | IUPACNAME |
|---|---|---|---|
| 197 | 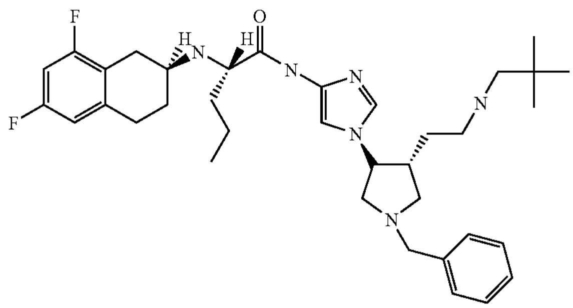 | M + 1 = 621.83 | N-{1-[(3S,4R)-1-benzyl-4-{2-[(2,2-dimethylpropyl)amino]ethyl}pyrrolidin-3-yl]-1H-imidazol-4-yl}-N-2-[(2S)-6,8-difluoro-1,2,3,4-tetrahydronaphthalen-2-yl]-L-norvalinamide |
| 198 | 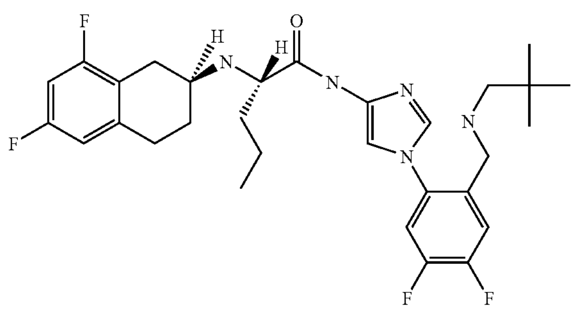 | M + 1 = 560.65 | N-2-[(2S)-6,8-difluoro-1,2,3,4-tetrahydronaphthalen-2-yl]-N-[1-(2-{[(2,2-dimethylpropyl)amino]-methyl}-45-difluorophenyl)-1H-imidazol-4-yl]-L-norvalinamide |
| 199 | 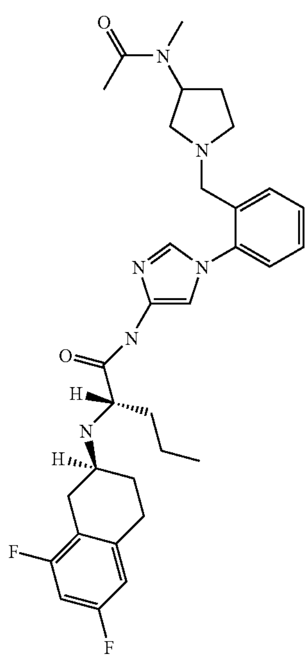 | M + 1 = 579.7 | N-{1-[2-({3-[acetyl(methyl)amino]-pyrrolidin-1-yl}methyl)phenyl]-1H-imidazol-4-yl}-N-2-[(2S)-6,8-difluoro-1,2,3,4-tetrahydronaphthalen-2-yl]-L-norvalinamide |

|     |           | MS or NMR   |           |
|-----|-----------|-------------|-----------|
| Ex  | Structure | data        | IUPACNAME |

200  M + 1 = 628.78  N-{1-[2-({[(1R,2R)-2-(benzyloxy)cyclopentyl]-amino}methyl)phenyl]-1H-imidazol-4-yl}-N-2-[(2S)-6,8-difluoro-1,2,3,4-tetrahydronaphthalen-2-yl]-L-norvalinamide 201  M + 1 = 579.7  N-(1-{2-[(4-acetyl-1,4-diazepan-1-yl)methyl]phenyl}-1H-imidazol-4-yl)-N-2-[(2S)-6,8-difluoro-1,2,3,4-tetrahydronaphthalen-2-yl]-L-norvalinamide -continued

| Ex | Structure | MS or NMR data | IUPACNAME |
|---|---|---|---|
| 202 | 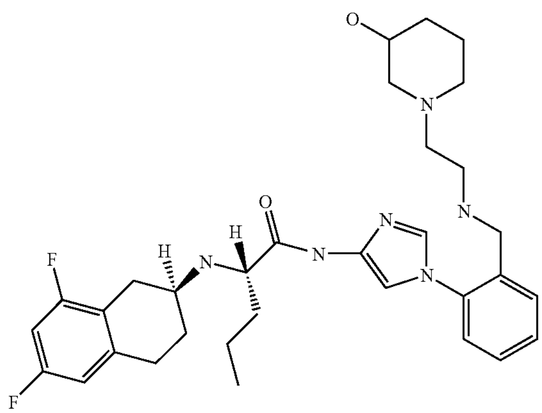 | M + 1 = 581.72 | N-2-[(2S)-6,8-difluoro-1,2,3,4-tetrahydronaphthalen-2-yl]-N-{1-[2-({[2-(3-hydroxypiperidin-1-yl)ethyl]amino}methyl)-phenyl]-1H-imidazol-4-yl}-L-norvalinamide |
| 203 | 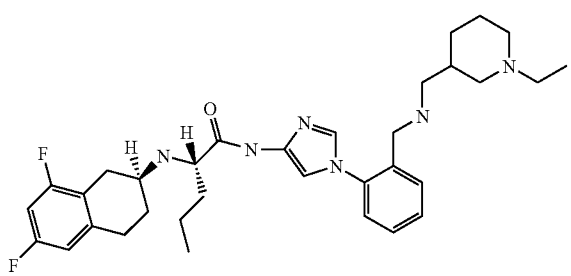 | M + 1 = 579.75 | N-2-[(2S)-6,8-difluoro-1,2,3,4-tetrahydronaphthalen-2-yl]-N-{1-[2-({[(1-ethylpiperidin-3-yl)methyl]amino}methyl)-phenyl]-1H-imidazol-4-yl}-L-norvalinamide |
| 204 | 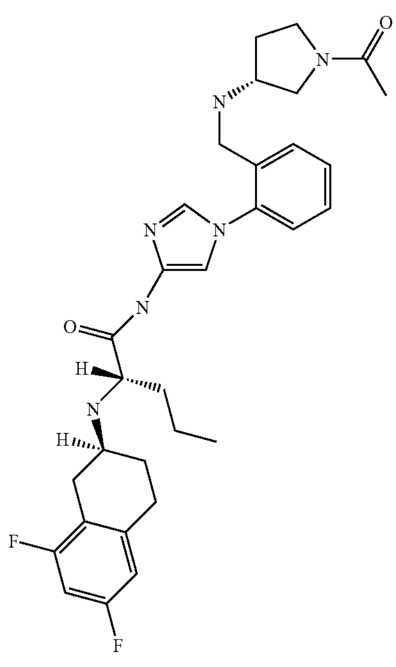 | M + 1 = 565.68 | N-{1-[2-({[(3R)-1-acetylpyrrolidin-3-yl]amino}methyl)phenyl]-1H-imidazol-4-yl}-N-2-[(2S)-6,8-difluoro-1,2,3,4-tetrahydronaphthalen-2-yl]-L-norvalinamide |

-continued

| Ex | Structure | MS or NMR data | IUPACNAME |
|---|---|---|---|
| 205 | 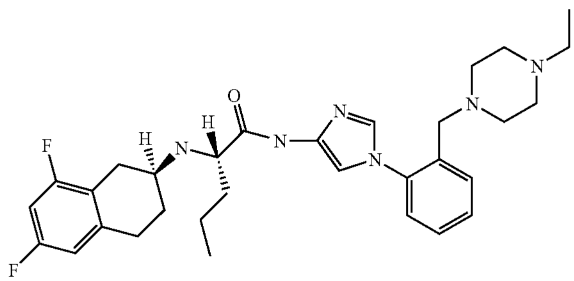 | M + 1 = 551.69 | N-2-[(2S)-6,8-difluoro-1,2,3,4-tetrahydronaphthalen-2-yl]-N-(1-{2-[(4-ethylpiperazin-1-yl)methyl]phenyl}-1H-imidazol-4-yl)-L-norvalinamide |
| 206 | 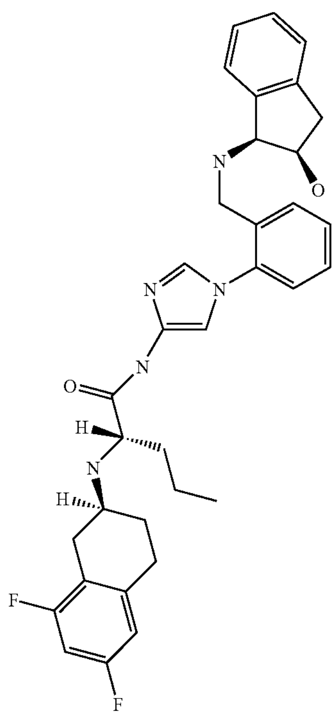 | M + 1 = 586.7 | N-2-[(2S)-6,8-difluoro-1,2,3,4-tetrahydronaphthalen-2-yl]-N-{1-[2-({[(1S,2R)-2-hydroxy-2,3-dihydro-1H inden-1-yl]amino}methyl)phenyl]-1H-imidazol-4-yl}-L-norvalinamide |
| 207 | 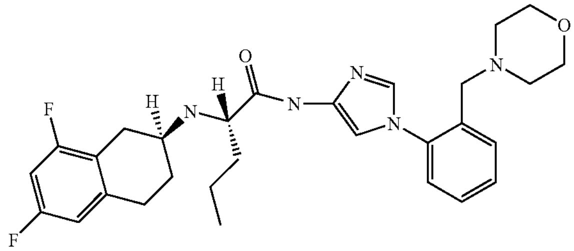 | M + 1 = 524.63 | N-2-[(2S)-6,8-difluoro-1,2,3,4-tetrahydronaphthalen-2-yl]-N-{1-[2-(morpholin-4-ylmethyl)phenyl]-1H-imidazol-4-yl}-L-norvalinamide |

| Ex | Structure | MS or NMR data | IUPACNAME |
|---|---|---|---|
| 208 | 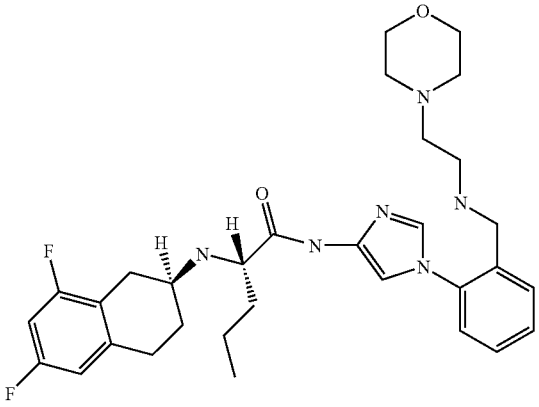 | M + 1 = 567.69 | N-2-[(2S)-6,8-difluoro-1,2,3,4-tetrahydronaphthalen-2-yl]-N-[1-(2-{[(2-morpholin-4-ylethyl)amino]methyl}-phenyl)-1H-imidazol-4-yl]-L-norvalinamide |
| 209 | 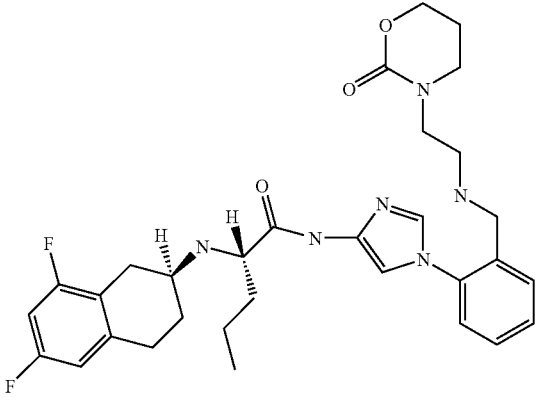 | M + 1 = 581.68 | N-2-[(2S)-6,8-difluoro-1,2,3,4-tetrahydronaphthalen-2-yl]-N-{1-[2-({[2-(2-oxo-1,3-oxazinan-3-yl)ethyl]amino}-methyl)-phenyl]-1H-imidazol-4-yl}-L-norvalinamide |
| 210 | 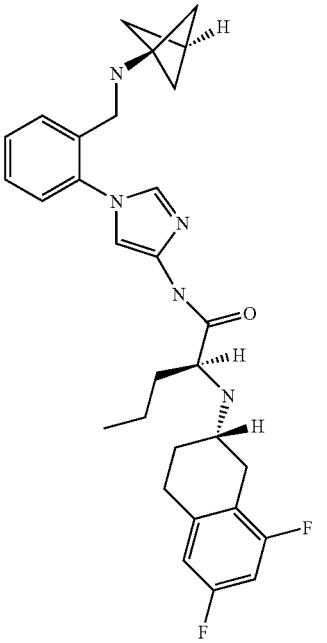 | M + 1 = 520.64 | N-(1-{2-[(bicyclo[1.1.1]pent-1-ylamino)methyl]phenyl}-1H-imidazol-4-yl)-N-2-[(2S)-6,8-difluoro-1,2,3,4-tetrahydronaphthalen-2-yl]-L-norvalinamide |

| Ex | Structure | MS or NMR data | IUPACNAME |
|---|---|---|---|
| 211 | 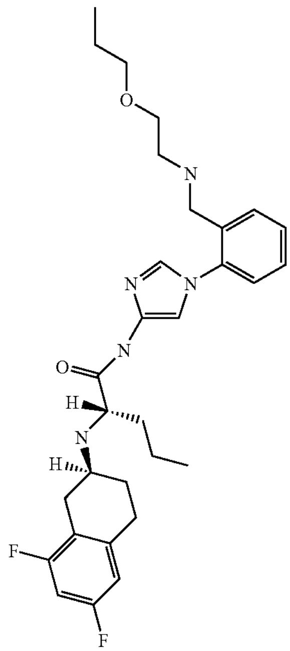 | M + 1 = 540.67 | N-2-[(2S)-6,8-difluoro-1,2,3,4-tetrahydronaphthalen-2-yl]-N-[1-(2-{[(2-propoxyethyl)amino]methyl}phenyl)-1H-imidazol-4-yl]-L-norvalinamide |
| 212 | 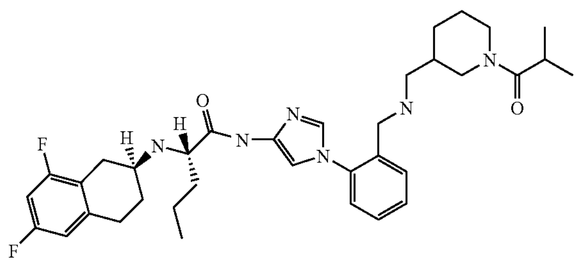 | M + 1 = 621.78 | N-2-[(2S)-6,8-difluoro-1,2,3,4-tetrahydronaphthalen-2-yl]-N-{1-[2-({[(1-isobutyrylpiperidin-3-yl)methyl]amino}methyl)-phenyl]-1H-imidazol-4-yl}-L-norvalinamide |
| 213 | 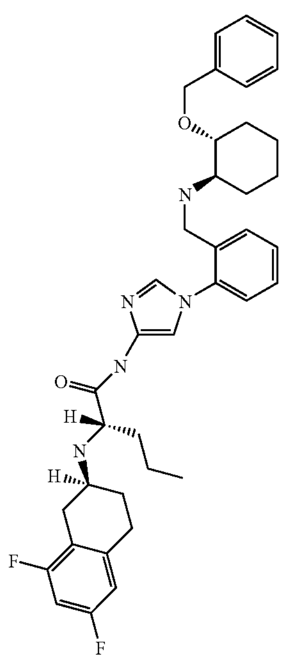 | M + 1 = 642.8 | N-{1-[2-({[(1R,2R)-2-(benzyloxy)cyclohexyl]-amino}methyl)phenyl]-1H-imidazol-4-yl}-N-2-[(2S)-6,8-difluoro-1,2,3,4-tetrahydropthalen-2-yl]-L-norvalinamide |

-continued

| Ex | Structure | MS or NMR data | IUPACNAME |
|---|---|---|---|
| 214 | 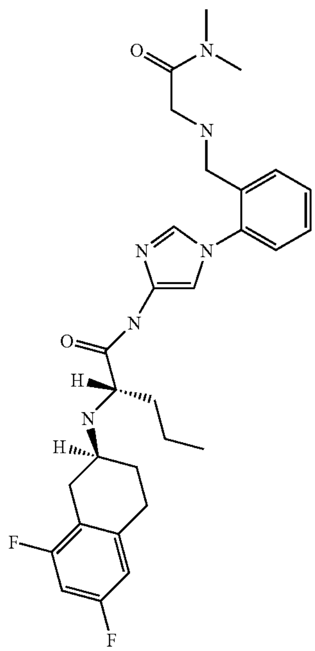 | M + 1 = 539.64 | N-2-[(2S)-6,8-difluoro-1,2,3,4-tetrahydronaphthalen-2-yl]-N-{1-[2-({[2-(dimethylamino)-2-oxoethyl]amino}methyl)-phenyl]-1H-imidazol-4-yl}-L-norvalinamide |
| 215 | 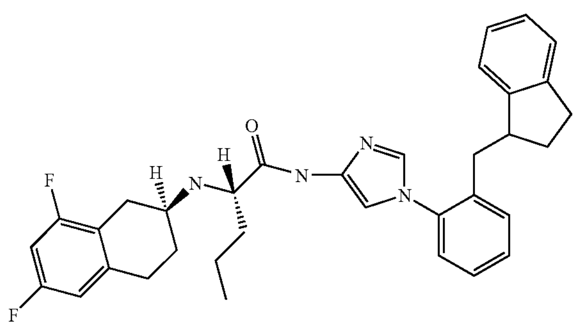 | M + 1 = 556.67 | N-2-[(2S)-6,8-difluoro-1,2,3,4-tetrahydronaphthalen-2-yl]-N-{1-[2-(2,3-dihydro-1H-indol-1-ylmethyl)phenyl]-1H-imidazol-4-yl}-L-norvalinamide |
| 216 | 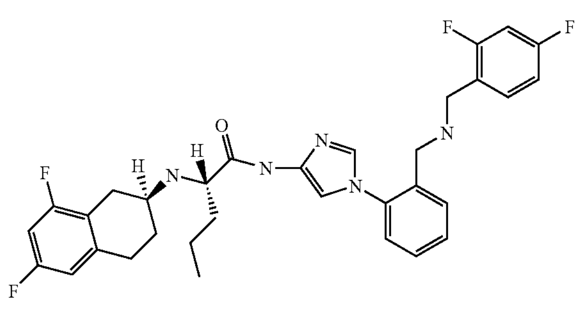 | M + 1 = 580.64 | N-[1-(2-{[(2,4-difluorobenzyl)amino]methyl}-phenyl)-1H-imidazol-4-yl]-N-2-[(2S)-6,8-difluoro-1,2,3,4-tetrahydronaphthalen-2-yl]-L-norvalinamide |

-continued

| Ex | Structure | MS or NMR data | IUPACNAME |
|---|---|---|---|
| 217 | 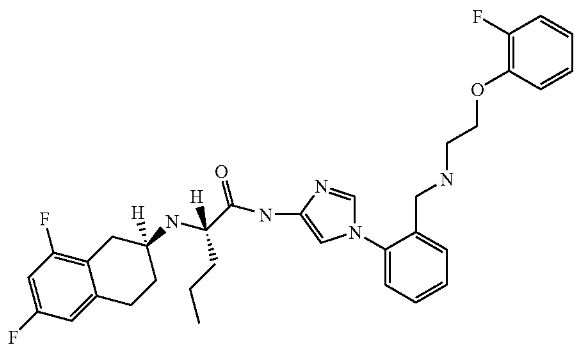 | M + 1 = 592.67 | N-2-[(2S)-6,8-difluoro-1,2,3,4-tetrahydronaphthalen-2-yl]-N-{1-[2-({[2-(2-fluorophenoxy)ethyl]amino}methyl)phenyl]-1H-imidazol-4-yl}-L-norvalinamide |
| 218 | 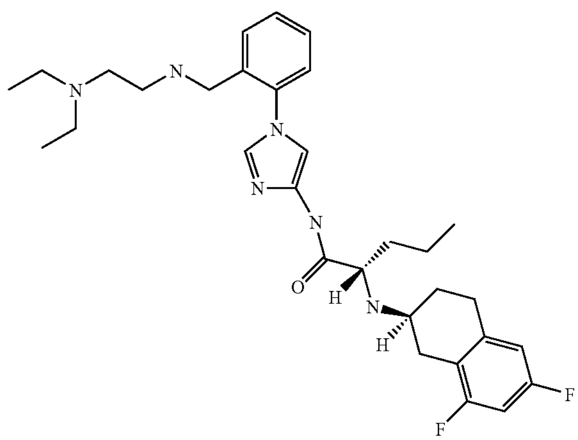 | M + 1 = 553.71 | N-{1-[2-({[2-(diethylamino)ethyl]amino}methyl)phenyl]-1H-imidazol-4-yl}-N-2-[(2S)-6,8-difluoro-1,2,3,4-tetrahydronaphthalen-2-yl]-L-norvalinamide |
| 219 | 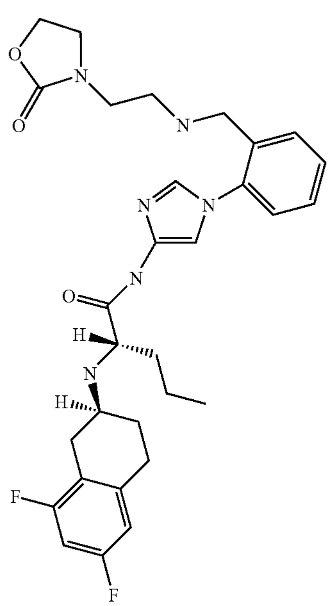 | M + 1 = 567.65 | N-2-[(2S)-6,8-difluoro-1,2,3,4-tetrahydronaphthalen-2-yl]-N-{1-[2-({[2-(2-oxo-1,3-oxazolidin-3-yl)ethyl]amino}methyl)-phenyl]-1H-imidazol-4-yl}-L-norvalinamide |

-continued

| Ex | Structure | MS or NMR data | IUPACNAME |
|---|---|---|---|
| 220 | 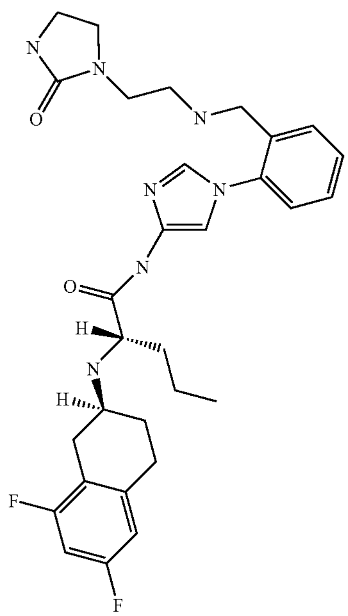 | M + 1 = 566.67 | N-2-[(2S)-6,8-difluoro-1,2,3,4-tetrahydronaphthalen-2-yl]-N-{1-[2-({[2-(2-oxoimidazolidin-1-yl)ethyl]amino}methyl)-phenyl]-1H-imidazol-4-yl}-L-norvalinamide |
| 221 | 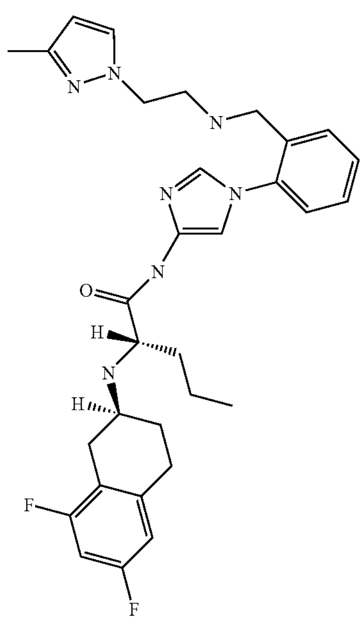 | M + 1 = 562.68 | N-2-[(2S)-6,8-difluoro-1,2,3,4-tetrahydronaphthalen-2-yl]-N-{1-[2-({[2-(3-methyl-1H-pyrazol-1-yl)ethyl]amino}methyl)-phenyl]-1H-imidazol-4-yl}-L-norvalinamide |

| Ex | Structure | MS or NMR data | IUPACNAME |
|---|---|---|---|
| 222 | 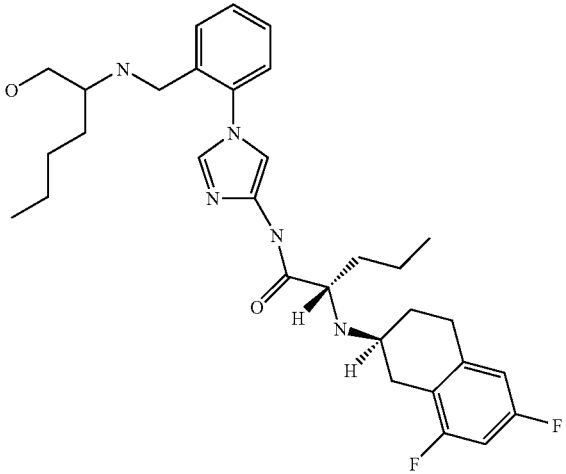 | M + 1 = 554.69 | N-2-[(2S)-6,8-difluoro-1,2,3,4-tetrahydronaphthalen-2-yl]-N-{1-[2-({[1-(hydroxymethyl)pentyl]-amino}methyl)phenyl]-1H-imidazol-4-yl}-L-norvalinamide |
| 223 | 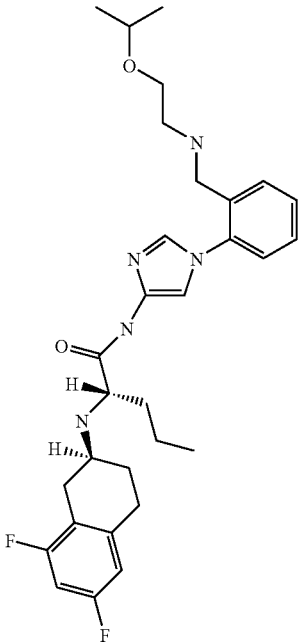 | M + 1 = 540.67 | N-2-[(2S)-6,8-difluoro-1,2,3,4-tetrahydronaphthalen-2-yl]-N-[1-(2-{[(2-isopropoxyethyl)amino]-methyl}phenyl)-1H-imidazol-4-yl]-L-norvalinamide |

-continued

| Ex | Structure | MS or NMR data | IUPACNAME |
|---|---|---|---|
| 224 | 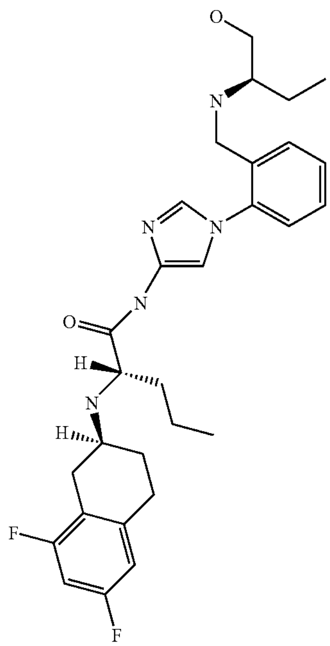 | M + 1 = 526.64 | N-2-[(2S)-6,8-difluoro-1,2,3,4-tetrahydronaphthalen-2-yl]-N-{1-[2-({[(1R)-1-(hydroxymethyl)propyl]-amino}methyl)phenyl]-1H-imidazol-4-yl}-L-norvalinamide |
| 225 | 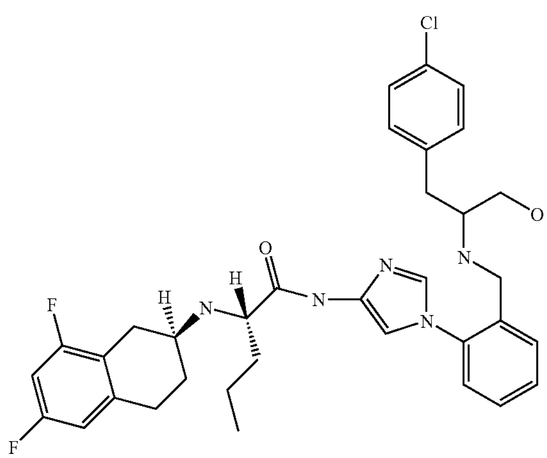 | M + 1 = 623.16 | N-{1-[2-({[1-(4-chlorobenzyl)-2-hydroxyethyl]amino}methyl)phenyl]-1H-imidazol-4-yl}-N-2-[(2S)-6,8-difluoro-1,2,3,4-tetrahydronaphthalen-2-yl]-L-norvalinamide |

-continued

| Ex | Structure | MS or NMR data | IUPACNAME |
|---|---|---|---|
| 226 | 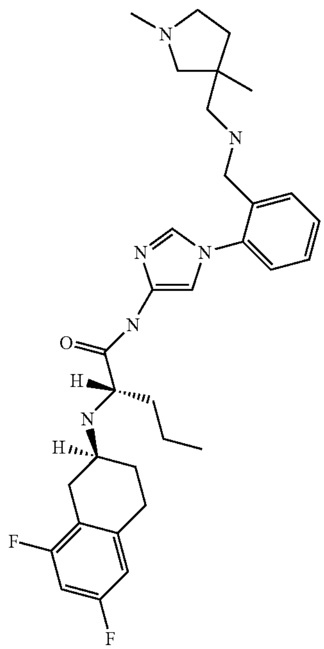 | M + 1 = 565.72 | N-2-[(2S)-6,8-difluoro-1,2,3,4-tetrahydronaphthalen-2-yl]-N-{1-[2-({[(1,3-dimethylpyrrolidin-3-yl)methyl]amino}methyl)-phenyl]-1H-imidazol-4-yl}-L-norvalinamide |
| 227 | 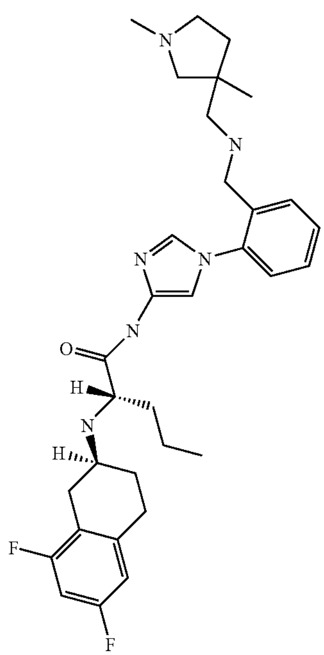 | M + 1 = 565.72 | N-2-[(2S)-6,8-difluoro-1,2,3,4-tetrahydronaphthalen-2-yl]-N-{1-[2-({[(1,3-dimethylpyrrolidin-3-yl)methyl]amino}methyl)-phenyl]-1H-imidazol-4-yl}-L-norvalinamide |
| 228 | 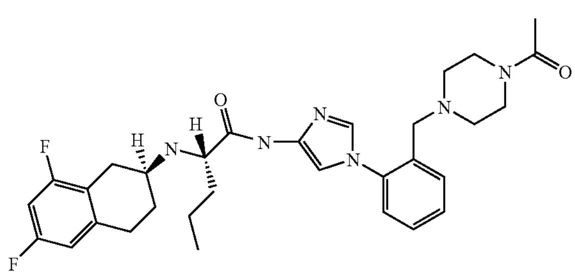 | M + 1 = 565.68 | N-(1-{2-[(4-acetylpiperazin-1-yl)methyl]phenyl}-1H-imidazol-4-yl)-N-2-[(2S)-6,8-difluoro-1,2,3,4-tetrahydronaphthalen-2-yl]-L-norvalinamide |

-continued

| Ex | Structure | MS or NMR data | IUPACNAME |
|---|---|---|---|
| 229 | 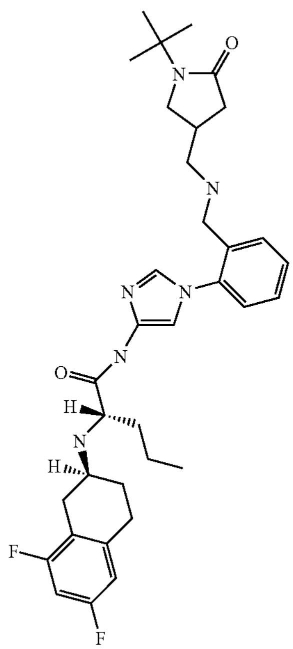 | M + 1 = 607.76 | N-{1-[2-({[(1-tert-butyl-5-oxopyrrolidin-3-yl)methyl]amino}methyl)-phenyl]-1H-imidazol-4-yl}-N-2-[(2S)-6,8-difluoro-1,2,3,4-tetrahydronaphthalen-2-yl]-L-norvalinamide |
| 230 | 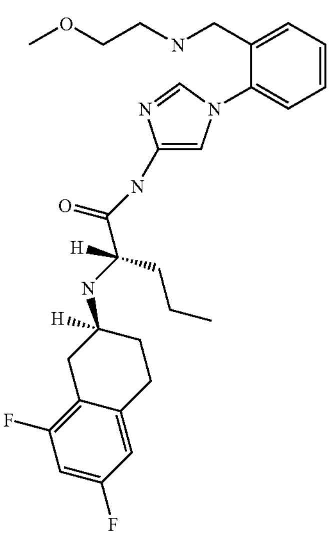 | M + 1 = 512.61 | N-2-[(2S)-6,8-difluoro-1,2,3,4-tetrahydronaphthalen-2-yl]-N-[1-(2-{[(2-methoxyethyl)amino]methyl}-phenyl)-1H-imidazol-4-yl]-L-norvalinamide |

-continued

| Ex | Structure | MS or NMR data | IUPACNAME |
|---|---|---|---|
| 231 | 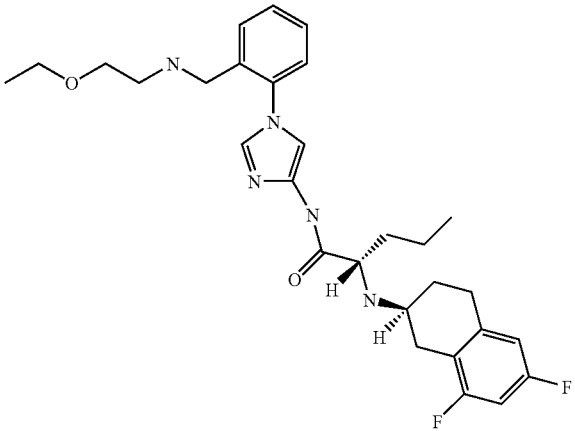 | M + 1 = 526.64 | N-2-[(2S)-6,8-difluoro-1,2,3,4-tetrahydronaphthalen-2-yl]-N-[1-(2-{[(2-ethoxyethyl)amino]methyl}-phenyl)-1H-imidazol-4-yl]-L-norvalinamide |
| 232 | 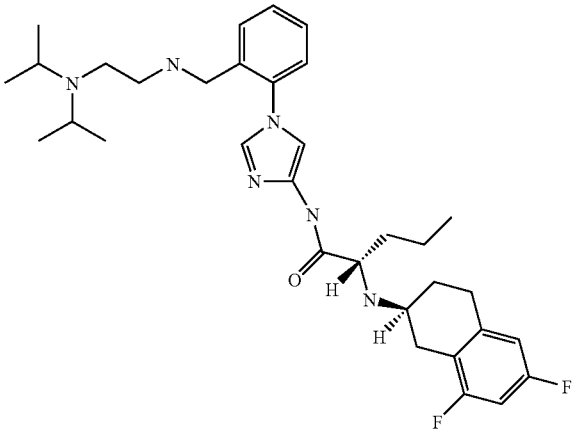 | M + 1 = 581.76 | N-2-[(2S)-6,8-difluoro-1,2,3,4-tetrahydronaphthalen-2-yl]-N-{1-[2-({[2-(diisopropylamino)ethyl]-amino}methyl)phenyl]-1H-imidazol-4-yl}-L-norvalinamide |
| 233 | 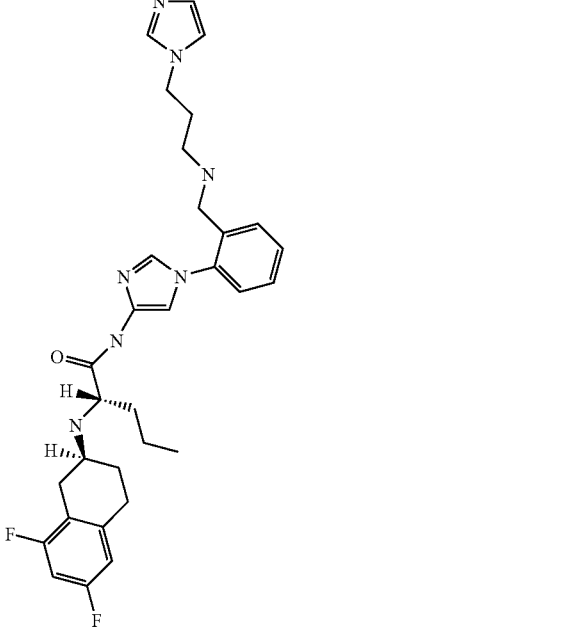 | M + 1 = 562.68 | N-2-[(2S)-6,8-difluoro-1,2,3,4-tetrahydronaphthalen-2-yl]-N-{1-[2-({[3-(1H-imidazol-1-yl)propyl]amino}methyl)-phenyl]-1H-imidazol-4-yl}-L-norvalinamide |

-continued

| Ex | Structure | MS or NMR data | IUPACNAME |
|---|---|---|---|
| 234 | 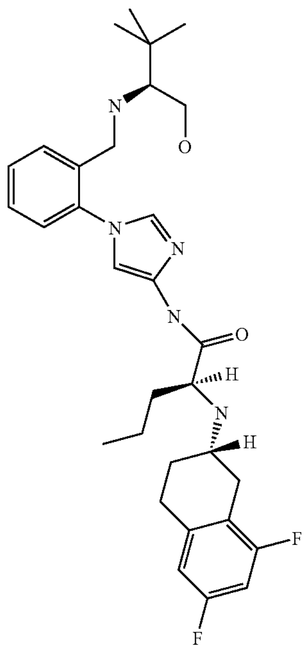 | M + 1 = 554.69 | N-2-[(2S)-6,8-difluoro-1,2,3,4-tetrahydronaphthalen-2-yl]-N-{1-[2-({[(1S)-1-(hydroxymethyl)-2,2-dimethylpropyl]amino}-methyl)phenyl]-1H-imidazol-4-yl}-L-norvalinamide |
| 235 | 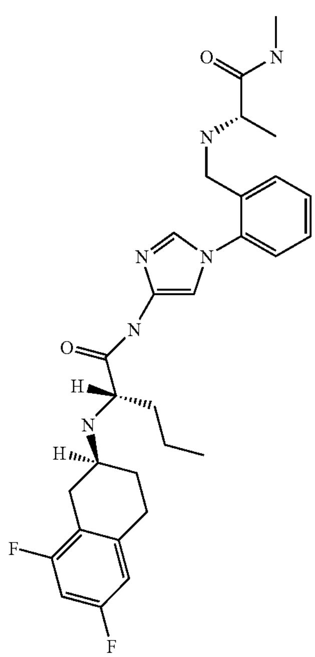 | M + 1 = 539.64 | N-2-[(2S)-6,8-difluoro-1,23,4-tetrahydronaphthalen-2-yl]-N-{1-[2-({[(1S)-1-methyl-2-(methylamino)-2-oxoethyl]amino}methyl)-phenyl]-1H-imidazol-4-yl}-L-norvalinamide |

-continued

| Ex | Structure | MS or NMR data | IUPACNAME |
|---|---|---|---|
| 236 | 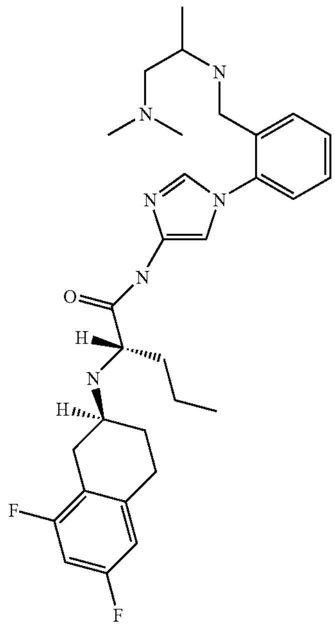 | M + 1 = 539.68 | N-2-[(2S)-6,8-difluoro-1,2,3,4-tetrahydronaphthalen-2-yl]-N-{1-[2-({[2-(dimethylamino)-1-methylethyl]amino}methyl)-phenyl]-1H-imidazol-4-yl}-L-norvalinamide |
| 237 | 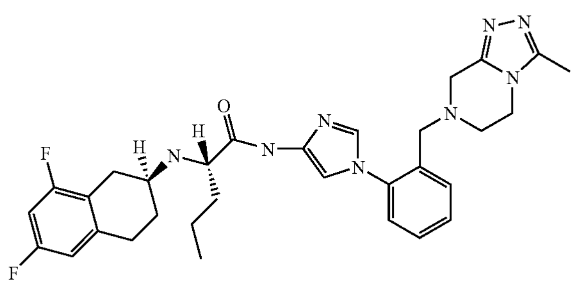 | M + 1 = 575.68 | N-2-[(2S)-6,8-difluoro-1,2,3,4-tetrahydronaphthalen-2-yl]-N-(1-{2-[(3-methyl-5,6-dihydro[1,2,4]triazolo[4,3-a]pyrazin-7(8H)-yl)methyl]phenyl}-1H-imidazol-4-yl)-L-norvalinamide |
| 238 | 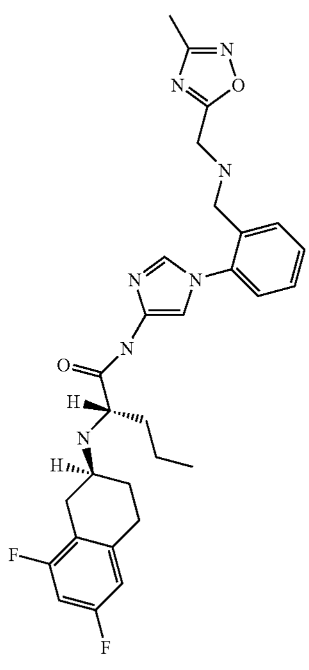 | M + 1 = 550.62 | N-2-[(2S)-6,8-difluoro-1,2,3,4-tetrahydronaphthalen-2-yl]-N-{1-[2-({[(3-methyl-1,2,4-oxadiazol-5-yl)methyl]amino}methyl)-phenyl]-1H-imidazol-4-yl}-L-norvalinamide |

-continued

| Ex | Structure | MS or NMR data | IUPACNAME |
|---|---|---|---|
| 239 | 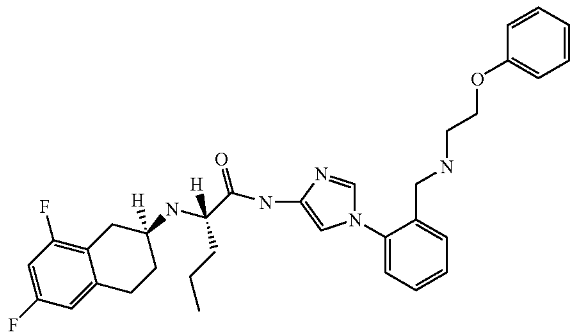 | M + 1 = 574.68 | N-2-[(2S)-6,8-difluoro-1,2,3,4-tetrahydronaphthalen-2-yl]-N-[1-(2-{[(2-phenoxyethyl)amino]methyl}-phenyl)-1H-imidazol-4-yl]-L-norvalinamide |
| 240 | 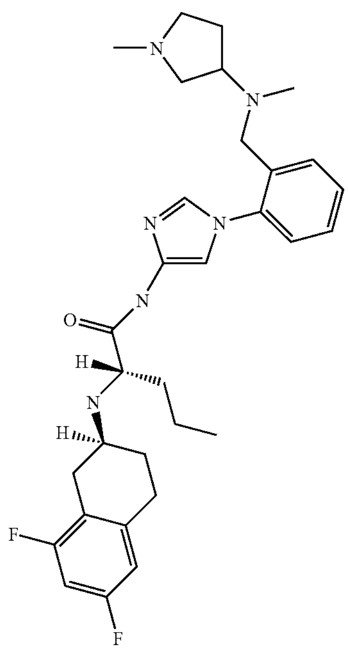 | M + 1 = 551.69 | N-2-[(2S)-6,8-difluoro-1,2,3,4-tetrahydronaphthalen-2-yl]-N-[1-(2-{[methyl(1-methylpyrrolidin-3-yl)amino]methyl}phenyl)-1H-imidazol-4-yl]-L-norvalinamide |
| 241 | 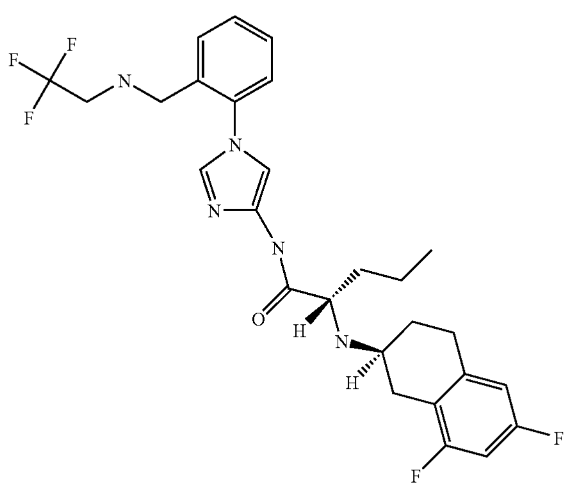 | M + 1 = 536.56 | N-2-[(2S)-6,8-difluoro-1,2,3,4-tetrahydronaphthalen-2-yl]-N-[1-(2-{[(2,2,2-trifluoroethyl)amino]methyl}phenyl)-1H-imidazol-4-yl]-L-norvalinamide |

-continued

| Ex | Structure | MS or NMR data | IUPACNAME |
|---|---|---|---|
| 242 | 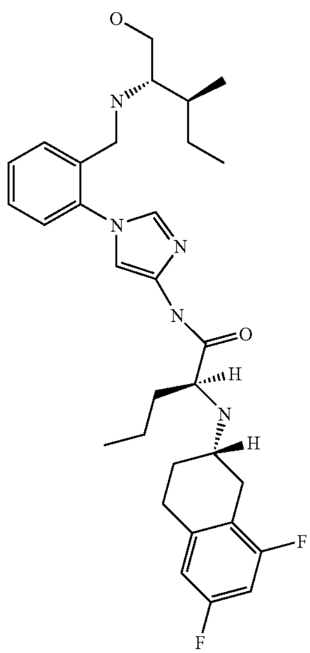 | M + 1 = 554.69 | N-2-[(2S)-6,8-difluoro-1,2,3,4-tetrahydronaphthalen-2-yl]-N-{1-[2-({[(1S,2S)-1-(hydroxymethyl)-2-methylbutyl]amino}methyl)-phenyl]-1H-imidazol-4-yl}-L-norvalinamide |
| 243 | 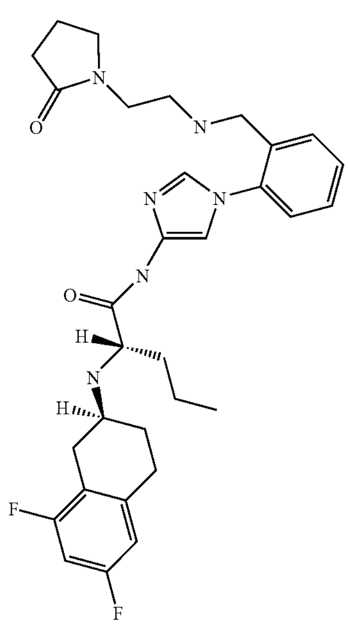 | M + 1 = 565.68 | N-2-[(2S)-6,8-difluoro-1,2,3,4-tetrahydronaphthalen-2-yl]-N-{1-[2-({[2-(2-oxopyrrolidin-1-yl)ethyl]amino}methyl)-phenyl]-1H-imidazol-4-yl}-L-norvalinamide |

-continued

| Ex | Structure | MS or NMR data | IUPACNAME |
|---|---|---|---|
| 244 | 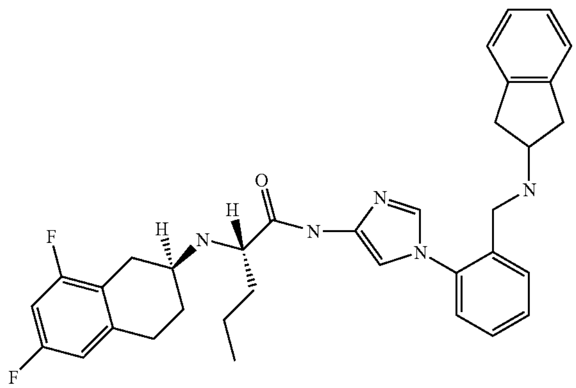 | M + 1 = 570.7 | N-2-[(2S)-6,8-difluoro-1,2,3,4-tetrahydronaphthalen-2-yl]-N-(1-{2-[(2,3-dihydro-1H-inden-2-ylamino)methyl]phenyl}-1H-imidazol-4-yl)-L-norvalinamide |
| 245 | 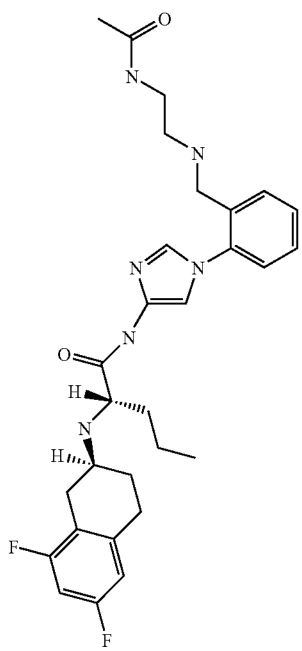 | M + 1 = 539.64 | N-{1-[2-({[2-(acetylamino)ethyl]amino}-methyl)phenyl]-1H-imidazol-4-yl}-N-2-[(2S)-6,8-difluoro-1,2,3,4-tetrahydronaphthalen-2-yl]-L-norvalinamide |
| 246 | 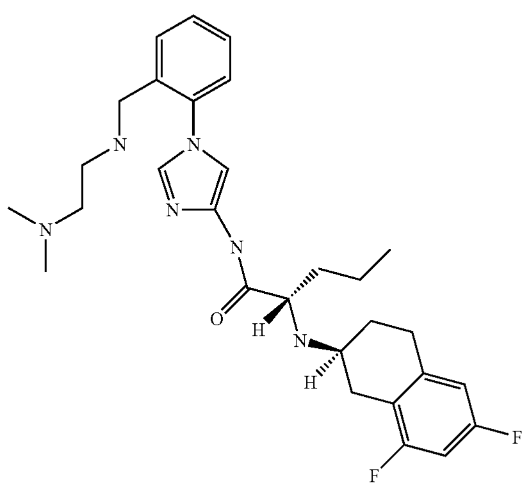 | M + 1 = 525.66 | N-2-[(2S)-6,8-difluoro-1,2,3,4-tetrahydronaphthalen-2-yl]-N-{1-[2-({[2-(dimethylamino)ethyl]-amino}methyl)phenyl]-1H-imidazol-4-yl}-L-norvalinamide |

-continued

| Ex | Structure | MS or NMR data | IUPACNAME |
|---|---|---|---|
| 247 | 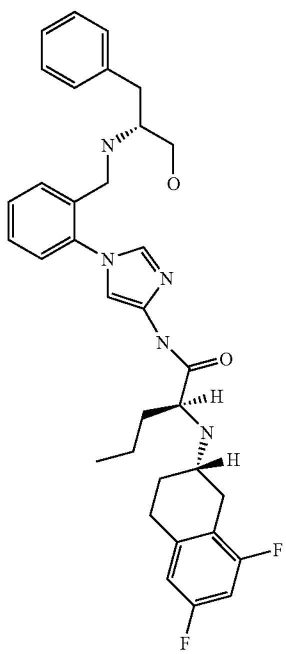 | M + 1 = 588.71 | N-{1-[2-({[(1R)-1-benzyl-2-hydroxyethyl]amino}methyl)phenyl]-1H-imidazol-4-yl}-N-2-[(2S)-6,8-difluoro-1,2,3,4-tetrahydronaphthalen-2-yl]-L-norvalinamide |
| 248 | 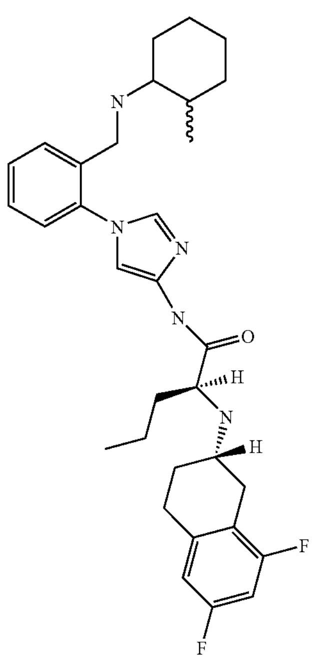 | M + 1 = 550.71 | N-2-[(2S)-6,8-difluoro-1,2,3,4-tetrahydronaphthalen-2-yl]-N-[1-(2-{[(2-methylcyclohexyl)amino]methyl}phenyl)-1H-imidazol-4-yl]-L-norvalinamide |

-continued

| Ex | Structure | MS or NMR data | IUPACNAME |
|---|---|---|---|
| 249 | 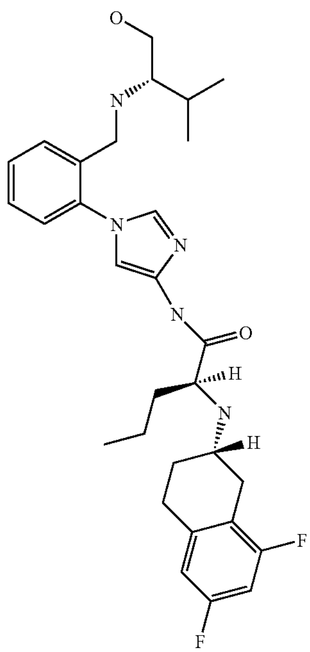 | M + 1 = 540.67 | N-2-[(2S)-6,8-difluoro-1,2,3,4-tetrahydronaphthalen-2-yl]-N-{1-[2-({[(1S)-1-(hydroxymethyl)-2-methylpropyl]amino}methyl)phenyl]-1H-imidazol-4-yl}-L-norvalinamide |
| 250 | 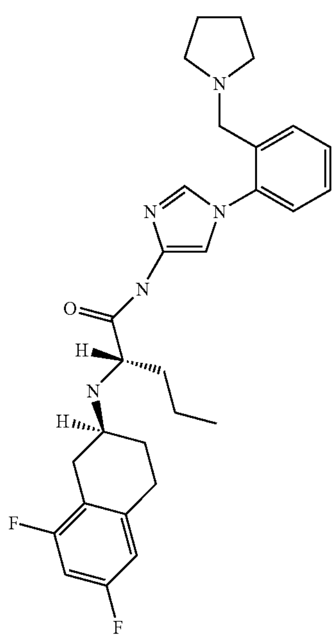 | M + 1 = 508.63 | N-2-[(2S)-6,8-difluoro-1,2,3,4-tetrahydronaphthalen-2-yl]-N-{1-[2-(pyrrolidin-1-ylmethyl)phenyl]-1H-imidazol-4-yl}-L-norvalinamide |

-continued

| Ex | Structure | MS or NMR data | IUPAC NAME |
|---|---|---|---|
| 251 | 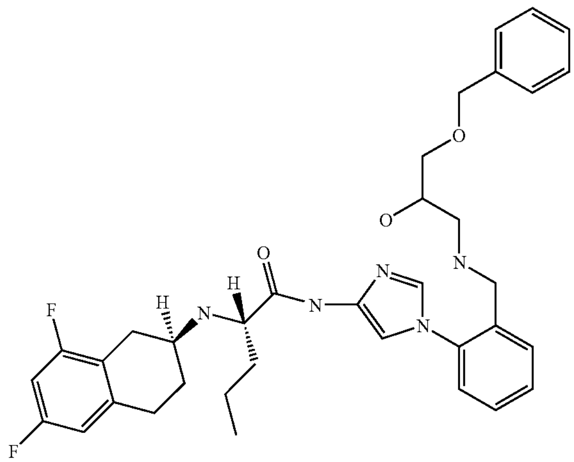 | M + 1 = 618.74 | N-{1-[2-({[3-(benzyloxy)-2-hydroxypropyl]amino}methyl)-phenyl]-1H-imidazol-4-yl}-N-2-[(2S)-6,8-difluoro-1,2,3,4-tetrahydronaphthalen-2-yl]-L-norvalinamide |
| 252 | 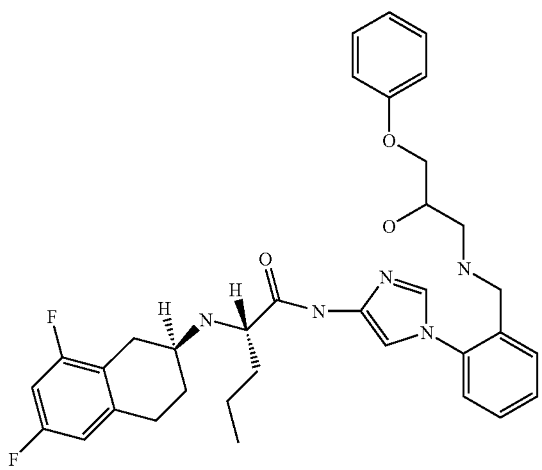 | M + 1 = 604.71 | N-2-[(2S)-6,8-difluoro-1,2,3,4-tetrahydronaphthalen-2-yl]-N-[1-(2-{[(2-hydroxy-3-phenoxypropyl)amino]-methyl}phenyl)-1H-imidazol-4-yl]-L-norvalinamide |
| 253 | 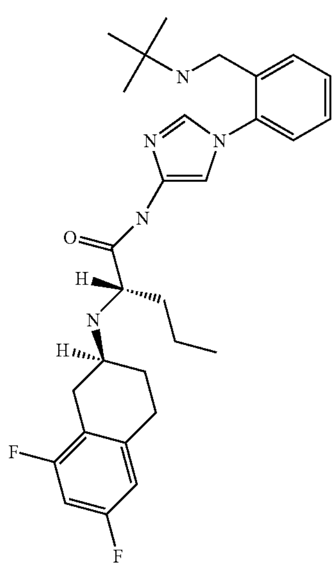 | M + 1 = 510.64 | N-(1-{2-[(tert-butylamino)methyl]phenyl}-1H-imidazol-4-yl)-N-2-[(2S)-6,8-difluoro-1,2,3,4-tetrahydronaphthalen-2-yl]-L-norvalinamide |

-continued

| Ex | Structure | MS or NMR data | IUPACNAME |
|---|---|---|---|
| 254 | 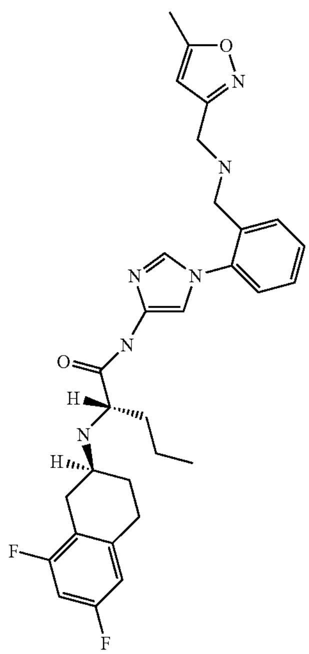 | M + 1 = 549.64 | N-2-[(2S)-6,8-difluoro-1,2,3,4-tetrahydronaphthalen-2-yl]-N-{1-[2-({[(5-methylisoxazol-3-yl)methyl]amino}methyl)-phenyl]-1H-imidazol-4-yl}-L-norvalinamide |
| 255 | 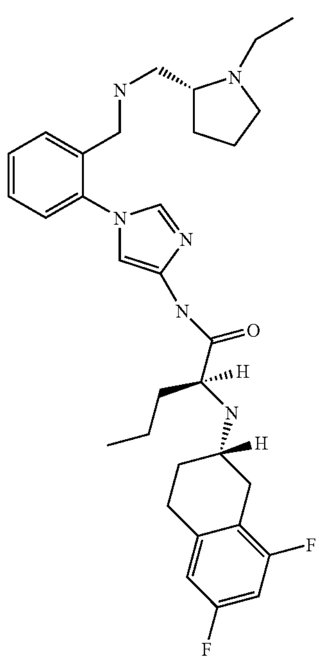 | M + 1 = 565.72 | N-2-[(2S)-6,8-difluoro-1,2,3,4-tetrahydronaphthalen-2-yl]-N-(1-{2-[({[(2R)-1-ethylpyrrolidin-2-yl]methyl}amino)methyl]-phenyl}-1H-imidazol-4-yl)-L-norvalinamide |

-continued

| Ex | Structure | MS or NMR data | IUPACNAME |
|---|---|---|---|
| 256 | 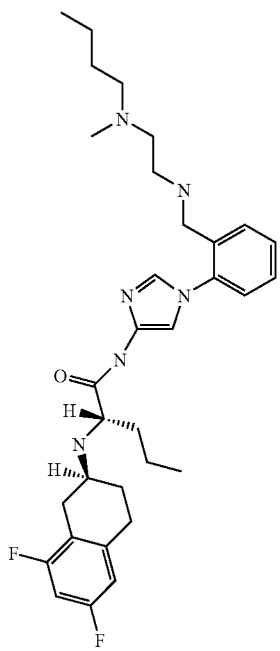 | M + 1 = 567.74 | N-(1-{2-[({2-[butyl(methyl)amino]ethyl}-amino)methyl]phenyl}-1H-imidazol-4-yl)-N-2-[(2S)-6,8-difluoro-1,2,3,4-tetrahydronaphthalen-2-yl]-L-norvalinamide |
| 257 | 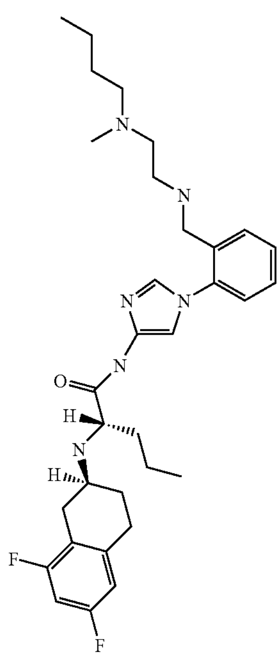 | M + 1 = 567.74 | N-(1-{2-[({2-[butyl(methyl)amino]ethyl}-amino)methyl]phenyl}-1H-imidazol-4-yl)-N-2-[(2S)-6,8-difluoro-1,2,3,4-tetrahydronaphthalen-2-yl]-L-norvalinamide |

-continued

| Ex | Structure | MS or NMR data | IUPACNAME |
|---|---|---|---|
| 258 | 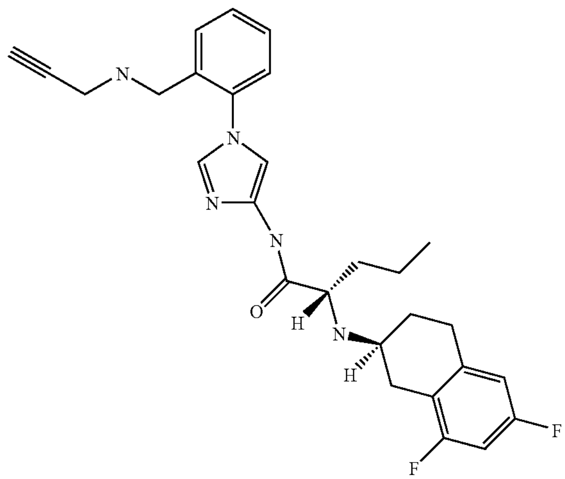 | M + 1 = 492.58 | N-2-[(2S)-6,8-difluoro-1,2,3,4-tetrahydronaphthalen-2-yl]-N-(1-{2-[(prop-2-yn-1-ylamino)methyl]phenyl}-1H-imidazol-4-yl)-L-norvalinamide |
| 259 | 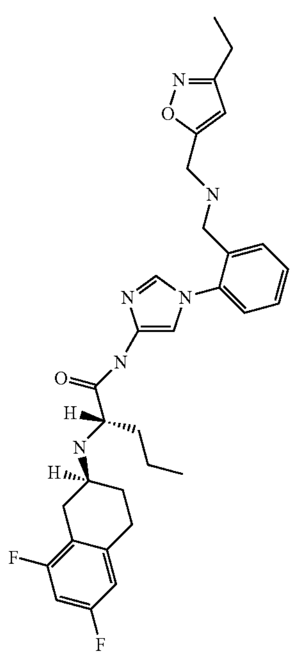 | M + 1 = 563.66 | N-2-[(2S)-6,8-difluoro-1,2,3,4-tetrahydronaphthalen-2-yl]-N-{1-[2-({[(3-ethylisoxazol-5-yl)methyl]amino}methyl)-phenyl]-1H-imidazol-4-yl}-L-norvalinamide |

-continued

| Ex | Structure | MS or NMR data | IUPACNAME |
|---|---|---|---|
| 260 | 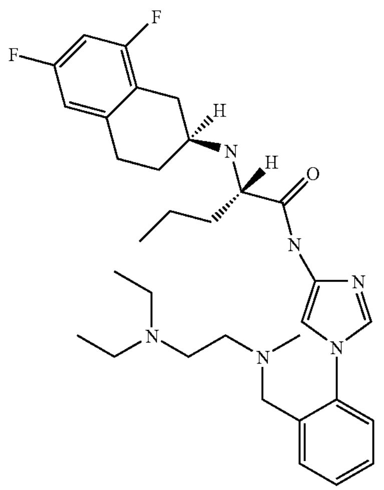 | M + 1 = 567.74 | N-{1-[2-({[2-(diethylamino)ethyl](methyl)amino}methyl)phenyl]-1H-imidazol-4-yl}-N-2-[(2S)-6,8-difluoro-1,2,3,4-tetrahydronaphthalen-2-yl]-L-norvalinamide |
| 261 | 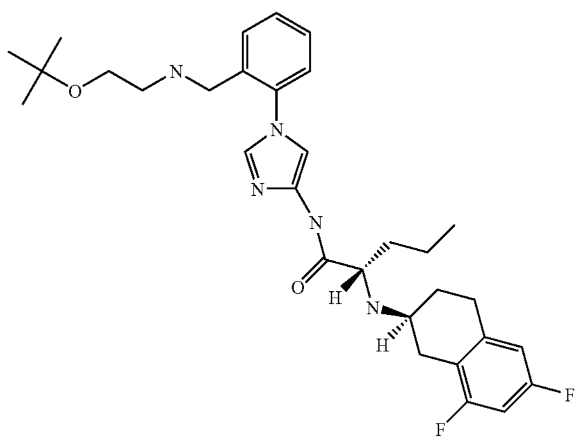 | M + 1 = 554.69 | N-[1-(2-{[(2-tert-butoxyethyl)amino]methyl}-phenyl)-1H-imidazol-4-yl]-N-2-[(2S)-6,8-difluoro-1,2,3,4-tetrahydronaphthalen-2-yl]-L-norvalinamide |
| 262 | 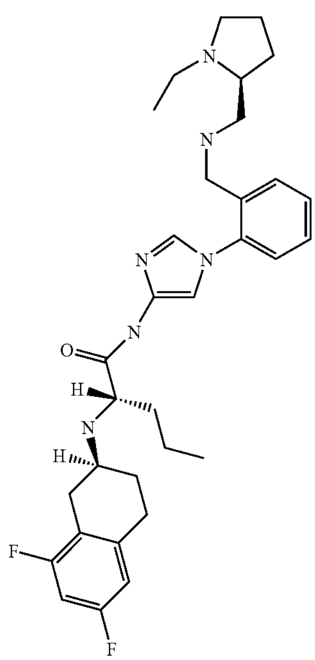 | M + 1 = 565.72 | N-2-[(2S)-6,8-difluoro-1,2,3,4-tetrahydronaphthalen-2-yl]-N-(1-{2-[({[(2S)-1-ethylpyrrolidin-2-yl]methyl}amino)methyl]-phenyl}-1H-imidazol-4-yl)-L-norvalinamide |

-continued

| Ex | Structure | MS or NMR data | IUPACNAME |
|---|---|---|---|
| 263 | 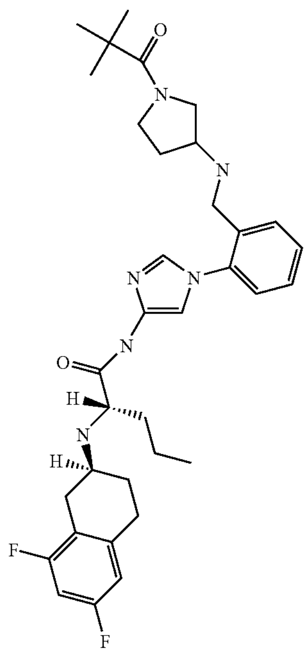 | M + 1 = 607.76 | N-2-[(2S)-6,8-difluoro-1,2,3,4-tetrahydronaphthalen-2-yl]-N-{1-[2-({[1-(2,2-dimethylpropanoyl)-pyrrolidin-3-yl]amino}methyl)phenyl]-1H-imidazol-4-yl}-L-norvalinamide |
| 264 | 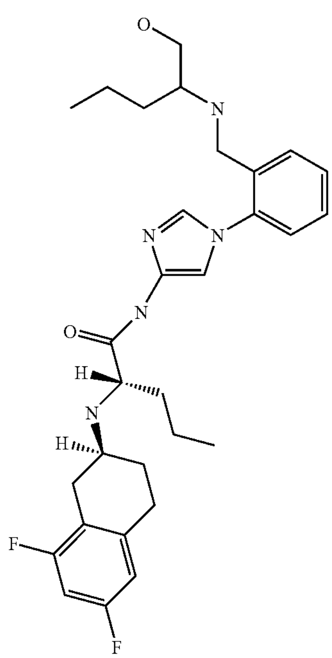 | M + 1 = 540.67 | N-2-[(2S)-6,8-difluoro-1,2,3,4-tetrahydronaphthalen-2-yl]-N-{1-[2-({[1-(hydroxymethyl)butyl]-amino}methyl)phenyl]-1H-imidazol-4-yl}-L-norvalinamide |

-continued

| Ex | Structure | MS or NMR data | IUPACNAME |
|---|---|---|---|
| 265 | 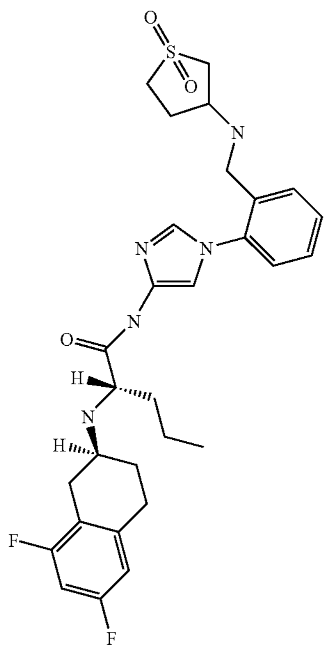 | M + 1 = 572.69 | N-2-[(2S)-6,8-difluoro-1,2,3,4-tetrahydronaphthalen-2-yl]-N-[1-(2-{[(1,1-dioxidotetrahydro-3-thienyl)amino]methyl}phenyl)-1H-imidazol-4-yl]-L-norvalinamide |
| 266 | 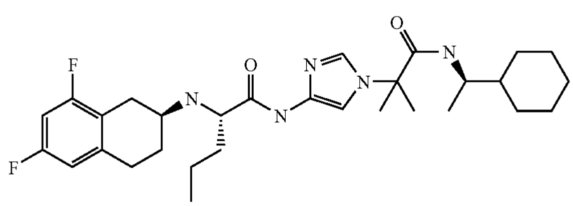 | M + 1 = 544.28 | N-[1-(2-{[(1R)-1-cyclohexylethyl]amino}-1,1-dimethyl-2-oxoethyl)-1H-imidazol-4-yl]-N-2-[(2S)-6,8-difluoro-1,2,3,4-tetrahydronaphthalen-2-yl]-L-norvalinamide |
| 267 | 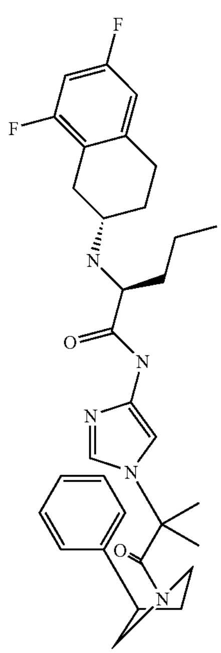 | M + 1 = 564.29 | N-2-[(2S)-6,8-difluoro-1,2,3,4-tetrahydronaphthalen-2-yl]-N-{1-[1,1-dimethyl-2-oxo-2-(3-phenylpyrrolidin-1-yl)ethyl]-1H-imidazol-4-yl}-L-norvalinamide |

-continued

| Ex | Structure | MS or NMR data | IUPACNAME |
|---|---|---|---|
| 268 | 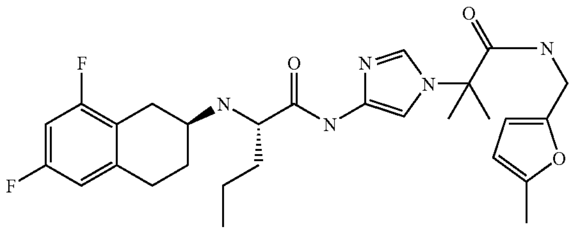 | M + 1 = 528.25 | N-2-[(2S)-6,8-difluoro-1,2,3,4-tetrahydronaphthalen-2-yl]-N-[1-(1,1-dimethyl-2-{[(5-methyl-2-furyl)methyl]amino}-2-oxoethyl)-1H-imidazol-4-yl]-L-norvalinamide |
| 269 | 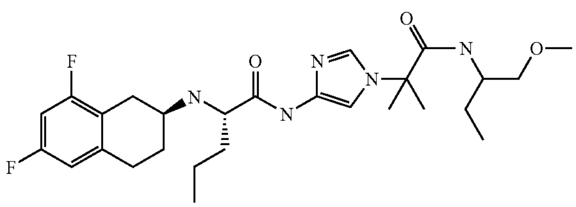 | M + 1 = 520.3 | N-2-[(2S)-6,8-difluoro-1,2,3,4-tetrahydronaphthalen-2-yl]-N-[1-(2-{[1-(methoxymethyl)propyl]amino}-1,1-dimethyl-2-oxoethyl)-1H-imidazol-4-yl]-L-norvalinamide |
| 270 | 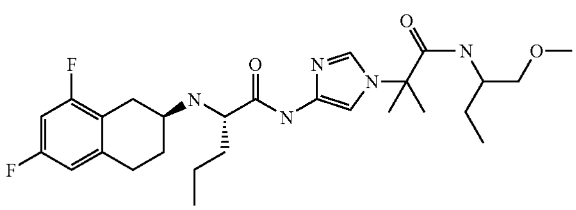 | M + 1 = 520.28 | N-2-[(2S)-6,8-difluoro-1,2,3,4-tetrahydronaphthalen-2-yl]-N-[1-(2-{[1-(methoxymethyl)propyl]amino}-1,1-dimethyl-2-oxoethyl)-1H-imidazol-4-yl]-L-norvalinamide |
| 271 | 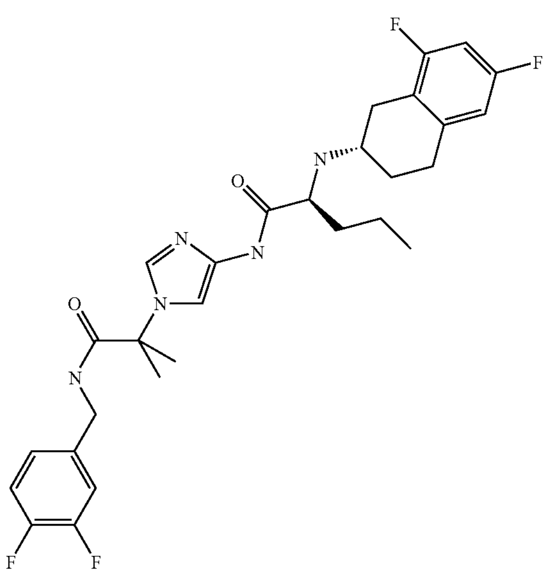 | M + 1 = 560.22 | N-(1-{2-[(3,4-difluorobenzyl)amino]-1,1-dimethyl-2-oxoethyl}-1H-imidazol-4-yl)-N-2-[(2S)-6,8-difluoro-1,2,3,4-tetrahydronaphthalen-2-yl]-L-norvalinamide |

-continued

| Ex | Structure | MS or NMR data | IUPACNAME |
|---|---|---|---|
| 272 | 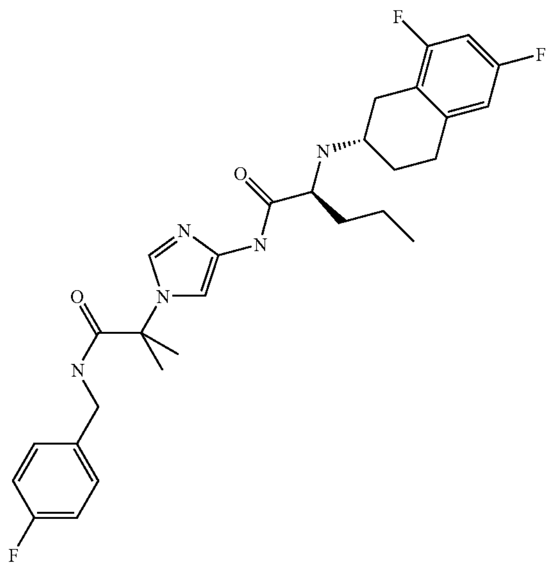 | M + 1 = 542.25 | N-2-[(2S)-6,8-difluoro-1,2,3,4-tetrahydronaphthalen-2-yl]-N-(1-{2-[(4-fluorobenzyl)amino]-1,1-dimethyl-2-oxoethyl}-1H-imidazol-4-yl)-L-norvalinamide |
| 273 | 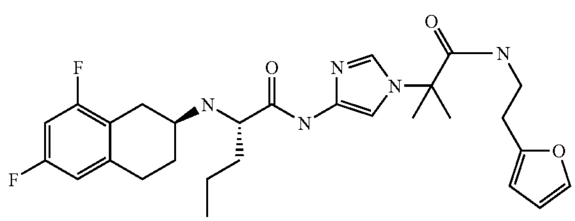 | M + 1 = 528.28 | N-2-[(2S)-6,8-difluoro-1,2,3,4-tetrahydronaphthalen-2-yl]-N-[1-(2-{[2-(2-furyl)ethyl]amino}-1,1-dimethyl-2-oxoethyl)-1H-imidazol-4-yl]-L-norvalinamide |
| 274 | 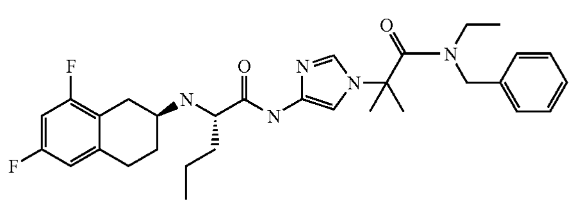 | M + 1 = 552.12 | N-(1-{2-[benzyl(ethyl)amino]-1,1-dimethyl-2-oxoethyl}-1H-imidazol-4-yl)-N-2-[(2S)-6,8-difluoro-1,2,3,4-tetrahydronaphthalen-2-yl]-L-norvalinamide |
| 275 | 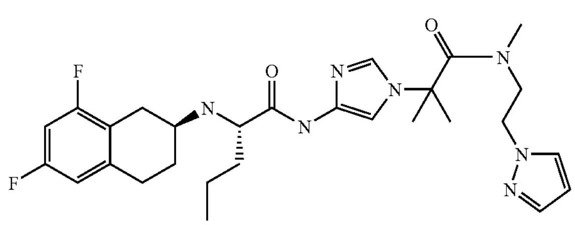 | M + 1 = 548.25 | N-2-[(2S)-6,8-difluoro-1,2,3,4-tetrahydronaphthalen-2-yl]-N-[1-(1,1-dimethyl-2-{methyl[2-(1H-pyrazol-1-yl)ethyl]amino}-2-oxoethyl)-1H-imidazol-4-yl]-L-norvalinamide |
| 276 | 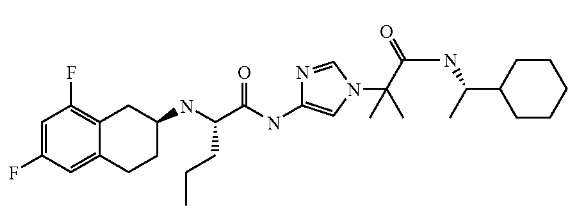 | M + 1 = 544.31 | N-[1-(2-{[(1S)-1-cyclohexylethyl]amino}-1,1-dimethyl-2-oxoethyl)-1H-imidazol-4-yl]-N-2-[(2S)-6,8-difluoro-1,2,3,4-tetrahydronaphthalen-2-yl]-L-norvalinamide |

-continued

| Ex | Structure | MS or NMR data | IUPACNAME |
|---|---|---|---|
| 277 | 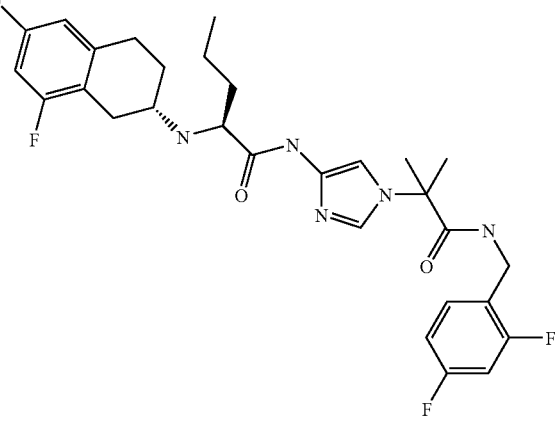 | M + 1 = 560.2 | N-(1-{2-[(2,4-difluorobenzyl)amino]-1,1-dimethyl-2-oxoethyl}-1H-imidazol-4-yl)-N-2-[(2S)-6,8-difluoro-1,2,3,4-tetrahydronaphthalen-2-yl]-L-norvalinamide |
| 278 | 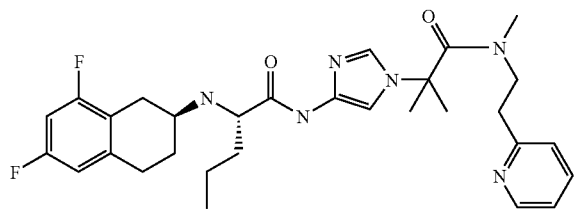 | M + 1 = 553.23 | N-2-[(2S)-6,8-difluoro-1,2,3,4-tetrahydronaphthalen-2-yl]-N-(1-{1,1-dimethyl-2-[methyl(2-pyridin-2-ylethyl)amino]-2-oxoethyl}-1H-imidazol-4-yl)-L-norvalinamide |
| 279 | 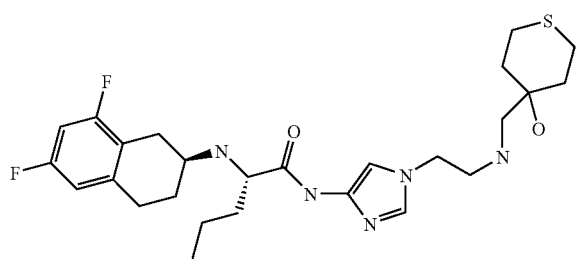 | data not available | N-2-[(2S)-6,8-difluoro-1,2,3,4-tetrahydronaphthalen-2-yl]-N-[1-(2-{[(4-hydroxytetrahydro-2H-thiopyran-4-yl)methyl]amino}ethyl)-1H-imidazol-4-yl]-L-norvalinamide |
| 280 | 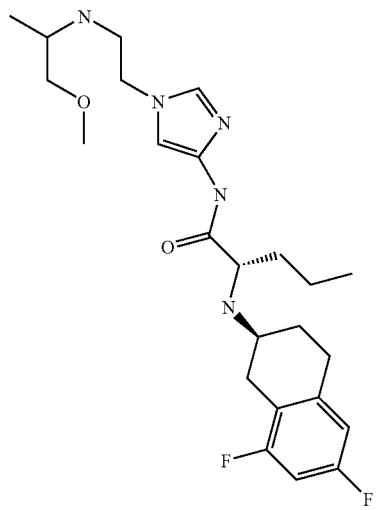 | M + 1 = 464.2 | N-2-[(2S)-6,8-difluoro-1,2,3,4-tetrahydronaphthalen-2-yl]-N-(1-{2-[(2-methoxy-1-methylethyl)amino]ethyl}-1H-imidazol-4-yl)-L-norvalinamide |

-continued

| Ex | Structure | MS or NMR data | IUPACNAME |
|---|---|---|---|
| 281 | 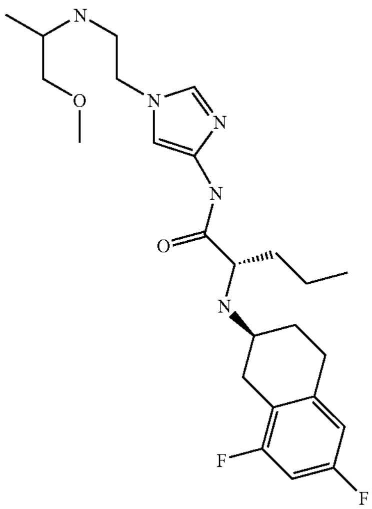 | data not available | N-2-[(2S)-6,8-difluoro-1,2,3,4-tetrahydronaphthalen-2-yl]-N-(1-{2-[(2-methoxy-1-methylethyl)amino]ethyl}-1H-imidazol-4-yl)-L-norvalinamide |
| 282 | 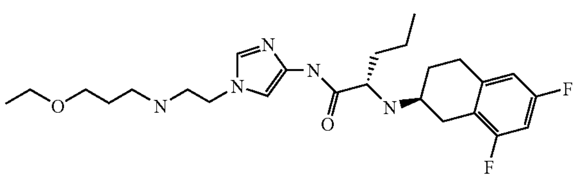 | data not available | N-2-[(2S)-6,8-difluoro-1,2,3,4-tetrahydronaphthalen-2-yl]-N-(1-{2-[(3-ethoxypropyl)amino]ethyl}-1H-imidazol-4-yl)-L-norvalinamide |
| 283 | 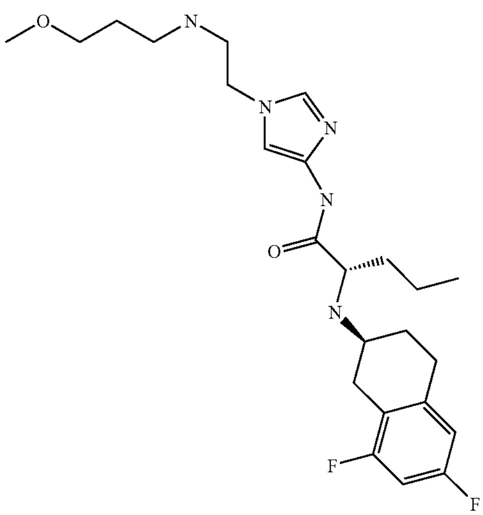 | M + 1 = 464.3 | N-2-[(2S)-6,8-difluoro-1,2,3,4-tetrahydronaphthalen-2-yl]-N-(1-{2-[(3-methoxypropyl)amino]ethyl}-1H-imidazol-4-yl)-L-norvalinamide |
| 284 | 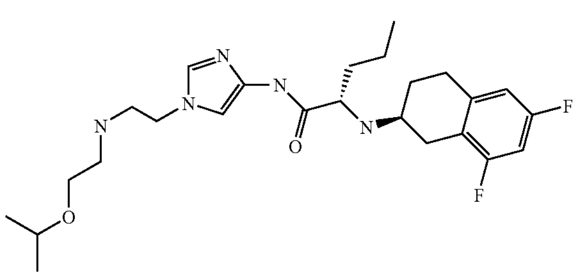 | M + 1 = 478.3 | N-2-[(2S)-6,8-difluoro-1,2,3,4-tetrahydronaphthalen-2-yl]-N-(1-{2-[(2-isopropoxyethyl)amino]ethyl}-1H-imidazol-4-yl)-L-norvalinamide |

-continued

| Ex | Structure | MS or NMR data | IUPACNAME |
|---|---|---|---|
| 285 | 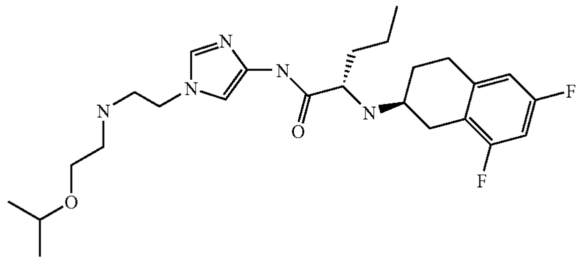 | data not available | N-2-[(2S)-6,8-difluoro-1,2,3,4-tetrahydronaphthalen-2-yl]-N-(1-{2-[(2-isopropoxyethyl)amino]-ethyl}-1H-imidazol-4-yl)-L-norvalinamide |
| 286 | 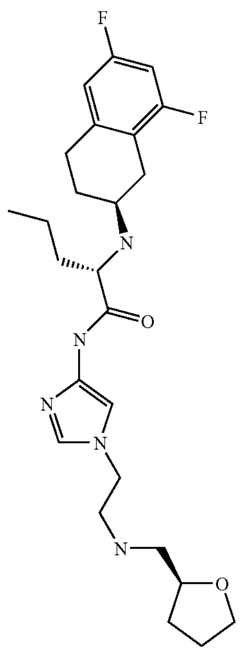 | M + 1 = 476.3 | N-2-[(2S)-6,8-difluoro-1,2,3,4-tetrahydronaphthalen-2-yl]-N-[1-(2-{[(2S)-tetrahydrofuran-2-ylmethyl]amino}ethyl)-1H-imidazol-4-yl]-L-norvalinamide |
| 287 | 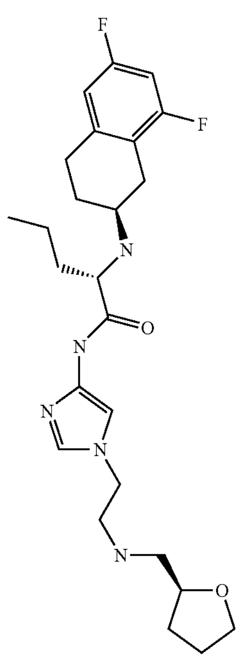 | data not available | N-2-[(2S)-6,8-difluoro-1,2,3,4-tetrahydronaphthalen-2-yl]-N-[1-(2-{[(2S)-tetrahydrofuran-2-ylmethyl]amino}ethyl)-1H-imidazol-4-yl]-L-norvalinamide |

-continued

| Ex | Structure | MS or NMR data | IUPACNAME |
|---|---|---|---|
| 288 | 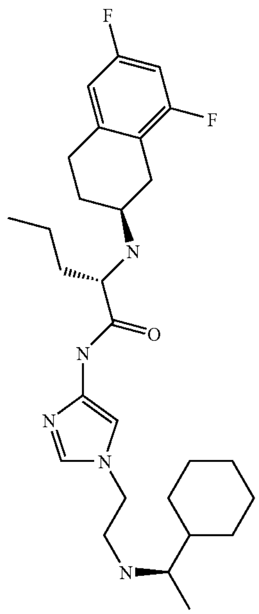 | data not available | N-[1-(2-{[(1R)-1-cyclohexylethyl]amino}-ethyl)-1H-imidazol-4-yl]-N-2-[(2S)-6,8-difluoro-1,2,3,4-tetrahydronaphthalen-2-yl]-L-norvalinamide |
| 289 | 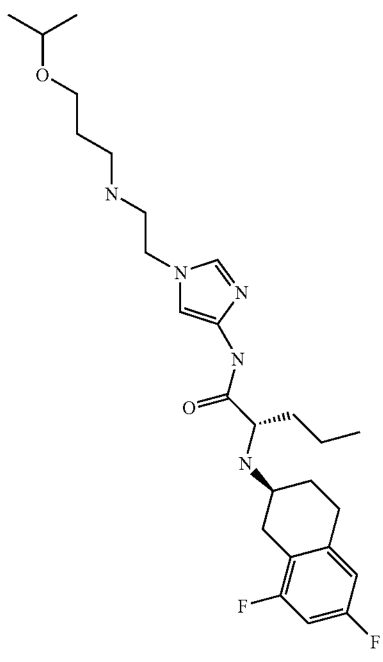 | data not available | N-2-[(2S)-6,8-difluoro-1,2,3,4-tetrahydronaphthalen-2-yl]-N-(1-{2-[(3-isopropoxypropyl)amino]-ethyl}-1H-imidazol-4-yl)-L-norvalinamide |
| 290 | 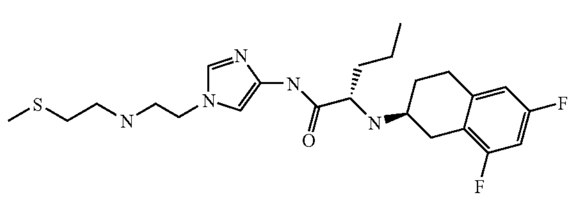 | data not available | N-2-[(2S)-6,8-difluoro-1,2,3,4-tetrahydronaphthalen-2-yl]-N-[1-(2-{[2-(methylthio)ethyl]amino}-ethyl)-1H-imidazol-4-yl]-L-norvalinamide |

-continued

| Ex | Structure | MS or NMR data | IUPACNAME |
|---|---|---|---|
| 291 | 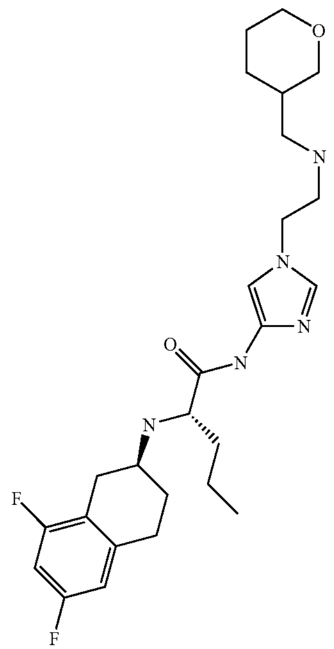 | data not available | N-2-[(2S)-6,8-difluoro-1,2,3,4-tetrahydronaphthalen-2-yl]-N-(1-{2-[(tetrahydro-2H-pyran-3-ylmethyl)amino]ethyl}-1H-imidazol-4-yl)-L-norvalinamide |
| 292 | 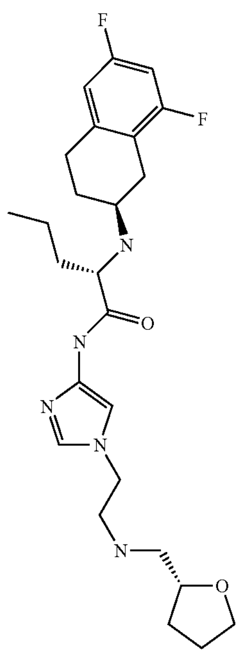 | data not available | N-2-[(2S)-6,8-difluoro-1,2,3,4-tetrahydronaphthalen-2-yl]-N-[1-(2-{[(2R)-tetrahydrofuran-2-ylmethyl]amino}ethyl)-1H-imidazol-4-yl]-L-norvalinamide |
| 293 | 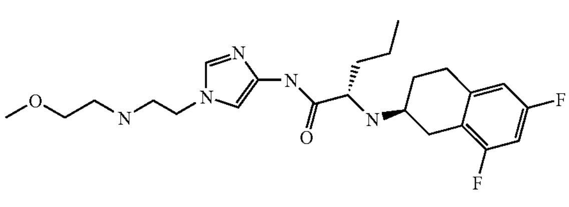 | data not available | N-2-[(2S)-6,8-difluoro-1,2,3,4-tetrahydronaphthalen-2-yl]-N-(1-{2-[(2-methoxyethyl)amino]ethyl}-1H-imidazol-4-yl)-L-norvalinamide |

-continued

| Ex | Structure | MS or NMR data | IUPACNAME |
|---|---|---|---|
| 294 | 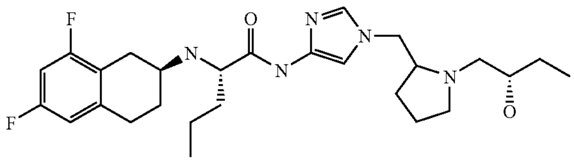 | M + 1 = 504.4 | N-2-[(2S)-6,8-difluoro-1,2,3,4-tetrahydronaphthalen-2-yl]-N-[1-({1-[(2S)-2-hydroxybutyl]pyrrolidin-2-yl}methyl)-1H-imidazol-4-yl]-L-norvalinamide |
| 295 | 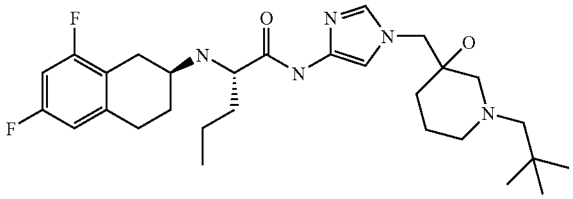 | M + 1 = 532.5 | N-2-[(2S)-6,8-difluoro-1,2,3,4-tetrahydronaphthalen-2-yl]-N-(1-{[1-(2,2-dimethylpropyl)-3-hydroxypiperidin-3-yl]methyl}-1H-imidazol-4-yl)-L-norvalinamide |
| 296 | 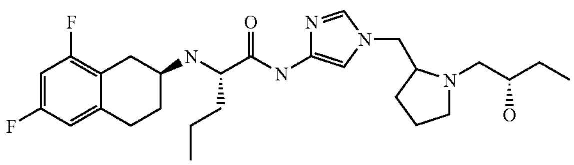 | M + 1 = 504.4 | N-2-[(2S)-6,8-difluoro-1,2,3,4-tetrahydronaphthalen-2-yl]-N-[1-({1-[(2S)-2-hydroxybutyl]pyrrolidin-2-yl}methyl)-1H-imidazol-4-yl]-L-norvalinamide |
| 297 | 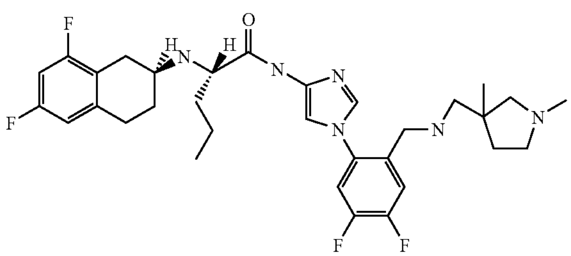 | M + 1 = 601.7 | N-2-[(2S)-6,8-difluoro-1,2,3,4-tetrahydronaphthalen-2-yl]-N-{1-[2-({[(1,3-dimethylpyrrolidin-3-yl)methyl]amino}methyl)-4,5-difluorophenyl]-1H-imidazol-4-yl}-L-norvalinamide |
| 298* | 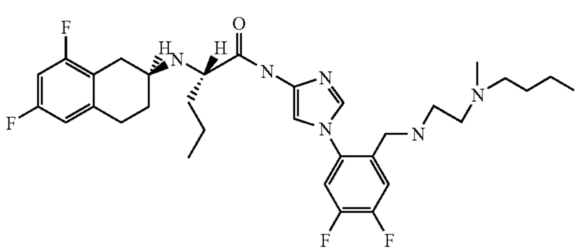 | M + 1 = 603.72 | N-(1-{2-[({2-[butyl(methyl)amino]ethyl}-amino)methyl]-45-difluorophenyl}-1H-imidazol-4-yl)-N-2-[(2S)-6,8-difluoro-1,2,3,4-tetrahydronaphthalen-2-yl]-L-norvalinamide |
| 299 | 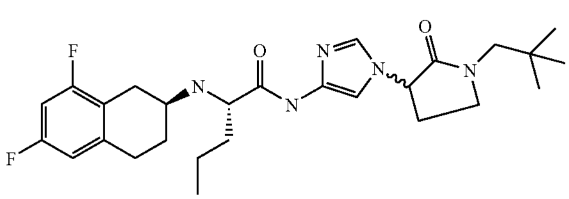 | M + 1 = 502.3 | N-2-[(2S)-6,8-difluoro-1,2,3,4-tetrahydronaphthalen-2-yl]-N-{1-[1-(2,2-dimethylpropyl)-2-oxopyrrolidin-3-yl]-1H-imidazol-4-yl}-L-norvalinamide |

-continued

| Ex | Structure | MS or NMR data | IUPACNAME |
|---|---|---|---|
| 300 | 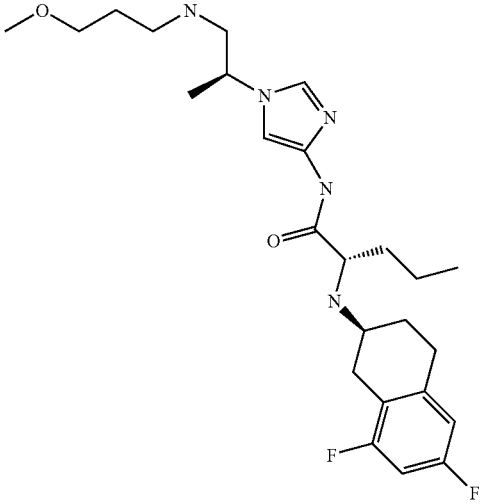 | M + 1 = 478.3 | N-2-[(2S)-6,8-difluoro-1,2,3,4-tetrahydronaphthalen-2-yl]-N-(1-{(1S)-2-[(3-methoxypropyl)amino]-1-methylethyl}-1H-imidazol-4-yl)-L-norvalinamide |
| 301 | 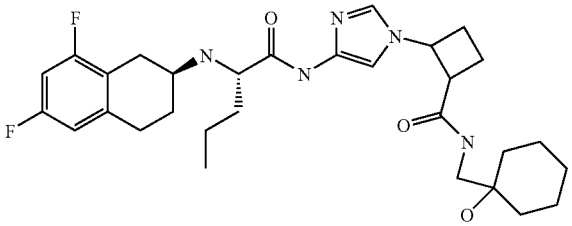 | M + 1 = 558.3 | N-2-[(2S)-6,8-difluoro-1,2,3,4-tetrahydronaphthalen-2-yl]-N-{1-[2-({[(1-hydroxycyclohexyl)methyl]amino}carbonyl)cyclobutyl]-1H-imidazol-4-yl}-L-norvalinamide |
| 302 | 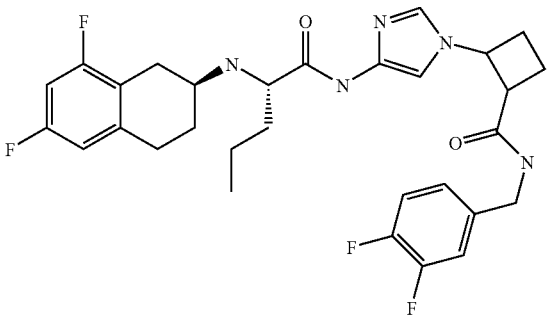 | M + 1 = 572.29 | N-[1-(2-{[(3,4-difluorobenzyl)amino]carbonyl}cyclobutyl)-1H-imidazol-4-yl]-N-2-[(2S)-6,8-difluoro-1,2,3,4-tetrahydronaphthalen-2-yl]-L-norvalinamide |
| 303 | 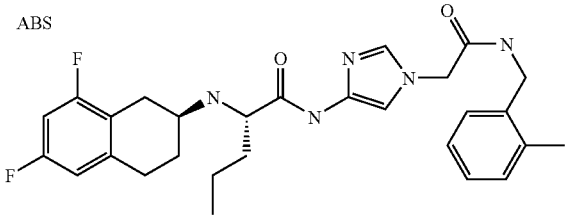 | M + 1 = 510.23 | N-2-[(2S)-6,8-difluoro-1,2,3,4-tetrahydronaphthalen-2-yl]-N-(1-{2-[(2-methylbenzyl)amino]-2-oxoethyl}-1H-imidazol-4-yl)-L-norvalinamide |
| 304 | 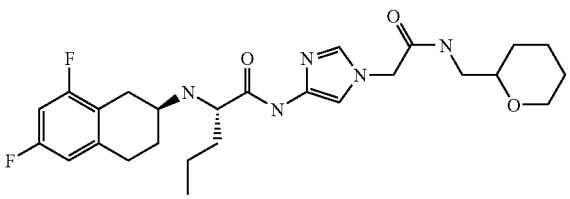 | M + 1 = 504.26 | N-2-[(2S)-6,8-difluoro-1,2,3,4-tetrahydronaphthalen-2-yl]-N-(1-{2-oxo-2-[(tetrahydro-2H-pyran-2-ylmethyl)amino]ethyl}-1H-imidazol-4-yl)-L-norvalinamide |

| Ex | Structure | MS or NMR data | IUPACNAME |
|---|---|---|---|
| 305 | 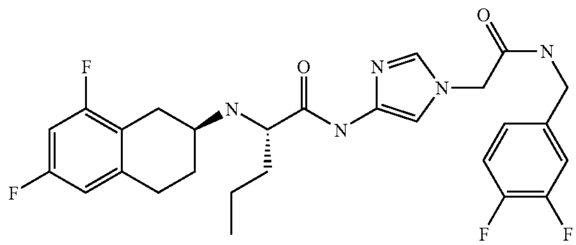 | M + 1 = 532.22 | N-(1-{2-[(34-difluorobenzyl)amino]-2-oxoethyl}-1H-imidazol-4-yl)-N-2-[(2S)-6,8-difluoro-1,2,3,4-tetrahydronaphthalen-2-yl]-L-norvalinamide |
| 306 | 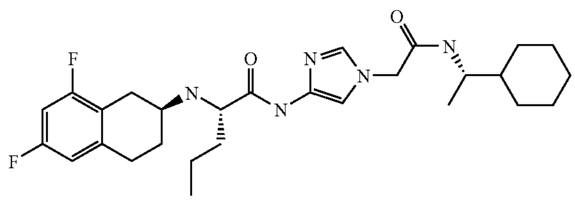 | M + 1 = 516.29 | N-[1-(2-{[(1S)-1-cyclohexylethyl]amino}-2-oxoethyl)-1H-imidazol-4-yl]-N-2-[(2S)-6,8-difluoro-1,2,3,4-tetrahydronaphthalen-2-yl]-L-norvalinamide |
| 307 | 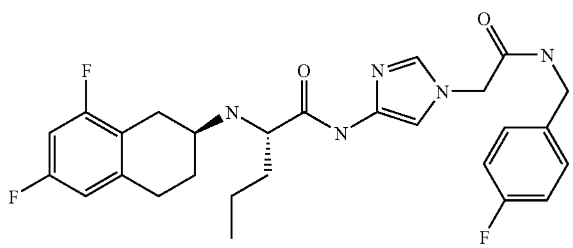 | M + 1 = 514.22 | N-2-[(2S)-6,8-difluoro-1,2,3,4-tetrahydronaphthalen-2-yl]-N-(1-{2-[(4-fluorobenzyl)amino]-2-oxoethyl}-1H-imidazol-4-yl)-L-norvalinamide |
| 308 | 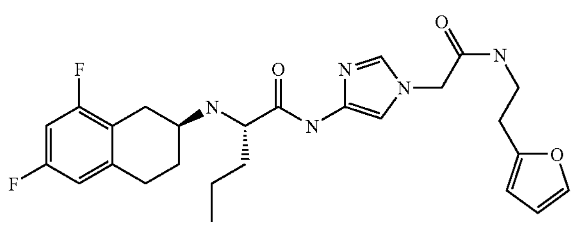 | M + 1 = 500.22 | N-2-[(2S)-6,8-difluoro-1,2,3,4-tetrahydronaphthalen-2-yl]-N-[1-(2-{[2-(2-furyl)ethyl]amino}-2-oxoethyl)-1H-imidazol-4-yl]-L-norvalinamide |
| 309 | 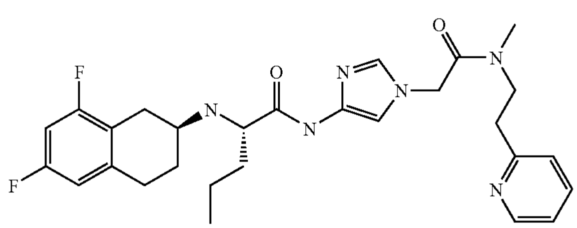 | M + 1 = 525.23 | N-2-[(2S)-6,8-difluoro-1,2,3,4-tetrahydronaphthalen-2-yl]-N-(1-{2-[methyl(2-pyridin-2-ylethyl)amino]-2-oxoethyl}-1H-imidazol-4-yl)-L-norvalinamide |
| 310 | 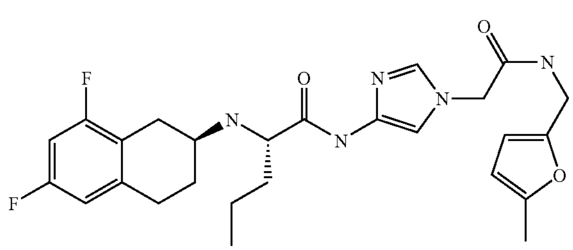 | M + 1 = 500.22 | N-2-[(2S)-6,8-difluoro-1,2,3,4-tetrahydronaphthalen-2-yl]-N-[1-(2-{[(5-methyl-2-furyl)methyl]amino}-2-oxoethyl)-1H-imidazol-4-yl]-L-norvalinamide |

-continued

| Ex | Structure | MS or NMR data | IUPACNAME |
|---|---|---|---|
| 311 | 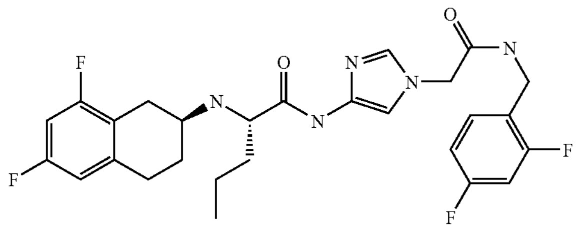 | M + 1 = 532.21 | N-(1-{2-[(24-difluorobenzyl)amino]-2-oxoethyl}-1H-imidazol-4-yl)-N-2-[(2S)-6,8-difluoro-1,2,3,4-tetrahydronaphthalen-2-yl]-L-norvalinamide |
| 312 | 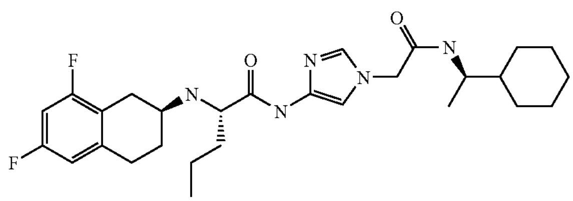 | M + 1 = 516.3 | N-[1-(2-{[(1R)-cyclohexylethyl]amino}-2-oxoethyl)-1H-imidazol-4-yl]-N-2-[(2S)-6,8-difluoro-1,2,3,4-tetrahydronaphthalen-2-yl]-L-norvalinamide |
| 313 | 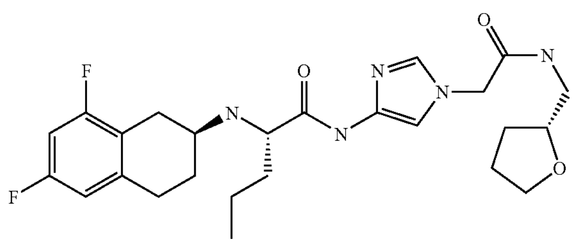 | M + 1 = 490.26 | N-2-[(2S)-6,8-difluoro-1,2,3,4-tetrahydronaphthalen-2-yl]-N-[1-(2-oxo-2-{[(2R)-tetrahydrofuran-2-ylmethyl]amino}ethyl)-1H-imidazol-4-yl]-L-norvalinamide |
| 314 | 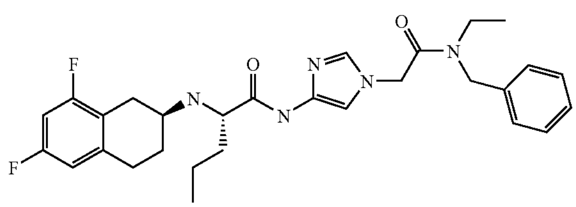 | M + 1 = 524.27 | N-(1-{2-[benzyl(ethyl)amino]-2-oxoethyl}-1H-imidazol-4-yl)-N-2-[(2S)-6,8-difluoro-1,2,3,4-tetrahydronaphthalen-2-yl]-L-norvalinamide |
| 315 | 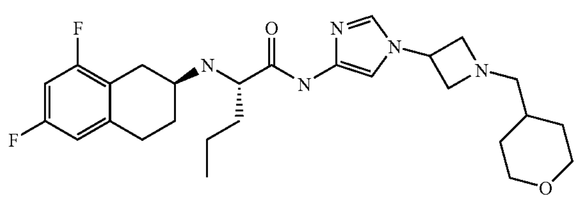 | M + 1 = 502.2 | N-2-[(2S)-6,8-difluoro-1,2,3,4-tetrahydronaphthalen-2-yl]-N-{1-[1-(tetrahydro-2H-pyran-4-ylmethyl)azetidin-3-yl]-1H-imidazol-4-yl}-L-norvalinamide |
| 316 | 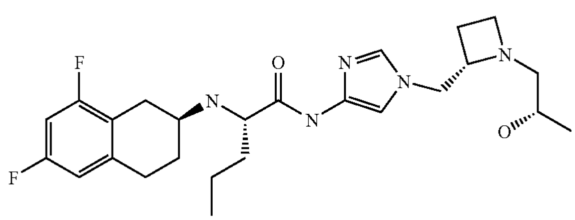 | M + 1 = 476.3 | N-2-[(2S)-6,8-difluoro-1,2,3,4-tetrahydronaphthalen-2-yl]-N-[1-({(2S)-1-[(2S)-2-hydroxypropyl]azetidin-2-yl}methyl)-1H-imidazol-4-yl]-L-norvalinamide |
| 317 | 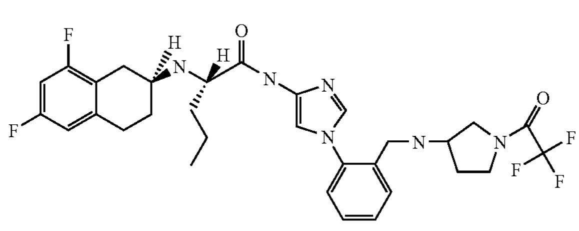 | M + 1 = 619.65 | N-2-[(2S)-6,8-difluoro-1,2,3,4-tetrahydronaphthalen-2-yl]-N-{1-[2-({[1-(trifluoroacetyl)pyrrolidin-3-yl]amino}methyl)phenyl]-1H-imidazol-4-yl}-L-norvalinamide |

-continued

| Ex | Structure | MS or NMR data | IUPAC NAME |
|---|---|---|---|
| 318 | 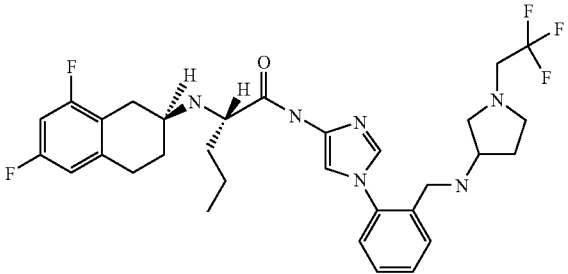 | M + 1 = 605.66 | N-2-[(2S)-6,8-difluoro-1,2,3,4-tetrahydronaphthalen-2-yl]-N-{1-[2-({[1-(2,2,2-trifluoroethyl)pyrrolidin-3-yl]amino}methyl)phenyl]-1H-imidazol-4-yl}-L-norvalinamide |
| 319 | 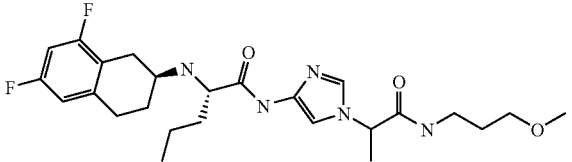 | M + 1 = 492.1 | N-2-[(2S)-6,8-difluoro-1,2,3,4-tetrahydronaphthalen-2-yl]-N-(1-{2-[(3-methoxypropyl)amino]-1-methyl-2-oxoethyl}-1H-imidazol-4-yl)-L-norvalinamide |
| 320 | 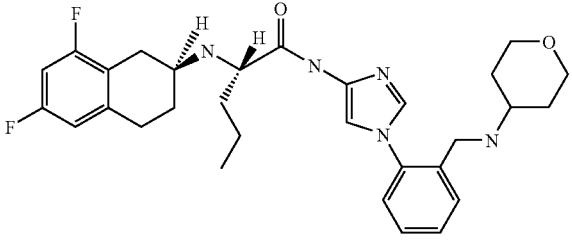 | M + 1 = 538.65 | N-2-[(2S)-6,8-difluoro-1,2,3,4-tetrahydronaphthalen-2-yl]-N-(1-{2-[(tetrahydro-2H-pyran-4-ylamino)methyl]phenyl}-1H-imidazol-4-yl)-L-norvalinamide |
| 321 | 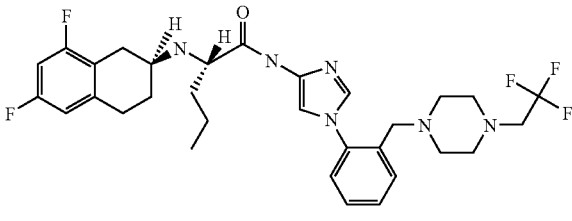 | M + 1 = 605.66 | N-2-[(2S)-6,8-difluoro-1,2,3,4-tetrahydronaphthalen-2-yl]-N-[1-(2-{[4-(2,2,2-trifluoroethyl)piperazin-1-yl]methyl}phenyl)-1H-imidazol-4-yl]-L-norvalinamide |
| 322 | 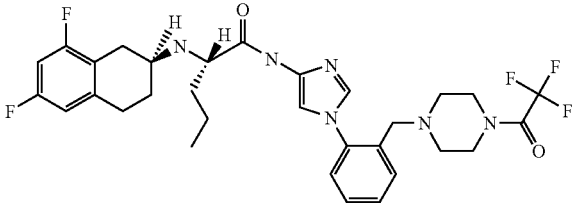 | M + 1 = 619.65 | N-2-[(2S)-6,8-difluoro-1,2,3,4-tetrahydronaphthalen-2-yl]-N-[1-(2-{[4-(trifluoroacetyl)piperazin-1-yl]methyl}phenyl)-1H-imidazol-4-yl]-L-norvalinamide |

-continued

| Ex | Structure | MS or NMR data | IUPACNAME |
|---|---|---|---|
| 323 | 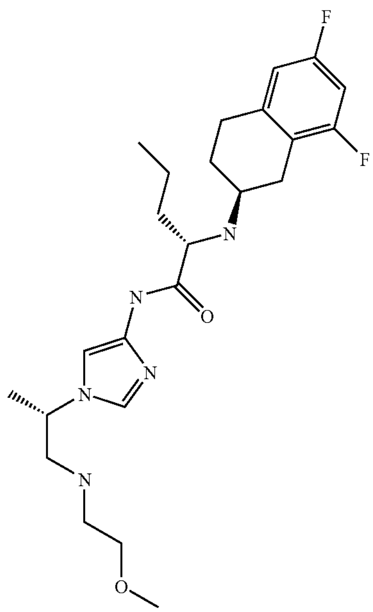 | M + 1 = 465.19 | N-2-[(2S)-6,8-difluoro-1,2,3,4-tetrahydronaphthalen-2-yl]-N-(1-{(1S)-2-[(2-methoxyethyl)amino]-1-methylethyl}-1H-imidazol-4-yl)-L-norvalinamide |
| 324 | 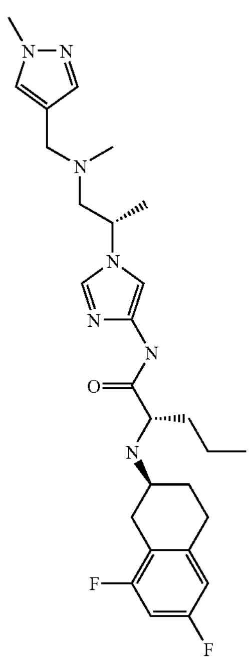 | M + 1 = 514.25 | N-2-[(2S)-6,8-difluoro-1,2,3,4-tetrahydronaphthalen-2-yl]-N-{1-[(1S)-1-methyl-2-{methyl[(1-methyl-1H-pyrazol-4-yl)methyl]amino}ethyl]-1H-imidazol-4-yl}-L-norvalinamide |

-continued

| Ex | Structure | MS or NMR data | IUPACNAME |
|---|---|---|---|
| 325 | 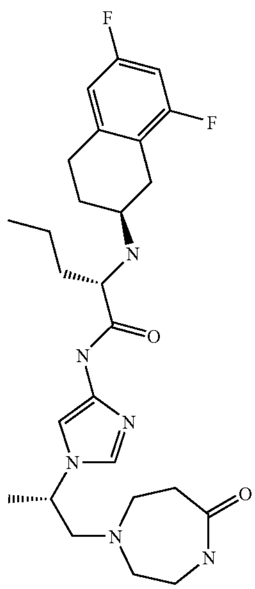 | M + 1 = 503.14 | N-2-[(2S)-6,8-difluoro-1,2,3,4-tetrahydronaphthalen-2-yl]-N-{1-[(1S)-1-methyl-2-(5-oxo-14-diazepan-1-yl)ethyl]-1H-imidazol-4-yl}-L-norvalinamide |
| 326 | 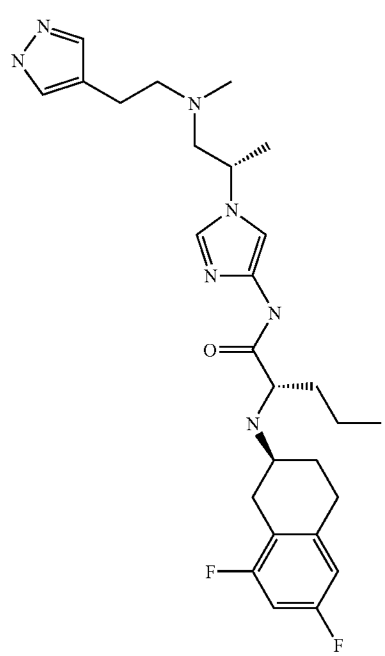 | M + 1 = 514.25 | N-2-[(2S)-6,8-difluoro-1,2,3,4-tetrahydronaphthalen-2-yl]-N-{1-[(1S)-1-methyl-2-{methyl[2-(1H-pyrazol-4-yl)ethyl]amino}ethyl]-1H-imidazol-4-yl}-L-norvalinamide |

-continued

| Ex | Structure | MS or NMR data | IUPACNAME |
|---|---|---|---|
| 327 | 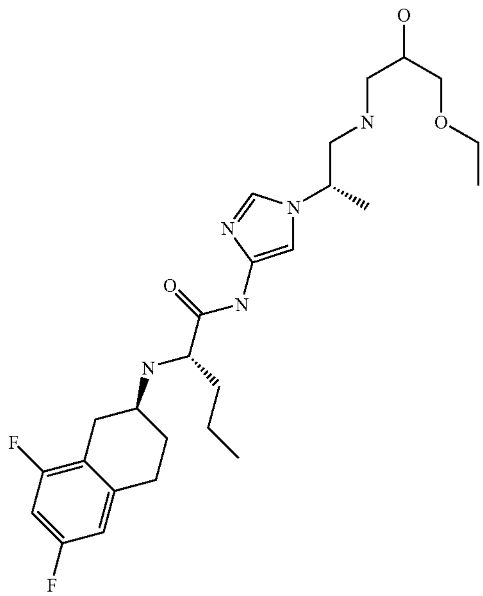 | M + 1 = 508.34 | N-2-[(2S)-6,8-difluoro-1,2,3,4-tetrahydronaphthalen-2-yl]-N-(1-{(1S)-2-[(3-ethoxy-2-hydroxypropyl)amino]-1-methylethyl}-1H-imidazol-4-yl)-L-norvalinamide |
| 328 | 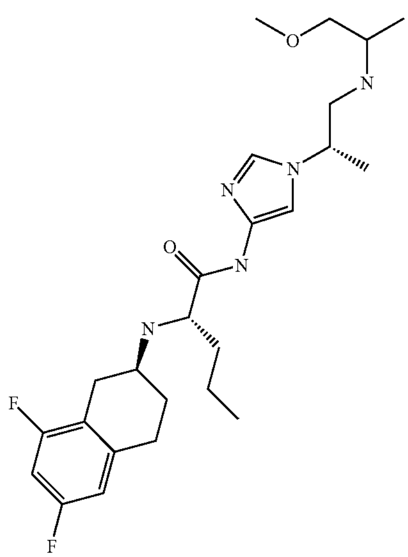 | M + 1 = 478.28 | N-2-[(2S)-6,8-difluoro-1,2,3,4-tetrahydronaphthalen-2-yl]-N-(1-{(1S)-2-[(2-methoxy-1-methylethyl)amino]-1-methylethyl}-1H-imidazol-4-yl)-L-norvalinamide |
| 329 | 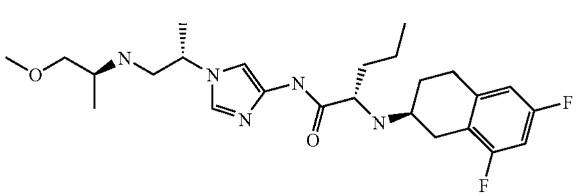 | M + 1 = 478.22 | N-2-[(2S)-6,8-difluoro-1,2,3,4-tetrahydronaphthalen-2-yl]-N-{1-[(1S)-2-{[(1S)-2-methoxy-1-methylethyl]amino}-1-methylethyl]-1H-imidazol-4-yl}-L-norvalinamide |

-continued

| Ex | Structure | MS or NMR data | IUPACNAME |
|---|---|---|---|
| 330 | 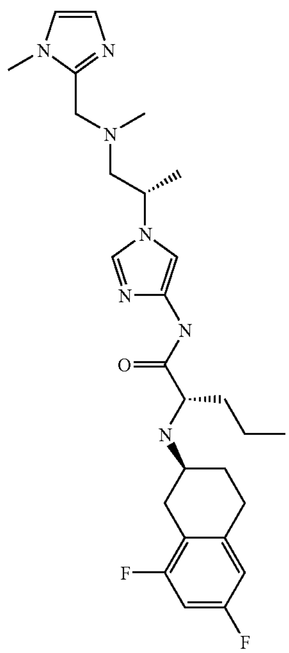 | M + 1 = 514.14 | N-2-[(2S)-6,8-difluoro-1,2,3,4-tetrahydronaphthalen-2-yl]-N-{1-[(1S)-1-methyl-2-{methyl[(1-methyl-1H-imidazol-2-yl)methyl]amino}ethyl]-1H-imidazol-4-yl}-L-norvalinamide |
| 331 | 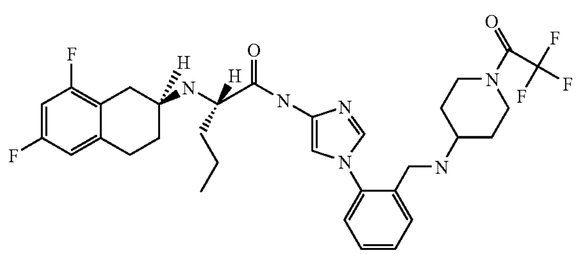 | M + 1 = 633.67 | N-2-[(2S)-6,8-difluoro-1,2,3,4-tetrahydronaphthalen-2-yl]-N-{1-[2-({[1-(trifluoroacetyl)piperidin-4-yl]amino}methyl)phenyl]-1H-imidazol-4-yl}-L-norvalinamide |
| 332 | 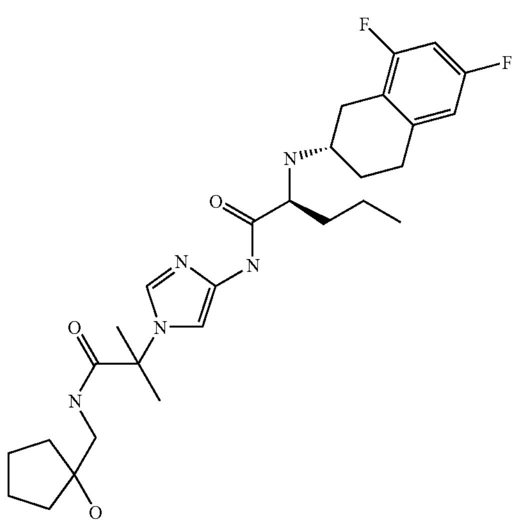 | M + 1 = 532.4 | N-2-[(2S)-6,8-difluoro-1,2,3,4-tetrahydronaphthalen-2-yl]-N-[1-(2-{[(1-hydroxycyclopentyl)methyl]amino}-1,1-dimethyl-2-oxoethyl)-1H-imidazol-4-yl]-L-norvalinamide |

| Ex | Structure | MS or NMR data | IUPACNAME |
|---|---|---|---|
| 333 | 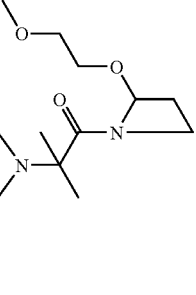 | M + 1 = 575.95 | N-2-[(2S)-6,8-difluoro-1,2,3,4-tetrahydronaphthalen-2-yl]-N-(1-{2-[4-(2-methoxyethoxy)piperidin-1-yl]-1,1-dimethyl-2-oxoethyl}-1H-imidazol-4-yl)-L-norvalinamide |
| 334 | 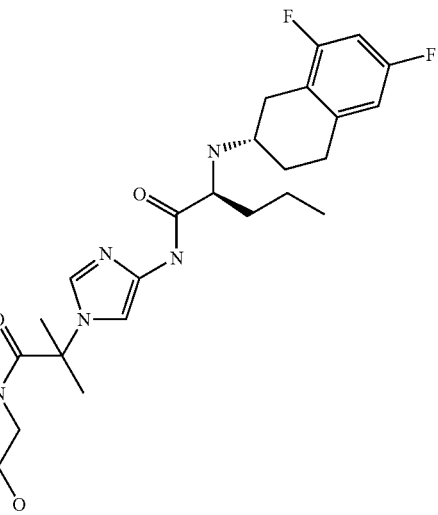 | M + 1 = 518.23 | N-2-[(2S)-6,8-difluoro-1,2,3,4-tetrahydronaphthalen-2-yl]-N-[1-(2-{[(1-hydroxycyclobutyl)methyl]amino}-1,1-dimethyl-2-oxoethyl)-1H-imidazol-4-yl]-L-norvalinamide |
| 335 | 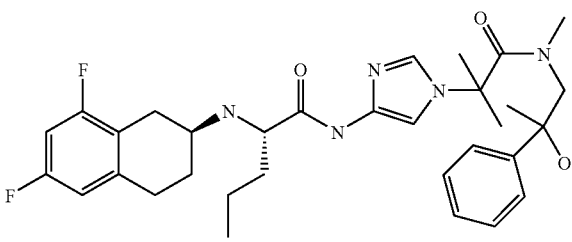 | M + 1 = 582.29 | N-2-[(2S)-6,8-difluoro-1,2,3,4-tetrahydronaphthalen-2-yl]-N-(1-{2-[(2-hydroxy-2-phenylpropyl)(methyl)amino]-1,1-dimethyl-2-oxoethyl}-1H-imidazol-4-yl)-L-norvalinamide |
| 336 | 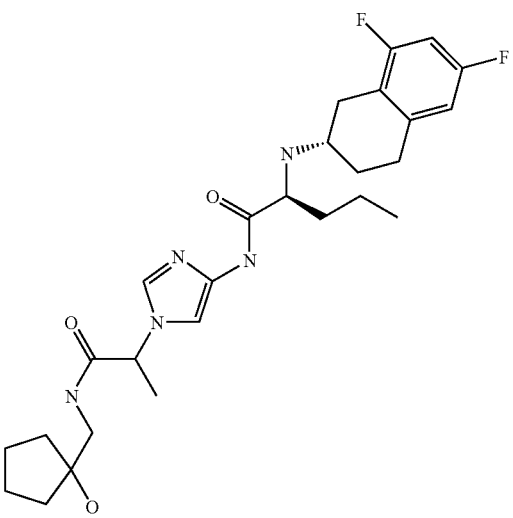 | M + 1 = 518.22 | N-2-[(2S)-6,8-difluoro-1,2,3,4-tetrahydronaphthalen-2-yl]-N-[1-(2-{[(1-hydroxycyclopentyl)methyl]amino}-1-methyl-2-oxoethyl)-1H-imidazol-4-yl]-L-norvalinamide |

-continued

| Ex | Structure | MS or NMR data | IUPACNAME |
|---|---|---|---|
| 337 | 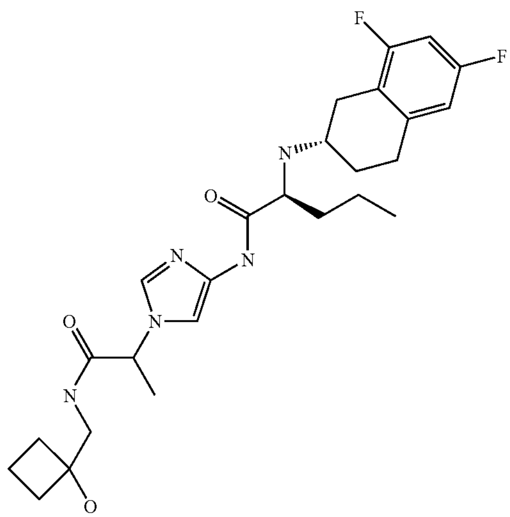 | M + 1 = 504.17 | N-2-[(2S)-6,8-difluoro-1,2,3,4-tetrahydronaphthalen-2-yl]-N-[1-(2-{[(1-hydroxycyclobutyl)methyl]amino}-1-methyl-2-oxoethyl)-1H-imidazol-4-yl]-L-norvalinamide |
| 338 | 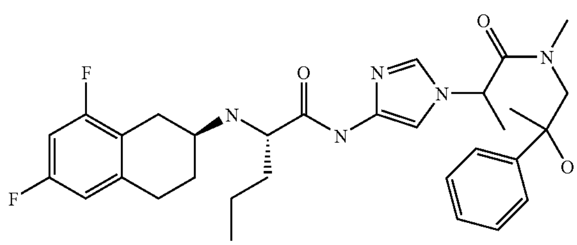 | M + 1 = 568.23 | N-2-[(2S)-6,8-difluoro-1,2,3,4-tetrahydronaphthalen-2-yl]-N-(1-{2-[(2-hydroxy-2-phenylpropyl)(methyl)amino]-1-methyl-2-oxoethyl}-1H-imidazol-4-yl)-L-norvalinamide |
| 339 | 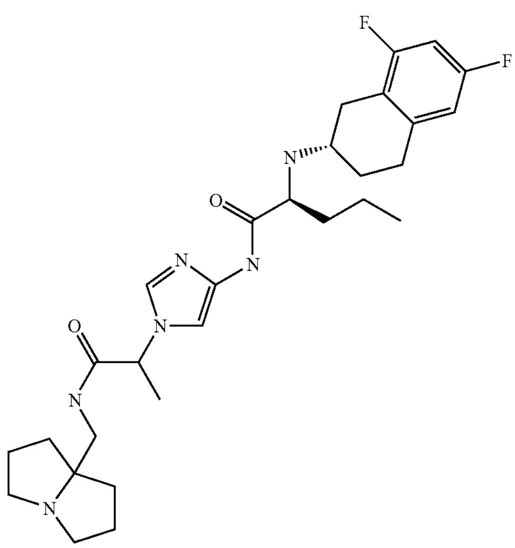 | M + 1 = 543.21 | N-2-[(2S)-6,8-difluoro-1,2,3,4-tetrahydronaphthalen-2-yl]-N-(1-{1-methyl-2-oxo-2-[(tetrahydro-1H-pyrrolizin-7a(5H)-ylmethyl)amino]ethyl}-1H-imidazol-4-yl)-L-norvalinamide |
| 340 | 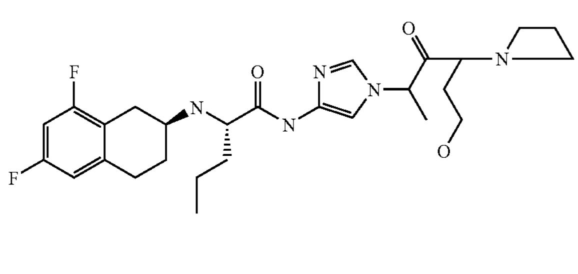 | M + 1 = 532.21 | N-2-[(2S)-6,8-difluoro-1,2,3,4-tetrahydronaphthalen-2-yl]-N-(1-{2-[2-(2-hydroxyethyl)piperidin-1-yl]-1-methyl-2-oxoethyl}-1H-imidazol-4-yl)-L-norvalinamide |

-continued

| Ex | Structure | MS or NMR data | IUPACNAME |
|---|---|---|---|
| 341 | 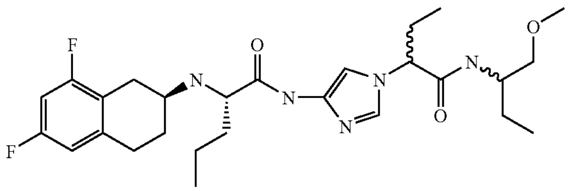 | M + 1 = 520.2 | N-2-[(2S)-6,8-difluoro-1,2,3,4-tetrahydronaphthalen-2-yl]-N-{1-[1-({[1-(methoxymethyl)propyl]-amino}carbonyl)propyl]-1H-imidazol-4-yl}-L-norvalinamide |
| 342 | 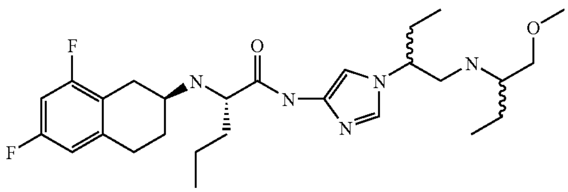 | M + 1 = 506.1 | N-2-[(2S)-6,8-difluoro-1,2,3,4-tetrahydronaphthalen-2-yl]-N-{1-[1-({[1-(methoxymethyl)propyl]-amino}methyl)propyl]-1H-imidazol-4-yl}-L-norvalinamide |
| 343 | 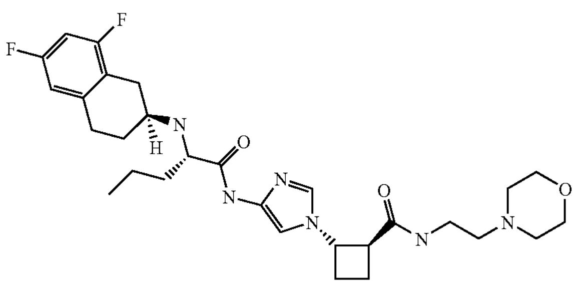 | M + 1 = 559.1 | N-2-[(2S)-6,8-difluoro-1,2,3,4-tetrahydronaphthalen-2-yl]-N-{1-[(1S,2S)-2-{[(2-morpholin-4-ylethyl)amino]carbonyl}-cyclobutyl]-1H-imidazol-4-yl}-L-norvalinamide |
| 344 | 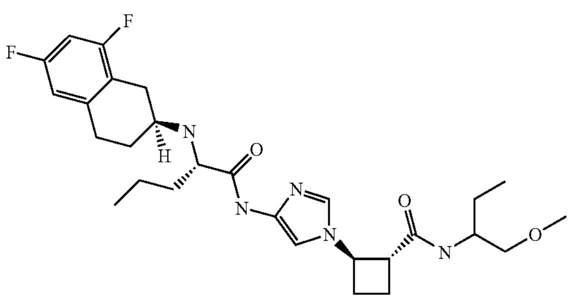 | M + 1 = 532.1 | N-2-[(2S)-6,8-difluoro-1,2,3,4-tetrahydronaphthalen-2-yl]-N-{1-[(1R,2R)-2-({[1-(methoxymethyl)propyl]-amino}carbonyl)cyclobutyl]-1H-imidazol-4-yl}-L-norvalinamide |
| 345 | 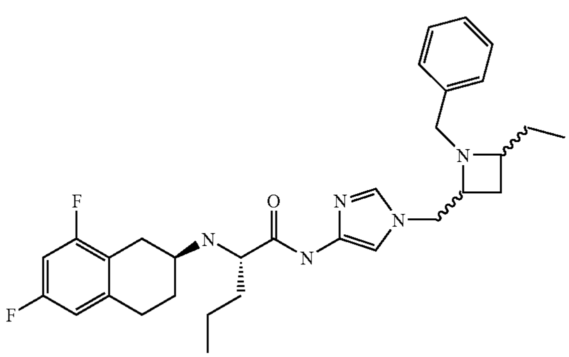 | M + 1 = 536.1 | N-{1-[(1-benzyl-4-ethylazetidin-2-yl)methyl]-1H-imidazol-4-yl}-N-2-[(2S)-6,8-difluoro-1,2,3,4-tetrahydronaphthalen-2-yl]-L-norvalinamide |

-continued

| Ex | Structure | MS or NMR data | IUPACNAME |
|---|---|---|---|
| 346 | 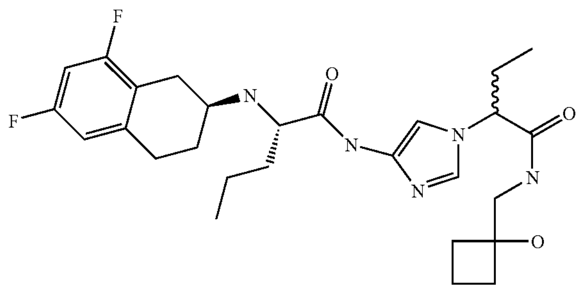 | M + 1 = 518.2 | N-2-[(2S)-6,8-difluoro-1,2,3,4-tetrahydronaphthalen-2-yl]-N-{1-[1-({[(1-hydroxycyclobutyl)methyl]-amino}carbonyl)propyl]-1H-imidazol-4-yl}-L-norvalinamide |
| 347 | 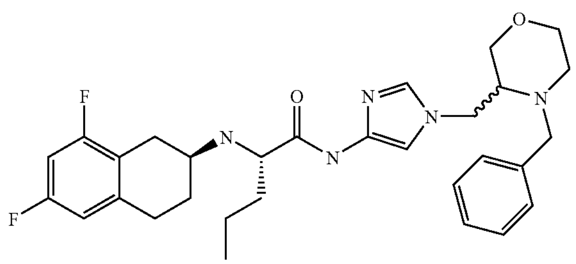 | M + 1 = 432 | N-{1-[(4-benzylmorpholin-3-yl)methyl]-1H-imidazol-4-yl}-N-2-[(2S)-6,8-difluoro-1,2,3,4-tetrahydronaphthalen-2-yl]-L-norvalinamide |
| 348 | 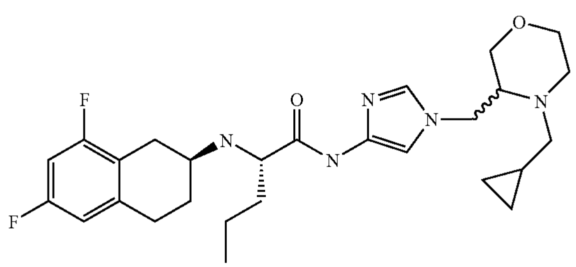 | M + 1 = 502 | N-(1-{[4-(cyclopropylmethyl)-morpholin-3-yl]methyl}-1H-imidazol-4-yl)-N-2-[(2S)-6,8-difluoro-1,2,3,4-tetrahydronaphthalen-2-yl]-L-norvalinamide |
| 349 | 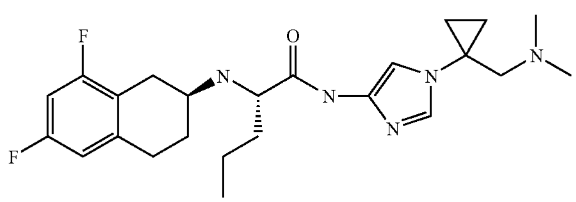 | M + 1 = 446.0 | N-2-[(2S)-6,8-difluoro-1,2,3,4-tetrahydronaphthalen-2-yl]-N-(1-{1-[(dimethylamino)methyl]-cyclopropyl}-1H-imidazol-4-yl)-L-norvalinamide |
| 350 | 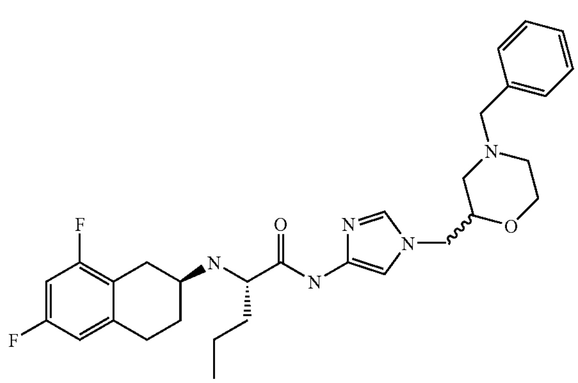 | M + 1 = 538 | N-{1-[(4-benzylmorpholin-2-yl)methyl]-1H-imidazol-4-yl}-N-2-[(2S)-6,8-difluoro-1,2,3,4-tetrahydronaphthalen-2-yl]-L-norvalinamide |

| Ex | Structure | MS or NMR data | IUPACNAME |
|---|---|---|---|
| 351 | 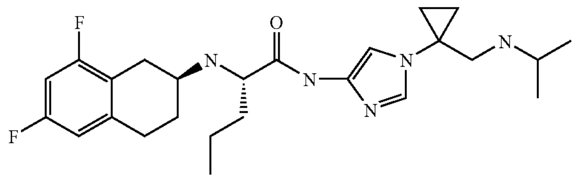 | M + 1 = 460.0 | N-2-[(2S)-6,8-difluoro-1,2,3,4-tetrahydronaphthalen-2-yl]-N-(1-{1-[(isopropylamino)methyl]-cyclopropyl}-1H-imidazol-4-yl)-L-norvalinamide |

Example 352

The following compounds are prepared utilizing the procedures described above:

(S)-2-[2-(3,5-Difluoro-phenyl)-acetylamino]-pentanoic acid {1-[2-(3-ethoxy-propylamino)-ethyl]-1H-imidazol-4-yl}-amide;

(S)-2-[2-(3,5-Difluoro-phenyl)-acetylamino]-pentanoic acid [1-(2-fluoro-benzyl)-1H-imidazol-4-yl]-amide;

(S)-2-[2-(3,5-Difluoro-phenyl)-acetylamino]-pentanoic acid [1-(3-fluoro-benzyl)-1H-imidazol-4-yl]-amide;

(S)-2-[2-(3,5-Difluoro-phenyl)-acetylamino]-pentanoic acid [1-(4-methyl-benzyl)-1H-imidazol-4-yl]-amide;

(S)-2-[2-(3,5-Difluoro-phenyl)-acetylamino]-pentanoic acid [1-(4-methoxy-benzyl)-1H-imidazol-4-yl]-amide;

(S)-2-[2-(3,5-Difluoro-phenyl)-acetylamino]-pentanoic acid [1-(4-tert-butyl-benzyl)-1H-imidazol-4-yl]-amide;

(S)-2-[2-(3,5-Difluoro-phenyl)-acetylamino]-pentanoic acid [1-(1-hydroxymethyl-cyclobutyl)-1H-imidazol-4-yl]-amide;

(S)-2-[2-(3,5-Difluoro-phenyl)-acetylamino]-pentanoic acid [1-(2-hydroxymethyl-cyclobutyl)-1H-imidazol-4-yl]-amide;

(S)-2-[2-(3,5-Difluoro-phenyl)-acetylamino]-pentanoic acid [1-(1-pyrrolidin-1-ylmethyl-cyclobutyl)-1H-imidazol-4-yl]-amide;

(S)-2-(6,8-Difluoro-1,2,3,4-tetrahydro-naphthalen-2-ylamino)-pentanoic acid {1-[2-((R)-1-cyclohexyl-ethylamino)-1,1-dimethyl-ethyl]-1H-imidazol-4-yl}-amide;

(S)-2-[2-(3,5-Difluoro-phenyl)-acetylamino]-pentanoic acid {1-[2-((R)-1-cyclohexyl-ethylamino)-1,1-dimethyl-ethyl]-1H-imidazol-4-yl}-amide;

(S)-2-[2-(2,4-Difluoro-phenyl)-2-hydroxy-ethylamino]-pentanoic acid [1-(1,1-dimethyl-2-pyrrolidin-1-yl-ethyl)-1H-imidazol-4-yl]-amide;

(S)-2-[2-(3,4-Difluoro-phenyl)-2-hydroxy-ethylamino]-pentanoic acid [1-(1,1-dimethyl-2-pyrrolidin-1-yl-ethyl)-1H-imidazol-4-yl]-amide;

(S)-2-(6,8-Difluoro-1,2,3,4-tetrahydro-naphthalen-2-ylamino)-pentanoic acid (1-{1,1-dimethyl-2-[(tetrahydro-pyran-4-ylmethyl)-amino]-ethyl}-1H-imidazol-4-yl)-amide;

(S)-2-[2-(3,5-Difluoro-phenyl)-acetylamino]-pentanoic acid (1-{1,1-dimethyl-2-[(tetrahydro-pyran-4-ylmethyl)-amino]-ethyl}-1H-imidazol-4-yl)-amide;

(S)-2-(6,8-Difluoro-1,2,3,4-tetrahydro-naphthalen-2-ylamino)-pentanoic acid {1-[3-((S)-1-phenyl-ethylamino)-butyl]-1H-imidazol-4-yl}-amide;

(S)-2-(6,8-Difluoro-1,2,3,4-tetrahydro-naphthalen-2-ylamino)-pentanoic acid [1-(3-methyl-oxetan-3-ylmethyl)-1H-imidazol-4-yl]-amide;

(S)-2-[2-(3,5-Difluoro-phenyl)-acetylamino]-pentanoic acid [1-(3-methyl-oxetan-3-ylmethyl)-1H-imidazol-4-yl]-amide;

(S)-2-[2-(3,5-Difluoro-phenyl)-2-hydroxy-ethylamino]-pentanoic acid [1-(1,1-dimethyl-2-pyrrolidin-1-yl-ethyl)-1H-imidazol-4-yl]-amide;

(S)-2-[2-(2,4-Difluoro-phenyl)-2-hydroxy-ethylamino]-pentanoic acid {1-[2-((2R,6S)-2,6-dimethyl-morpholin-4-yl)-1,1-dimethyl-ethyl]-1H-imidazol-4-yl}-amide;

(S)-2-[2-(3,5-Difluoro-phenyl)-acetylamino]-pentanoic acid {1-[2-(octahydro-pyrazino[1,2-a]azepin-2-yl)-ethyl]-1H-imidazol-4-yl}-amide;

(S)-2-[2-(3,5-Difluoro-phenyl)-acetylamino]-pentanoic acid {1-[2-([1,4]dioxan-2-ylmethyl-methyl-amino)-ethyl]-1H-imidazol-4-yl}-amide;

(S)-2-[2-(3,5-Difluoro-phenyl)-acetylamino]-pentanoic acid {1-[2-(2-methoxy-1-methyl-ethylamino)-ethyl]-1H-imidazol-4-yl}-amide;

(S)-2-[2-(3,5-Difluoro-phenyl)-acetylamino]-pentanoic acid {1-[2-(3-oxo-piperazin-1-yl)-ethyl]-1H-imidazol-4-yl}-amide;

(S)-2-[2-(3,5-Difluoro-phenyl)-acetylamino]-pentanoic acid [1-(2-benzylamino-ethyl)-1H-imidazol-4-yl]-amide;

(S-2-[2-(3,5-Difluoro-phenyl)-acetylamino]-pentanoic acid {1-[2-(3-butoxy-propylamino)-ethyl]-1H-imidazol-4-yl}-amide;

(S)-2-[2-(3,5-Difluoro-phenyl)-acetylamino]-pentanoic acid {1-[2-((1R,2S)-2-hydroxymethyl-cyclohexylamino)-ethyl]-1H-imidazol-4-yl}-amide;

2-[2-(3,5-Difluoro-phenyl)-acetylamino]-pentanoic acid {1-[(4aS,8aS)-2-(octahydro-isoquinolin-2-yl)-ethyl]-1H-imidazol-4-yl}-amide;

(S)-2-[2-(3,5-Difluoro-phenyl)-acetylamino]-pentanoic acid {1-[2-(3-isopropoxy-propylamino)-ethyl]-1H-imidazol-4-yl}-amide;

(S)-2-[2-(3,5-Difluoro-phenyl)-acetylamino]-pentanoic acid {1-[2-(octahydro-isoquinolin-2-yl)-ethyl]-1H-imidazol-4-yl}-amide;

(S)-2-[2-(3,5-Difluoro-phenyl)-acetylamino]-pentanoic acid {1-[2-(3,4,5,6-tetrahydro-2H-[4,4]bipyridinyl-1-yl)-ethyl]-1H-imidazol-4-yl}-amide;

S)-2-[2-(3,5-Difluoro-phenyl)-acetylamino]-pentanoic acid {1-[2-(2-hydroxy-2-phenyl-ethylamino)-ethyl]-1H-imidazol-4-yl}-amide;

(S)-2-[2-(3,5-Difluoro-phenyl)-acetylamino]-pentanoic acid {1-[2-(indan-1-ylamino)-ethyl]-1H-imidazol-4-yl}-amide;

(S)-2-[2-(3,5-Difluoro-phenyl)-acetylamino]-pentanoic acid {1-[2-(benzyl-methyl-amino)-ethyl]-1H-imidazol-4-yl}-amide;

(S)-2-[2-(3,5-Difluoro-phenyl)-acetylamino]-pentanoic acid {1-[2-(indan-2-ylamino)-ethyl]-1H-imidazol-4-yl}-amide;

(S)-2-[2-(3,5-Difluoro-phenyl)-acetylamino]-pentanoic acid {1-[2-(3,4-dihydro-1#H!-isoquinolin-2-yl)-ethyl]-1H-imidazol-4-yl}-amide;

(S)-2-[2-(3,5-Difluoro-phenyl)-acetylamino]-pentanoic acid {1-[2-(2-propoxy-ethylamino)-ethyl]-1H-imidazol-4-yl}-amide;

(S)-2-[2-(3,5-Difluoro-phenyl)-acetylamino]-pentanoic acid {1-[2-(3-benzyl-pyrrolidin-1-yl)-ethyl]-1H-imidazol-4-yl}-amide;

(S)-2-[2-(3,5-Difluoro-phenyl)-acetylamino]-pentanoic acid {1-[2-(3-pyridin-2-yl-pyrrolidin-1-yl)-ethyl]-1H-imidazol-4-yl}-amide;

(S)-2-[2-(3,5-Difluoro-phenyl)-acetylamino]-pentanoic acid {1-[2-(methyl-pyridin-4-ylmethyl-amino)-ethyl]-1H-imidazol-4-yl}-amide;

(S)-2-[2-(3,5-Difluoro-phenyl)-acetylamino]-pentanoic acid (1-{2-[(2-methanesulfonyl-ethyl)-methyl-amino]-ethyl}-1H-imidazol-4-yl)-amide;

(S)-2-[2-(3,5-Difluoro-phenyl)-acetylamino]-pentanoic acid {1-[2-(2-tert-butoxy-ethylamino)-ethyl]-1H-imidazol-4-yl}-amide;

(S)-2-[2-(3,5-Difluoro-phenyl)-acetylamino]-pentanoic acid {1-[2-(3-pyridin-4-yl-pyrrolidin-1-yl)-ethyl]-1H-imidazol-4-yl}-amide;

(S)-2-[(1-Hydroxy-cyclohexylmethyl)-amino]-pentanoic acid [1-(1,1-dimethyl-2-pyrrolidin-1-yl-ethyl)-1H-imidazol-4-yl]-amide;

(S)-2-[2-(3,5-Difluoro-phenyl)-acetylamino]-N-[1-(1,1-dimethyl-2-pyrrolidin-1-yl-ethyl)-1H-imidazol-4-yl]-2-phenyl-acetamide;

(S)-2-(Dicyclopropylmethyl-amino)-pentanoic acid [1-(1,1-dimethyl-2-pyrrolidin-1-yl-ethyl)-1H-imidazol-4-yl]-amide;

(S)-2-(6,8-Difluoro-1,2,3,4-tetrahydro-naphthalen-2-ylamino)-pentanoic acid {1-[3-((R)-1-phenyl-ethylamino)-propyl]-1H-imidazol-4-yl}-amide;

(S)-2-(6,8-Difluoro-1,2,3,4-tetrahydro-naphthalen-2-ylamino)-pentanoic acid (1-{2-[(1-hydroxy-cyclohexylmethyl)-amino]-1,1-dimethyl-ethyl}-1H-imidazol-4-yl)-amide;

(S)-2-[2-(3,5-Difluoro-phenyl)-acetylamino]-N-{1-[2-((2S,6R)-2,6-dimethyl-morpholin-4-yl)-1,1-dimethyl-ethyl]-1H-imidazol-4-yl}-2-phenyl-acetamide;

(S)-2-(6,8-Difluoro-1,2,3,4-tetrahydro-naphthalen-2-ylamino)-pentanoic acid (1-{2-[(4-hydroxy-tetrahydro-pyran-4-ylmethyl)-amino]-1,1-dimethyl-ethyl}-1H-imidazol-4-yl)-amide;

(S)-2-[2-(3,5-Difluoro-phenyl)-acetylamino]-pentanoic acid [1-(1-dimethylaminomethyl-cyclobutyl)-1H-imidazol-4-yl]-amide;

(S)-2-[2-(3,5-Difluoro-phenyl)-acetylamino]-pentanoic acid [1-(1-piperidin-1-ylmethyl-cyclobutyl)-1H-imidazol-4-yl]-amide;

(S)-2-[2-(3,5-Difluoro-phenyl)-acetylamino]-pentanoic acid [1-(1-morpholin-4-ylmethyl-cyclobutyl)-1H-imidazol-4-yl]-amide;

(S)-2-[2-(3,5-Difluoro-phenyl)-acetylamino]-pentanoic acid (1-{1-[((2R,6S)-2,6-dimethyl-morpholin-4-yl)methyl]-cyclobutyl}-1H-imidazol-4-yl)-amide;

(S)-2-[2-(3,5-Difluoro-phenyl)-acetylamino]-pentanoic acid (1-{1-[(2,2,2-trifluoro-ethylamino)-methyl]-cyclobutyl}-1H-imidazol-4-yl)-amide;

(S)-2-[2-(3,5-Difluoro-phenyl)-acetylamino]-pentanoic acid (1-{1-[((R)-1-cyclohexyl-ethylamino)-methyl]-cyclobutyl}-1H-imidazol-4-yl)-amide;

(S)-2-(5,7-Difluoro-1,2,3,4-tetrahydro-naphthalen-2-ylamino)-pentanoic acid [1-(1-hydroxymethyl-cyclobutyl)-1H-imidazol-4-yl]-amide;

(S)-2-(5,7-Difluoro-1,2,3,4-tetrahydro-naphthalen-2-ylamino)-pentanoic acid [1-(1-pyrrolidin-1-ylmethyl-cyclobutyl)-1H-imidazol-4-yl]-amide;

(S)-2-[2-(3,5-Difluoro-phenyl)-acetylamino]-pentanoic acid (1-{1-[(2,2-dimethyl-propylamino)-methyl]-cyclobutyl}-1H-imidazol-4-yl)-amide;

(S)-2-(6,8-Difluoro-1,2,3,4-tetrahydro-naphthalen-2-ylamino)-N-{1-[2-(2,2-dimethyl-propylamino)-1,1-dimethyl-ethyl]-1H-imidazol-4-yl}-2-phenyl-acetamide;

(S)-2-(6,8-Difluoro-1,2,3,4-tetrahydro-naphthalen-2-ylamino)-pentanoic acid {1-[1-(4-trifluoromethyl-phenyl)-ethyl]-1H-imidazol-4-yl}-amide;

(S)-2-[2-(3,5-Difluoro-phenyl)-acetylamino]-pentanoic acid {1-[1-(4-trifluoromethyl-phenyl)-ethyl]-1H-imidazol-4-yl}-amide;

(S)-2-(6,8-Difluoro-1,2,3,4-tetrahydro-naphthalen-2-ylamino)-pentanoic acid {1-[2-(2-methoxy-2-methyl-propylamino)-1,1-dimethyl-ethyl]-1H-imidazol-4-yl}-amide;

(S)-2-(6,8-Difluoro-1,2,3,4-tetrahydro-naphthalen-2-ylamino)-pentanoic acid (1-{1,1-dimethyl-2-[(3-methyl-oxetan-3-ylmethyl)-amino]-ethyl}-1H-imidazol-4-yl)-amide;

(S)-2-(6,8-Difluoro-1,2,3,4-tetrahydro-naphthalen-2-ylamino)-pentanoic acid {1-[2-(cyclohexylmethyl-amino)-1,1-dimethyl-ethyl]-1H-imidazol-4-yl}-amide;

(S)-2-(6,8-Difluoro-1,2,3,4-tetrahydro-naphthalen-2-ylamino)-pentanoic acid {1-1-methyl-2-[(tetrahydro-pyran-4-ylmethyl)-amino]-ethyl}-1H-imidazol-4-yl)-amide;

(S)-2-[2-(3,5-Difluoro-phenyl)-acetylamino]-pentanoic acid (1-indan-1-yl-1H-imidazol-4-yl)-amide;

(S)-2-[2-(3,5-Difluoro-phenyl)-acetylamino]-pentanoic acid [(S)-1-((1S,2R)-2-hydroxy-indan-1-yl)-1H-imidazol-4-yl]-amide;

(S)-2-[2-(3,5-Difluoro-phenyl)-acetylamino]-pentanoic acid [(R)-1-((1R,2S)-2-hydroxy-indan-1-yl)-1H-imidazol-4-yl]-amide;

(S)-2-[2-(3,5-Difluoro-phenyl)-acetylamino]-pentanoic acid [1-(2-pyrrolidin-1-ylmethyl-cyclobutyl)-1H-imidazol-4-yl]-amide;

(S)-2-(6,8-Difluoro-1,2,3,4-tetrahydro-naphthalen-2-ylamino)-pentanoic acid [1-(2-pyrrolidin-1-ylmethyl-cyclobutyl)-1H-imidazol-4-yl]-amide;

(S)-2-[2-(3,5-Difluoro-phenyl)acetylamino]-pentanoic acid {1-[1-(4-fluoro-phenyl)-2-hydroxy-ethyl]-1H-imidazol-4-yl}-amide;

(S)-2-(6,8-Difluoro-1,2,3,4-tetrahydro-naphthalen-2-ylamino)-pentanoic acid {1-[3-(3-methyl-benzylamino)-propyl]-1H-imidazol-4-yl}-amide;

(S)-2-(6,8-Difluoro-1,2,3,4-tetrahydro-naphthalen-2-ylamino)-pentanoic acid {1-[3-(2-hydroxy-2-phenyl-ethylamino)-propyl]-1H-imidazol-4-yl}-amide;

(S)-2-(6,8-Difluoro-1,2,3,4-tetrahydro-naphthalen-2-ylamino)-pentanoic acid {1-[3-(2-chloro-benzylamino)-propyl]-1H-imidazol-4-yl}-amide;

(S)-2-(6,8-Difluoro-1,2,3,4-tetrahydro-naphthalen-2-ylamino)-pentanoic acid {1-[3-(3,4-dihydro-1H-isoquinolin-2-yl)-propyl]-1H-imidazol-4-yl}-amide;

(S)-2-(6,8-Difluoro-1,2,3,4-tetrahydro-naphthalen-2-ylamino)-pentanoic acid {1-[3-(indan-2-ylamino)-propyl]-1H-imidazol-4-yl}-amide;

(S)-2-(6,8-Difluoro-1,2,3,4-tetrahydro-naphthalen-2-ylamino)-pentanoic acid {1-[3-(1-methoxymethyl-propylamino)-propyl]-1H-imidazol-4-yl}-amide;

(S)-2-(6,8-Difluoro-1,2,3,4-tetrahydro-naphthalen-2-ylamino)-pentanoic acid {1-[3-(4-chloro-benzylamino)-propyl]-1H-imidazol-4-yl}-amide;

(S)-2-(6,8-Difluoro-1,2,3,4-tetrahydro-naphthalen-2-ylamino)-pentanoic acid {1-[3-(2-methyl-benzylamino)-propyl]-1H-imidazol-4-yl}-amide;

(S)-2-(6,8-Difluoro-1,2,3,4-tetrahydro-naphthalen-2-ylamino)-pentanoic acid {1-[3-(2-methoxy-ethylamino)-propyl]-1H-imidazol-4-yl}-amide;

(S)-2-(6,8-Difluoro-1,2,3,4-tetrahydro-naphthalen-2-ylamino)-pentanoic acid (1-{3-[(pyridin-3-ylmethyl)-amino]-propyl}-1H-imidazol-4-yl)-amide;

(S)-2-(6,8-Difluoro-1,2,3,4-tetrahydro-naphthalen-2-ylamino)-pentanoic acid {1-[3-((S)-1-p-tolyl-ethylamino)-propyl]-1H-imidazol-4-yl}-amide;

(S)-2-(6,8-Difluoro-1,2,3,4-tetrahydro-naphthalen-2-ylamino)-pentanoic acid {1-[3-(4-methoxy-benzylamino)-propyl]-1H-imidazol-4-yl}-amide;

(S)-2-(6,8-Difluoro-1,2,3,4-tetrahydro-naphthalen-2-ylamino)-pentanoic acid {1-[3-(cyclopropylmethyl-amino)-propyl]-1H-imidazol-4-yl}-amide;

(S)-2-(6,8-Difluoro-1,2,3,4-tetrahydro-naphthalen-2-ylamino)-pentanoic acid {1-[3-(4-methyl-benzylamino)-propyl]-1H-imidazol-4-yl}-amide;

(S)-2-(6,8-Difluoro-1,2,3,4-tetrahydro-naphthalen-2-ylamino)-pentanoic acid (1-{2-[(1-hydroxy-cyclohexylmethyl)-carbamoyl]-1,1-dimethyl-ethyl}-1H-imidazol-4-yl)-amide;

(S)-2-(1,2,3,4-Tetrahydro-naphthalen-2-ylamino)-pentanoic acid (1-{1,1-dimethyl-2-[(tetrahydro-pyran-4-ylmethyl)-amino]-ethyl}-1H-imidazol-4-yl)-amide;

(S)-2-(6,8-Difluoro-1,2,3,4-tetrahydro-naphthalen-2-ylamino)-pentanoic acid (1-{2-[(1-hydroxy-cyclohexylmethyl)-amino]-ethyl}-1H-imidazol-4-yl)-amide;

(S)-2-(6,8-Difluoro-1,2,3,4-tetrahydro-naphthalen-2-ylamino)-pentanoic acid (1-{1-[(2,2,2-trifluoro-ethylamino)-methyl]-cyclobutyl}-1H-imidazol-4-yl)-amide;

(S)-2-(6,8-Difluoro-1,2,3,4-tetrahydro-naphthalen-2-ylamino)-pentanoic acid (1-{1-[(2,2-dimethyl-propylamino)-methyl]-cyclobutyl}-1H-imidazol-4-yl)-amide;

(S)-2-(6,8-Difluoro-1,2,3,4-tetrahydro-naphthalen-2-ylamino)-pentanoic acid (1-{1-[((R)-1-cyclohexyl-ethylamino)-methyl]-cyclobutyl}-1H-imidazol-4-yl)-amide;

(S)-2-(6,8-Difluoro-1,2,3,4-tetrahydro-naphthalen-2-ylamino)-pentanoic acid [1-(1-dimethylaminomethyl-cyclobutyl)-1H-imidazol-4-yl]-amide;

(S)-2-(6,8-Difluoro-1,2,3,4-tetrahydro-naphthalen-2-ylamino)-pentanoic acid [1-(1-piperidin-1-ylmethyl-cyclobutyl)-1H-imidazol-4-yl]-amide;

(S)-2-(6,8-Difluoro-1,2,3,4-tetrahydro-naphthalen-2-ylamino)-pentanoic acid [1-(1-morpholin-4-ylmethyl-cyclobutyl)-1H-imidazol-4-yl]-amide;

(S)-2-(6,8-Difluoro-1,2,3,4-tetrahydro-naphthalen-2-ylamino)-pentanoic acid (1-{1-[((2R,6S)-2,6-dimethyl-morpholin-4-yl)methyl]-cyclobutyl}-1H-imidazol-4-yl)-amide;

(S)-2-(6,8-Difluoro-1,2,3,4-tetrahydro-naphthalen-2-ylamino)-pentanoic acid (1-{2-[(4-hydroxy-tetrahydro-pyran-4-ylmethyl)-amino]-ethyl}-1H-imidazol-4-yl)-amide;

(S)-2-(6,8-Difluoro-1,2,3,4-tetrahydro-naphthalen-2-ylamino)-pentanoic acid (1-{2-[(tetrahydro-pyran-4-ylmethyl)-amino]-ethyl}-1H-imidazol-4-yl)-amide;

(S)-2-(6,8-Difluoro-1,2,3,4-tetrahydro-naphthalen-2-ylamino)-pentanoic acid (1-{2-[(3-methyl-oxetan-3-ylmethyl)-amino]-ethyl}-1H-imidazol-4-yl)-amide;

(S)-2-(6,8-Difluoro-1,2,3,4-tetrahydro-naphthalen-2-ylamino)-pentanoic acid (1-{2-[(1-hydroxy-cyclohexylmethyl)-amino]-1-methyl-ethyl}-1H-imidazol-4-yl)-amide;

(S)-2-(6,8-Difluoro-1,2,3,4-tetrahydro-naphthalen-2-ylamino)-pentanoic acid (1-{1,1-dimethyl-3-[(pyridin-2-ylmethyl)-amino]-propyl}-1H-imidazol-4-yl)-amide;

(S)-2-(6,8-Difluoro-1,2,3,4-tetrahydro-naphthalen-2-ylamino)-pentanoic acid (1-{1-[(1-hydroxy-cyclohexylmethyl)-carbamoyl]-1-methyl-ethyl}-1H-imidazol-4-yl)-amide;

(S)-2-{[(2-Fluoro-3-trifluoromethyl-phenyl)methyl]-amino}-pentanoic acid {1-[2-((2R,6S)-2,6-dimethyl-morpholin-4-yl)-1,1-dimethyl-ethyl]-1H-imidazol-4-yl}-amide;

(S)-2-(6,8-Difluoro-1,2,3,4-tetrahydro-naphthalen-2-ylamino)-pentanoic acid {1-[1,1-dimethyl-3-((S)-2,2,2-trifluoro-1-phenyl-ethylamino)-propyl]-1H-imidazol-4-yl}-amide;

(S)-2-(6,8-Difluoro-1,2,3,4-tetrahydro-naphthalen-2-ylamino)-pentanoic acid {1-[1,1-dimethyl-3-((R)-1-phenyl-ethylamino)-propyl]-1H-imidazol-4-yl}-amide;

(S)-2-(2-Trifluoromethyl-benzylamino)-pentanoic acid {1-[2-((2R,6S)-2,6-dimethyl-morpholin-4-yl)-1,1-dimethyl-ethyl]-1H-imidazol-4-yl}-amide;

(S)-2-(6,8-Difluoro-1,2,3,4-tetrahydro-naphthalen-2-ylamino)-pentanoic acid (1-{1-methyl-1-[(tetrahydro-pyran-4-ylmethyl)-carbamoyl]-ethyl}-1H-imidazol-4-yl)-amide;

(S)-2-(6,8-Difluoro-1,2,3,4-tetrahydro-naphthalen-2-ylamino)-pentanoic acid {1-[2-(2-ethoxy-ethylamino)-ethyl]-1H-imidazol-4-yl}-amide;

(S)-2-[2-(3,5-Difluoro-phenyl)-acetylamino]-pentanoic acid {(R)-1-[(R)-1-(4-fluoro-phenyl)-2-hydroxy-ethyl]-1H-imidazol-4-yl}-amide;

(S)-2-[2-(3,5-Difluoro-phenyl)-acetylamino]-pentanoic acid [1-(2-hydroxymethyl-phenyl)-1H-imidazol-4-yl]-amide;

(S)-2-(6,8-Difluoro-1,2,3,4-tetrahydro-naphthalen-2-ylamino)-pentanoic acid {1-[2-(2-ethoxy-ethylamino)-1,1-dimethyl-ethyl]-1H-imidazol-4-yl}-amide;

(S)-2-(6,8-Difluoro-1,2,3,4-tetrahydro-naphthalen-2-ylamino)-N-{1-[2-(2-ethoxy-ethylamino)-1,1-dimethyl-ethyl]-1H-imidazol-4-yl}-propionamide;

(S)-2-[2-(3,5-Difluoro-phenyl)-acetylamino]-N-{1-[2-(2,2-dimethyl-propylamino)-1,1-dimethyl-ethyl]-1H-imidazol-4-yl}-2-phenyl-acetamide;

(S)-2-(6,8-Difluoro-1,2,3,4-tetrahydro-naphthalen-2-ylamino)-pentanoic acid {1-[1-methyl-1-(2-methyl-benzylcarbamoyl)-ethyl]-1H-imidazol-4-yl}-amide;

(S)-2-(6,8-Difluoro-1,2,3,4-tetrahydro-naphthalen-2-ylamino)-pentanoic acid {1-[1-(2-methoxy-1-methyl-ethylcarbamoyl)-1-methyl-ethyl]-1H-imidazol-4-yl}-amide;

(S)-2-(6,8-Difluoro-1,2,3,4-tetrahydro-naphthalen-2-ylamino)-pentanoic acid {(S)-1-[2-(2,2-dimethyl-propylamino)-1-phenyl-ethyl]-1H-imidazol-4-yl}-amide;

(S)-2-(6,8-Difluoro-1,2,3,4-tetrahydro-naphthalen-2-ylamino)-pentanoic acid [1-(3-benzylamino-propyl)-1H-imidazol-4-yl]-amide;

(S)-2-(6,8-Difluoro-1,2,3,4-tetrahydro-naphthalen-2-ylamino)-pentanoic acid (1-{2-[(2,2-dimethyl-propylamino)-methyl]-phenyl}-1H-imidazol-4-yl)-amide;

(S)-2-(6,8-Difluoro-1,2,3,4-tetrahydro-naphthalen-2-ylamino)-pentanoic acid {(S)-1-[2-(2,2-dimethyl-propylamino)-1-phenyl-ethyl]-1H-imidazol-4-yl}-amide;

(S)-2-(6,8-Difluoro-1,2,3,4-tetrahydro-naphthalen-2-ylamino)-pentanoic acid (1-{2-[(2-hydroxy-butylamino)-methyl]-phenyl}-1H-imidazol-4-yl)-amide;

2-[2-(3,5-Difluoro-phenyl)-acetylamino]-N-{1-[2-(2,2-dimethyl-propylamino)-1,1-dimethyl-ethyl]-1H-imidazol-4-yl}-2-pyridin-3-yl-acetamide;

2-[2-(3,5-Difluoro-phenyl)-acetylamino]-N-{1-[2-(2,2-dimethyl-propylamino)-1,1-dimethyl-ethyl]-1H-imidazol-4-yl}-2-(4-fluoro-phenyl)-acetamide;

(S)-2-(6,8-Difluoro-1,2,3,4-tetrahydro-naphthalen-2-ylamino)-pentanoic acid {1-[1-methyl-1-(methyl-phenethyl-carbamoyl)-ethyl]-1H-imidazol-4-yl}-amide;

(S)-2-(6,8-Difluoro-1,2,3,4-tetrahydro-naphthalen-2-ylamino)-pentanoic acid {1-[1-(1,3-dihydro-isobenzofuran-5-ylcarbamoyl)-1-methyl-ethyl]-1H-imidazol-4-yl}-amide;

(S)-2-(6,8-Difluoro-1,2,3,4-tetrahydro-naphthalen-2-ylamino)-pentanoic acid {1-[1-(indan-1-ylcarbamoyl)-1-methyl-ethyl]-1H-imidazol-4-yl}-amide;

(S)-2-(6,8-Difluoro-1,2,3,4-tetrahydro-naphthalen-2-ylamino)-pentanoic acid {1-[1,1-dimethyl-2-oxo-2-(3-pyridin-4-yl-pyrrolidin-1-yl)-ethyl]-1H-imidazol-4-yl}-amide;

(S)-2-(6,8-Difluoro-1,2,3,4-tetrahydro-naphthalen-2-ylamino)-pentanoic acid (1-{1-[2-(3-fluoro-phenyl)-ethylcarbamoyl]-1-methyl-ethyl}-1H-imidazol-4-yl)-amide;

2-{4-[(S)-2-(6,8-Difluoro-1,2,3,4-tetrahydro-naphthalen-2-ylamino)-propionylamino]-imidazol-1-yl}-N-indan-1-yl-isobutyramide;

(S)-2-(6,8-Difluoro-1,2,3,4-tetrahydro-naphthalen-2-ylamino)-pentanoic acid {1-[2-(3-cyano-piperidin-1-yl)-1,1-dimethyl-2-oxo-ethyl]-1H-imidazol-4-yl}-amide;

(S)-2-(6,8-Difluoro-1,2,3,4-tetrahydro-naphthalen-2-ylamino)-pentanoic acid (1-{1-methyl-1-[methyl-(tetrahydro-pyran-2-ylmethyl)-carbamoyl]-ethyl}-1H-imidazol-4-yl)-amide;

(S)-2-(6,8-Difluoro-1,2,3,4-tetrahydro-naphthalen-2-ylamino)-pentanoic acid (1-{1-[ethyl-(2-pyrazol-1-yl-ethyl)-carbamoyl]-1-methyl-ethyl}-1H-imidazol-4-yl)-amide;

(S)-2-(6,8-Difluoro-1,2,3,4-tetrahydro-naphthalen-2-ylamino)-pentanoic acid {1-[1,1-dimethyl-2-oxo-2-(2-phenyl-pyrrolidin-1-yl)-ethyl]-1H-imidazol-4-yl}-amide;

(S)-2-(6,8-Difluoro-1,2,3,4-tetrahydro-naphthalen-2-ylamino)-N-{1-[1,1-dimethyl-2-oxo-2-(3-pyridin-4-yl-pyrrolidin-1-yl)-ethyl]-1H-imidazol-4-yl}-propionamide;

(S)-2-(6,8-Difluoro-1,2,3,4-tetrahydro-naphthalen-2-ylamino)-pentanoic acid (1-{1-[(furan-2-ylmethyl)-carbamoyl]-1-methyl-ethyl}-1H-imidazol-4-yl)-amide;

(S)-2-(6,8-Difluoro-1,2,3,4-tetrahydro-naphthalen-2-ylamino)-pentanoic acid (1-{2-[3-(acetyl-methyl-amino)-pyrrolidin-1-yl]-1,1-dimethyl-2-oxo-ethyl}-1H-imidazol-4-yl)-amide;

(S)-2-(6,8-Difluoro-1,2,3,4-tetrahydro-naphthalen-2-ylamino)-pentanoic acid {1-[1-methyl-1-((3R,4S)-4-methylsulfanyl-tetrahydro-furan-3-ylcarbamoyl)-ethyl]-1H-imidazol-4-yl}-amide;

(S)-2-(6,8-Difluoro-1,2,3,4-tetrahydro-naphthalen-2-ylamino)-pentanoic acid {1-[2-(4-acetyl-[1,4]diazepan-1-yl)-1,1-dimethyl-2-oxo-ethyl]-1H-imidazol-4-yl}-amide;

2-{4-[(S)-2-(6,8-Difluoro-1,2,3,4-tetrahydro-naphthalen-2-ylamino)-propionylamino]-imidazol-1-yl}-N-[2-(3-fluoro-phenyl)-ethyl]-isobutyramide;

(S)-2-(6,8-Difluoro-1,2,3,4-tetrahydro-naphthalen-2-ylamino)-pentanoic acid (1-{1-methyl-1-[1-(1-methyl-1H-pyrazol-4-yl)-ethylcarbamoyl]-ethyl}-1H-imidazol-4-yl)-amide;

2-{4-[(S)-2-(6,8-Difluoro-1,2,3,4-tetrahydro-naphthalen-2-ylamino)-propionylamino]-imidazol-1-yl}-N-methyl-N-phenethyl-isobutyramide;

(S)-2-(6,8-Difluoro-1,2,3,4-tetrahydro-naphthalen-2-ylamino)-pentanoic acid {1-[1-(3-methoxy-propylcarbamoyl)-1-methyl-ethyl]-1H-imidazol-4-yl}-amide;

(S)-2-(6,8-Difluoro-1,2,3,4-tetrahydro-naphthalen-2-ylamino)-pentanoic acid (1-{1-methyl-1-[(3-methyl-[1,2,4]oxadiazol-5-ylmethyl)-carbamoyl]-ethyl}-1H-imidazol-4-yl)-amide;

(S)-2-(6,8-Difluoro-1,2,3,4-tetrahydro-naphthalen-2-ylamino)-pentanoic acid (1-{1-[(2-cyano-ethyl)-methylcarbamoyl]-1-methyl-ethyl}-1H-imidazol-4-yl)-amide;

2-{4-[(S)-2-(6,8-Difluoro-1,2,3,4-tetrahydro-naphthalen-2-ylamino)-propionylamino]-imidazol-1-yl}-N-ethyl-N-(2-pyrazol-1-yl-ethyl)-isobutyramide;

(S)-2-(6,8-Difluoro-1,2,3,4-tetrahydro-naphthalen-2-ylamino)-pentanoic acid {1-[1,1-dimethyl-2-(3-methyl-5,6-dihydro-8H-[1,2,4]triazolo[4,3-a]pyrazin-7-yl)-2-oxo-ethyl]-1H-imidazol-4-yl}-amide;

(S)-2-(6,8-Difluoro-1,2,3,4-tetrahydro-naphthalen-2-ylamino)-pentanoic acid (1-{1-methyl-1-[methyl-(1-methyl-1H-imidazol-2-ylmethyl)-carbamoyl]-ethyl}-1H-imidazol-4-yl)-amide;

(S)-2-(6,8-Difluoro-1,2,3,4-tetrahydro-naphthalen-2-ylamino)-N-{1-[2-(4-hydroxymethyl-4-methyl-piperidin-1-yl)-1,1-dimethyl-2-oxo-ethyl]-1H-imidazol-4-yl}-propionamide;

2-{4-[(S)-2-(6,8-Difluoro-1,2,3,4-tetrahydro-naphthalen-2-ylamino)-propionylamino]-imidazol-1-yl}-N-(4-methyl-benzyl)-isobutyramide;

2-{4-[(S)-2-(6,8-Difluoro-1,2,3,4-tetrahydro-naphthalen-2-ylamino)-propionylamino]-imidazol-1-yl}-N-(1,3-dihydro-isobenzofuran-5-yl)-isobutyramide;

(S)-2-(6,8-Difluoro-1,2,3,4-tetrahydro-naphthalen-2-ylamino)-N-{1-[1,1-dimethyl-2-oxo-2-(2-phenyl-pyrrolidin-1-yl)-ethyl]-1H-imidazol-4-yl}-propionamide;

(S)-2-(6,8-Difluoro-1,2,3,4-tetrahydro-naphthalen-2-ylamino)-pentanoic acid (1-{1-[(2-diethylamino-ethyl)-methyl-carbamoyl]-1-methyl-ethyl}-1H-imidazol-4-yl)-amide;

(S)-N-{1-[2-(3-Cyano-piperidin-1-yl)-1,1-dimethyl-2-oxo-ethyl]-1H-imidazol-4-yl}-2-(6,8-difluoro-1,2,3,4-tetrahydro-naphthalen-2-ylamino)-propionamide;

(S)-N-(1-{2-[3-(Acetyl-methyl-amino)-pyrrolidin-1-yl]-1,1-dimethyl-2-oxo-ethyl}-1H-imidazol-4-yl)-2-(6,8-difluoro-1,2,3,4-tetrahydro-naphthalen-2-ylamino)-propionamide;

2-{4-[(S)-2-(6,8-Difluoro-1,2,3,4-tetrahydro-naphthalen-2-ylamino)-propionylamino]-imidazol-1-yl}-N-((1R,2S)-2-hydroxymethyl-cyclohexyl)-isobutyramide;

2-{4-[(S)-2-(6,8-Difluoro-1,2,3,4-tetrahydro-naphthalen-2-ylamino)-propionylamino]-imidazol-1-yl}-N-(3-methyl-[1,2,4]oxadiazol-5-ylmethyl)-isobutyramide;

2-{4-[(S)-2-(6,8-Difluoro-1,2,3,4-tetrahydro-naphthalen-2-ylamino)-propionylamino]-imidazol-1-yl}-N-((S)-2-methoxy-1-methyl-ethyl)-isobutyramide;

2-{4-[(S)-2-(6,8-Difluoro-1,2,3,4-tetrahydro-naphthalen-2-ylamino)-propionylamino]-imidazol-1-yl}-N-(3-methoxy-propyl)-isobutyramide;

2-{4-[(S)-2-(6,8-Difluoro-1,2,3,4-tetrahydro-naphthalen-2-ylamino)-propionylamino]-imidazol-1-yl}-N-[1-(1-methyl-1H-pyrazol-4-yl)-ethyl]-isobutyramide;

2-{4-[(S)-2-(6,8-Difluoro-1,2,3,4-tetrahydro-naphthalen-2-ylamino)-propionylamino]-imidazol-1-yl}-N-(3-imidazol-1-yl-propyl)-isobutyramide; and 2-{4-[(S)-2-(6,8-Difluoro-1,2,3,4-tetrahydro-naphthalen-2-ylamino)-propionylamino]-imidazol-1-yl}-N-(3-morpholin-4-yl-propyl)-isobutyramide;

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A compound of Formula I

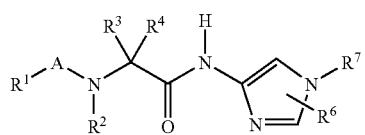

wherein A is absent or is selected from

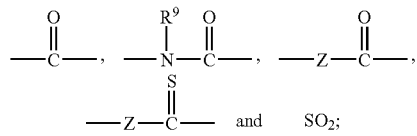

Z is selected from —$CH_2$, —CH(OH), —CH($C_1$-$C_6$ alkyl), —CH($C_1$-$C_6$ alkoxy), —CH($NR^9R^{10}$), —CH($CH_2$(OH)), —CH(CH($C_1$-$C_4$ alkyl)(OH)) and —CH(C($C_1$-$C_4$ alkyl)($C_1$-$C_4$alkyl)(OH));

$R^1$ is selected from —$C_1$-$C_{20}$ alkyl, —$C_2$-$C_{20}$ alkenyl, —$C_2$-$C_{20}$ alkynyl, —$C_1$-$C_{20}$ alkoxy, —$C_2$-$C_{20}$ alkenoxy, —$C_1$-$C_{20}$ hydroxyalkyl, —$C_3$-$C_8$ cycloalkyl, benzo($C_3$-$C_8$ cycloalkyl), benzo($C_3$-$C_8$ heterocycloalkyl), —$C_4$-$C_8$ cycloalkenyl, —($C_5$-$C_{11}$)bi- or tricycloalkyl, benzo($C_5$-$C_{11}$)bi- or tricycloalkyl, ($C_7$-$C_{11}$)bi- or tricycloalkenyl, (3-8 membered) heterocycloalkyl, —$C_6$-$C_{14}$ aryl and (5-14 membered) heteroaryl, wherein $R^1$ is optionally substituted by $R^{1a}$;

wherein $R^{1a}$ in each instance is independently selected from —OH, halo, —$C_1$-$C_6$ alkoxy, —CN, —$NO_2$, —$NR^9R^{10}$, —C(=O)$NR^9R^{10}$, —C(=O)$R^{11}$, —C(=O)$OR^{12}$, —$SO_2$—$NR^9R^{10}$, —S(O)$_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy;

wherein said alkoxy, cycloalkyl, cycloalkenyl, bi- or tricycloalkyl, bi- or tricycloalkenyl, heterocycloalkyl, aryl, heteroaryl, aryloxy and heteroaryloxy of $R^{1a}$ are each optionally independently substituted with from one to six substituents independently selected from the group $R^{1b}$;

wherein $R^{1b}$ in each instance is independently selected from —OH, —$C_1$-$C_{12}$ alkyl, —$C_2$-$C_{12}$ alkenyl, —$C_2$-$C_{12}$ alkynyl, —$C_1$-$C_6$ alkoxy, —$C_1$-$C_{12}$ alkoxyalkyl, —$C_1$-$C_{12}$ hydroxyalkyl, —$C_2$-$C_6$ alkenoxy, —$C_2$-$C_6$ alkynoxy, halo, —CN, —$NO_2$, —$NR^9R^{10}$, —C(=O)$NR^9R^{10}$, —C(=O)$R^{11}$, —C(=O)$OR^{12}$, —$SO_2$—$NR^9R^{10}$, —S(O)$_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy;

$R^2$ is selected from H, —$C_1$-$C_6$ alkyl, —$C_2$-$C_6$ alkenyl, —$C_3$-$C_8$ cycloalkyl and —$C_3$-$C_8$ cycloalkenyl, wherein $R^2$ is optionally independently substituted with from one to three substituents independently selected from —$C_1$-$C_4$ alkyl optionally substituted with from one to three halo atoms, —$C_1$-$C_4$ alkoxy optionally substituted with from one to three halo atoms, halo and —OH;

or $R^1$ and $R^2$ together with the A group when present and the nitrogen atom to which $R^2$ is attached, or $R^1$ and $R^2$ together with the nitrogen atom to which $R^1$ and $R^2$ are attached when A is absent, may optionally form a four to eight membered ring;

$R^3$ is selected from H, —$C_1$-$C_6$ alkyl, —$C_2$-$C_6$ alkenyl, —$C_2$-$C_6$ alkynyl, —$C_3$-$C_6$ cycloalkyl, —$C_5$-$C_6$ cycloalkenyl and (3-8 membered) heterocycloalkyl, —$C_6$-$C_{14}$ aryl and -(5-14 membered) heteroaryl, wherein said alkyl, alkenyl, alkynyl, cycloalkyl, cycloalkenyl, heterocycloalkyl, aryl or heteroaryl are each optionally independently substituted with from one to three substituents independently selected from —$C_1$-$C_4$ alkoxy, halo, —OH, —S($C_1$-$C_4$)alkyl, —$C_1$-$C_4$ alkyl —C(=O)$OR^9$, —$SO_2R^9$ and -(3-8 membered) heterocycloalkyl wherein said alkyl, alkoxy, and heterocycloalkyl may be further substituted by one to six halo;

$R^4$ is H, —$C_1$-$C_6$ alkyl or halo;

or $R^3$ and $R^4$ may together with the carbon atom to which they are attached optionally form a moiety selected from cyclopropyl, cyclobutyl, cyclopentyl, cyclohexyl, morpholino, piperidino, pyrrolidino, tetrahydrofuranyl and perhydro-2H-pyran, wherein said moiety formed by $R^3$ and $R^4$ is optionally substituted with from one to three substituents independently selected from —$C_1$-$C_6$ alkyl optionally substituted with from one to three halo atoms, —$C_1$-$C_6$ alkoxy optionally substituted with from one to three halo atoms, halo, —OH, —CN and allyl;

$R^6$ is selected from H, —$C_1$-$C_6$ alkyl, —$C_2$-$C_6$ alkylene, —$C_1$-$C_6$ alkoxy, halo, —CN, —$C_3$-$C_{12}$ cycloalkyl, —$C_4$-$C_{12}$ cycloalkenyl (5-10 membered) heteroaryl and —$C_6$-$C_{10}$ aryl, wherein said alkyl, alkylene and alkoxy of $R^6$ are each optionally independently substituted with from one to three substituents independently selected from halo and —CN, and wherein said cycloalkyl, cycloalkenyl, heteroaryl and aryl of $R^6$ are each optionally independently substituted with from one to three substituents independently selected from —$C_1$-$C_4$ alkyl optionally substituted with from one to three halo atoms, —$C_1$-$C_4$ alkoxy optionally substituted with from one to three halo atoms, halo and —CN;

$R^7$ is —$C_1$-$C_{20}$ alkyl substituted by —$C_3$-$C_{12}$ cycloalkyl, —$C_4$-$C_{12}$ cycloalkenyl, —($C_5$-$C_{20}$)bi- or tricycloalkyl, —($C_7$-$C_{20}$)bi- or tricycloalkenyl, -(3-12 membered) heterocycloalkyl, -(7-20 membered) heterobi- or heterotricycloalkyl, benzo($C_3$-$C_8$ heterocycloalkyl), -(5-15 membered) heteroaryl, —$C_6$-$C_{15}$ aryloxy and -(5-15 membered) heteroaryloxy, wherein $R^7$ is independently substituted with from one to six substituents independently selected from $R^{7a}$;

or $R^7$ is —$C_3$-$C_{20}$ cycloalkyl, —$C_4$-$C_{12}$ cycloalkenyl, —($C_5$-$C_{20}$)bi- or tricycloalkyl, —($C_7$-$C_{20}$)bi- or tricycloalkenyl, -(3-12 membered) heterocycloalkyl, -(7-20 membered)heterobi- or heterotricycloalkyl, —$C_6$-$C_{14}$ aryl, benzo($C_3$-$C_8$ cycloalkyl), -(5-15 membered) heteroaryl, —$C_6$-$C_{15}$ aryloxy and -(5-15 membered) heteroaryloxy substituted by at least one —$C_1$-$C_{20}$ alkyl, wherein said cycloalkyl, cycloalkenyl, bi- or tricycloalkyl, bi- or tricycloalkenyl, heterocycloalkyl, heterobi- or heterotricycloalkyl, aryl, benzocycloalkyl, heteroaryl, aryloxy and heteroaryloxy is optionally independently substituted with from one to six substituents independently selected from $R^{7a}$; and wherein said alkyl is substituted by $R^{7C}$;

wherein $R^{7a}$ in each instance is independently selected from —OH, —$C_1$-$C_{12}$ alkyl, —$C_2$-$C_{12}$ alkenyl, —$C_2$-$C_{12}$ alkynyl, —$C_1$-$C_6$ alkoxy, —$C_1$-$C_{12}$ alkoxyalkyl, —$C_1$-$C_{12}$ hydroxyalkyl, —$C_2$-$C_6$ alkenoxy, —$C_2$-$C_6$ alkynoxy, halo, —CN, —$NO_2$, —$NR^9R^{10}$, —C(=O)$NR^9R^{10}$, —C(=O)$R^{11}$, —C(=O)$OR^{12}$, —$SO_2$—$NR^9R^{10}$, —S(O)$_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy; wherein said alkyl, alkenyl, alkynyl, alkoxy, alkenoxy, alkynoxy, cycloalkyl, cycloalkenyl, bi- or tricycloalkyl, bi- or tricycloalkenyl, heterocycloalkyl, aryl, heteroaryl, aryloxy and heteroaryloxy of $R^{7a}$ are each optionally independently substituted with from one to six substituents independently selected from the group $R^{7b}$;

wherein $R^{7b}$ in each instance is independently selected from —OH, —$C_1$-$C_{12}$ alkyl, —$C_2$-$C_{12}$ alkenyl, —$C_2$-$C_{12}$ alkynyl, —$C_1$-$C_6$ alkoxy, —$C_1$-$C_{12}$ alkoxyalkyl, —$C_1$-$C_{12}$ hydroxyalkyl, —$C_2$-$C_6$ alkenoxy, —$C_2$-$C_6$ alkynoxy, halo, —CN, —$NO_2$, —$NR^9R^{10}$, —C(=O)$NR^9R^{10}$, —C(=O)$R^{11}$, —C(=O)$OR^{12}$, —$SO_2$—$NR^9R^{10}$, —S(O)$_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy;

wherein $R^{7C}$ in each instance is independently selected from —$C_1$-$C_6$ alkoxy, —CN, —$NO_2$, —$NR^9R^{10}$, —C(=O)$NR^9R^{10}$, —C(=O)$R^{11}$, —C(=O)$OR^{12}$, —$SO_2$—$NR^9R^{10}$, —S(O)$_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy; wherein said alkenoxy, cycloalkyl, cycloalkenyl, bi- or tricycloalkyl, bi- or tricycloalkenyl, heterocycloalkyl, aryl, heteroaryl, aryloxy and heteroaryloxy of $R^{7c}$ are each optionally independently substituted with from one to six substituents independently selected from the group $R^{7b}$;

or $R^6$ and $R^7$ may together with the carbon and nitrogen atoms to which they are respectively attached optionally form a -(5-8 membered) heterocycloalkyl ring, a -(5-8 membered) heterocycloalkenyl ring or a -(6-8 membered) heteroaryl ring, wherein said heterocycloalkyl, heterocycloalkenyl and heteroaryl rings are each optionally independently substituted with from one to three substituents independently selected from halo, —$C_1$-$C_6$ alkyl, optionally subsituted with from one to three halo atoms, —$C_1$-$C_6$ alkoxy optionally substituted with from one to three halo atoms, —$C_1$-$C_6$ hydroxyalkyl, —OH, —(CH$_2$)$_{zero-10}$$NR^9R^{10}$, —(CH$_2$)$_{zero-10}$C(=O)$NR^9R^{10}$, —$SO_2NR^9R^{10}$ and —$C_3$-$C_{12}$ cycloalkyl;

$R^9$ and $R^{10}$ in each instance are each independently selected from H, —OH, —$C_1$-$C_{12}$ alkyl, —$C_2$-$C_{12}$ alkenyl, —$C_2$-$C_{12}$ alkynyl, —$C_1$-$C_6$ alkoxy, —$C_1$-$C_{12}$ alkoxyalkyl —$C_1$-$C_{12}$ hydroxyalkyl, —$C_2$-$C_6$ alkenoxy, —$C_2$-$C_6$ alkynoxy, —C(=O)$NR^{11}R^{12}$, —C(=O)$R^{11}$, —C(=O)$OR^{12}$, —$SO_2$—$NR^{11}R^{12}$, —S(O)$_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy, wherein said alkyl, alkenyl, alkynyl, alkoxy, alkenoxy, alkynoxy, cycloalkyl, cycloalkenyl, bi- or tricycloalkyl, bi- or tricycloalkenyl, heterocycloalkyl, aryl, heteroaryl, aryloxy and heteroaryloxy of $R^9$ of $R^{10}$ are each optionally independently substituted with from one to six substituents independently selected from the group $R^{10a}$;

wherein $R^{10a}$ in each instance is independently selected from —OH, halo, —$C_1$-$C_{12}$ hydroxyalkyl, —$C_1$-$C_6$ alkoxy, —CN, —$NO_2$, —$NR^{11}R^{12}$, —C(=O)$NR^{11}R^{12}$, —C(=O)$R^{11}$, —C(=O)$OR^{11}$, —$SO_2$—$NR^{11}R^{12}$, —S(O)$_n$$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy; wherein said alkoxy, cycloalkyl, cycloalkenyl, bi- or tricycloalkyl, bi- or tricycloalkenyl, heterocycloalkyl, aryl, heteroaryl, aryloxy and heteroaryloxy of $R^{10a}$ are each optionally independently substituted with from one to six substituents independently selected from the group $R^{10b}$;

wherein $R^{10b}$ in each instance is independently selected from —OH, halo, —$C_1$-$C_{12}$ alkyl, —$C_2$-$C_{12}$ alkenyl, —$C_2$-$C_{12}$ alkynyl, —$C_1$-$C_6$ alkoxy, —$C_1$-$C_{12}$ alkoxyalkyl —$C_1$-$C_{12}$ hydroxyalkyl, —$C_2$-$C_6$ alkenoxy, —$C_2$-$C_6$ alkynoxy, halo, —CN, —$NO_2$, —$NR^{11}R^{12}$, —C(=O)$NR^{11}R^{12}$, —C(=O)$R^{11}$, —C(=O)$OR^{11}$, —$SO_2$—$NR^{11}R^{12}$, —S(O)$_n$$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy;

or $NR^9R^{10}$ may form a (4-20 membered) heterocycloalkyl, (5-18 membered) heterobi- or tricycloalkyl (5-18 membered) heterobi- or tricycloalkenyl, or -(5-15 membered) heteroaryl, wherein said heterocycloalkyl, heterobi- or tricycloalkyl, heterobi- or tricycloalkenyl or heteroaryl are optionally independently substituted with from one to six substituents independently selected from —$C_1$-$C_6$ alkyl, —$C_2$-$C_6$ alkenyl, —$C_2$-$C_6$ alkenyl, —$C_1$-$C_6$ alkoxy, —$C_2$-$C_6$ alkenoxy, —$C_2$-$C_6$ alkynoxy, —$C_1$-$C_6$ hydroxyalkyl, —$C_2$-$C_6$ hydroxyalkenyl, —$C_2$-$C_6$ hydroxyalkenyl, halo, —OH, —CN, —$NO_2$, —$NR^{11}R^{12}$, —C(=O)$NR^{11}R^{12}$, —C(=O)$R^{11}$, —C(=O)$OR^{11}$, —S(O)$_n$$R^{11}$ and —S(O)$_n$—$NR^{11}R^{12}$;

$R^{11}$ and $R^{12}$ in each instance are each independently selected from H, —$C_1$-$C_8$ alkyl, —$C_3$-$C_8$ cycloalkyl, —$C_4$-$C_8$ cycloalkenyl, —($C_5$-$C_{11}$)bi- or tricycloalkyl, —($C_7$-$C_{11}$)bi- or tricycloalkenyl, (3-8 membered) heterocycloalkyl, —$C_6$-$C_{10}$ aryl and -(5-14 membered) heteroaryl, wherein said alkyl of $R^{11}$ is optionally independently substituted with from one to three substituents independently selected from —OH, —CN and —$C_3$-$C_8$ cycloalkyl, and wherein each hydrogen atom of said alkyl is optionally independently replaced with a halo atom, and wherein said cylcoalkyl, cycloalkenyl, heterocycloalkyl, aryl and hetereoaryl of $R^{11}$ are each optionally independently substituted with from one to three substituents independently selected from halo, —$C_1$-$C_8$ alkyl optionally substituted with from one to three halo atoms, —OH, —CN and —$C_3$-$C_8$ cycloalkyl; and n is in each instance an integer independently selected from zero, 1 and 2;

or a pharmaceutically acceptable salt thereof.

2. A compound according to claim 1, or a pharmaceutically acceptable salt thereof, wherein $R^7$ is —$C_4$-$C_8$ cycloalkyl, -(4-10 membered) heterocycloalkyl, —$C_6$-$C_{14}$ aryl or -(5-15 membered) heteroaryl substituted by a —$C_1$-$C_4$ alkyl and wherein said alkyl is further substituted by $R^{7C}$, wherein $R^{7C}$ is —$NR^9R^{10}$.

3. A compound according to claim 2, or a pharmaceutically acceptable salt thereof, wherein $R^9$ is hydrogen or methyl, $R^{10}$ is —$C_1$-$C_8$ alkyl or —$C_4$-$C_8$ cycloalkyl, wherein said alkyl or cycloalkyl of $R^{10}$ is optionally substituted with from one to six $R^{10a}$, wherein each $R^{10a}$ is independently selected from halo, —$C_1$-$C_4$ alkyl, —$C_4$-$C_8$ cycloalkyl, -(5-15 membered) heteroaryl and —$C_1$-$C_4$ hydroxyalkyl;

or —$NR^9R^{10}$ is -(4-6 membered) heterocycloalkyl optionally substituted with from one to six substituents independently selected from halo, —$C_1$-$C_4$ alkyl and —$C_1$-$C_4$ hydroxyalkyl.

4. A compound according to claim 1, or a pharmaceutically acceptable salt thereof, wherein $R^7$ is —$C_1$-$C_8$ alkyl substituted by —$C_4$-$C_8$ cycloalkyl, —$(C_5$-$C_{20})$bi- or tricycloalkyl, -(4-8 membered) heterocycloalkyl, -(7-12 membered) heterobi- or heterotricycloalkyl, benzo($C_3$-$C_8$ cycloalkyl), or -(5-15 membered) heteroaryl, wherein $R^7$ is optionally substituted with from one to six from $R^{7a}$, wherein each $R^{7a}$ is independently selected from —$NR^9R^{10}$, halo, —$C_1$-$C_4$ alkyl and —$C_1$-$C_4$ hydroxyalkyl.

5. A compound according to claim 4, or a pharmaceutically acceptable salt thereof, wherein $R^7$ is —$C_1$-$C_6$ alkyl substituted by -(4-8 membered) heterocycloalkyl, wherein $R^7$ is optionally substituted with from one to six $R^{7a}$, wherein each $R^{7a}$ is independently selected from —$NR^9R^{10}$, halo, —OH, —$C_1$-$C_4$ alkyl and —$C_1$-$C_4$ hydroxyalkyl, wherein said alkyl or hydroxyalkyl is optionally substituted with from one to six halo.

6. A compound according to claim 1, or a pharmaceutically acceptable salt thereof, wherein A is absent and $R^1$ is benzo($C_5$-$C_6$ cycloalkyl) optionally substituted with from one to three substituents independently selected from —$C_1$-$C_6$ alkyl, halo and —OH; or A is

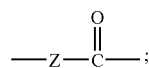

Z is —$CH_2$, —CH(OH) or —CH($C_1$-$C_6$ alkyl) and $R^1$ is —$C_1$-$C_{10}$ alkyl, —$C_6$-$C_{10}$ aryl or (6-10 membered) heteroaryl, wherein said alkyl, aryl and heteroaryl are optionally substituted with from one to three substituents independently selected from —$C_1$-$C_6$ alkyl, halo and —OH; $R^2$ is H or —$C_1$-$C_6$ alkyl; $R^3$ is H, —$CH_2CH_2SCH_3$, —$CH_2CH_2OCH_3$ or —$C_1$-$C_6$ alkyl; $R^4$ is H and $R^6$ is H or —$C_1$-$C_6$ alkyl.

7. A compound of Formula I

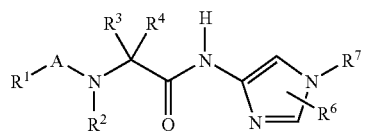

wherein A is absent or is selected from

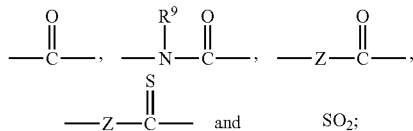

Z is selected from —$CH_2$, —CH(OH), —CH($C_1$-$C_6$ alkyl), —CH($C_1$-$C_6$ alkoxyl), —CH($NR^9R^{10}$), —CH($CH_2$(OH)), —CH(CH($C_1$-$C_4$ alkyl)(OH)) and —CH(C($C_1$-$C_4$ alkyl)($C_1$-$C_4$alkyl)(OH));

$R^1$ is selected from —$C_1$-$C_{20}$ alkyl, —$C_2$-$C_{20}$ alkenyl, —$C_2$-$C_{20}$ alkynyl, —$C_1$-$C_{20}$ alkoxy, —$C_2$-$C_{20}$ alkenoxy, —$C_1$-$C_{20}$ hydroxyalkyl, —$C_3$-$C_8$ cycloalkyl, benzo($C_3$-$C_8$ cycloalkyl), benzo($C_3$-$C_8$ heterocycloalkyl), —$C_4$-$C_8$ cycloalkenyl, —$(C_5$-$C_{11})$bi- or tricycloalkyl, benzo($C_5$-$C_{11}$)bi- or tricycloalkenyl, $(C_7$-$C_{11})$bi- or tricycloalkenyl, -(3-8 membered) heterocycloalkyl, —$C_6$-$C_{14}$ aryl and -(5-14 membered) heteroaryl, wherein $R^1$ is optionally substituted by $R^{1a}$;

wherein $R^{1a}$ in each instance is independently selected from —OH, halo, —$C_1$-$C_6$ alkoxy, —CN, —$NO_2$, —$NR^9R^{10}$, —C(=O)$NR^9R^{10}$, —C(=O)$R^{11}$, —C(=O)$OR^{12}$, —$SO_2$—$NR^9R^{10}$, —S(O)$_n$—$R^{11}$, —$C_3$-$C_{15}$ cycloalkyl, —$C_4$-$C_{15}$ cycloalkenyl, —$(C_5$-$C_{11})$bi- or tricycloalkyl, —$(C_7$-$C_{11})$bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy;

wherein said alkoxy, cycloalkyl, cycloalkenyl, bi- or tricycloalkyl, bi- or tricycloalkenyl, heterocycloalkyl, aryl, heteroaryl, aryloxy and heteroaryloxy of $R^{1a}$ are each optionally independently substituted with from one to six substituents independently selected from the group $R^{1b}$;

wherein $R^{1b}$ in each instance is independently selected from —OH, —$C_1$-$C_{12}$ alkyl, —$C_2$-$C_{12}$ alkenyl, —$C_2$-$C_{12}$ alkynyl, —$C_1$-$C_6$ alkoxy, —$C_1$-$C_{12}$ alkoxyalkyl —$C_1$-$C_{12}$ hydroxyalkyl, —$C_2$-$C_6$ alkenoxy, —$C_2$-$C_6$ alkynoxy, halo, —CN, —$NO_2$, —$NR^9R^{10}$, —C(=O)$NR^9R^{10}$, —C(=O)$R^{11}$, —C(=O)$OR^{12}$, —$SO_2$—$NR^9R^{10}$, —S(O)$_n$—$R^{11}$, —$C_3$-$C_{15}$ cycloalkyl, —$C_4$-$C_{15}$ cycloalkenyl, —$(C_5$-$C_{11})$bi- or tricycloalkyl, —$(C_7$-$C_{11})$bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy;

$R^2$ is selected from H, —$C_1$-$C_6$ alkyl, —$C_2$-$C_6$ alkenyl, —$C_3$-$C_8$ cycloalkyl and $C_3$-$C_8$ cycloalkenyl, wherein $R^2$ is optionally independently substituted with from one to three substituents independently selected from —$C_1$-$C_4$ alkyl optionally substituted with from one to three halo atoms, —$C_1$-$C_4$ alkoxy optionally substituted with from one to three halo atoms, halo and —OH;

or $R^1$ and $R^2$ together with the A group when present and the nitrogen atom to which $R^2$ is attached, or $R^1$ and $R^2$ together with the nitrogen atom to which $R^1$ and $R^2$ are attached when A is absent, may optionally form a four to eight membered ring;

$R^3$ is selected from H, —$C_1$-$C_6$ alkyl, —$C_2$-$C_6$ alkenyl, —$C_2$-$C_6$ alkynyl, —$C_3$-$C_6$ cycloalkyl, —$C_5$-$C_6$ cycloalkenyl and (3-8 membered) heterocycloalkyl —$C_6$-$C_{14}$ aryl and (5-14 membered) heteroaryl, wherein said alkyl, alkenyl, alkynyl, cycloalkyl, cycloalkenyl, heterocycloalkyl aryl or heteroaryl are each optionally independently substituted with from one to three substituents independently selected from —$C_1$-$C_4$ alkoxy, halo, —OH, —S($C_1$-$C_4$)alkyl —$C_1$-$C_4$ alkyl —C(=O) $OR^9$, —$SO_2R^9$ and -(3-8 membered) heterocycloalkyl wherein said alkyl, alkoxy, and heterocyloalkyl may be further substituted by one to six halo;

$R^4$ is H, —$C_1$-$C_6$ alkyl or halo;

or $R^3$ and $R^4$ may together with the carbon atom to which they are attached optionally form a moiety selected from cyclopropyl, cyclobutyl, cyclopentyl, cyclohexyl, morpholino, piperidino, pyrrolidino, tetrahydrofuranyl and perhydro-2H-pyran, wherein said moiety formed by $R^3$ and $R^4$ is optionally substituted with from one to three substituents independently selected from —$C_1$-$C_6$ alkyl optionally substituted with from one to three halo atoms, —$C_1$-$C_6$ alkoxy optionally substituted with from one to three halo atoms, halo, —OH, —CN and allyl;

$R^6$ is selected from H, —$C_1$-$C_6$ alkyl, —$C_2$-$C_6$ alkylene, —$C_1$-$C_6$ alkoxy, halo, —CN, —$C_3$-$C_{12}$ cycloalkyl, —$C_4$-$C_{12}$ cycloalkenyl -(5-10 membered) heteroaryl and —$C_6$-$C_{10}$ aryl, wherein said alkyl, alkylene and alkoxy of $R^6$ are each optionally independently substituted with from one to three substituents independently selected from halo and —CN, and wherein said cycloalkyl, cycloalkenyl, heteroaryl and aryl of $R^6$ are each optionally independently substituted with from one to three substituents independently selected from —$C_1$-$C_4$ alkyl optionally substituted with from one to three halo atoms, —$C_1$-$C_4$ alkoxy optionally substituted with from one to three halo atoms, halo and —CN;

$R^7$ is selected from —$C_1$-$C_{20}$ alkyl, —$C_1$-$C_{20}$ alkoxy, —$C_1$-$C_{20}$ hydroxyalkyl, —$C_3$-$C_{12}$ cycloalkyl, —$C_4$-$C_{12}$ cycloalkenyl, —($C_5$-$C_{20}$)bi- or tricycloalkyl, —($C_7$-$C_{20}$) bi- or tricycloalkenyl, (3-12 membered) heterocycloalkyl, -(7-20 membered) heterobi- or heterotricycloalkyl, —$C_6$-$C_{14}$ aryl, -(5-15 membered) heteroaryl —$C_6$-$C_{15}$ aryloxy and -(5-15 membered) heteroaryloxy, wherein said alkyl, alkenyl, alkynyl, alkoxy, alkenoxy, alkynoxy, cycloalkyl, cycloalkenyl, bi- or tricycloalkyl, bi- or tricycloalkenyl, heterocycloalkyl, aryl, heteroaryl, aryloxy and heteroaryloxy of $R^7$ are each independently substituted with from one to six substituents independently selected from the group $R^{7a}$;

wherein $R^{7a}$ in each instance is independently selected from —$C_1$-$C_6$ alkoxy, —$C_1$-$C_{12}$ alkoxyalkyl, —$NR^9R^{10}$, —C(=O)$NR^9R^{10}$, —$C_3$-$C_{15}$ cycloalkyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy, wherein said alkyl, alkoxy, alkoxyalkyl, cycloalkyl, heterocycloalkyl, aryl heteroaryl, aryloxy, and heteroaryloxy of $R^{7a}$ are each independently substituted by $R^{7b}$;

wherein $R^{7d}$ in each instance is independently selected from: —$C_2$-$C_{12}$ alkenyl, —$C_2$-$C_{12}$ alkynyl, —$C_1$-$C_{12}$ hydroxyalkyl, —$C_2$-$C_6$ alkenoxy, —$C_2$-$C_6$ alkynoxy, —$NR^9R^{10}$, —C(=O)$NR^9R^{10}$, —$SO_2$—$NR^9R^{10}$, —$C_4$-$C_{15}$ cycloalkenyl, —($C_5$-$C_{11}$) bi- or tricycloalkyl, —($C_7$-$C_{11}$) bi- or tricycloalkenyl, wherein said alkenyl, alkynyl, hydroxyalkyl, alkenoxy, alkynoxy, cycloalkenyl, bi- or tricycloalkyl, bi- or tricycloalkenyl, of $R^{7d}$ are each optionally independently substituted with from one to six substituents independently selected from the group $R^{7b}$;

wherein $R^{7b}$ in each instance is independently selected from —$C_2$-$C_{12}$ alkenyl, —$C_2$-$C_{12}$ alkynyl, —$C_1$-$C_6$ alkoxy, —$C_1$-$C_{12}$ alkoxyalkyl —$C_1$-$C_{12}$ hydroxyalkyl, —$C_2$-$C_6$ alkenoxy, —$C_2$-$C_6$ alkynoxy, halo, —CN, —$NO_2$, —$NR^9R^{10}$, —C(=O)$NR^9R^{10}$, —C(=O)$R^{11}$, —C(=O)$OR^{12}$, —$SO_2$—$NR^9R^{10}$, —S(O)$_n$—$R^{11}$, —$C_3$-$C_{15}$ cycloalkyl, —$C_4$-$C_{15}$ cycloalkenyl, —($C_5$-$C_{11}$) bi or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy;

or $R^6$ and $R^7$ may together with the carbon and nitrogen atoms to which they are respectively attached optionally form a (5-8 membered) heterocycloalkyl ring, a (5-8 membered) heterocycloalkenyl ring or a (6-8 membered) heteroaryl ring, wherein said heterocycloalkyl, heterocycloalkenyl and heteroaryl rings are each optionally independently substituted with from one to three substituents independently selected from halo, —$C_1$-$C_6$ alkyl, optionally subsituted with from one to three halo atoms, —$C_1$-$C_6$ alkoxy optionally substituted with from one to three halo atoms, —$C_1$-$C_6$ hydroxyalkyl, —OH, —($CH_2$)$_{zero-10}$$NR^9R^{10}$, —($CH_2$)$_{zero-10}$C(=O)$NR^9R^{10}$, —$SO_2NR^9R^{10}$ and —$C_3$-$C_{12}$ cycloalkyl;

$R^9$ and $R^{10}$ in each instance are each independently selected from —H, —C(=O)$R^{13}$ or —$C_1$-$C_{20}$ alkyl, wherein at least one of $R^9$ and $R^{10}$ are —C(=O)$R^{13}$ or —$C_1$-$C_{20}$ alkyl, and wherein each —$C_1$-$C_{20}$ alkyl is substituted with $R^{10a}$ wherein $R^{10a}$ in each instance is independently selected from —$C_1$-$C_6$ alkoxy, —CN, —$NO_2$, —$NR^{11}R^{11}$, —C(=O)$NR^{11}R^{12}$, —C(=O)$R^{11}$, —C(=O)$OR^{11}$, —$SO_2$—$NR^{11}R^{12}$, —S(O)$_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy; wherein said alkoxy, cycloalkyl, cycloalkenyl, bi- or tricycloalkyl, bi- or tricycloalkenyl, heterocycloalkyl, aryl, heteroaryl, aryloxy and heteroaryloxy of $R^{10a}$ are each optionally independently substituted with from one to six substituents independently selected from the group $R^{10b}$ wherein $R^{10b}$ in each instance is independently selected from —OH, —$C_1$-$C_{12}$ alkyl, —$C_2$-$C_{12}$ alkenyl, —$C_2$-$C_{12}$ alkynyl, —$C_1$-$C_6$ alkoxy, —$C_1$-$C_{12}$ alkoxyalkyl —$C_1$-$C_{12}$ hydroxyalkyl, —$C_2$-$C_6$ alkenoxy, —$C_2$-$C_6$ alkynoxy, halo, —CN, —$NO_2$, —$NR^{11}R^{12}$, —C(=O)$NR^{11}R^{12}$, —C(=O)$R^{11}$, —C(=O)$OR^{11}$, —$SO_2$—$NR^{11}R^{12}$, —S(O)$_n$$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy;

$R^{11}$ and $R^{12}$ in each instance are each independently selected from H, —$C_1$-$C_8$ alkyl, —$C_3$-$C_8$ cycloalkyl, —$C_4$-$C_8$ cycloalkenyl, ($C_5$-$C_{11}$) bi- or tricycloalkyl, —($C_7$-$C_{11}$) bi- or tricycloalkenyl, (3-8 membered) heterocycloalkyl, —$C_6$-$C_{10}$ aryl and (5-14 membered) heteroaryl, wherein said alkyl of $R^{11}$ and $R^{12}$ is optionally independently substituted with from one to three substituents independently selected from —OH, —CN and —$C_3$-$C_8$ cycloalkyl, and wherein each hydrogen atom of said alkyl is optionally independently replaced with a halo atom, and wherein said cylcoalkyl, cycloalkenyl, heterocycloalkyl, aryl and hetereoaryl of $R^{11}$ and $R^{12}$ are each optionally independently substituted with from one to three substituents independently selected from halo, —$C_1$-$C_8$ alkyl optionally substituted with from one to three halo atoms, —OH, —CN and —$C_3$-$C_8$ cycloalkyl;

$R^{13}$ is in each instance is independently selected from alkyl substituted by —$C_1$-$C_{12}$ alkoxy, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$) bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy; wherein said alkoxy, cycloalkyl, cycloalkenyl, bi- or tricycloalkyl, bi- or tricycloalkenyl, heterocycloalkyl, aryl, heteroaryl, aryloxy and heteroaryloxy of $R^{13}$ is optionally substituted by one to three substituents independently selected from halo, —$C_1$-$C_8$ alkyl optionally substituted with from one to three halo atoms, —OH, —CN and —$C_3$-$C_8$ cycloalkyl;

n is in each instance an integer independently selected from zero, 1 and 2;

or a pharmaceutically acceptable salt thereof.

8. A compound according to claim 7, or a pharmaceutically acceptable salt thereof, wherein $R^7$ is —$C_1$-$C_8$ alkyl substituted by $R^{7a}$; $R^{7a}$ is —$NR^9R^{10}$; $R^9$ is H or methyl; $R^{10}$ is —$C_1$-$C_8$ alkyl; $R^{10a}$ is —$C_1$-$C_6$ alkoxy, —$C_4$-$C_8$ cycloalkyl, -(4-8 membered) heterocycloalkyl, —$C_6$-$C_{15}$ aryl or -(5-15 membered) heteroaryl, wherein said alkoxy, cycloalkyl, heterocycloalkyl, aryl, and heteroaryl of $R^{10a}$ are each optionally independently substituted with from one to six $R^{10b}$; wherein $R^{10b}$ is independently selected from halo, —OH, —$C_1$-$C_4$ alkyl and —$C_1$-$C_4$ hydroxyalkyl, and wherein each said alkyl and hydroxyalkyl of $R^{10b}$ is optionally substituted by one to six halo.

9. A compound according to claim 7, or a pharmaceutically acceptable salt thereof, wherein $R^7$ is —$C_1$-$C_8$ alkyl substituted by $R^{7a}$; $R^{7a}$ is —$C(\!=\!O)NR^9R^{10}$; $R^9$ is H or methyl; $R^{10}$ is —$C_1$-$C_8$ alkyl; $R^{10a}$ is —$C_1$-$C_6$ alkoxy, —$C_4$-$C_8$ cycloalkyl, -(4-8 membered) heterocycloalkyl, —$C_6$-$C_{15}$ aryl or -(5-15 membered) heteroaryl, wherein said alkoxy, cycloalkyl, heterocycloalkyl, aryl, heteroaryl, aryloxy and heteroaryloxy of $R^{10a}$ are each optionally independently substituted with from one to six $R^{10b}$; wherein $R^{10b}$ is halo, —OH, —$C_1$-$C_4$ alkyl or —$C_1$-$C_4$ hydroxyalkyl, and wherein said alkyl or hydroxyalkyl of $R^{10b}$ is optionally substituted by one to six halo.

10. A compound according to claim 7, or a pharmaceutically acceptable salt thereof, wherein A is absent and $R^1$ is benzo($C_5$-$C_6$ cycloalkyl) optionally substituted with from one to three substituents independently selected from —$C_1$-$C_6$ alkyl, halo and OH; or A is

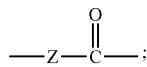

Z is $CH_2$, —CH(OH) or —CH($C_1$-$C_6$ alkyl) and $R^1$ is —$C_1$-$C_{10}$ alkyl, —$C_6$-$C_{10}$ aryl or (6-10 membered) heteroaryl, wherein said alkyl, aryl and heteroaryl are optionally independently substituted with from one to three substituents independently selected from —$C_1$-$C_6$ alkyl, halo and OH; $R^2$ is H or —$C_1$-$C_6$ alkyl; $R^3$ is H, —$CH_2CH_2SCH_3$, —$CH_2CH_2OCH_3$ or —$C_1$-$C_6$ alkyl; $R^4$ is H and $R^6$ is H or —$C_1$-$C_6$ alkyl.

11. A compound of Formula I

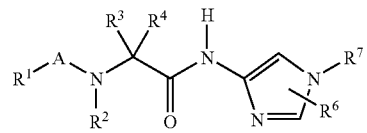

wherein A is absent or is selected from

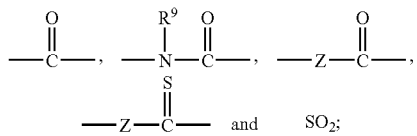

Z is selected from —$CH_2$, —CH(OH), —CH($C_1$-$C_6$ alkyl), —CH($C_1$-$C_6$ alkoxyl), —CH($NR^9R^{10}$), —CH($CH_2$(OH)), —CH(CH($C_1$-$C_4$ alkyl)(OH)) and —CH(C($C_1$-$C_4$ alkyl)($C_1$-$C_4$alkyl)(OH));

$R^1$ is selected from —$C_1$-$C_{20}$ alkyl, —$C_2$-$C_{20}$ alkenyl, —$C_2$-$C_{20}$ alkynyl, —$C_1$-$C_{20}$ alkoxy, —$C_2$-$C_{20}$ alkenoxy, —$C_1$-$C_{20}$ hydroxyalkyl, —$C_3$-$C_8$ cycloalkyl, benzo($C_3$-$C_8$ cycloalkyl), benzo($C_3$-$C_8$ heterocycloalkyl), —$C_4$-$C_8$ cycloalkenyl, —($C_5$-$C_{11}$)bi- or tricycloalkyl, benzo($C_5$-$C_{11}$)bi- or tricycloalkyl, —($C_7$-$C_{11}$) bi- or tricycloalkenyl, -(3-8 membered) heterocycloalkyl, —$C_6$-$C_{14}$ aryl and -(5-14 membered) heteroaryl, wherein $R^1$ is optionally substituted by $R^{1a}$;

wherein $R^{1a}$ in each instance is independently selected from —OH, halo, —$C_1$-$C_6$ alkoxy, —CN, —$NO_2$, —$NR^9R^{10}$, —$C(\!=\!O)NR^9R^{10}$, —$C(\!=\!O)R^{11}$, —$C(\!=\!O)OR^{12}$, —$SO_2$—$NR^9R^{10}$, —S(O)$_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy, wherein said alkoxy, cycloalkyl, cycloalkenyl, bi- or tricycloalkyl, bi- or tricycloalkenyl, heterocycloalkyl, aryl, heteroaryl, aryloxy and heteroaryloxy of $R^{1a}$ are each optionally independently substituted with from one to six substituents independently selected from the group $R^{1b}$;

wherein $R^{1b}$ in each instance is independently selected from —OH, —$C_1$-$C_{12}$ alkyl, —$C_2$-$C_{12}$ alkenyl, —$C_2$-$C_{12}$ alkynyl, —$C_1$-$C_6$ alkoxy, —$C_1$-$C_{12}$ alkoxyalkyl —$C_1$-$C_{12}$ hydroxyalkyl, —$C_2$-$C_6$ alkenoxy, —$C_2$-$C_6$ alkynoxy, halo, —CN, —$NO_2$, —$NR^9R^{10}$, —$C(\!=\!O)NR^9R^{10}$, —$C(\!=\!O)R^{11}$, —$C(\!=\!O)OR^{12}$, —$SO_2$—$NR^9R^{10}$, —S(O)$_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, (5-15 membered) heteroaryl, —$C_6$-$C_{15}$ aryloxy and -(5-15 membered) heteroaryloxy;

$R^2$ is selected from H, —$C_1$-$C_6$ alkyl, —$C_2$-$C_6$ alkenyl, —$C_3$-$C_8$ cycloalkyl and —$C_3$-$C_8$ cycloalkenyl, wherein $R^2$ is optionally independently substituted with from one to three substituents independently selected from —$C_1$-

$C_4$ alkyl optionally substituted with from one to three halo atoms, —$C_1$-$C_4$ alkoxy optionally substituted with from one to three halo atoms, halo and —OH;

or $R^1$ and $R^2$ together with the A group when present and the nitrogen atom to which $R^2$ is attached, or $R^1$ and $R^2$ together with the nitrogen atom to which $R^1$ and $R^2$ are attached when A is absent, may optionally form a four to eight membered ring;

$R^3$ is selected from —$C_6$-$C_{14}$ aryl and (5-14 membered) heteroaryl, wherein said aryl or heteroaryl are each optionally independently substituted with from one to three substituents independently selected from —$C_1$-$C_4$ alkoxy, halo, —OH, —$S(C_1$-$C_4)$alkyl —$C_1$-$C_4$ alkyl —$C(=O)OR^9$, —$SO_2R^9$ and (3-8 membered) heterocycloalkyl wherein said alkyl, alkoxy, and heterocyloalkyl may be further substituted by one to six halo;

$R^4$ is H, —$C_1$-$C_6$ alkyl or halo;

or $R^3$ and $R^4$ may together with the carbon atom to which they are attached optionally form a moiety selected from cyclopropyl, cyclobutyl, cyclopentyl, cyclohexyl, morpholino, piperidino, pyrrolidino, tetrahydrofuranyl and perhydro-2H-pyran, wherein said moiety formed by $R^3$ and $R^4$ is optionally substituted with from one to three substituents independently selected from —$C_1$-$C_6$ alkyl optionally substituted with from one to three halo atoms, —$C_1$-$C_6$ alkoxy optionally substituted with from one to three halo atoms, halo, —OH, —CN and allyl;

$R^6$ is selected from H, —$C_1$-$C_6$ alkyl, —$C_2$-$C_6$ alkylene, —$C_1$-$C_6$ alkoxy, halo, —CN, —$C_3$-$C_{12}$ cycloalkyl, —$C_4$-$C_{12}$ cycloalkenyl (5-10 membered) heteroaryl and —$C_6$-$C_{10}$ aryl, wherein said alkyl, alkylene and alkoxy of $R^6$ are each optionally independently substituted with from one to three substituents independently selected from halo and —CN, and wherein said cycloalkyl, cycloalkenyl, heteroaryl and aryl of $R^6$ are each optionally independently substituted with from one to three substituents independently selected from —$C_1$-$C_4$ alkyl optionally substituted with from one to three halo atoms, —$C_1$-$C_4$ alkoxy optionally substituted with from one to three halo atoms, halo and —CN;

$R^7$ is selected from H, —$C_1$-$C_{20}$ alkyl, —$C_1$-$C_{20}$ alkoxy, —$C_1$-$C_{20}$ hydroxyalkyl, —$C_3$-$C_{12}$ cycloalkyl, —$C_4$-$C_{12}$ cycloalkenyl, ($C_5$-$C_{20}$)bi- or tricycloalkyl, —$C_7$-$C_{20}$)bi- or tricycloalkenyl, (3-12 membered) heterocycloalkyl, -(7-20 membered) heterobi- or heterotricycloalkyl, —$C_6$-$C_{14}$ aryl and -(5-15 membered) heteroaryl, wherein said alkyl, alkenyl, alkynyl, alkoxy, alkenoxy, alkynoxy, cycloalkyl, cycloalkenyl, bi- or tricycloalkyl, bi- or tricycloalkenyl, heterocycloalkyl, aryl, heteroaryl, aryloxy and heteroaryloxy of $R^7$ are each optionally independently substituted with from one to six substituents independently selected from the group $R^{7a}$;

wherein $R^{7a}$ in each instance is independently selected from —OH, —$C_1$-$C_{12}$ alkyl, —$C_2$-$C_{12}$ alkenyl, —$C_2$-$C_{12}$ alkynyl, —$C_1$-$C_6$ alkoxy, —$C_1$-$C_{12}$ alkoxyalkyl, —$C_1$-$C_{12}$ hydroxyalkyl, —$C_2$-$C_6$ alkenoxy, —$C_2$-$C_6$ alkynoxy, halo, —CN, —$NO_2$, —$NR^9R^{10}$, —$C(=O)NR^9R^{10}$, —$C(=O)R^{11}$, —$C(=O)OR^{12}$, —$SO_2$—$NR^9R^{10}$, —$S(O)_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, (5-15 membered) heteroaryl, —$C_6$-$C_{15}$ aryloxy and -(5-15 membered) heteroaryloxy; wherein said alkyl, alkenyl, alkynyl, alkoxy, alkenoxy, alkynoxy, cycloalkyl, cycloalkenyl, bi- or tricycloalkyl, bi- or tricycloalkenyl, heterocycloalkyl, aryl, heteroaryl, aryloxy and heteroaryloxy of $R^{7a}$ are each optionally independently substituted with from one to six substituents independently selected from the group $R^{7b}$;

wherein $R^{7b}$ in each instance is independently selected from —OH, —$C_1$-$C_{12}$ alkyl, —$C_2$-$C_{12}$ alkenyl, —$C_2$-$C_{12}$ alkynyl, —$C_1$-$C_6$ alkoxy, —$C_1$-$C_{12}$ alkoxyalkyl —$C_1$-$C_{12}$ hydroxyalkyl, —$C_2$-$C_6$ alkenoxy, —$C_2$-$C_6$ alkynoxy, halo, —CN, —$NO_2$, —$NR^9R^{10}$, —$C(=O)NR^9R^{10}$, —$C(=O)R^{11}$, —$C(=O)OR^{11}$, —$SO_2$—$NR^9R^{10}$, —$S(O)_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy;

or $R^6$ and $R^7$ may together with the carbon and nitrogen atoms to which they are respectively attached optionally form a (5-8 membered) heterocycloalkyl ring, a (5-8 membered) heterocycloalkenyl ring or a (6-8 membered) heteroaryl ring, wherein said heterocycloalkyl, heterocycloalkenyl and heteroaryl rings are each optionally independently substituted with from one to three substituents independently selected from halo, —$C_1$-$C_6$ alkyl, optionally subsituted with from one to three halo atoms, —$C_1$-$C_6$ alkoxy optionally substituted with from one to three halo atoms, —$C_1$-$C_6$ hydroxyalkyl, —OH, —$(CH_2)_{zero-10}NR^9R^{10}$, —$(CH_2)_{zero-10}C(=O)NR^9R^{10}$, —$SO_2NR^9R^{10}$ and —$C_3$-$C_{12}$ cycloalkyl;

$R^9$ and $R^{10}$ in each instance are each independently selected from H, —OH, —$C_1$-$C_{12}$ alkyl, —$C_2$-$C_{12}$ alkenyl, —$C_2$-$C_{12}$ alkynyl, —$C_1$-$C_6$ alkoxy, —$C_1$-$C_{12}$ alkoxyalkyl —$C_1$-$C_{12}$ hydroxyalkyl, —$C_2$-$C_6$ alkenoxy, —$C_2$-$C_6$ alkynoxy, —$C(=O)NR^{11}R^{12}$, —$C(=O)R^{11}$, —$C(=O)OR^{12}$, —$SO_2$—$NR^{10}R^{11}$, —$S(O)_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy, wherein said alkyl, alkenyl, alkynyl, alkoxy, alkenoxy, alkynoxy, cycloalkyl, cycloalkenyl, bi- or tricycloalkyl, bi- or tricycloalkenyl, heterocycloalkyl, aryl, heteroaryl, aryloxy and heteroaryloxy of $R^9$ of $R^{10}$ are each optionally independently substituted with from one to six substituents independently selected from the group $R^{10a}$;

wherein $R^{10a}$ in each instance is independently selected from —OH, halo, —$C_1$-$C_6$ alkoxy, —CN, —$NO_2$, —$NR^{11}R^{12}$, —$C(=O)NR^{11}R^{12}$, —$C(=O)R^{11}$, —$C(=O)OR^{12}$, —$SO_2$—$NR^{11}R^{12}$, —$S(O)_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy; wherein said alkoxy, cycloalkyl, cycloalkenyl, bi- or tricycloalkyl, bi- or tricycloalkenyl, heterocycloalkyl, aryl, heteroaryl, aryloxy and heteroaryloxy of $R^{10a}$ are each optionally independently substituted with from one to six substituents independently selected from the group $R^{10b}$;

wherein $R^{10b}$ in each instance is independently selected from —OH, halo; —$C_1$-$C_{12}$ alkyl, —$C_2$-$C_{12}$ alkenyl, —$C_2$-$C_{12}$ alkynyl, —$C_1$-$C_6$ alkoxy, —$C_1$-$C_{12}$ alkoxyalkyl —$C_1$-$C_{12}$ hydroxyalkyl, —$C_2$-$C_6$ alkenoxy, —$C_2$-$C_6$ alkynoxy, halo, —CN, —$NO_2$, —$NR^{11}R^{12}$, —$C(=O)NR^{11}R^{12}$, —$C(=O)R^{11}$, —$C(=O)OR^{12}$, —$SO_2$—$NR^{11}R^{12}$, —$S(O)_n$—$R^{11}$, —$C_3$-$C_{15}$ cycloalkyl, $C_4$-$C_{15}$ cycloalkenyl,—($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy;

or $NR^9R^{10}$ may form may form a -(4-20 membered) heterocycloalkyl, -(5-18 membered) heterobi- or tricycloalkyl, -(5-18 membered) heterobi- or tricycloalkenyl, or -(5-15 membered) heteroaryl, wherein said heterocycloalkyl, heterobi- or tricycloalkyl, heterobi- or tricycloalkenyl or heteroaryl are optionally independently substituted with from one to six substituents independently selected from —$C_1$-$C_6$ alkyl, —$C_2$-$C_6$ alkenyl, —$C_2$-$C_6$ alkenyl, —$C_1$-$C_6$ alkoxy, —$C_2$-$C_6$ alkenoxy, —$C_2$-$C_6$ alkynoxy, —$C_1$-$C_6$ hydroxyalkyl, —$C_2$-$C_6$ hydroxyalkenyl, —$C_2$-$C_6$ hydroxyalkynyl, halo, —OH, —CN, —$NO_2$, —$NR^{11}R^{12}$, —C(=O)$NR^{11}R^{12}$, —C(=O)$R^{11}$, —C(=O)$OR^{11}$, —S(O)$_n$$R^{11}$ and —S(O)$_n$$NR^{11}R^{12}$;

wherein $R^{11}$ and $R^{12}$ in each instance are each independently selected from H, —$C_1$-$C_8$ alkyl, —$C_3$-$C_8$ cycloalkyl, —$C_4$-$C_8$ cycloalkenyl, —($C_5$-$C_{11}$)bi- or tricycloalkyl,—($C_7$-$C_{11}$) bi- or tricycloalkenyl, -(3-8 membered) heterocycloalkyl, —$C_6$-$C_{10}$ aryl and -(5-14 membered) heteroaryl, wherein said alkyl of $R^{11}$ is optionally independently substituted with from one to three substituents independently selected from —OH, —CN and —$C_3$-$C_8$ cycloalkyl, and wherein each hydrogen atom of said alkyl is optionally independently replaced with a halo atom, and wherein said cylcoalkyl, cycloalkenyl, heterocycloalkyl, aryl and hetereoaryl of $R^{11}$ are each optionally independently substituted with from one to three substituents independently selected from halo, —$C_1$-$C_8$ alkyl optionally substituted with from one to three halo atoms, —OH, —CN and —$C_3$-$C_8$ cycloalkyl; and n is in each instance an integer independently selected from zero, 1 and 2;

or a pharmaceutically acceptable salt thereof.

12. A compound of Formula I

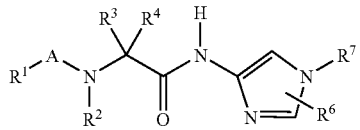

I wherein A is absent;

$R^1$ is —$C_1$-$C_{20}$ alkyl; wherein $R^1$ is independently substituted with from one to six substituents independently selected from $R^{1a}$;

$R^{1a}$ in each instance is independently selected from —$C_1$-$C_6$ alkoxy, —CN, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$) bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy;

wherein said cycloalkyl, cycloalkenyl, bi- or tricycloalkyl, bi- or tricycloalkenyl, heterocycloalkyl, aryl, heteroaryl, aryloxy and heteroaryloxy of $R^{1a}$ are each optionally independently substituted with from one to six substituents independently selected from the group $R^{1b}$;

wherein $R^{1b}$ in each instance is independently selected from —OH, —$C_1$-$C_{12}$ alkyl, —$C_2$-$C_{12}$ alkenyl, —$C_2$-$C_{12}$ alkynyl, —$C_1$-$C_6$ alkoxy, —$C_1$-$C_{12}$ alkoxyalkyl —$C_1$-$C_{12}$ hydroxyalkyl, —$C_2$-$C_6$ alkenoxy, —$C_2$-$C_6$ alkynoxy, halo, —CN, —$NO_2$, —$NR^9R^{10}$, —C(=O)$NR^9R^{10}$, —C(=O)$R^{11}$, —C(=O)$OR^{12}$, —$SO_2$—$NR^9R^{10}$, —S(O)$_n$—$R^{11}$, —$C_3$-$C_{15}$ cycloalkyl, —$C_4$-$C_{15}$ cycloalkenyl,—($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy;

$R^2$ is selected from H, —$C_1$-$C_6$ alkyl, —$C_2$-$C_6$ alkenyl, —$C_3$-$C_8$ cycloalkyl and —$C_3$-$C_8$ cycloalkenyl, wherein $R^2$ is optionally independently substituted with from one to three substituents independently selected from —$C_1$-$C_4$ alkyl optionally substituted with from one to three halo atoms, —$C_1$-$C_4$ alkoxy optionally substituted with from one to three halo atoms, halo and —OH;

$R^3$ is selected from H, —$C_1$-$C_6$ alkyl, —$C_2$-$C_6$ alkenyl, —$C_2$-$C_6$ alkynyl, —$C_3$-$C_6$ cycloalkyl, —$C_5$-$C_6$ cycloalkenyl and (3-8 membered) heterocycloalkyl, —$C_6$-$C_{14}$ aryl and (5-14 membered) heteroaryl, wherein said alkyl, alkenyl, alkynyl, cycloalkyl, cycloalkenyl, heterocycloalkyl aryl or heteroaryl are each optionally independently substituted with from one to three substituents independently selected from —$C_1$-$C_4$ alkoxy, halo, —OH, —S($C_1$-$C_4$)alkyl —$C_1$-$C_4$ alkyl —C(=O)$OR^9$, —$SO_2R^9$ and (3-8 membered) heterocycloalkyl wherein said alkyl, alkoxy, and heterocyloalkyl may be further substituted by one to six halo;

$R^4$ is H, —$C_1$-$C_6$ alkyl or halo;

or $R^3$ and $R^4$ may together with the carbon atom to which they are attached optionally form a moiety selected from cyclopropyl, cyclobutyl, cyclopentyl, cyclohexyl, morpholino, piperidino, pyrrolidino, tetrahydrofuranyl and perhydro-2H-pyran, wherein said moiety formed by $R^3$ and $R^4$ is optionally substituted with from one to three substituents independently selected from —$C_1$-$C_6$ alkyl optionally substituted with from one to three halo atoms, —$C_1$-$C_6$ alkoxy optionally substituted with from one to three halo atoms, halo, —OH, —CN and allyl;

$R^6$ is selected from H, —$C_1$-$C_6$ alkyl, —$C_2$-$C_6$ alkylene, —$C_1$-$C_6$ alkoxy, halo, —CN, —$C_3$-$C_{12}$ cycloalkyl, —$C_4$-$C_{12}$ cycloalkenyl (5-10 membered) heteroaryl and —$C_6$-$C_{10}$ aryl, wherein said alkyl, alkylene and alkoxy of $R^6$ are each optionally independently substituted with from one to three substituents independently selected from halo and —CN, and wherein said cycloalkyl, cycloalkenyl, heteroaryl and aryl of $R^6$ are each optionally independently substituted with from one to three substituents independently selected from —$C_1$-$C_4$ alkyl optionally substituted with from one to three halo atoms, —$C_1$-$C_4$ alkoxy optionally substituted with from one to three halo atoms, halo and —CN;

$R^7$ is selected from H, —$C_1$-$C_{20}$ alkyl, —$C_1$-$C_{20}$ alkoxy, —$C_1$-$C_{20}$ hydroxyalkyl, —$C_3$-$C_{12}$ cycloalkyl, —$C_4$-$C_{12}$ cycloalkenyl, —($C_5$-$C_{20}$)bi- or tricycloalkyl, —($C_7$-$C_{20}$)bi- or tricycloalkenyl, (3-12 membered) heterocycloalkyl, (-7-20 membered) heterobi- or heterotricycloalkyl, —$C_6$-$C_{14}$ aryl and (5-15 membered) heteroaryl, wherein said alkyl, alkenyl, alkynyl, alkoxy, alkenoxy, alkynoxy, cycloalkyl, cycloalkenyl, bi- or tricycloalkyl, bi- or tricycloalkenyl, heterocycloalkyl, aryl, heteroaryl, aryloxy and heteroaryloxy of $R^7$ are each optionally independently substituted with from one to six substituents independently selected from the group $R^{7a}$;

wherein $R^{7a}$ in each instance is independently selected from —OH, —$C_1$-$C_{12}$ alkyl, —$C_2$-$C_{12}$ alkenyl, —$C_2$-

$C_{12}$ alkynyl, —$C_1$-$C_6$ alkoxy, —$C_1$-$C_{12}$ alkoxyalkyl, —$C_1$-$C_{12}$ hydroxyalkyl, —$C_2$-$C_6$ alkenoxy, —$C_2$-$C_6$ alkynoxy, halo, —CN, —$NO_2$, —$NR^9R^{10}$, —C(=O)$NR^9R^{10}$, —C(=O)$R^{11}$, —C(=O)$OR^{12}$, —$SO_2$—$NR^9R^{10}$, —S(O)$_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, (5-15 membered) heteroaryl, —$C_6$-$C_{15}$ aryloxy and -(5-15 membered) heteroaryloxy; wherein said alkyl, alkenyl, alkynyl, alkoxy, alkenoxy, alkynoxy, cycloalkyl, cycloalkenyl, bi- or tricycloalkyl, bi- or tricycloalkenyl, heterocycloalkyl, aryl, heteroaryl, aryloxy and heteroaryloxy of $R^{7a}$ are each optionally independently substituted with from one to six substituents independently selected from the group $R^{7b}$;

wherein $R^{7b}$ in each instance is independently selected from —OH, —$C_1$-$C_{12}$ alkyl, —$C_2$-$C_{12}$ alkenyl, —$C_2$-$C_{12}$ alkynyl, —$C_1$-$C_6$ alkoxy, —$C_1$-$C_{12}$ alkoxyalkyl —$C_1$-$C_{12}$ hydroxyalkyl, —$C_2$-$C_6$ alkenoxy, —$C_2$-$C_6$ alkynoxy, halo, —CN, —$NO_2$, —$NR^9R^{10}$, —C(=O)$NR^9R^{10}$, —C(=O)$R^{11}$, —C(=O)$OR^{11}$, —$SO_2$—$NR^9R^{10}$, —S(O)$_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy;

or $R^6$ and $R^7$ may together with the carbon and nitrogen atoms to which they are respectively attached optionally form a -(5-8 membered) heterocycloalkyl ring, a -(5-8 membered) heterocycloalkenyl ring or a -(6-8 membered) heteroaryl ring, wherein said heterocycloalkyl, heterocycloalkenyl and heteroaryl rings are each optionally independently substituted with from one to three substituents independently selected from halo, —$C_1$-$C_6$ alkyl, optionally subsituted with from one to three halo atoms, —$C_1$-$C_6$ alkoxy optionally substituted with from one to three halo atoms, —$C_1$-$C_6$ hydroxyalkyl, —OH, —($CH_2$)$_{zero-10}$$NR^9R^{10}$, —($CH_2$)$_{zero-10}$C(=O)$NR^9R^{10}$, —$SO_2NR^9R^{10}$ and —$C_3$-$C_{12}$ cycloalkyl;

$R^9$ and $R^{10}$ in each instance are each independently selected from H, —OH, —$C_1$-$C_{12}$ alkyl, —$C_2$-$C_{12}$ alkenyl, —$C_2$-$C_{12}$ alkynyl, —$C_1$-$C_6$ alkoxy, —$C_1$-$C_{12}$ alkoxyalkyl —$C_1$-$C_{12}$ hydroxyalkyl, —$C_2$-$C_6$ alkenoxy, —$C_2$-$C_6$ alkynoxy, —C(=O)$NR^{11}R^{12}$, —C(=O)$R^{11}$, —C(=O)$OR^{11}$, —$SO_2$—$NR^{11}R^{12}$, —S(O)$_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy, wherein said alkyl, alkenyl, alkynyl, alkoxy, alkenoxy, alkynoxy, cycloalkyl, cycloalkenyl, bi- or tricycloalkyl, bi- or tricycloalkenyl, heterocycloalkyl, aryl, heteroaryl, aryloxy and heteroaryloxy of $R^9$ of $R^{10}$ are each optionally independently substituted with from one to six substituents independently selected from the group $R^{10a}$;

wherein $R^{10a}$ in each instance is independently selected from —OH, Halo, —$C_1$-$C_6$ alkoxy, —CN, —$NO_2$, —$NR^{11}R^{12}$, —C(=O)$NR^{11}R^{12}$, —C(=O)$R^{11}$, —C(=O)$OR^{12}$, —$SO_2$—$NR^{11}R^{12}$, —S(O)$_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy; wherein said alkoxy, cycloalkyl, cycloalkenyl, bi- or tricycloalkyl, bi- or tricycloalkenyl, heterocycloalkyl, aryl, heteroaryl, aryloxy and heteroaryloxy of $R^{10a}$ are each optionally independently substituted with from one to six substituents independently selected from the group $R^{10b}$;

wherein $R^{10b}$ in each instance is independently selected from —OH, halo; —$C_1$-$C_{12}$ alkyl, —$C_2$-$C_{12}$ alkenyl, —$C_2$-$C_{12}$ alkynyl, —$C_1$-$C_6$ alkoxy, —$C_1$-$C_{12}$ alkoxyalkyl —$C_1$-$C_{12}$ hydroxyalkyl, —$C_2$-$C_6$ alkenoxy, —$C_2$-$C_6$ alkynoxy, halo, —CN, —$NO_2$, —$NR^{11}R^{12}$, —C(=O)$NR^{11}R^{12}$, —C(=O)$R^{11}$, —C(=O)$OR^{11}$, —$SO_2$—$NR^{11}R^{12}$, —S(O)$_n$—$R^{11}$, —$C_3$-$C_{15}$ cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy;

or $NR^9R^{10}$ may form a (4-20 membered) heterocycloalkyl, (5-18 membered) heterobi- or tricycloalkyl (5-18 membered) heterobi- or tricycloalkenyl, or -(5-15 membered) heteroaryl, wherein said a heterocycloalkyl, heterobi- or tricycloalkyl, heterobi- or tricycloalkenyl or heteroaryl are optionally independently substituted with from one to six substituents independently selected from —$C_1$-$C_6$ alkyl, —$C_2$-$C_6$ alkenyl, —$C_2$-$C_6$ alkenyl, —$C_1$-$C_6$ alkoxy, —$C_2$-$C_6$ alkenoxy, —$C_2$-$C_6$ alkynoxy, —$C_1$-$C_6$ hydroxyalkyl, —$C_2$-$C_6$ hydroxyalkenyl, —$C_2$-$C_6$ hydroxyalkenyl, halo, —OH, —CN, —$NO_2$, —$NR^{11}R^{12}$, —C(=O)$NR^{11}R^{12}$, —C(=O)$R^{11}$, —C(=O)$OR^{11}$, —S(O)$_n$$R^{11}$ and —S(O)$_n$$NR^{11}R^{12}$;

$R^{11}$ and $R^{12}$ in each instance are each independently selected from H, —$C_1$-$C_8$ alkyl, —$C_3$-$C_8$ cycloalkyl, —$C_4$-$C_8$ cycloalkenyl, —($C_5$-$C_{11}$)bi- or tricycloalkyl, —($C_7$-$C_{11}$) bi- or tricycloalkenyl, -(3-8 membered) heterocycloalkyl, —$C_6$-$C_{10}$ aryl and -(5-14 membered) heteroaryl, wherein said alkyl of $R^{11}$ is optionally independently substituted with from one to three substituents independently selected from —OH, —CN and —$C_3$-$C_8$ cycloalkyl, and wherein each hydrogen atom of said alkyl is optionally independently replaced with a halo atom, and wherein said cycloalkyl, cycloalkenyl, heterocycloalkyl, aryl and hetereoaryl of $R^{11}$ are each optionally independently substituted with from one to three substituents independently selected from halo, —$C_1$-$C_8$ alkyl optionally substituted with from one to three halo atoms, —OH, —CN and —$C_3$-$C_8$ cycloalkyl; and n is in each instance an integer independently selected from zero, 1 and 2;

or a pharmaceutically acceptable salt thereof.

13. A compound selected from the group consisting of:

(S)-2-[2-(3,5-Difluoro-phenyl)-acetylamino]-pentanoic acid {1-[2-(3-ethoxy-propylamino) -ethyl]-1H-imidazol-4-yl}-amide;

(S)-2-[2-(3,5-Difluoro-phenyl)-acetylamino]-pentanoic acid {1-[2-(octahydro-pyrazino [1,2-a]azepin-2-yl)-ethyl]-1H-imidazol-4-yl}-amide;

(S)-2-[2-(3,5-Difluoro-phenyl)-acetylamino]-pentanoic acid {1-[2-([1,4]dioxan-2-ylmethyl-methyl-amino)-ethyl]-1H-imidazol-4-yl}-amide;

(S)-2-[2-(3,5-Difluoro-phenyl)-acetylamino]-pentanoic acid {1-[2-(2 -methoxy-1-methyl-ethylamino)-ethyl]-1H-imidazol-4-yl}-amide;

(S)-2-[2-(3,5-Difluoro-phenyl)-acetylamino]-pentanoic acid {1-[2-(3-oxo-piperazin-1-yl)-ethyl]-1H-imidazol-4-yl}-amide;

(S)-2-[2-(3,5-Difluoro-phenyl)-acetylamino]-pentanoic acid [1-(2-benzylamino-ethyl)-1H-imidazol-4-yl]-amide;
(S)-2-[2-(3,5-Difluoro-phenyl)-acetylamino]-pentanoic acid {1-[2-(3-butoxy -propylamino)-ethyl]-1H-imidazol-4-yl}-amide;
(S)-2-[2-(3,5-Difluoro-phenyl)-acetylamino]-pentanoic acid {1-[2-((1R,2S)-2-hydroxymethyl-cyclohexylamino)-ethyl]-1H-imidazol-4-yl}-amide;
2-[2-(3,5-Difluoro-phenyl)-acetylamino]-pentanoic acid {1-[(4aS,8aS)-2-(octahydro-isoquinolin-2-yl)-ethyl]-1H-imidazol-4-yl}-amide;
(S)-2-[2-(3,5-Difluoro-phenyl)-acetylamino]-pentanoic acid {1-[2-(3-isopropoxy -propylamino)-ethyl]-1H-imidazol-4-yl}-amide;
(S)-2-[2-(3,5-Difluoro-phenyl)-acetylamino]-pentanoic acid {1-[2-(octahydro -isoquinolin-2-yl)-ethyl]-1H-imidazol-4-yl}-amide;
(S)-2-[2-(3,5-Difluoro-phenyl)-acetylamino]-pentanoic acid {1-[2-(3,4,5,6-tetrahydro-2H-[4,4]bipyridinyl-1-yl)-ethyl]-1H-imidazol-4-yl}-amide;
(S)-2-[2-(3,5-Difluoro-phenyl)-acetylamino]-pentanoic acid {1-[2-(2-hydroxy-2-phenyl-ethylamino)-ethyl]-1H-imidazol-4-yl}-amide;
(S)-2-[2-(3,5-Difluoro-phenyl)-acetylamino]-pentanoic acid {1-[2-(indan-1-ylamino)-ethyl]-1H-imidazol-4-yl}-amide;
(S)-2-[2-(3,5-Difluoro-phenyl)-acetylamino]-pentanoic acid {1-[2-(benzyl-methyl -amino)-ethyl]-1H-imidazol-4-yl}-amide;
(S)-2-[2-(3,5-Difluoro-phenyl)-acetylamino]-pentanoic acid {1-[2-(indan-2-ylamino)-ethyl]-1H-imidazol-4-yl}-amide;
(S)-2-[2-(3,5-Difluoro-phenyl)-acetylamino]-pentanoic acid {1-[2-(3,4-dihydro -1#H!-isoquinolin-2-yl)-ethyl]-1H-imidazol-4-yl}-amide;
(S)-2-[2-(3,5-Difluoro-phenyl)-acetylamino]-pentanoic acid {1-[2-(2-propoxy -ethylamino)-ethyl]-1H-imidazol-4-yl}-amide;
(S)-2-[2-(3,5-Difluoro-phenyl)-acetylamino]-pentanoic acid {1-[2-(3-benzyl -pyrrolidin-1-yl)-ethyl]-1H-imidazol-4-yl}-amide;
(S)-2-[2-(3,5-Difluoro-phenyl)-acetylamino]-pentanoic acid {1-[2-(3-pyridin-2-yl -pyrrolidin-1-yl)-ethyl]-1H-imidazol-4-yl}-amide;
(S)-2-[2-(3,5-Difluoro-phenyl)-acetylamino]-pentanoic acid {1-[2-(methyl-pyridin -4-ylmethyl-amino)-ethyl]-1H-imidazol-4-yl}-amide;
(S)-2-[2-(3,5-Difluoro-phenyl)-acetylamino]-pentanoic acid (1-{2-[(2-methanesulfonyl-ethyl)-methyl-amino]-ethyl}-1H-imidazol-4-yl)-amide;
(S)-2-[2-(3,5-Difluoro-phenyl)-acetylamino]-pentanoic acid {1-[2-(2-tert-butoxy -ethylamino)-ethyl]-1H-imidazol-4-yl}-amide;
(S)-2-[2-(3,5-Difluoro-phenyl)-acetylamino]-pentanoic acid {1-[2-(3-pyridin-4-yl -pyrrolidin-1-yl)-ethyl]-1H-imidazol-4-yl}-amide;
(S)-2-[2-(3,5-Difluoro-phenyl)-acetylamino]-pentanoic acid [1-(2-fluoro-benzyl) -1H-imidazol-4-yl]-amide;
(S)-2-[2-(3,5-Difluoro-phenyl)-acetylamino]-pentanoic acid [1-(3-fluoro-benzyl) -1H-imidazol-4-yl]-amide;
(S)-2-[2-(3,5-Difluoro-phenyl)-acetylamino]-pentanoic acid [1-(1-dimethylaminomethyl-cyclobutyl)-1H-imidazol-4-yl]-amide;
(S)-2-[2-(3,5-Difluoro-phenyl)-acetylamino]-pentanoic acid [1-(1-piperidin-1-ylmethyl-cyclobutyl)-1H-imidazol-4-yl]-amide;
(S)-2-[2-(3,5-Difluoro-phenyl)-acetylamino]-pentanoic acid [1-(1-morpholin-4-ylmethyl-cyclobutyl)-1H-imidazol-4-yl]-amide;
(S)-2-[2-(3,5-Difluoro-phenyl)-acetylamino]-pentanoic acid (1-{1-[((2R,6S)-2,6-dimethyl-morpholin-4-yl)methyl]-cyclobutyl}-1H-imidazol-4-yl)-amide;
(S)-2-[2-(3,5-Difluoro-phenyl)-acetylamino]-pentanoic acid (1-{1-[(2,2,2-trifluoro -ethylamino)-methyl]-cyclobutyl}-1H-imidazol-4-yl)-amide;
(S)-2-[2-(3,5-Difluoro-phenyl)-acetylamino]-pentanoic acid (1-{1-[((R)-1-cyclohexyl-ethylamino)-methyl]-cyclobutyl}-1H-imidazol-4-yl)-amide;
(S)-2-(5,7-Difluoro-1,2,3,4-tetrahydro-naphthalen-2-ylamino) pentanoic acid [1-(1-pyrrolidin-1-ylmethyl-cyclobutyl)-1H-imidazol-4-yl]-amide;
(S)-2-[2-(3,5-Difluoro-phenyl)-acetylamino]-pentanoic acid (1-{1-[(2,2-dimethyl -propylamino)-methyl]-cyclobutyl}-1H-imidazol-4-yl)-amide;
(S)-2-(6,8-Difluoro-1,2,3,4-tetrahydro-naphthalen-2-ylamino)-pentanoic acid (1-{1-[(2,2,2-trifluoro-ethylamino)-methyl]-cyclobutyl}-1H-imidazol-4-yl)-amide;
(S)-2-(6,8-Difluoro-1,2,3,4-tetrahydro-naphthalen-2-ylamino)-pentanoic acid (1-{1-[(2,2-dimethyl -propylamino)-methyl]-cyclobutyl}-1H-imidazol-4-yl)-amide;
(S)-2-(6,8-Difluoro-1,2,3,4-tetrahydro-naphthalen-2-ylamino)-pentanoic acid (1-{1-[((R)-1-cyclohexyl-ethylamino)-methyl]-cyclobutyl}-1H-imidazol-4-yl)-amide;
(S)-2-(6,8-Difluoro-1,2,3,4-tetrahydro-naphthalen-2-ylamino)-pentanoic acid [1-(1-dimethylaminomethyl-cyclobutyl)-1H-imidazol-4-yl]-amide;
(S)-2-(6,8-Difluoro-1,2,3,4-tetrahydro-naphthalen-2-ylamino)-pentanoic acid [1-(1-piperidin-1-ylmethyl-cyclobutyl)-1H-imidazol-4-yl]-amide;
(S)-2-(6,8-Difluoro-1,2,3,4-tetrahydro-naphthalen-2-ylamino)-pentanoic acid [1-(1-morpholin-4-ylmethyl-cyclobutyl)-1H-imidazol-4-yl]-amide;
(S)-2-(6,8-Difluoro-1,2,3,4-tetrahydro-naphthalen-2-ylamino)-pentanoic acid (1-{1-[((2R,6S)-2,6-dimethyl-morpholin-4-yl)methyl]-cyclobutyl}-1H-imidazol-4-yl)-amide;
(S)-2-(6,8-Difluoro-1,2,3,4-tetrahydro-naphthalen-2-ylamino)-pentanoic acid {1-[2-((R)-1-cyclohexyl-ethylamino)-1,1-dimethyl-ethyl]-1H-imidazol-4-yl}-amide;
(S)-2-(6,8-Difluoro-1,2,3,4-tetrahydro-naphthalen-2-ylamino)-pentanoic acid (1-{1,1-dimethyl-2-[(tetrahydro-pyran-4-ylmethyl)-amino]-ethyl}-1H-imidazol-4-yl)-amide;
(S)-2-(6,8-Difluoro-1,2,3,4-tetrahydro-naphthalen-2-ylamino)-pentanoic acid (1-{2-[(1-hydroxy-cyclohexylmethyl)-amino]-1,1-dimethyl-ethyl}-1H-imidazol-4-yl)-amide;
(S)-2-(6,8-Difluoro-1,2,3,4-tetrahydro-naphthalen-2-ylamino)-pentanoic acid (1-{2-[(4-hydroxy-tetrahydro-pyran-4-ylmethyl)-amino]-1,1-dimethyl-ethyl}-1H-imidazol-4-yl) -amide;
(S)-2-(6,8-Difluoro-1,2,3,4-tetrahydro-naphthalen-2-ylamino)-pentanoic acid {1-[2-(2-methoxy-2-methyl-propylamino)-1,1-dimethyl-ethyl]-1H-imidazol-4-yl}-amide;
(S)-2-(6,8-Difluoro-1,2,3,4-tetrahydro-naphthalen-2-ylamino)-pentanoic acid (1-{1,1-dimethyl-2-[(3-methyl-oxetan-3-ylmethyl)-amino]-ethyl}-1H-imidazol-4-yl)-amide;

(S)-2-(6,8-Difluoro-1,2,3,4-tetrahydro-naphthalen-2-ylamino)-pentanoic acid {1-[2-(cyclohexylmethyl-amino)-1,1-dimethyl-ethyl]-1H-imidazol-4-yl}-amide;

(S)-2-[2-(3,5-Difluoro-phenyl)-acetylamino]-pentanoic acid {1-[2-((R)-1-cyclohexyl-ethylamino)-1,1-dimethyl-ethyl]-1H-imidazol-4-yl}-amide;

(S)-2-[2-(3,5-Difluoro-phenyl)-acetylamino]-pentanoic acid (1-{1,1-dimethyl-2-[(tetrahydro-pyran-4-ylmethyl)-amino]-ethyl}-1H-imidazol-4-yl)-amide;

(S)-2-(6,8-Difluoro-1,2,3,4-tetrahydro-naphthalen-2-ylamino)-pentanoic acid {1-[3-((S)-1-phenyl-ethylamino)-butyl]-1H-imidazol-4-yl}-amide;

(S)-2-(Dicyclopropylmethyl-amino)-pentanoic acid [1-(1,1-dimethyl-2-pyrrolidin-1-yl-ethyl)-1H-imidazol-4-yl]-amide;

(S)-2-[2-(3,5-Difluoro-phenyl)-acetylamino]-pentanoic acid [1-(1-hydroxymethyl-cyclobutyl)-1H-imidazol-4-yl]-amide;

(S)-2-[2-(3,5-Difluoro-phenyl)-acetylamino]-pentanoic acid [1-(2-hydroxymethyl-cyclobutyl)-1H-imidazol-4-yl]-amide;

(S)-2-(5,7-Difluoro-1,2,3,4-tetrahydro-naphthalen-2-ylamino-pentanoic acid [1-(1-hydroxymethyl-cyclobutyl)-1H-imidazol-4-yl]-amide;

(S)-2-[2-(2,4-Difluoro-phenyl)-2-hydroxy-ethylamino]-pentanoic acid [1-(1,1-dimethyl-2-pyrrolidin-1-yl-ethyl)-1H-imidazol-4-yl]-amide;

(S)-2-[2-(3,4-Difluoro-phenyl)-2-hydroxy-ethylamino]-pentanoic acid [1-(1,1-dimethyl-2-pyrrolidin-1-yl-ethyl)-1H-imidazol-4-yl]-amide;

(S)-2-[2-(3,5-Difluoro-phenyl)-2-hydroxy-ethylamino]-pentanoic acid [1-(1,1-dimethyl-2-pyrrolidin-1-yl-ethyl)-1H-imidazol-4-yl]-amide;

(S)-2-[2-(2,4-Difluoro-phenyl)-2-hydroxy-ethylamino]-pentanoic acid {1-[2-((2R,6S)-2,6-dimethyl-morpholin-4-yl)-1,1-dimethyl-ethyl]-1H-imidazol-4-yl}-amide;

(S)-2-[(1-Hydroxy-cyclohexylmethyl)-amino]-pentanoic acid [1-(1,1-dimethyl-2-pyrrolidin-1-yl-ethyl)-1H-imidazol-4-yl]-amide;

(S-2-(6,8-Difluoro-1,2,3,4-tetrahydro-naphthalen-2-ylamino)-pentanoic acid {1-[3-((R)-1-phenyl-ethylamino)-propyl]-1H-imidazol-4-yl}-amide;

(S)-2-(6,8-Difluoro-1,2,3,4-tetrahydro-naphthalen-2-ylamino)-pentanoic acid {1-[3-(3-methyl-benzylamino)-propyl]-1H-imidazol-4-yl}-amide;

(S)-2-(6,8-Difluoro-1,2,3,4-tetrahydro-naphthalen-2-ylamino)-pentanoic acid {1-[3-(2-hydroxy-2-phenylethylamino)-propyl]-1H-imidazol-4-yl}-amide;

(S)-2-(6,8-Difluoro-1,2,3,4-tetrahydro-naphthalen-2-ylamino)-pentanoic acid {1-[3-(2-chloro-benzylamino)-propyl]-1H-imidazol-4-yl}-amide;

(S)-2-(6,8-Difluoro-1,2,3,4-tetrahydro-naphthalen-2-ylamino)-pentanoic acid {1-[3-(3,4-dihydro-1H-isoquinolin-2-yl)-propyl]-1H-imidazol-4-yl}-amide;

(S)-2-(6,8-Difluoro-1,2,3,4-tetrahydro-naphthalen-2-ylamino)-pentanoic acid {1-[3-(indan-2-ylamino)-propyl]-1H-imidazol-4-yl}-amide;

(S)-2-(6,8-Difluoro-1,2,3,4-tetrahydro-naphthalen-2-ylamino)-pentanoic acid {1-[3-(1-methoxymethyl-propylamino)-propyl]-1H-imidazol-4-yl}-amide;

(S)-2-(6,8-Difluoro-1,2,3,4-tetrahydro-naphthalen-2-ylamino)-pentanoic acid {1-[3-(4-chloro-benzylamino)-propyl]-1H-imidazol-4-yl}-amide;

(S)-2-(6,8-Difluoro-1,2,3,4-tetrahydro-naphthalen-2-ylamino)-pentanoic acid {1-[3-(2-methyl-benzylamino)-propyl]-1H-imidazol-4-yl}-amide;

(S)-2-(6,8-Difluoro-1,2,3,4-tetrahydro-naphthalen-2-ylamino)-pentanoic acid {1-[3-(2-methoxy-ethylamino)-propyl]-1H-imidazol-4-yl}-amide;

(S)-2-(6,8-Difluoro-1,2,3,4-tetrahydro-naphthalen-2-ylamino)-pentanoic acid (1-{3-[(pyridin-3-ylmethyl)-amino]-propyl}-1H-imidazol-4-yl)-amide;

(S)-2-(6,8-Difluoro-1,2,3,4-tetrahydro-naphthalen-2-ylamino)-pentanoic acid {1-[3-((S)-1-p-tolyl-ethylamino)-propyl]-1H-imidazol-4-yl}-amide;

(S)-2-(6,8-Difluoro-1,2,3,4-tetrahydro-naphthalen-2-ylamino)-pentanoic acid {1-[3-(4-methoxy-benzylamino)-propyl]-1H-imidazol-4-yl}-amide;

(S)-2-(6,8-Difluoro-1,2,3,4-tetrahydro-naphthalen-2-ylamino)-pentanoic acid {1-[3-(cyclopropylmethylamino)-propyl]-1H-imidazol-4-yl}-amide;

(S)-2-(6,8-Difluoro-1,2,3,4-tetrahydro-naphthalen-2-ylamino)-pentanoic acid {1-[3-(4-methyl-benzylamino)-propyl]-1H-imidazol-4-yl}-amide;

(S)-2-(6,8-Difluoro-1,2,3,4-tetrahydro-naphthalen-2-ylamino)-pentanoic acid {1-[1-methyl-1-(methyl-phenethyl-carbamoyl)-ethyl]-1H-imidazol-4-yl}-amide;

(S)-2-(6,8-Difluoro-1,2,3,4-tetrahydro-naphthalen-2-ylamino)-pentanoic acid {1-[1-(1,3-dihydro-isobenzofuran-5-ylcarbamoyl)-1-methyl-ethyl]-1H-imidazol-4-yl}-amide;

(S)-2-(6,8-Difluoro-1,2,3,4-tetrahydro-naphthalen-2-ylamino)-pentanoic acid {1-[1-(indan-1-ylcarbamoyl)-1-methyl-ethyl]-1H-imidazol-4-yl}-amide;

(S)-2-(6,8-Difluoro-1,2,3,4-tetrahydro-naphthalen-2-ylamino)-pentanoic acid {1-[1,1-dimethyl-2-oxo-2-(3-pyridin-4-yl-pyrrolidin-1-yl)-ethyl]-1H-imidazol-4-yl}-amide;

(S)-2-(6,8-Difluoro-1,2,3,4-tetrahydro-naphthalen-2-ylamino)-pentanoic acid (1-{1-[2-(3-fluoro-phenyl)-ethylcarbamoyl]-1-methyl-ethyl}-1H-imidazol-4-yl)-amide;

(S)-2-(6,8-Difluoro-1,2,3,4-tetrahydro-naphthalen-2-ylamino)-pentanoic acid (1-{1-methyl-1-[methyl-(tetrahydro-pyran-2-ylmethyl)-carbamoyl]-ethyl}-1H-imidazol-4-yl)-amide;

(S)-2-(6,8-Difluoro-1,2,3,4-tetrahydro-naphthalen-2-ylamino)-pentanoic acid (1-{1-[ethyl-(2-pyrazol-1-yl-ethyl)-carbamoyl]-1-methyl-ethyl}-1H-imidazol-4-yl)-amide;

(S)-2-(6,8-Difluoro-1,2,3,4-tetrahydro-naphthalen-2-ylamino)-pentanoic acid (1-{1-[(furan-2-ylmethyl)-carbamoyl]-1-methyl-ethyl}-1H-imidazol-4-yl)-amide;

(S)-2-(6,8-Difluoro-1,2,3,4-tetrahydro-naphthalen-2-ylamino)-pentanoic acid (1-{2-[3-(acetyl-methyl-amino)-pyrrolidin-1-yl]-1,1-dimethyl-2-oxo-ethyl}-1H-imidazol-4-yl)-amide;

(S)-2-(6,8-Difluoro-1,2,3,4-tetrahydro-naphthalen-2-ylamino)-pentanoic acid {1-[1-methyl-1-((3R,4S)-4-methylsulfanyl-tetrahydro-furan-3-ylcarbamoyl)-ethyl]-1H-imidazol-4-yl}-amide;

(S)-2-(6,8-Difluoro-1,2,3,4-tetrahydro-naphthalen-2-ylamino)-pentanoic acid {1-[2-(4-acetyl-[1,4]diazepan-1-yl)-1,1-dimethyl-2-oxo-ethyl]-1H-imidazol-4-yl)-amide;

(S)-2-(6,8-Difluoro-1,2,3,4-tetrahydro-naphthalen-2-ylamino)-pentanoic acid (1-{1-methyl-1-[1-(1-methyl-1H-pyrazol-4-yl)-ethylcarbamoyl]-ethyl}-1H-imidazol-4-yl)-amide;

(S)-2-(6,8-Difluoro-1,2,3,4-tetrahydro-naphthalen-2-ylamino)-pentanoic acid {1-[1-(3-methoxy-propylcarbamoyl)-1-methyl-ethyl]-1H-imidazol-4-yl}-amide;

(S)-2-(6,8-Difluoro-1,2,3,4-tetrahydro-naphthalen-2-ylamino)-pentanoic acid (1-{1-methyl-1-[(3-methyl-[1,2,4]oxadiazol-5-ylmethyl)-carbamoyl]-ethyl}-1H-imidazol-4-yl) -amide;

(S)-2-(6,8-Difluoro-1,2,3,4-tetrahydro-naphthalen-2-ylamino)-pentanoic acid (1-{1-[(2-cyano-ethyl)-methyl-carbamoyl]-1-methyl-ethyl}-1H-imidazol-4-yl)-amide;

(S)-2-(6,8-Difluoro-1,2,3,4-tetrahydro-naphthalen-2-ylamino)-pentanoic acid (1-{1-methyl-1-[methyl-(1-methyl-1H-imidazol-2-ylmethyl)-carbamoyl]-ethyl}-1H-imidazol-4-yl)-amide;

(S)-2-(6,8-Difluoro-1,2,3,4-tetrahydro-naphthalen-2-ylamino)-pentanoic acid (1-{1-[(2-diethylamino-ethyl)-methyl-carbamoyl]-1-methyl-ethyl}-1H-imidazol-4-yl)-amide;

2-{4-[(S)-2-(6,8-Difluoro-1,2,3,4-tetrahydro-naphthalen-2-ylamino) -propionylamino]-imidazol-1-yl}-N-indan-1-yl-isobutyramide;

2-{4-[(S)-2-(6,8-Difluoro-1,2,3,4-tetrahydro-naphthalen-2-ylamino) -propionylamino]-imidazol-1-yl}-N-methyl-N-phenethyl-isobutyramide;

2-{4-[(S)-2-(6,8-Difluoro-1,2,3,4-tetrahydro-naphthalen-2-ylamino) -propionylamino]-imidazol-1-yl}-N-ethyl-N-(2-pyrazol-1-yl-ethyl)-isobutyramide;

2-{4-[(S)-2-(6,8-Difluoro-1,2,3,4-tetrahydro-naphthalen-2-ylamino) -propionylamino]-imidazol-1-yl}-N-(4-methyl-benzyl)-isobutyramide;

2-{4-[(S)-2-(6,8-Difluoro-1,2,3,4-tetrahydro-naphthalen-2-ylamino) -propionylamino]-imidazol-1-yl}-N-(1,3-dihydro-isobenzofuran-5-yl)-isobutyramide;

2-{4-[(S)-2-(6,8-Difluoro-1,2,3,4-tetrahydro-naphthalen-2-ylamino) -propionylamino]-imidazol-1-yl}-N-((1R,2S)-2-hydroxymethyl-cyclohexyl)-isobutyramide;

2-{4-[(S)-2-(6,8-Difluoro-1,2,3,4-tetrahydro-naphthalen-2-ylamino) -propionylamino]-imidazol-1-yl}-N-(3-methyl-[1,2,4]oxadiazol-5-ylmethyl)-isobutyramide;

2-{4-[(S)-2-(6,8-Difluoro-1,2,3,4-tetrahydro-naphthalen-2-ylamino) -propionylamino]-imidazol-1-yl}-N-((S)-2-methoxy-1-methyl-ethyl)-isobutyramide;

2-{4-[(S)-2-(6,8-Difluoro-1,2,3,4-tetrahydro-naphthalen-2-ylamino) -propionylamino]-imidazol-1-yl}-N-(3-methoxy-propyl)-isobutyramide;

2-{4-[(S)-2-(6,8-Difluoro-1,2,3,4-tetrahydro-naphthalen-2-ylamino) -propionylamino]-imidazol-1-yl}-N-[1-(1-methyl-1H-pyrazol-4-yl)-ethyl]-isobutyramide;

2-{4-[(S)-2-(6,8-Difluoro-1,2,3,4-tetrahydro-naphthalen-2-ylamino) -propionylamino]-imidazol-1-yl}-N-(3-imidazol-1-yl-propyl)-isobutyramide;

2-{4-[(S)-2-(6,8-Difluoro-1,2,3,4-tetrahydro-naphthalen-2-ylamino) -propionylamino]-imidazol-1-yl}-N-(3-morpholin-4-yl-propyl)-isobutyramide;

(S)-2-(6,8-Difluoro-1,2,3,4-tetrahydro-naphthalen-2-ylamino)-pentanoic acid [1-(3-methyl-oxetan-3-ylmethyl)-1H-imidazol-4-yl]-amide;

(S)-2-[2-(3,5-Difluoro-phenyl)-acetylamino]-pentanoic acid [1-(3-methyl-oxetan-3-ylmethyl)-1H-imidazol-4-yl]-amide;

(S)-2-[2-(3,5-Difluoro-phenyl)-acetylamino]-pentanoic acid [1-(2-pyrrolidin-1-ylmethyl-cyclobutyl)-1H-imidazol-4-yl]-amide;

(S)-2-(6,8-Difluoro-1,2,3,4-tetrahydro-naphthalen-2-ylamino)-pentanoic acid [1-(2-pyrrolidin-1-ylmethyl-cyclobutyl)-1H-imidazol-4-yl]-amide;

(S)-2-(1,2,3,4-Tetrahydro-naphthalen-2-ylamino)-pentanoic acid (1-{1,1-dimethyl -2-[(tetrahydro-pyran-4-ylmethyl)-amino]-ethyl}-1H-imidazol-4-yl)-amide;

(S)-2-(6,8-Difluoro-1,2,3,4-tetrahydro-naphthalen-2-ylamino)-pentanoic acid {1-[2-(2-ethoxy-ethylamino)-1,1-dimethyl-ethyl]-1H-imidazol-4-yl}-amide;

(S)-2-(6,8-Difluoro-1,2,3,4-tetrahydro-naphthalen-2-ylamino)-N-{1-[2-(2-ethoxy-ethylamino)-1,1-dimethyl-ethyl]-1H-imidazol-4-yl}-propionamide;

(S)-2-(6,8-Difluoro-1,2,3,4-tetrahydro-naphthalen-2-ylamino)-pentanoic acid (1-{2-[(1-hydroxy-cyclohexylmethyl)-carbamoyl]-1,1-dimethyl-ethyl}-1H-imidazol-4-yl) -amide;

(S)-2-(6,8-Difluoro-1,2,3,4-tetrahydro-naphthalen-2-ylamino)-pentanoic acid (1-{1-[(1-hydroxy-cyclohexylmethyl)-carbamoyl]-1-methyl-ethyl}-1H-imidazol-4-yl)-amide;

(S)-2-(6,8-Difluoro-1,2,3,4-tetrahydro-naphthalen-2-ylamino)-pentanoic acid (1-{1-methyl-1-[(tetrahydro-pyran-4-ylmethyl)-carbamoyl]-ethyl}-1H-imidazol-4-yl)-amide;

(S)-2-(6,8-Difluoro-1,2,3,4-tetrahydro-naphthalen-2-ylamino)-pentanoic acid {1-[1-methyl-1-(2-methyl-benzylcarbamoyl)-ethyl]-1H-imidazol-4-yl}-amide;

(S)-2-(6,8-Difluoro-1,2,3,4-tetrahydro-naphthalen-2-ylamino)-pentanoic acid {1-[1-(2-methoxy-1-methyl-ethylcarbamoyl)-1-methyl-ethyl]-1H-imidazol-4-yl}-amide;

(S)-2-(6,8-Difluoro-1,2,3,4-tetrahydro-naphthalen-2-ylamino)-pentanoic acid (1-{1-methyl-2-[(tetrahydro-pyran-4-ylmethyl)-amino]-ethyl}-1H-imidazol-4-yl)-amide;

(S)-2-(6,8-Difluoro-1,2,3,4-tetrahydro-naphthalen-2-ylamino)-pentanoic acid (1-{2-[(1-hydroxy-cyclohexylmethyl)-amino]-ethyl}-1H-imidazol-4-yl)-amide;

(S)-2-(6,8-Difluoro-1,2,3,4-tetrahydro-naphthalen-2-ylamino)-pentanoic acid (1-{2-[(4-hydroxy-tetrahydro-pyran-4-ylmethyl)-amino]-ethyl}-1H-imidazol-4-yl)-amide;

(S)-2-(6,8-Difluoro-1,2,3,4-tetrahydro-naphthalen-2-ylamino)-pentanoic acid (1-{2-[(tetrahydro-pyran-4-ylmethyl)-amino]-ethyl}-1H-imidazol-4-yl)-amide;

(S)-2-(6,8-Difluoro-1,2,3,4-tetrahydro-naphthalen-2-ylamino)-pentanoic acid (1-{2-[(3-methyl-oxetan-3-ylmethyl)-amino]-ethyl}-1H-imidazol-4-yl)-amide;

(S)-2-(6,8-Difluoro-1,2,3,4-tetrahydro-naphthalen-2-ylamino)-pentanoic acid (1-{2-[(1-hydroxy-cyclohexylmethyl)-amino]-1-methyl-ethyl}-1H-imidazol-4-yl)-amide;

(S)-2-(6,8-Difluoro-1,2,3,4-tetrahydro-naphthalen-2-ylamino)-pentanoic acid {1-[2-(2-ethoxy-ethylamino)-ethyl]-1H-imidazol-4-yl}-amide;

(S)-2-(6,8-Difluoro-1,2,3,4-tetrahydro-naphthalen-2-ylamino)-pentanoic acid [1-(3-benzylamino-propyl)-1H-imidazol-4-yl]-amide;

(S)-2-(6,8-Difluoro-1,2,3,4-tetrahydro-naphthalen-2-ylamino)-pentanoic acid (1-{1,1-dimethyl-3-[(pyridin-2-ylmethyl)-amino]-propyl}-1H-imidazol-4-yl)-amide;

(S)-2-(6,8-Difluoro-1,2,3,4-tetrahydro-naphthalen-2-ylamino)-pentanoic acid {1-[1,1-dimethyl-3-((S)-2,2,2-trifluoro-1-phenyl-ethylamino)-propyl]-1H-imidazol-4-yl}-amide;

(S)-2-(6,8-Difluoro-1,2,3,4-tetrahydro-naphthalen-2-ylamino)-pentanoic acid {1-[1,1-dimethyl-3-((R)-1-phenyl-ethylamino)-propyl]-1H-imidazol-4-yl}-amide;

(S)-2-(2-Trifluoromethyl-benzylamino)-pentanoic acid {1-[2-((2R,6S)-2,6-dimethyl-morpholin-4-yl)-1,1-dimethyl-ethyl]-1H-imidazol-4-yl}-amide;

(S)-2-{[(2-Fluoro-3-trifluoromethyl-phenyl)methyl]-amino}-pentanoic acid {1-[2-((2R,6S)-2,6-dimethyl-morpholin-4-yl)-1,1-dimethyl-ethyl]-1H-imidazol-4-yl}-amide;

(S)-2-[2-(3,5-Difluoro-phenyl)-acetylamino]-N-[1-(1,1-dimethyl-2-pyrrolidin-1-yl ethyl)-1H-imidazol-4-yl]-2-phenyl-acetamide (S)-2-[2-(3,5-Difluoro-phenyl)-acetylamino]-N-{1-[2-((2S,6R)-2,6-dimethyl-morpholin-4-yl)-1,1-dimethyl-ethyl]-1H-imidazol-4-yl}-2-phenyl-acetamide (S)-2-(6,8-Difluoro-1,2,3,4-tetrahydro-naphthalen-2-ylamino)-N-{1-[2-(2,2-dimethyl-propylamino)-1,1-dimethyl-ethyl]-1H-imidazol-4-yl}-2-phenyl-acetamide (S)-2-[2-(3,5-Difluoro-phenyl)-acetylamino]-pentanoic acid (1-indan-1-yl-1H-imidazol-4-yl)-amide;

(S)-2-[2-(3,5-Difluoro-phenyl)-acetylamino]-pentanoic acid [(S)-1-((1S,2R)-2-hydroxy-indan-1-yl)-1H-imidazol-4-yl]-amide;

(S)-2-[2-(3,5-Difluoro-phenyl)-acetylamino]-pentanoic acid [(R)-1-((1R,2S)-2-hydroxy-indan-1-yl)-1H-imidazol-4-yl]-amide;

(S)-2-[2-(3,5-Difluoro-phenyl)-acetylamino]-pentanoic acid [1-(2-hydroxymethyl-phenyl)-1H-imidazol-4-yl]-amide;

(S)-2-[2-(3,5-Difluoro-phenyl)-acetylamino]-N-{1-[2-(2,2-dimethyl-propylamino)-1,1-dimethyl-ethyl]-1H-imidazol-4-yl}-2-phenyl-acetamide;

2-[2-(3,5-Difluoro-phenyl)-acetylamino]-N-{1-[2-(2,2-dimethyl-propylamino)-1,1-dimethyl-ethyl]-1H-imidazol-4-yl}-2-(4-fluoro-phenyl)-acetamide;

2-[2-(3,5-Difluoro-phenyl)-acetylamino]-N-{1-[2-(2,2-dimethyl-propylamino)-1,1-dimethyl-ethyl]-1H-imidazol-4-yl}-2-pyridin-3-yl-acetamide;

(S)-2-(6,8-Difluoro-1,2,3,4-tetrahydro-naphthalen-2-ylamino)-pentanoic acid (1-{2-[(2,2-dimethyl-propylamino)-methyl]-phenyl}-1H-imidazol-4-yl)-amide;

(S)-2-(6,8-Difluoro-1,2,3,4-tetrahydro-naphthalen-2-ylamino)-pentanoic acid (1-{2-[(2-hydroxy-butylamino)-methyl]-phenyl}-1H-imidazol-4-yl)-amide;

(S)-2-[2-(3,5-Difluoro-phenyl)-acetylamino]-pentanoic acid {1-[2-(3-ethoxy-propylamino)-ethyl]-1H-imidazol-4-yl}-amide;

(S)-2-[2-(3,5-Difluoro-phenyl)-acetylamino]-pentanoic acid [1-(1-hydroxymethyl-cyclobutyl)-1H-imidazol-4-yl]-amide;

(S)-2-[2-(3,5-Difluoro-phenyl)-acetylamino]-pentanoic acid [1-(2-hydroxymethyl-cyclobutyl)-1H-imidazol-4-yl]-amide;

(S)-2-[2-(3,5-Difluoro-phenyl)-acetylamino]-pentanoic acid [1-(1-pyrrolidin-1-ylmethyl-cyclobutyl)-1H-imidazol-4-yl]-amide;

(S)-2-(6,8-Difluoro-1,2,3,4-tetrahydro-naphthalen-2-ylamino)-pentanoic acid {1-[2-((R)-1-cyclohexyl-ethylamino)-1,1-dimethyl-ethyl]-1H-imidazol-4-yl}-amide;

(S)-2-[2-(3,5-Difluoro-phenyl)-acetylamino]-pentanoic acid {1-[2-((R)-1-cyclohexyl-ethylamino)-1,1-dimethyl-ethyl]-1H-imidazol-4-yl}-amide;

(S)-2-[2-(2,4-Difluoro-phenyl)-2-hydroxy-ethylamino]-pentanoic acid [1-(1,1-dimethyl-2-pyrrolidin-1-yl-ethyl)-1H-imidazol-4-yl]-amide;

(S)-2-[2-(3,4-Difluoro-phenyl)-2-hydroxy-ethylamino]-pentanoic acid [1-(1,1-dimethyl-2-pyrrolidin-1-yl-ethyl)-1H-imidazol-4-yl]-amide;

(S)-2-(6,8-Difluoro-1,2,3,4-tetrahydro-naphthalen-2-ylamino)-pentanoic acid (1-{1,1-dimethyl-2-[(tetrahydro-pyran-4-ylmethyl)-amino]-ethyl}-1H-imidazol-4-yl)-amide;

(S)-2-[2-(3,5-Difluoro-phenyl)-acetylamino]-pentanoic acid (1-{1,1-dimethyl-2-[(tetrahydro-pyran-4-ylmethyl)-amino]-ethyl}-1H-imidazol-4-yl)-amide;

(S)-2-(6,8-Difluoro-1,2,3,4-tetrahydro-naphthalen-2-ylamino)-pentanoic acid {1-[3-((S)-1-phenyl-ethylamino)-butyl]-1H-imidazol-4-yl}-amide;

(S)-2-(6,8-Difluoro-1,2,3,4-tetrahydro-naphthalen-2-ylamino)-pentanoic acid [1-(3-methyl-oxetan-3-ylmethyl)-1H-imidazol-4-yl]-amide;

(S)-2-[2-(3,5-Difluoro-phenyl)-acetylamino]-pentanoic acid [1-(3-methyl-oxetan-3-ylmethyl)-1H-imidazol-4-yl]-amide;

(S)-2-[2-(3,5-Difluoro-phenyl)-2-hydroxy-ethylamino]-pentanoic acid [1-(1,1-dimethyl-2-pyrrolidin-1-yl-ethyl)-1H-imidazol-4-yl]-amide;

(S)-2-[2-(2,4-Difluoro-phenyl)-2-hydroxy-ethylamino]-pentanoic acid {1-[2-((2R,6S)-2,6-dimethyl-morpholin-4-yl)-1,1-dimethyl-ethyl]-1H-imidazol-4-yl}-amide;

(S)-2-[2-(3,5-Difluoro-phenyl)-acetylamino]-pentanoic acid {1-[2-(octahydro-pyrazino[1,2-a]azepin-2-yl)-ethyl]-1H-imidazol-4-yl}-amide;

(S)-2-[2-(3,5-Difluoro-phenyl)-acetylamino]-pentanoic acid {1-[2-([1,4]dioxan-2-ylmethyl-methyl-amino)-ethyl]-1H-imidazol-4-yl}-amide;

(S)-2-[2-(3,5-Difluoro-phenyl)-acetylamino]-pentanoic acid {1-[2-(2-methoxy-1-methyl-ethylamino)-ethyl]-1H-imidazol-4-yl}-amide;

(S)-2-[2-(3,5-Difluoro-phenyl)-acetylamino]-pentanoic acid {1-[2-(3-oxo-piperazin-1-yl)-ethyl]-1H-imidazol-4-yl}-amide;

(S)-2-[2-(3,5-Difluoro-phenyl)-acetylamino]-pentanoic acid [1-(2-benzylamino-ethyl)-1H-imidazol-4-yl]-amide;

(S)-2-[2-(3,5-Difluoro-phenyl)-acetylamino]-pentanoic acid {1-[2-(3-butoxy-propylamino)-ethyl]-1H-imidazol-4-yl}-amide;

(S)-2-[2-(3,5-Difluoro-phenyl)-acetylamino]-pentanoic acid {1-[2-((1R,2S)-2-hydroxymethyl-cyclohexylamino)-ethyl]-1H-imidazol-4-yl}-amide;

2-[2-(3,5-Difluoro-phenyl)-acetylamino]-pentanoic acid {1-[(4aS,8aS)-2-(octahydro-isoquinolin-2-yl)-ethyl]-1H-imidazol-4-yl}-amide;

(S)-2-[2-(3,5-Difluoro-phenyl)-acetylamino]-pentanoic acid {1-[2-(3-isopropoxy-propylamino)-ethyl]-1H-imidazol-4-yl}-amide;

(S)-2-[2-(3,5-Difluoro-phenyl)-acetylamino]-pentanoic acid {1-[2-(octahydro-isoquinolin-2-yl)-ethyl]-1H-imidazol-4-yl}-amide;

(S)-2-[2-(3,5-Difluoro-phenyl)-acetylamino]-pentanoic acid {1-[2-(3,4,5,6-tetrahydro-2H-[4,4']bipyridinyl-1-yl)-ethyl]-1H-imidazol-4-yl}-amide;

S)-2-[2-(3,5-Difluoro-phenyl)-acetylamino]-pentanoic acid {1-[2-(2-hydroxy-2-phenyl-ethylamino)-ethyl]-1H-imidazol-4-yl}-amide;

(S)-2-[2-(3,5-Difluoro-phenyl)-acetylamino]-pentanoic acid {1-[2-(indan-1-ylamino)-ethyl]-1H-imidazol-4-yl}-amide;

(S)-2-[2-(3,5-Difluoro-phenyl)-acetylamino]-pentanoic acid {1-[2-(benzyl-methyl-amino)-ethyl]-1H-imidazol-4-yl}-amide;

(S)-2-[2-(3,5-Difluoro-phenyl)-acetylamino]-pentanoic acid {1-[2-(indan-2-ylamino)-ethyl]-1H-imidazol-4-yl}-amide;

(S)-2-[2-(3,5-Difluoro-phenyl)-acetylamino]-pentanoic acid {1-[2-(3,4-dihydro -1H-isoquinolin-2-yl)-ethyl]-1H-imidazol-4-yl}-amide;

(S)-2-[2-(3,5-Difluoro-phenyl)-acetylamino]-pentanoic acid {1-[2-(2-propoxy -ethylamino)-ethyl]-1H-imidazol-4-yl}-amide;

(S)-2-[2-(3,5-Difluoro-phenyl)-acetylamino]-pentanoic acid {1-[2-(3-benzyl -pyrrolidin-1-yl)-ethyl]-1H-imidazol-4-yl}-amide;

(S)-2-[2-(3,5-Difluoro-phenyl)-acetylamino]-pentanoic acid {1-[2-(3-pyridin-2-yl -pyrrolidin-1-yl)-ethyl]-1H-imidazol-4-yl}-amide;

(S)-2-[2-(3,5-Difluoro-phenyl)-acetylamino]-pentanoic acid {1-[2-(methyl-pyridin -4-ylmethyl-amino)-ethyl]-1H-imidazol-4-yl}-amide;

(S)-2-[2-(3,5-Difluoro-phenyl)-acetylamino]-pentanoic acid (1-{2-[(2-methanesulfonyl-ethyl)-methyl-amino]-ethyl}-1H-imidazol-4-yl)-amide;

(S)-2-[2-(3,5-Difluoro-phenyl)-acetylamino]-pentanoic acid {1-[2-(2-tert-butoxy -ethylamino)-ethyl]-1H-imidazol-4-yl}-amide;

(S)-2-[2-(3,5-Difluoro-phenyl)-acetylamino]-pentanoic acid {1-[2-(3-pyridin-4-yl -pyrrolidin-1-yl)-ethyl]-1H-imidazol-4-yl}-amide;

(S)-2-[(1-Hydroxy-cyclohexylmethyl)-amino]-pentanoic acid [1-(1,1-dimethyl-2-pyrrolidin-1-yl-ethyl)-1H-imidazol-4-yl]-amide;

(S)-2-[2-(3,5-Difluoro-phenyl)-acetylamino]-N-[1-(1,1-dimethyl-2-pyrrolidin-1-yl -ethyl)-1H-imidazol-4-yl]-2-phenyl-acetamide;

(S)-2-(Dicyclopropylmethyl-amino)-pentanoic acid [1-(1,1-dimethyl-2-pyrrolidin-1-yl-ethyl)-1H-imidazol-4-yl]-amide;

(S)-2-(6,8-Difluoro-1,2,3,4-tetrahydro-naphthalen-2-ylamino)-pentanoic acid {1-[3-((R)-1-phenyl-ethylamino)-propyl]-1H-imidazol-4-yl}-amide;

(S)-2-(6,8-Difluoro-1,2,3,4-tetrahydro-naphthalen-2-ylamino)-pentanoic acid (1-{2-[(1-hydroxy-cyclohexylmethyl)-amino]-1,1-dimethyl-ethyl}-1H-imidazol-4-yl)-amide;

(S)-2-[2-(3,5-Difluoro-phenyl)-acetylamino]-N-{1-[2-((2S,6R)-2,6-dimethyl -morpholin-4-yl)-1,1-dimethyl-ethyl]-1H-imidazol-4-yl}-2-phenyl-acetamide;

(S)-2-(6,8-Difluoro-1,2,3,4-tetrahydro-naphthalen-2-ylamino)-pentanoic acid (1-{2-[(4-hydroxy-tetrahydro-pyran-4-ylmethyl)-amino]-1,1-dimethyl-ethyl}-1H-imidazol-4-yl) -amide;

(S)-2-[2-(3,5-Difluoro-phenyl)-acetylamino]-pentanoic acid [1-(1-dimethylaminomethyl-cyclobutyl)-1H-imidazol-4-yl]-amide;

(S)-2-[2-(3,5-Difluoro-phenyl)-acetylamino]-pentanoic acid [1-(1-piperidin-1-ylmethyl-cyclobutyl)-1H-imidazol-4-yl]-amide;

(S)-2-[2-(3,5-Difluoro-phenyl)-acetylamino]-pentanoic acid [1-(1-morpholin-4-ylmethyl-cyclobutyl)-1H-imidazol-4-yl]-amide;

(S)-2-[2-(3,5-Difluoro-phenyl)-acetylamino]-pentanoic acid (1-{1-[((2R,6S)-2,6-dimethyl-morpholin-4-yl)methyl]-cyclobutyl}-1H-imidazol-4-yl)-amide;

(S)-2-[2-(3,5-Difluoro-phenyl)-acetylamino]-pentanoic acid (1-{1-[(2,2,2-trifluoro -ethylamino)-methyl]-cyclobutyl}-1H-imidazol-4-yl)-amide;

(S)-2-[2-(3,5-Difluoro-phenyl)-acetylamino]-pentanoic acid (1-{1-[((R)-1-cyclohexyl-ethylamino)-methyl]-cyclobutyl}-1H-imidazol-4-yl)-amide;

(S)-2-(5,7-Difluoro-1,2,3,4-tetrahydro-naphthalen-2-ylamino)-pentanoic acid [1-(1-hydroxymethyl-cyclobutyl)-1H-imidazol-4-yl]-amide;

(S)-2-(5,7-Difluoro-1,2,3,4-tetrahydro-naphthalen-2-ylamino)-pentanoic acid [1-(1-pyrrolidin-1-ylmethyl-cyclobutyl)-1H-imidazol-4-yl]-amide;

(S)-2-[2-(3,5-Difluoro-phenyl)-acetylamino]-pentanoic acid (1-{1-[(2,2-dimethyl -propylamino)-methyl]-cyclobutyl}-1H-imidazol-4-yl)-amide;

(S)-2-(6,8-Difluoro-1,2,3,4-tetrahydro-naphthalen-2-ylamino)-N-{1-[2-(2,2-dimethyl-propylamino)-1,1-dimethyl-ethyl]-1H-imidazol-4-yl}-2-phenyl-acetamide;

(S)-2-(6,8-Difluoro-1,2,3,4-tetrahydro-naphthalen-2-ylamino)-pentanoic acid {1-[2-(2-methoxy-2-methyl-propylamino)-1,1-dimethyl-ethyl]-1H-imidazol-4-yl}-amide;

(S)-2-(6,8-Difluoro-1,2,3,4-tetrahydro-naphthalen-2-ylamino)-pentanoic acid (1-{1,1-dimethyl-2-[(3-methyl-oxetan-3-ylmethyl)-amino]-ethyl}-1H-imidazol-4-yl)-amide;

(S)-2-(6,8-Difluoro-1,2,3,4-tetrahydro-naphthalen-2-ylamino)-pentanoic acid {1-[2-(cyclohexylmethyl-amino)-1,1-dimethyl-ethyl]-1H-imidazol-4-yl}-amide;

(S)-2-(6,8-Difluoro-1,2,3,4-tetrahydro-naphthalen-2-ylamino)-pentanoic acid (1-{1-methyl-2-[(tetrahydro-pyran-4-ylmethyl)-amino]-ethyl}-1H-imidazol-4-yl)-amide;

(S)-2-[2-(3,5-Difluoro-phenyl)-acetylamino]-pentanoic acid (1-indan-1-yl-1H -imidazol-4-yl)-amide;

(S)-2-[2-(3,5-Difluoro-phenyl)-acetylamino]-pentanoic acid [(S)-1-((1S,2R)-2-hydroxy-indan-1-yl)-1H-imidazol-4-yl]-amide;

(S)-2-[2-(3,5-Difluoro-phenyl)-acetylamino]-pentanoic acid [(R)-1-((1R,2S)-2-hydroxy-indan-1-yl)-1H-imidazol-4-yl]-amide;

(S)-2-[2-(3,5-Difluoro-phenyl)-acetylamino]-pentanoic acid [1-(2-pyrrolidin-1-ylmethyl-cyclobutyl)-1H-imidazol-4-yl]-amide;

(S)-2-(6,8-Difluoro-1,2,3,4-tetrahydro-naphthalen-2-ylamino)-pentanoic acid [1-(2-pyrrolidin-1-ylmethyl-cyclobutyl)-1H-imidazol-4-yl]-amide;

(S)-2-(6,8-Difluoro-1,2,3,4-tetrahydro-naphthalen-2-ylamino)-pentanoic acid {1-[3-(3-methyl-benzylamino)-propyl]-1H-imidazol-4-yl}-amide;

(S)-2-(6,8-Difluoro-1,2,3,4-tetrahydro-naphthalen-2-ylamino)-pentanoic acid{1-[3-(2-hydroxy-2-phenyl-ethylamino)-propyl]-1H-imidazol-4-yl}-amide;

(S)-2-(6,8-Difluoro-1,2,3,4-tetrahydro-naphthalen-2-ylamino)-pentanoic acid {1-[3-(2-hydroxy-2-phenyl-ethylamino)-propyl]-1H-imidazol-4-yl}-amide;

(S)-2-(6,8-Difluoro-1,2,3,4-tetrahydro-naphthalen-2-ylamino)-pentanoic acid {1-[3-(3,4-dihydro-1H-isoquinolin-2-yl)-propyl]-1H-imidazol-4-yl}-amide;

(S)-2-(6,8-Difluoro-1,2,3,4-tetrahydro-naphthalen-2-ylamino)-pentanoic acid {1-[3-(indan-2-ylamino)-propyl]-1H-imidazol-4-yl}-amide;

(S)-2-(6,8-Difluoro-1,2,3,4-tetrahydro-naphthalen-2-ylamino)-pentanoic acid {1-[3-(1-methoxymethyl-propylamino)-propyl]-1H-imidazol-4-yl}-amide;

(S)-2-(6,8-Difluoro-1,2,3,4-tetrahydro-naphthalen-2-ylamino)-pentanoic acid {1-[3-(4-chloro-benzylamino)-propyl]-1H-imidazol-4-yl}-amide;

(S)-2-(6,8-Difluoro-1,2,3,4-tetrahydro-naphthalen-2-ylamino)-pentanoic acid {1-[3-(2-methyl-benzylamino)-propyl]-1H-imidazol-4-yl}-amide;

(S)-2-(6,8-Difluoro-1,2,3,4-tetrahydro-naphthalen-2-ylamino)-pentanoic acid {1-[3-(2-methoxy-ethylamino)-propyl]-1H-imidazol-4-yl}-amide;

(S)-2-(6,8-Difluoro-1,2,3,4-tetrahydro-naphthalen-2-ylamino)-pentanoic acid (1-{3-[(pyridin-3-ylmethyl)-amino]-propyl}-1H-imidazol-4-yl)-amide;

(S)-2-(6,8-Difluoro-1,2,3,4-tetrahydro-naphthalen-2-ylamino)-pentanoic acid {1-[3-((S)-1-p-tolyl-ethylamino)-propyl]-1H-imidazol-4-yl}-amide;

(S)-2-(6,8-Difluoro-1,2,3,4-tetrahydro-naphthalen-2-ylamino)-pentanoic acid {1-[3-(4-methoxy-benzylamino)-propyl]-1H-imidazol-4-yl}-amide;

(S)-2-(6,8-Difluoro-1,2,3,4-tetrahydro-naphthalen-2-ylamino)-pentanoic acid {1-[3-(cyclopropylmethylamino)-propyl]-1H-imidazol-4-yl}-amide;

(S)-2-(6,8-Difluoro-1,2,3,4-tetrahydro-naphthalen-2-ylamino)-pentanoic acid {1-[3-(4-methyl-benzylamino)-propyl]-1H-imidazol-4-yl}-amide;

(S)-2-(6,8-Difluoro-1,2,3,4-tetrahydro-naphthalen-2-ylamino)-pentanoic acid (1-{2-[(1-hydroxy-cyclohexylmethyl)-carbamoyl]-1,1-dimethyl-ethyl}-1H-imidazol-4-yl)-amide;

(S)-2-(1,2,3,4-Tetrahydro-naphthalen-2-ylamino)-pentanoic acid (1-{1,1-dimethyl-2-[(tetrahydro-pyran-4-ylmethyl)-amino]-ethyl}-1H-imidazol-4-yl)-amide;

(S)-2-(6,8-Difluoro-1,2,3,4-tetrahydro-naphthalen-2-ylamino)-pentanoic acid (1-{2-[(1-hydroxy-cyclohexylmethyl)-amino]-ethyl}-1H-imidazol-4-yl)-amide;

(S)-2-(6,8-Difluoro-1,2,3,4-tetrahydro-naphthalen-2-ylaminoypentanoic acid (1-{1-[(2,2,2-trifluoro-ethylamino)-methyl]-cyclobutyl}-1H-imidazol-4-yl)-amide;

(S)-2-(6,8-Difluoro-1,2,3,4-tetrahydro-naphthalen-2-ylamino)-pentanoic acid (1-{1-[(2,2-dimethyl-propylamino)-methyl]-cyclobutyl}-1H-imidazol-4-yl)-amide;

(S)-2-(6,8-Difluoro-1,2,3,4-tetrahydro-naphthalen-2-ylamino)-pentanoic acid (1-{1-[((R)-1-cyclohexyl-ethylamino)-methyl]-cyclobutyl}-1H-imidazol-4-yl)-amide;

(S)-2-(6,8-Difluoro-1,2,3,4-tetrahydro-naphthalen-2-ylamino)-pentanoic acid [1-(1-dimethylaminomethyl-cyclobutyl)-1H-imidazol-4-yl]-amide;

(S)-2-(6,8-Difluoro-1,2,3,4-tetrahydro-naphthalen-2-ylamino)-pentanoic acid [1-(1-piperidin-1-ylmethyl-cyclobutyl)-1H-imidazol-4-yl]-amide;

(S)-2-(6,8-Difluoro-1,2,3,4-tetrahydro-naphthalen-2-ylamino)-pentanoic acid [1-(1-morpholin-4-ylmethyl-cyclobutyl)-1H-imidazol-4-yl]-amide;

(S)-2-(6,8-Difluoro-1,2,3,4-tetrahydro-naphthalen-2-ylamino)-pentanoic acid (1-{1-[((2R,6S)-2,6-dimethyl-morpholin-4-yl)methyl]-cyclobutyl}-1H-imidazol-4-yl)-amide;

(S)-2-(6,8-Difluoro-1,2,3,4-tetrahydro-naphthalen-2-ylamino)-pentanoic acid (1-{2-[(4-hydroxy-tetrahydro-pyran-4-ylmethyl)-amino]-ethyl}-1H-imidazol-4-yl)-amide;

(S)-2-(6,8-Difluoro-1,2,3,4-tetrahydro-naphthalen-2-ylamino)-pentanoic acid (1-{2-[(tetrahydro-pyran-4-ylmethyl)-amino]-ethyl}-1H-imidazol-4-yl)-amide;

(S)-2-(6,8-Difluoro-1,2,3,4-tetrahydro-naphthalen-2-ylamino)-pentanoic acid (1-{2-[(3-methyl-oxetan-3-ylmethyl)-amino]-ethyl}-1H-imidazol-4-yl)-amide;

(S)-2-(6,8-Difluoro-1,2,3,4-tetrahydro-naphthalen-2-ylamino)-pentanoic acid (1-{2-[(1-hydroxy-cyclohexylmethyl)-amino]-1-methyl-ethyl}-1H-imidazol-4-yl)-amide;

(S)-2-(6,8-Difluoro-1,2,3,4-tetrahydro-naphthalen-2-ylamino)-pentanoic acid (1-{1,1-dimethyl-3-[(pyridin-2-ylmethyl)-amino]-propyl}-1H-imidazol-4-yl)-amide;

(S)-2-(6,8-Difluoro-1,2,3,4-tetrahydro-naphthalen-2-ylamino)-pentanoic acid (1-{1-[(1-hydroxy-cyclohexylmethyl)-carbamoyl]-1-methyl-ethyl}-1H-imidazol-4-yl)-amide;

(S)-2-{[(2-Fluoro-3-trifluoromethyl-phenyl)methyl]-amino}-pentanoic acid {1-[2-((2R,6S)-2,6-dimethyl-morpholin-4-yl)-1,1-dimethyl-ethyl]-1H-imidazol-4-yl}-amide;

(S)-2-(6,8-Difluoro-1,2,3,4-tetrahydro-naphthalen-2-ylamino)-pentanoic acid {1-[1,1-dimethyl-3-((S)-2,2,2-trifluoro-1-phenyl-ethylamino)-propyl]-1H-imidazol-4-yl}-amide;

(S)-2-(6,8-Difluoro-1,2,3,4-tetrahydro-naphthalen-2-ylamino)-pentanoic acid {1-[1,1-dimethyl-3-((R)-1-phenyl-ethylamino)-propyl]-1H-imidazol-4-yl}-amide;

(S)-2-(2-Trifluoromethyl-benzylamino)-pentanoic acid {1-[2-((2R,6S)-2,6-dimethyl-morpholin-4-yl)-1,1-dimethyl-ethyl]-1H-imidazol-4-yl}-amide;

(S)-2-(6,8-Difluoro-1,2,3,4-tetrahydro-naphthalen-2-ylamino)-pentanoic acid (1-{1-methyl-1-[(tetrahydro-pyran-4-ylmethyl)-carbamoyl]-ethyl}-1H-imidazol-4-yl)-amide;

(S)-2-(6,8-Difluoro-1,2,3,4-tetrahydro-naphthalen-2-ylamino)-pentanoic acid {1-[2-(2-ethoxy-ethylamino)-ethyl]-1H-imidazol-4-yl}-amide;

(S)-2-[2-(3,5-Difluoro-phenyl)-acetylamino]-pentanoic acid [1-(2-hydroxymethyl -phenyl)-1H-imidazol-4-yl]-amide;

(S)-2-(6,8-Difluoro-1,2,3,4-tetrahydro-naphthalen-2-ylamino)-pentanoic acid {1-[2-(2-ethoxy-ethylamino)-1,1-dimethyl-ethyl]-1H-imidazol-4-yl}-amide;

(S)-2-(6,8-Difluoro-1,2,3,4-tetrahydro-naphthalen-2-ylamino)-N-{1-[2-(2-ethoxy -ethylamino)-1,1-dimethyl-ethyl]-1H-imidazol-4-yl}-propionamide;

(S)-2-[2-(3,5-Difluoro-phenyl)-acetylamino]-N-{1-[2-(2,2-dimethyl-propylamino)-1,1-dimethyl-ethyl]-1H-imidazol-4-yl}-2-phenyl-acetamide;

(S)-2-(6,8-Difluoro-1,2,3,4-tetrahydro-naphthalen-2-ylamino)-pentanoic acid {1-[1-methyl-1-(2-methyl-benzylcarbamoyl)-ethyl]-1H-imidazol-4-yl}-amide;

(S)-2-(6,8-Difluoro-1,2,3,4-tetrahydro-naphthalen-2-ylamino)-pentanoic acid {1-[1-(2-methoxy-1-methyl-ethylcarbamoyl)-1-methyl-ethyl]-1H-imidazol-4-yl}-amide;

(S)-2-(6,8-Difluoro-1,2,3,4-tetrahydro-naphthalen-2-ylamino)-pentanoic acid [1-(3-benzylamino-propyl)-1H-imidazol-4-yl]-amide;

(S)-2-(6,8-Difluoro-1,2,3,4-tetrahydro-naphthalen-2-ylamino)-pentanoic acid (1-{2-[(2,2-dimethyl-propylamino)-methyl]-phenyl}-1H-imidazol-4-yl)-amide;

(S)-2-(6,8-Difluoro-1,2,3,4-tetrahydro-naphthalen-2-ylamino)-pentanoic acid {(S) -1-[2-(2,2-dimethyl-propylamino)-1-phenyl-ethyl]-1H-imidazol-4-yl}-amide;

(S)-2-(6,8-Difluoro-1,2,3,4-tetrahydro-naphthalen-2-ylamino)-pentanoic acid (1-{2-[(2-hydroxy-butylamino)-methyl]-phenyl}-1H-imidazol-4-yl)-amide;

2-[2-(3,5-Difluoro-phenyl)-acetylamino]-N-{1-[2-(2,2-dimethyl-propylamino)-1,1-dimethyl-ethyl]-1H-imidazol-4-yl}-2-pyridin-3-yl-acetamide;

2-[2-(3,5-Difluoro-phenyl)-acetylamino]-N-{1-[2-(2,2-dimethyl-propylamino)-1,1-dimethyl-ethyl]-1H-imidazol-4-yl}-2-(4-fluoro-phenyl)-acetamide;

(S)-2-(6,8-Difluoro-1,2,3,4-tetrahydro-naphthalen-2-ylamino)-pentanoic acid {1-[1-methyl-1-(methyl-phenethyl-carbamoyl)-ethyl]-1H-imidazol-4-yl}-amide;

(S)-2-(6,8-Difluoro-1,2,3,4-tetrahydro-naphthalen-2-ylamino)-pentanoic acid {1-[1-(1,3-dihydro-isobenzofuran-5-ylcarbamoyl)-1-methyl-ethyl]-1H-imidazol-4-yl}-amide;

(S)-2-(6,8-Difluoro-1,2,3,4-tetrahydro-naphthalen-2-ylamino)-pentanoic acid {1-[1-(indan-1-ylcarbamoyl)-1-methyl-ethyl]-1H-imidazol-4-yl}-amide;

(S)-2-(6,8-Difluoro-1,2,3,4-tetrahydro-naphthalen-2-ylamino)-pentanoic acid (1-{1-[2-(3-fluoro-phenyl)-ethylcarbamoyl]-1-methyl-ethyl}-1H-imidazol-4-yl)-amide;

2-{4-[(S)-2-(6,8-Difluoro-1,2,3,4-tetrahydro-naphthalen-2-ylamino)-propionylamino]-imidazol-1-yl}-N-indan-1-yl-isobutyramide;

(S)-2-(6,8-Difluoro-1,2,3,4-tetrahydro-naphthalen-2-ylamino)-pentanoic acid (1-{1-methyl-1-[methyl-(tetrahydro-pyran-2-ylmethyl)-carbamoyl]-ethyl}-1H-imidazol-4-yl)-amide;

(S)-2-(6,8-Difluoro-1,2,3,4-tetrahydro-naphthalen-2-ylamino)-pentanoic acid (1-{1-[ethyl-(2-pyrazol-1-yl-ethyl)-carbamoyl]-1-methyl-ethyl}-1H-imidazol-4-yl)-amide;

(S)-2-(6,8-Difluoro-1,2,3,4-tetrahydro-naphthalen-2-ylamino)-pentanoic acid (1-{1-[(furan-2-ylmethyl)-carbamoyl]-1-methyl-ethyl}-1H-imidazol-4-yl)-amide;

(S)-2-(6,8-Difluoro-1,2,3,4-tetrahydro-naphthalen-2-ylamino)-pentanoic acid {1-[1-methyl-1-((3R,4S)-4-methylsulfanyl-tetrahydro-furan-3-ylcarbamoyl)-ethyl]-1H-imidazol-4-yl}-amide;

(S)-2-(6,8-Difluoro-1,2,3,4-tetrahydro-naphthalen-2-ylamino)-pentanoic acid {1-[2-(4-acetyl-[1,4]diazepan-1-yl)-1,1-dimethyl-2-oxo-ethyl]-1H-imidazol-4-yl}-amide;

2-{4-[(S)-2-(6,8-Difluoro-1,2,3,4-tetrahydro-naphthalen-2-ylamino)-propionylamino]-imidazol-1-yl}-N-[2-(3-fluoro-phenyl)-ethyl]-isobutyramide;

(S)-2-(6,8-Difluoro-1,2,3,4-tetrahydro-naphthalen-2-ylamino)-pentanoic acid (1-{1-methyl-1-[1-(1-methyl-1H-pyrazol-4-yl)-ethylcarbamoyl]-ethyl}-1H-imidazol-4-yl)-amide;

2-{4-[(S)-2-(6,8-Difluoro-1,2,3,4-tetrahydro-naphthalen-2-ylamino)-propionylamino]-imidazol-1-yl}-N-methyl-N-phenethyl-isobutyramide;

(S)-2-(6,8-Difluoro-1,2,3,4-tetrahydro-naphthalen-2-ylamino)-pentanoic acid {1-[1-(3-methoxy-propylcarbamoyl)-1-methyl-ethyl]-1H-imidazol-4-yl}-amide;

(S)-2-(6,8-Difluoro-1,2,3,4-tetrahydro-naphthalen-2-ylamino)-pentanoic acid (1-{1-methyl-1-[(3-methyl-[1,2,4]oxadiazol-5-ylmethyl)-carbamoyl]-ethyl}-1H-imidazol-4-yl)-amide;

(S)-2-(6,8-Difluoro-1,2,3,4-tetrahydro-naphthalen-2-ylamino)-pentanoic acid (1-{1-[(2-cyano-ethyl)-methyl-carbamoyl]-1-methyl-ethyl}-1H-imidazol-4-yl)-amide;

2-{4-[(S-2-(6,8-Difluoro-1,2,3,4-tetrahydro-naphthalen-2-ylamino)-propionylamino]-imidazol-1-yl}-N-ethyl-N-(2-pyrazol-1-yl-ethyl)-isobutyramide;

(S)-2-(6,8-Difluoro-1,2,3,4-tetrahydro-naphthalen-2-ylamino)-pentanoic acid (1-{1-methyl-1-[methyl-(1-methyl-1H-imidazol-2-ylmethyl)-carbamoyl]-ethyl}-1H-imidazol-4-yl)-amide;

2-{4-[(S)-2-(6,8-Difluoro-1,2,3,4-tetrahydro-naphthalen-2-ylamino)-propionylamino]-imidazol-1-yl}-N-(4-methyl-benzyl)-isobutyramide;

2-{4-[(S)-2-(6,8-Difluoro-1,2,3,4-tetrahydro-naphthalen-2-ylamino)-propionylamino]-imidazol-1-yl}-N-(1,3-dihydro-isobenzofuran-5-yl)-isobutyramide;

(S)-2-(6,8-Difluoro-1,2,3,4-tetrahydro-naphthalen-2-ylamino)-pentanoic acid (1-{1-[(2-diethylamino-ethyl)-methyl-carbamoyl]-1-methyl-ethyl}-1H-imidazol-4-yl)-amide;

2-{4-[(S)-2-(6,8-Difluoro-1,2,3,4-tetrahydro-naphthalen-2-ylamino)-propionylamino]-imidazol-1-yl}-N-((1R,2S)-2-hydroxymethyl-cyclohexyl)-isobutyramide;

2-{4-[(S)-2-(6,8-Difluoro-1,2,3,4-tetrahydro-naphthalen-2-ylamino)-propionylamino]-imidazol-1-yl}-N-(3-methyl-[1,2,4]oxadiazol-5-ylmethyl)-isobutyramide;

2-{4-[(S)-2-(6,8-Difluoro-1,2,3,4-tetrahydro-naphthalen-2-ylamino)-propionylamino]-imidazol-1-yl}-N-((S)-2-methoxy-1-methyl-ethyl)-isobutyramide;

2-{4-[(S)-2-(6,8-Difluoro-1,2,3,4-tetrahydro-naphthalen-2-ylamino)-propionylamino]-imidazol-1-yl}-N-(3-methoxy-propyl)-isobutyramide;

2-{4-[(S)-2-(6,8-Difluoro-1,2,3,4-tetrahydro-naphthalen-2-ylamino)-propionylamino]-imidazol-1-yl}-N-[1-(1-methyl-1H-pyrazol-4-yl)-ethyl]-isobutyramide;

2-{4-[(S)-2-(6,8-Difluoro-1,2,3,4-tetrahydro-naphthalen-2-ylamino)-propionylamino]-imidazol-1-yl}-N-(3-imidazol-1-yl-propyl)-isobutyramide;

2-{4-[(S)-2-(6,8-Difluoro-1,2,3,4-tetrahydro-naphthalen-2-ylamino)-propionylamino]-imidazol-1-yl}-N-(3-morpholin-4-yl-propyl)-isobutyramide;

N-2-[(2S)-6,8-difluoro-1,2,3,4-tetrahydronaphthalen-2-yl]-N-[1-(2-{[(1-hydroxycyclohexyl)methyl]amino}-11-dimethylethyl)-1H-imidazol-4-yl]-L-norvalinamide;

N-2-[(3,5-difluorophenyl)acetyl]-N-{1-[1-(piperidin-1-ylmethyl)cyclobutyl]-1H-imidazol-4-yl}-L-norvalinamide;

N-2-[(2S)-6,8-difluoro-1,2,3,4-tetrahydronaphthalen-2-yl]-N-{1-[1-(pyrrolidin-1-ylmethyl)cyclobutyl]-1H-imidazol-4-yl}-L-norvalinamide;

N-2-[(3,5-difluorophenyl)acetyl]-N-[1-(1-{[(2,2-dimethylpropyl)amino]methyl}cyclobutyl)-1H-imidazol-4-yl]-L-norvalinamide;

N-2-[(3,5-difluorophenyl)acetyl]-N-[1-(1-{[(2,2-dimethylpropyl)amino]methyl}cyclobutyl)-1H-imidazol-4-yl]-L-norvalinamide;

N-2-[(2S)-6,8-difluoro-1,2,3,4-tetrahydronaphthalen-2-yl]-N-[1-(1-{[(22-dimethylpropyl)amino]methyl}cyclobutyl)-1H-imidazol-4-yl]-L-norvalinamide;

N-2-[(2S)-6,8-difluoro-1,2,3,4-tetrahydronaphthalen-2-yl]-N-(1-{1,1-dimethyl-2-[(2-methylbenzyl)amino]-2-oxoethyl}-1H-imidazol-4-yl)-L-norvalinamide;

N-2-[(2S)-6,8-difluoro-1,2,3,4-tetrahydronaphthalen-2-yl]-N-(1-{1-methyl-2-[(tetrahydro-2H-pyran-4-ylmethyl)amino]ethyl}-1H-imidazol-4-yl)-L-norvalinamide;

N-2-[(2S)-6,8-difluoro-1,2,3,4-tetrahydronaphthalen-2-yl]-N-(1-{2-[(3-methoxypropyl)amino]-1,1-dimethyl-2-oxoethyl}-1H-imidazol-4-yl)-L-norvalinamide;

N-2-[(2S)-6,8-difluoro-1,2,3,4-tetrahydronaphthalen-2-yl]-N-[1-(2-{[(2-hydroxybutyl)amino]methyl}phenyl)-1H-imidazol-4-yl]-L-norvalinamide;

tert-butyl 3-{[4-({N-[(2S)-6,8-difluoro-1,2,3,4-tetrahydronaphthalen-2-yl]-L-norvalyl}amino)-1H-imidazol-1-yl]methyl}azetidine-1-carboxylate;

N-2-[(2S)-6,8-difluoro-1,2,3,4-tetrahydronaphthalen-2-yl]-N-(1-{[1-(2,2-dimethylpropyl)azetidin-3-yl]methyl}-1H-imidazol-4-yl)-L-norvalinamide;

2-[4-({(2S)-2-[(6,8-difluoro-1,2,3,4-tetrahydronaphthalen-2-yl)amino]-2-phenylacetyl}amino)-1H-imidazol-1-yl]-N-(2,2-dimethylpropyl)-2-methylpropanamide;

N-(2-chlorobenzyl)-2-[4-({(2S)-2-[(6,8-difluoro-1,2,3,4-tetrahydronaphthalen-2-yl)amino]-2-phenylacetyl}amino)-1H-imidazol-1-yl]-2-methylpropanamide;

2-[4-({(2S)-2-[(6,8-difluoro-1,2,3,4-tetrahydronaphthalen-2-yl)amino]-2-phenylacetyl}amino)-1H-imidazol-1-yl]-N-(2,3-dihydro-1H-inden-1-yl)-2-methylpropanamide;

N-[(1R)-1-cyclohexylethyl]-2-[4-({(2S)-2-[(6,8-difluoro-1,2,3,4-tetrahydronaphthalen-2-yl)amino]-2-phenylacetyl}amino)-1H-imidazol-1-yl]-2-methylpropanamide;

2-[4-({(2S)-2-[(6,8-difluoro-1,2,3,4-tetrahydronaphthalen-2-yl)amino]-2-phenylacetyl}amino)-1H-imidazol-1-yl]-2-methyl-N-(2-methylcyclohexyl)propanamide;

(2S)-N-(1-{2-[(1R,4S)-2-azabicyclo[2.2.1]hept-2-yl]-1,1-dimethyl-2-oxoethyl}-1H-imidazol-4-yl)-2-[(6,8-difluoro-1,2,3,4-tetrahydronaphthalen-2-yl)amino]-2-phenylacetamide;

N-(3,4-difluorobenzyl)-2-[4-({(2S)-2-[(6,8-difluoro-1,2,3,4-tetrahydronaphthalen-2-yl)amino]-2-phenylacetyl}amino)-1H-imidazol-1-yl]-2-methylpropanamide;

2-[4-({(2S)-2-[(6,8-difluoro-1,2,3,4-tetrahydronaphthalen-2-yl)amino]-2-phenylacetyl}amino)-1H-imidazol-1-yl]-N-(2,2-dimethylpropyl)-2-methylpropanamide;

N-cyclohexyl-2-[4-({(2S)-2-[(6,8-difluoro-1,2,3,4-tetrahydronaphthalen-2-yl)amino]-2-phenylacetyl}amino)-1H-imidazol-1-yl]-2-methylpropanamide;

2-[4-({(2S)-2-[(6,8-difluoro-1,2,3,4-tetrahydronaphthalen-2-yl)amino]-2-phenylacetyl}amino)-1H-imidazol-1-yl]-2-methyl-N-(2-methylbenzyl)propanamide;

N-(2,4-difluorobenzyl)-2-[4-({(2S)-2-[(6,8-difluoro-1,2,3,4-tetrahydronaphthalen-2-yl)amino]-2-phenylacetyl}amino)-1H-imidazol-1-yl]-2-methylpropanamide;

2-[4-({(2S)-2-[(6,8-difluoro-1,2,3,4-tetrahydronaphthalen-2-yl)amino]-2-phenylacetyl}amino)-1H-imidazol-1-yl]-2-methyl-N-(4-methylcyclohexyl)propanamide;

2-[4-({(2S)-2-[(6,8-difluoro-1,2,3,4-tetrahydronaphthalen-2-yl)amino]-2-phenylacetyl}amino)-1H-imidazol-1-yl]-2-methyl-N-(3,3,5,5-tetramethylcyclohexyl)propanamide;

N-2-(6,8-difluoro-1,2,3,4-tetrahydronaphthalen-2-yl)-N-(1-{1,1-dimethyl-2-[(2-methylbenzyl)amino]-2-oxoethyl}-1H-imidazol-4-yl)-O-methyl-L-serinamide;

N-2-[(2S)-6,8-difluoro-1,2,3,4-tetrahydronaphthalen-2-yl]-N-(1-{[1-(2,2-dimethylpropyl)pyrrolidin-2-yl]methyl}-1H-imidazol-4-yl)-L-norvalinamide;

N-2-[(2S)-6,8-difluoro-1,2,3,4-tetrahydronaphthalen-2-yl]-N-(1-{[1-(2,2-dimethylpropanoyl)pyrrolidin-2-yl]methyl}-1H-imidazol-4-yl)-L-norvalinamide;

(2S)-2-{[(2S)-6,8-difluoro-1,2,3,4-tetrahydronaphthalen-2-yl]amino}-N-{1-[1-(2,2-dimethylpropyl)-2-oxopiperidin-3-yl]-1H-imidazol-4-yl}pentanamide (2S)-N-[1-(1-benzyl-2-oxopiperidin-3-yl)-1H-imidazol-4-yl]-2-{[(2S)-6,8-difluoro-1,2,3,4-tetrahydronaphthalen-2-yl]amino}pentanamide N-2-[(2S)-6,8-difluoro-1,2,3,4-tetrahydronaphthalen-2-yl]-N-(1-{[(2S)-1-(2,2-dimethylpropyl)azetidin-2-yl]methyl}-1H-imidazol-4-yl)-L-norvalinamide;

N-2-[(2S)-6,8-difluoro-1,2,3,4-tetrahydronaphthalen-2-yl]-N-[-({(2S)-1-[(2S)-2-hydroxybutyl]azetidin-2-yl}methyl)-1H-imidazol-4-yl]-L-norvalinamide;

tert-butyl 3-{[4-({N-[(2S)-6,8-difluoro-1,2,3,4-tetrahydronaphthalen-2-yl]-L -norvalyl}amino)-1H-imidazol-1-yl]methyl}-3-hydroxyazetidine-1-carboxylate N-2-[(2S)-6,8-difluoro-1,2,3,4-tetrahydronaphthalen-2-yl]-N-(1-{[1-(2,2-dimethylpropyl)-3-hydroxyazetidin-3-yl]methyl}-1H-imidazol-4-yl)-L-norvalinamide;

N-{1-[(3S,4R)-1-benzyl-4-{2-[(2,2-dimethylpropyl)amino]ethyl}pyrrolidin-3-yl]-1H -imidazol-4-yl}-N-2-[(2S)-6,8-difluoro-1,2,3,4-tetrahydronaphthalen-2-yl]-L-norvalinamide;

N-2-[(2S)-6,8-difluoro-1,2,3,4-tetrahydronaphthalen-2-yl]-N-[1-(2-{[(2,2-dimethylpropyl)amino]methyl}-4,5-difluorophenyl)-1H-imidazol-4-yl]-L-norvalinamide;

N-{1-[2-({3-[acetyl(methyl)amino]pyrrolidin-1-yl}methyl)phenyl]-1H-imidazol-4-yl}-N-2-[(2S)-6,8-difluoro-1,2,3,4-tetrahydronaphthalen-2-yl]-L-norvalinamide;

N-{1-[2-({[(1R,2R)-2-(benzyloxy)cyclopentyl]amino}methyl)phenyl]-1H-imidazol-4-yl}-N-2-[(2S)-6,8-difluoro-1,2,3,4-tetrahydronaphthalen-2-yl]-L-norvalinamide;

N-(1-{2-[(4-acetyl-1,4-diazepan-1-yl)methyl]phenyl}-1H-imidazol-4-yl)-N-2-[(2S)-6,8-difluoro-1,2,3,4-tetrahydronaphthalen-2-yl]-L-norvalinamide;

N-2[(2S)-6,8-difluoro-1,2,3,4-tetrahydronaphthalen-2-yl]-N-{1-[2-({[2-(3-hydroxypiperidin-1-yl)ethyl]amino}methyl)phenyl]-1H-imidazol-4-yl}-L-norvalinamide;

N-2-[(2S)-6,8-difluoro-1,2,3,4-tetrahydronaphthalen-2-yl]-N-{1-[2-({[(1-ethylpiperidin-3-yl)methyl]amino}methyl)phenyl]-1H-imidazol-4-yl}-L-norvalinamide;

N-{1-[2-({[(3R)-1-acetylpyrrolidin-3-yl]amino}methyl)phenyl]-1H-imidazol-4-yl}-N-2-[(2S)-6,8-difluoro-1,2,3,4-tetrahydronaphthalen-2-yl]-L-norvalinamide;

N-2-[(2S)-6,8-difluoro-1,2,3,4-tetrahydronaphthalen-2-yl]-N-(1-{2-[(4-ethylpiperazin-1-yl)methyl]phenyl}-1H-imidazol-4-yl)-L-norvalinamide;

N-2-[(2S)-6,8-difluoro-1,2,3,4-tetrahydronaphthalen-2-yl]-N-{1-[2-({[(1S,2R)-2-hydroxy-2,3-dihydro-1H-inden-1-yl]amino}methyl)phenyl]-1H-imidazol-4-yl}-L -norvalinamide;

N-2-[(2S)-6,8-difluoro-1,2,3,4-tetrahydronaphthalen-2-yl]-N{1-[2-(morpholin-4-ylmethyl)phenyl]-1H-imidazol-4-yl}-L-norvalinamide;

N-2-[(2S)-6,8-difluoro-1,2,3,4-tetrahydronaphthalen-2-yl]-N-[1-(2-{[(2-morpholin -4-ylethyl)amino]methyl}phenyl)-1H-imidazol-4-yl]-L-norvalinamide;

N-2-[(2S)-6,8-difluoro-1,2,3,4-tetrahydronaphthalen-2-yl]-N-{1-[2-({[2-(2-oxo-1,3-oxazinan-3-yl)ethyl]amino}methyl)phenyl]-1H-imidazol-4-yl}-L-norvalinamide;

N-(1-{2-[(bicyclo[1.1.1]pent-1-ylamino)methyl]phenyl}-1H-imidazol-4-yl)-N-2-[(2S)-6,8-difluoro-1,2,3,4-tetrahydronaphthalen-2-yl]-L-norvalinamide;

N-2-[(2S)-6,8-difluoro-1,2,3,4-tetrahydronaphthalen-2-yl]-N-[1-(2-{[(2-propoxyethyl)amino]methyl}phenyl)-1H-imidazol-4-yl]-L-norvalinamide;

N-2-[(2S)-6,8-difluoro-1,2,3,4-tetrahydronaphthalen-2-yl]-N-{1-[2-({[(1-isobutyrylpiperidin-3-yl)methyl]amino}methyl)phenyl]-1H-imidazol-4-yl}-L-norvalinamide;

N-{1-[2-({[(1R,2R)-2-(benzyloxy)cyclohexyl]amino}methyl)phenyl]-1H-imidazol-4-yl}-N-2-[(2S)-6,8-difluoro-1,2,3,4-tetrahydronaphthalen-2-yl]-L-norvalinamide;

N-2-[(2S-6,8-difluoro-1,2,3,4-tetrahydronaphthalen-2-yl]-N-{1-[2-({[2-(dimethylamino)-2-oxoethyl]amino}methyl)phenyl]-1H-imidazol-4-yl}-L-norvalinamide;

N-2-[(2S)-6,8-difluoro-1,2,3,4-tetrahydronaphthalen-2-yl]-N-{1-[2-(2,3-dihydro-1H-indol-1-ylmethyl)phenyl]-1H-imidazol-4-yl}-L-norvalinamide;

N-{1-(2-{[(2,4-difluorobenzyl)amino]methyl}phenyl)-1H-imidazol-4-yl]-N-2-[(2S)-6,8-difluoro-1,2,3,4-tetrahydronaphthalen-2-yl]-L-norvalinamide;

N-2-[(2S)-6,8-difluoro-1,2,3,4-tetrahydronaphthalen-2-yl]-N-{1-[2-({[2-(2-fluorophenoxyl)ethyl]amino}methyl)phenyl]-1H-imidazol-4-yl}-L-norvalinamide;

N-{1-[2-({[2-(diethylamino)ethyl]amino}methyl)phenyl]-1H-imidazol-4-yl}-N-2-[(2S)-6,8-difluoro-1,2,3,4-tetrahydronaphthalen-2-yl]-L-norvalinamide;

N-2-[(2S)-6,8-difluoro-1,2,3,4-tetrahydronaphthalen-2-yl]-N-{1-[2-({[2-(2-oxo-1,3-oxazolidin-3-yl)ethyl]amino}methyl)phenyl]-1H-imidazol-4-yl}-L-norvalinamide;

N-2-[(2S)-6,8-difluoro-1,2,3,4-tetrahydronaphthalen-2-yl]-N-{1-[2-({[2-(2-oxoimidazolidin-1-yl)ethyl]amino}methyl)phenyl]-1H-imidazol-4-yl}-L-norvalinamide;

N-2-[(2S)-6,8-difluoro-1,2,3,4-tetrahydronaphthalen-2-yl]-N-{1-[2-({[2-(3-methyl-1H-pyrazol-1-yl)ethyl]amino}methyl)phenyl]-1H-imidazol-4-yl}-L-norvalinamide;

N-2-[(2S)-6,8-difluoro-1,2,3,4-tetrahydronaphthalen-2-yl]-N-{1-[2-({[1-(hydroxymethyl)pentyl]amino}methyl)phenyl]-1H-imidazol-4-yl}-L-norvalinamide;

N-2-[(2S)-6,8-difluoro-1,2,3,4-tetrahydronaphthalen-2-yl]-N-[1-(2-{[(2-isopropoxyethyl)amino]methyl}phenyl)-1H-imidazol-4-yl]-L-norvalinamide;

N-2-[(2S)-6,8-difluoro-1,2,3,4-tetrahydronaphthalen-2-yl]-N-{1-[2-({[(1R)-1-(hydroxymethyl)propyl]amino}methyl)phenyl]-1H-imidazol-4-yl}-L-norvalinamide;

N-{1-[2-({[1-(4-chlorobenzyl)-2-hydroxyethyl]amino}methyl)phenyl]-1H-imidazol-4-yl}-N-2-[(2S)-6,8-difluoro-1,2,3,4-tetrahydronaphthalen-2-yl]-L-norvalinamide;

N-2-[(2S)-6,8-difluoro-1,2,3,4-tetrahydronaphthalen-2-yl]-N-{1-[2-({[(1,3-dimethylpyrrolidin-3-yl)methyl]amino}methyl)phenyl]-1H-imidazol-4-yl}-L-norvalinamide;

N-2-[(2S)-6,8-difluoro-1,2,3,4-tetrahydronaphthalen-2-yl]-N-{1-[2-({[(1,3-dimethylpyrrolidin-3-yl)methyl]amino}methyl)phenyl]-1H-imidazol-4-yl}-L-norvalinamide;

N-(1-{2-[(4-acetylpiperazin-1-yl)methyl]phenyl}-1H-imidazol-4-yl)-N-2-[(2S)-6,8-difluoro-1,2,3,4-tetrahydronaphthalen-2-yl]-L-norvalinamide;

N-{1-[2-({[(1-tert-butyl-5-oxopyrrolidin-3-yl)methyl]amino}methyl)phenyl]-1H-imidazol-4-yl}-N-2-[(2S)-6,8-difluoro-1,2,3,4-tetrahydronaphthalen-2-yl]-L-norvalinamide;

N-2-[(2S)-6,8-difluoro-1,2,3,4-tetrahydronaphthalen-2-yl]-N-[1-(2-{[(2-methoxyethyl)amino]methyl}phenyl)-1H-imidazol-4-yl]-L-norvalinamide;

N-2-[(2S)-6,8-difluoro-1,2,3,4-tetrahydronaphthalen-2-yl]-N-[1-(2-{[(2-ethoxyethyl)amino]methyl}phenyl)-1H-imidazol-4-yl]-L-norvalinamide;

N-2-[(2S)-6,8-difluoro-1,2,3,4-tetrahydronaphthalen-2-yl]-N-{1-[2-({[2-(diisopropylamino)ethyl]amino}methyl)phenyl]-1H-imidazol-4-yl}-L-norvalinamide;

N-2-[(2S)-6,8-difluoro-1,2,3,4-tetrahydronaphthalen-2-yl]-N-{1-[2-({[3-(1H-imidazol-1-yl)propyl]amino}methyl)phenyl]-1H-imidazol-4-yl}-L-norvalinamide;

N-2-[(2S)-6,8-difluoro-1,2,3,4-tetrahydronaphthalen-2-yl]-N-{1-[2-({[(1S)-1-(hydroxymethyl)-2,2-dimethylpropyl]amino}methyl)phenyl]-1H-imidazol-4-yl}-L-norvalinamide;

N-2-[(2S)-6,8-difluoro-1,2,3,4-tetrahydronaphthalen-2-yl]-N-{1-[2-({[(1S)-1-methyl-2-(methylamino)-2-oxoethyl]amino}methyl)phenyl]-1H-imidazol-4-yl}-L-norvalinamide;

N-2-[(2S)-6,8-difluoro-1,2,3,4-tetrahydronaphthalen-2-yl]-N-{1-[2-({[2-(dimethylamino)-1-methylethyl]amino}methyl)phenyl]-1H-imidazol-4-yl}-L-norvalinamide;

N-2-[(2S)-6,8-difluoro-1,2,3,4-tetrahydronaphthalen-2-yl]-N-(1-{2-[(3-methyl-5,6-dihydro[1,2,4]triazolo[4,3-a]pyrazin-7(8H)-yl)methyl]phenyl}-1H-imidazol-4-yl)-L-norvalinamide;

N-2-[(2S)-6,8-difluoro-1,2,3,4-tetrahydronaphthalen-2-yl]-N-{1-[2-({[(3-methyl-1,2,4-oxadiazol-5-yl)methyl]amino}methyl)phenyl]-1H-imidazol-4-yl}-L-norvalinamide;

N-2-[(2S)-6,8-difluoro-1,2,3,4-tetrahydronaphthalen-2-yl]-N-[1-(2-{[(2-phenoxyethyl)amino]methyl}phenyl)-1H-imidazol-4-yl]-L-norvalinamide;

N-2-[(2S)-6,8-difluoro-1,2,3,4-tetrahydronaphthalen-2-yl]-N-[1-(2-{[methyl(1-methylpyrrolidin-3-yl)amino]methyl}phenyl)-1H-imidazol-4-yl]-L-norvalinamide;

N-2-[(2S)-6,8-difluoro-1,2,3,4-tetrahydronaphthalen-2-yl]-N-[1-(2-{[(2,2,2-trifluoroethyl)amino]methyl}phenyl)-1H-imidazol-4-yl]-L-norvalinamide;

N-2-[(2S)-6,8-difluoro-1,2,3,4-tetrahydronaphthalen-2-yl]-N-{1-[2-({[(1S,2S)-1-(hydroxymethyl)-2-methylbutyl]amino}methyl)phenyl]-1H-imidazol-4-yl}-L-norvalinamide;

N-2-[(2S)-6,8-difluoro-1,2,3,4-tetrahydronaphthalen-2-yl]-N-{1-[2-({[2-(2-oxopyrrolidin-1-yl)ethyl]amino}methyl)phenyl]-1H-imidazol-4-yl}-L-norvalinamide;

N-2-[(2S)-6,8-difluoro-1,2,3,4-tetrahydronaphthalen-2-yl]-N-(1-{2-[(2,3-dihydro-1H-inden-2-ylamino)methyl]phenyl}-1H-imidazol-4-yl)-L-norvalinamide;

N-{1-[2-({[2-(acetylamino)ethyl]amino}methyl)phenyl]-1H-imidazol-4-yl}-N-2-[(2S)-6,8-difluoro-1,2,3,4-tetrahydronaphthalen-2-yl]-L-norvalinamide;

N-2-[(2S)-6,8-difluoro-1,2,3,4-tetrahydronaphthalen-2-yl]-N-{1-[2-({[2-(dimethylamino)ethyl]amino}methyl)phenyl]-1H-imidazol-4-yl}-L-norvalinamide;

N-{1-[2-({[(1R)-1-benzyl-2-hydroxyethyl]amino}methyl)phenyl]-1H-imidazol-4-yl}-N-2-[(2S)-6,8-difluoro-1,2,3,4-tetrahydronaphthalen-2-yl]-L-norvalinamide;

N-2-[(2S)-6,8-difluoro-1,2,3,4-tetrahydronaphthalen-2-yl]-N-[1-(2-{[(2-methylcyclohexyl)amino]methyl}phenyl)-1H-imidazol-4-yl]-L-norvalinamide;

N-2-[(2S)-6,8-difluoro-1,2,3,4-tetrahydronaphthalen-2-yl]-N-{1-[2-({[(1S)-1-(hydroxymethyl)-2-methylpropyl]amino}methyl)phenyl]-1H-imidazol-4-yl}-L-norvalinamide;

N-2-[(2S)-6,8-difluoro-1,2,3,4-tetrahydronaphthalen-2-yl]-N-{1-[2-(pyrrolidin-1-ylmethyl)phenyl]-1H-imidazol-4-yl}-L-norvalinamide;

N-{1-[2-({[3-(benzyloxy)-2-hydroxypropyl]amino}methyl)phenyl]-1H-imidazol-4-yl}-N-2-[(2S)-6,8-difluoro-1,2,3,4-tetrahydronaphthalen-2-yl]-L-norvalinamide;

N-2-[(2S)-6,8-difluoro-1,2,3,4-tetrahydronaphthalen-2-yl]-N-[1-(2-{[(2-hydroxy-3-phenoxypropyl)amino]methyl}phenyl)-1H-imidazol-4-yl]-L-norvalinamide;

N-(1-{2-[(tert-butylamino)methyl]phenyl}-1H-imidazol-4-yl)-N~2~-[(2S)-6,8-difluoro-1,2,3,4-tetrahydronaphthalen-2-yl]-L-norvalinamide;

N-2-[(2S)-6,8-difluoro-1,2,3,4-tetrahydronaphthalen-2-yl]-N-{1-[2-({[(5-methylisoxazol-3-yl)methyl]amino}methyl)phenyl]-1H-imidazol-4-yl}-L-norvalinamide;

N-2-[(2S)-6,8-difluoro-1,2,3,4-tetrahydronaphthalen-2-yl]-N-(1-{2-[({[(2R)-1-ethylpyrrolidin-2-yl]methyl}amino)methyl]phenyl}-1H-imidazol-4-yl)-L-norvalinamide;

N-(1-{2-[({2-[butyl(methyl)amino]ethyl}amino)methyl]phenyl}-1H-imidazol-4-yl)-N-2-[(2S)-6,8-difluoro-1,2,3,4-tetrahydronaphthalen-2-yl]-L-norvalinamide;

N-(1-{2-[({2-[butyl(methyl)amino]ethyl}amino)methyl]phenyl}-1H-imidazol-4-yl)-N-2-[(2S)-6,8-difluoro-1,2,3,4-tetrahydronaphthalen-2-yl]-L-norvalinamide;

N-2-[(2S)-6,8-difluoro-1,2,3,4-tetrahydronaphthalen-2-yl]-N-(1-{2-[(prop-2-yn-1-ylamino)methyl]phenyl}-1H-imidazol-4-yl)-L-norvalinamide;

N-2-[(2S)-6,8-difluoro-1,2,3,4-tetrahydronaphthalen-2-yl]-N-{1-[2-({[(3-ethylisoxazol-5-yl)methyl]amino}methyl)phenyl]-1H-imidazol-4-yl}-L-norvalinamide;

N-{1-[2-({[2-(diethylamino)ethyl](methyl)amino}methyl)phenyl]-1H-imidazol-4-yl}-N-2-[(2S)-6,8-difluoro-1,2,3,4-tetrahydronaphthalen-2-yl]-L-norvalinamide;

N-[1-(2-{[(2-tert-butoxyethyl)amino]methyl}phenyl)-1H-imidazol-4-yl]-N-2-[(2S)-6,8-difluoro-1,2,3,4-tetrahydronaphthalen-2-yl]-L-norvalinamide;

N-2-[(2S)-6,8-difluoro-1,2,3,4-tetrahydronaphthalen-2-yl]-N-(1-{2-[({[(2S)-1-ethylpyrrolidin-2-yl]methyl}amino)methyl]phenyl}-1H-imidazol-4-yl)-L-norvalinamide;

N-2-[(2S)-6,8-difluoro-1,2,3,4-tetrahydronaphthalen-2-yl]-N-{1-[2-({[1-(2,2-dimethylpropanoyl)pyrrolidin-3-yl]amino}methyl)phenyl]-1H-imidazol-4-yl}-L-norvalinamide;

N-2-[(2S)-6,8-difluoro-1,2,3,4-tetrahydronaphthalen-2-yl]-N-{1-[2-({[1-(hydroxymethyl)butyl]amino}methyl)phenyl]-1H-imidazol-4-yl}-L-norvalinamide;

N-2-[(2S)-6,8-difluoro-1,2,3,4-tetrahydronaphthalen-2-yl]-N-[1-(2-{[(1,1-dioxidotetrahydro-3-thienyl)amino]methyl}phenyl)-1H-imidazol-4-yl]-L-norvalinamide;

N-[1-(2-{[(1R)-1-cyclohexylethyl]amino}-1,1-dimethyl-2-oxoethyl)-1H-imidazol-4-yl]-N-2-[(2S)-6,8-difluoro-1,2,3,4-tetrahydronaphthalen-2-yl]-L-norvalinamide;

N-2-[(2S)-6,8-difluoro-1,2,3,4-tetrahydronaphthalen-2-yl]-N-{1-[1,1-dimethyl-2-oxo-2-(3-phenylpyrrolidin-1-yl)ethyl]-1H-imidazol-4-yl}-L-norvalinamide;

N-2-[(2S)-6,8-difluoro-1,2,3,4-tetrahydronaphthalen-2-yl]-N-[1-(1,1-dimethyl-2-{[(5-methyl-2-furyl)methyl]amino}-2-oxoethyl)-1H-imidazol-4-yl]-L-norvalinamide;

N-2-[(2S)-6,8-difluoro-1,2,3,4-tetrahydronaphthalen-2-yl]-N-[1-(2-{[1-(methoxymethyl)propyl]amino}-1,1-dimethyl-2-oxoethyl)-1H-imidazol-4-yl]-L-norvalinamide;

N-2-[(2S)-6,8-difluoro-1,2,3,4-tetrahydronaphthalen-2-yl]-N-[1-(2-{[1-(methoxymethyl)propyl]amino}-1,1-dimethyl-2-oxoethyl)-1H-imidazol-4-yl]-L -norvalinamide;

N-(1-{2-[(3,4-difluorobenzyl)amino]-1,1-dimethyl-2-oxoethyl}-1H-imidazol-4-yl)-N-2-[(2S)-6,8-difluoro-1,2,3,4-tetrahydronaphthalen-2-yl]-L-norvalinamide;

N-2-[(2S)-6,8-difluoro-1,2,3,4-tetrahydronaphthalen-2-yl]-N-(1-{2-[(4-fluorobenzyl)amino]-1,1-dimethyl-2-oxoethyl}-1H-imidazol-4-yl)-L-norvalinamide;

N-2-[(2S)-6,8-difluoro-1,2,3,4-tetrahydronaphthalen-2-yl]-N-[1-(2-{[2-(2-furyl)ethyl]amino}-1,1-dimethyl-2-oxoethyl)-1H-imidazol-4-yl]-L-norvalinamide;

N-(1-{2-[benzyl(ethyl)amino]-1,1-dimethyl-2-oxoethyl}-1H-imidazol-4-yl)-N-2-[(2S)-6,8-difluoro-1,2,3,4-tetrahydronaphthalen-2-yl]-L-norvalinamide;

N-2-[(2S)-6,8-difluoro-1,2,3,4-tetrahydronaphthalen-2-yl]-N-[1-(1,1-dimethyl-2-{methyl[2-(1H-pyrazol-1-yl)ethyl]amino}-2-oxoethyl)-1H-imidazol-4-yl]-L-norvalinamide;

N-[1-(2-{[(1S)-1-cyclohexylethyl]amino}-1,1-dimethyl-2-oxoethyl)-1H-imidazol-4-yl]-N-2-[(2S)-6,8-difluoro-1,2,3,4-tetrahydronaphthalen-2-yl]-L-norvalinamide;

N-(1-{2-[(2,4-difluorobenzyl)amino]-1,1-dimethyl-2-oxoethyl}-1H-imidazol-4-yl)-N -2-[(2S)-6,8-difluoro-1,2,3,4-tetrahydronaphthalen-2-yl]-L-norvalinamide;

N-2-[(2S)-6,8-difluoro-1,2,3,4-tetrahydronaphthalen-2-yl]-N-(1-{1,1-dimethyl-2-[methyl(2-pyridin-2-ylethyl)amino]-2-oxoethyl}-1H-imidazol-4-yl)-L-norvalinamide;

N-2-[(2S)-6,8-difluoro-1,2,3,4-tetrahydronaphthalen-2-yl]-N-[1-(2-{[(4-hydroxytetrahydro-2H-thiopyran-4-yl)methyl]amino}ethyl)-1H-imidazol-4-yl]-L -norvalinamide;

N-2-[(2S)-6,8-difluoro-1,2,3,4-tetrahydronaphthalen-2-yl]-N-(1-{2-[(2-methoxy-1-methylethyl)amino]ethyl}-1H-imidazol-4-yl)-L-norvalinamide;

N-2-[(2S)-6,8-difluoro-1,2,3,4-tetrahydronaphthalen-2-yl]-N-(1-{2-[(2-methoxy-1-methylethyl)amino]ethyl}-1H-imidazol-4-yl)-L-norvalinamide;

N-2-[(2S)-6,8-difluoro-1,2,3,4-tetrahydronaphthalen-2-yl]-N-(1-{2-[(3-ethoxypropyl)amino]ethyl}-1H-imidazol-4-yl)-L-norvalinamide;

N-2-[(2S)-6,8-difluoro-1,2,3,4-tetrahydronaphthalen-2-yl]-N-(1-{2-[(3-methoxypropyl)amino]ethyl}-1H-imidazol-4-yl)-L-norvalinamide;

N-2-[(2S)-6,8-difluoro-1,2,3,4-tetrahydronaphthalen-2-yl]-N-(1-{2-[(2-isopropoxyethyl)amino]ethyl}-1H-imidazol-4-yl)-L-norvalinamide;

N-2-[(2S)-6,8-difluoro-1,2,3,4-tetrahydronaphthalen-2-yl]-N-(1-{2-[(2-isopropoxyethyl)amino]ethyl}-1H-imidazol-4-yl)-L-norvalinamide;

N-2-[(2S)-6,8-difluoro-1,2,3,4-tetrahydronaphthalen-2-yl]-N-[1-(2-{[(2S)-tetrahydrofuran-2-ylmethyl]amino}ethyl)-1H-imidazol-4-yl]-L-norvalinamide;

N-2-[(2S)-6,8-difluoro-1,2,3,4-tetrahydronaphthalen-2-yl]-N-[1-(2-{[(2S) -tetrahydrofuran-2-ylmethyl]amino}ethyl)-1H-imidazol-4-yl]-L-norvalinamide;

N-[1-(2-{[(1R)-1-cyclohexylethyl]amino}ethyl)-1H-imidazol-4-yl]-N-2-[(2S)-6,8-difluoro-1,2,3,4-tetrahydronaphthalen-2-yl]-L-norvalinamide;

N-2-[(2S)-6,8-difluoro-1,2,3,4-tetrahydronaphthalen-2-yl]-N-(1-{2-[(3-isopropoxypropyl)amino]ethyl}-1H-imidazol-4-yl)-L-norvalinamide;

N-2-[(2S)-6,8-difluoro-1,2,3,4-tetrahydronaphthalen-2-yl]-N-[1-(2-{[2-(methylthio)ethyl]amino}ethyl)-1H-imidazol-4-yl]-L-norvalinamide;

N-2-[(2S)-6,8-difluoro-1,2,3,4-tetrahydronaphthalen-2-yl]-N-(1-{2-[(tetrahydro-2H-pyran-3-ylmethyl)amino]ethyl}-1H-imidazol-4-yl)-L-norvalinamide;

N-2-[(2S)-6,8-difluoro-1,2,3,4-tetrahydronaphthalen-2-yl]-N-[1-(2-{[(2R) -tetrahydrofuran-2-ylmethyl]amino}ethyl)-1H-imidazol-4-yl]-L-norvalinamide;

N-2-[(2S)-6,8-difluoro-1,2,3,4-tetrahydronaphthalen-2-yl]-N-(1-{2-[(2-methoxyethyl)amino]ethyl}-1H-imidazol-4-yl)-L-norvalinamide;

N-2-[(2S)-6,8-difluoro-1,2,3,4-tetrahydronaphthalen-2-yl]-N-[1-({1-[(2S)-2-hydroxybutyl]pyrrolidin-2-yl}methyl)-1H-imidazol-4-yl]-L-norvalinamide;

N-2-[(2S)-6,8-difluoro-1,2,3,4-tetrahydronaphthalen-2-yl]-N-(1-{[1-(2,2-dimethylpropyl)-3-hydroxypiperidin-3-yl]methyl}-1H-imidazol-4-yl)-L-norvalinamide;

N-2-[(2S)-6,8-difluoro-1,2,3,4-tetrahydronaphthalen-2-yl]-N-[1-({1-[(2S)-2-hydroxybutyl]pyrrolidin-2-yl}methyl)-1H-imidazol-4-yl]-L-norvalinamide;

N-2-[(2S)-6,8-difluoro-1,2,3,4-tetrahydronaphthalen-2-yl]-N-{1-[2-({[(1,3-dimethylpyrrolidin-3-yl)methyl]amino}methyl)-4,5-difluorophenyl]-1H-imidazol-4-yl}-L-norvalinamide;

N-(1-{2-[({2-[butyl(methyl)amino]ethyl}amino)methyl]-4,5-difluorophenyl}-1H-imidazol-4-yl)-N-2-[(2S)-6,8-difluoro-1,2,3,4-tetrahydronaphthalen-2-yl]-L-norvalinamide;

N-2-[(2S)-6,8-difluoro-1,2,3,4-tetrahydronaphthalen-2-yl]-N-{1-[1-(2,2-dimethylpropyl)-2-oxopyrrolidin-3-yl]-1H-imidazol-4-yl}-L-norvalinamide;

N-2-[(2S)-6,8-difluoro-1,2,3,4-tetrahydronaphthalen-2-yl]-N-(1-{(1S)-2-[(3-methoxypropyl)amino]-1-methylethyl}-1H-imidazol-4-yl)-L-norvalinamide;

N-2-[(2S)-6,8-difluoro-1,2,3,4-tetrahydronaphthalen-2-yl]-N-{1-[2-({[(1-hydroxycyclohexyl)methyl]amino}carbonyl)cyclobutyl]-1H-imidazol-4-yl}-L-norvalinamide;

N-[1-(2-{[(3,4-difluorobenzyl)amino]carbonyl}cyclobutyl)-1H-imidazol-4-yl]-N-2-[(2S)-6,8-difluoro-1,2,3,4-tetrahydronaphthalen-2-yl]-L-norvalinamide;

N-2-[(2S)-6,8-difluoro-1,2,3,4-tetrahydronaphthalen-2-yl]-N-(1-{2-[(2-methylbenzyl)amino]-2-oxoethyl}-1H-imidazol-4-yl)-L-norvalinamide;

N-2-[(2S)-6,8-difluoro-1,2,3,4-tetrahydronaphthalen-2-yl]-N-(1-{2-oxo-2-[(tetrahydro-2H-pyran-2-ylmethyl)amino]ethyl}-1H-imidazol-4-yl)-L-norvalinamide;

N-(1-{2-[(34-difluorobenzyl)amino]-2-oxoethyl}-1H-imidazol-4-yl)-N-2-[(2S) -6,8-difluoro-1,2,3,4-tetrahydronaphthalen-2-yl]-L-norvalinamide;

N-[1-(2-{[(1S)-1-cyclohexylethyl]amino}-2-oxoethyl)-1H-imidazol-4-yl]-N-2-[(2S) -6,8-difluoro-1,2,3,4-tetrahydronaphthalen-2-yl]-L-norvalinamide;

N-2-[(2S)-6,8-difluoro-1,2,3,4-tetrahydronaphthalen-2-yl]-N-(1-{2-[(4-fluorobenzyl)amino]-2-oxoethyl}-1H-imidazol-4-yl)-L-norvalinamide;

N-2-[(2S)-6,8-difluoro-1,2,3,4-tetrahydronaphthalen-2-yl]-N-[1-(2-{[2-(2-furyl)ethyl]amino}-2-oxoethyl)-1H-imidazol-4-yl]-L-norvalinamide;

N-2-[(2S)-6,8-difluoro-1,2,3,4-tetrahydronaphthalen-2-yl]-N-(1-{2-[methyl(2-pyridin-2-ylethyl)amino]-2-oxoethyl}-1H-imidazol-4-yl)-L-norvalinamide;

N-2-[(2S)-6,8-difluoro-1,2,3,4-tetrahydronaphthalen-2-yl]-N-[1-(2-{[(5-methyl-2-furyl)methyl]amino}-2-oxoethyl)-1H-imidazol-4-yl]-L-norvalinamide;

N-(1-{2-[(24-difluorobenzyl)amino]-2-oxoethyl}-1H-imidazol-4-yl)-N-2-[(2S)-6,8-difluoro-1,2,3,4-tetrahydronaphthalen-2-yl]-L-norvalinamide;

N-[1-(2-{[(1R)-1-cyclohexylethyl]amino}-2-oxoethyl)-1H-imidazol-4-yl]-N-2-[(2S) -6,8-difluoro-1,2,3,4-tetrahydronaphthalen-2-yl]-L-norvalinamide;

N-2-[(2S)-6,8-difluoro-1,2,3,4-tetrahydronaphthalen-2-yl]-N-[1-(2-oxo-2-{[(2R) -tetrahydrofuran-2-ylmethyl]amino}ethyl)-1H-imidazol-4-yl]-L-norvalinamide;

N-(1-{2-[benzyl(ethyl)amino]-2-oxoethyl}-1H-imidazol-4-yl)-N-2-[(2S)-6,8-difluoro-1,2,3,4-tetrahydronaphthalen-2-yl]-L-norvalinamide;

N-2-[(2S)-6,8-difluoro-1,2,3,4-tetrahydronaphthalen-2-yl]-N-{1-[1-(tetrahydro-2H-pyran-4-ylmethyl)azetidin-3-yl]-1H-imidazol-4-yl}-L-norvalinamide;

N-2-[(2S)-6,8-difluoro-1,2,3,4-tetrahydronaphthalen-2-yl]-N-[1-({(2S)-1-[(2S)-2-hydroxypropyl]azetidin-2-yl}methyl)-1H-imidazol-4-yl]-L-norvalinamide;

N-2-[(2S)-6,8-difluoro-1,2,3,4-tetrahydronaphthalen-2-yl]-N-{1-[2-({[1-(trifluoroacetyl)pyrrolidin-3-yl]amino}methyl)phenyl]-1H-imidazol-4-yl}-L-norvalinamide;

N-2-[(2S)-6,8-difluoro-1,2,3,4-tetrahydronaphthalen-2-yl]-N-{1-[2-({[1-(2,2,2-trifluoroethyl)pyrrolidin-3-yl]amino}methyl)phenyl]-1H-imidazol-4-yl}-L-norvalinamide;

N-2-[(2S)-6,8-difluoro-1,2,3,4-tetrahydronaphthalen-2-yl]-N-(1-{2-[(3-methoxypropyl)amino]-1-methyl-2-oxoethyl}-1H-imidazol-4-yl)-L-norvalinamide;

N-2-[(2S)-6,8-difluoro-1,2,3,4-tetrahydronaphthalen-2-yl]-N-(1-{2-[(tetrahydro-2H-pyran-4-ylamino)methyl]phenyl}-1H-imidazol-4-yl)-L-norvalinamide;

N-2-[(2S)-6,8-difluoro-1,2,3,4-tetrahydronaphthalen-2-yl]-N-[1-(2-{[4-(2,2,2-trifluoroethyl)piperazin-1-yl]methyl}phenyl)-1H-imidazol-4-yl]-L-norvalinamide;

N-2-[(2S)-6,8-difluoro-1,2,3,4-tetrahydronaphthalen-2-yl]-N-[1-(2-{[4-(trifluoroacetyl)piperazin-1-yl]methyl}phenyl)-1H-imidazol-4-yl]-L-norvalinamide;

N-2-[(2S)-6,8-difluoro-1,2,3,4-tetrahydronaphthalen-2-yl]-N-(1-{(1S)-2-[(2-methoxyethyl)amino]-1-methylethyl}-1H-imidazol-4-yl)-L-norvalinamide;

N-2-[(2S)-6,8-difluoro-1,2,3,4-tetrahydronaphthalen-2-yl]-N-{1-[(1S)-1-methyl-2-{methyl[(1-methyl-1H-pyrazol-4-yl)methyl]amino}ethyl]-1H-imidazol-4-yl}-L-norvalinamide;

N-2-[(2S)-6,8-difluoro-1,2,3,4-tetrahydronaphthalen-2-yl]-N-{1-[(1S)-1-methyl-2-(5-oxo-14-diazepan-1-yl)ethyl]-1H-imidazol-4-yl}-L-norvalinamide;

N-2-[(2S)-6,8-difluoro-1,2,3,4-tetrahydronaphthalen-2-yl]-N-{1-[(1S)-1-methyl-2-{methyl[2-(1H-pyrazol-4-yl)ethyl]amino}ethyl]-1H-imidazol-4-yl}-L-norvalinamide;

N-2-[(2S)-6,8-difluoro-1,2,3,4-tetrahydronaphthalen-2-yl]-N-(1-{(1S)-2-[(3-ethoxy-2-hydroxypropyl)amino]-1-methylethyl}-1H-imidazol-4-yl)-L-norvalinamide;

N-2-[(2S)-6,8-difluoro-1,2,3,4-tetrahydronaphthalen-2-yl]-N-(1-{(1S)-2-[(2-methoxy-1-methylethyl)amino]-1-methylethyl}-1H-imidazol-4-yl)-L-norvalinamide;

N-2-[(2S)-6,8-difluoro-1,2,3,4-tetrahydronaphthalen-2-yl]-N-{1-[(1S)-2-{[(1S)-2-methoxy-1-methylethyl]amino}-1-methylethyl]-1H-imidazol-4-yl}-L-norvalinamide;

N-2-[(2S)-6,8-difluoro-1,2,3,4-tetrahydronaphthalen-2-yl]-N-{1-[(1S)-1-methyl-2-{methyl[(1-methyl-1H-imidazol-2-yl)methyl]amino}ethyl]-1H-imidazol-4-yl}-L-norvalinamide;

N-2-[(2S)-6,8-difluoro-1,2,3,4-tetrahydronaphthalen-2-yl]-N-{1-[2-({[1-(trifluoroacetyl)piperidin-4-yl]amino}methyl)phenyl]-1H-imidazol-4-yl}-L-norvalinamide;

N-2-[(2S)-6,8-difluoro-1,2,3,4-tetrahydronaphthalen-2-yl]-N-[1-(2-{[(1-hydroxycyclopentyl)methyl]amino}-1,1-dimethyl-2-oxoethyl)-1H-imidazol-4-yl]-L -norvalinamide;

N-2-[(2S)-6,8-difluoro-1,2,3,4-tetrahydronaphthalen-2-yl]-N-[1-(2-{[(1-hydroxycyclobutyl)methyl]amino}-1,1-dimethyl-2-oxoethyl)-1H-imidazol-4-yl]-L -norvalinamide;

N-2-[(2S)-6,8-difluoro-1,2,3,4-tetrahydronaphthalen-2-yl]-N-(1-{2-[(2-hydroxy-2-phenylpropyl)(methyl)amino]-1,1-dimethyl-2-oxoethyl}-1H-imidazol-4-yl)-L -norvalinamide;

N-2-[(2S)-6,8-difluoro-1,2,3,4-tetrahydronaphthalen-2-yl]-N-[1-(2-{[(1-hydroxycyclopentyl)methyl]amino}-1-methyl-2-oxoethyl)-1H-imidazol-4-yl]-L -norvalinamide;

N-2-[(2S)-6,8-difluoro-1,2,3,4-tetrahydronaphthalen-2-yl]-N-[1-(2-{[(1-hydroxycyclobutyl)methyl]amino}-1-methyl-2-oxoethyl)-1H-imidazol-4-yl]-L -norvalinamide;

N-2-[(2S)-6,8-difluoro-1,2,3,4-tetrahydronaphthalen-2-yl]-N-(1-{2-[(2-hydroxy-2-phenylpropyl)(methyl)amino]-1-methyl-2-oxoethyl}-1H-imidazol-4-yl)-L-norvalinamide;

N-2-[(2S)-6,8-difluoro-1,2,3,4-tetrahydronaphthalen-2-yl]-N-(1-{1-methyl-2-oxo-2-[(tetrahydro-1H-pyrrolizin-7a(5H)-ylmethyl)amino]ethyl}-1H-imidazol-4-yl)-L -norvalinamide;

N-2-[(2S)-6,8-difluoro-1,2,3,4-tetrahydronaphthalen-2-yl]-N-{1-[1-({[1-(methoxymethyl)propyl]amino}carbonyl)propyl]-1H-imidazol-4-yl}-L-norvalinamide;

N-2-[(2S)-6,8-difluoro-1,2,3,4-tetrahydronaphthalen-2-yl]-N-{1-[1-({[1-(methoxymethyl)propyl]amino}methyl)propyl]-1H-imidazol-4-yl}-L-norvalinamide;

N-2-[(2S)-6,8-difluoro-1,2,3,4-tetrahydronaphthalen-2-yl]-N-{1-[(1S,2S)-2-{[(2-morpholin-4-ylethyl)amino]carbonyl}cyclobutyl]-1H-imidazol-4-yl}-L-norvalinamide;

N-2-[(2S)-6,8-difluoro-1,2,3,4-tetrahydronaphthalen-2-yl]-N-{1-[(1R,2R)-2-({[1-(methoxymethyl)propyl]amino}carbonyl)cyclobutyl]-1H-imidazol-4-yl}-L-norvalinamide;

N-{1-[(1-benzyl-4-ethylazetidin-2-yl)methyl]-1H-imidazol-4-yl}-N-2-[(2S)-6,8-difluoro-1,2,3,4-tetrahydronaphthalen-2-yl]-L-norvalinamide;

N-2-[(2S)-6,8-difluoro-1,2,3,4-tetrahydronaphthalen-2-yl]-N-{1-[1-({[(1-hydroxycyclobutyl)methyl]amino}carbonyl)propyl]-1H-imidazol-4-yl}-L-norvalinamide;

N-{1-[(4-benzylmorpholin-3-yl)methyl]-1H-imidazol-4-yl}-N-2-[(2S)-6,8-difluoro -1,2,3,4-tetrahydronaphthalen-2-yl]-L-norvalinamide;

N-(1-{[4-(cyclopropylmethyl)morpholin-3-yl]methyl}-1H-imidazol-4-yl)-N-2-[(2S) -6,8-difluoro-1,2,3,4-tetrahydronaphthalen-2-yl]-L-norvalinamide;

N-2-[(2S)-6,8-difluoro-1,2,3,4-tetrahydronaphthalen-2-yl]-N-(1-{1-[(dimethylamino)methyl]cyclopropyl}-1H-imidazol-4-yl)-L-norvalinamide;

N-{1-[(4-benzylmorpholin-2-yl)methyl]-1H-imidazol-4-yl}-N-2-[(2S)-6,8-difluoro -1,2,3,4-tetrahydronaphthalen-2-yl]-L-norvalinamide; and N-2-[(2S)-6,8-difluoro-1,2,3,4-tetrahydronaphthalen-2-yl]-N-(1-{1-[(isopropylamino)methyl]cyclopropyl}-1H-imidazol-4-yl)-L-norvalinamide;

or a pharmaceutically acceptable salt thereof.

14. A pharmaceutical composition, comprising an effective amount of a compound according claim 1, or a pharmaceutically acceptable salt thereof, and a pharmaceutically acceptable carrier.

15. A pharmaceutical composition, comprising an effective amount of a compound according claim 1, or a pharmaceutically acceptable salt thereof, and a pharmaceutically acceptable carrier.

\* \* \* \* \*